United States Patent [19]

Young et al.

[11] Patent Number: 5,204,358
[45] Date of Patent: Apr. 20, 1993

[54] HETARYL STYRYL QUINOLINES AS LEUKOTRIENE INHIBITORS

[75] Inventors: Robert N. Young, Senneville; Robert Zamboni, Pointe-Claire; Jacques-Yves Gauthier, Laval Des Rapides Laval; Michel L. Belley, St.-Laurent, all of Canada

[73] Assignee: Merck Frosst Canada, Inc., Kirkland, Canada

[21] Appl. No.: 818,598

[22] Filed: Jan. 9, 1992

Related U.S. Application Data

[60] Division of Ser. No. 527,236, May 22, 1990, Pat. No. 5,104,882, which is a continuation-in-part of Ser. No. 356,478, May 24, 1989, abandoned, which is a continuation-in-part of Ser. No. 275,160, Nov. 22, 1988, abandoned, which is a continuation-in-part of Ser. No. 125,050, Nov. 25, 1987, abandoned.

[51] Int. Cl.$^5$ ............................................ C07D 215/18
[52] U.S. Cl. .................................. 514/314; 514/311; 514/312; 514/313; 544/128; 546/176; 546/178; 546/180
[58] Field of Search ............... 514/311, 314, 312, 313; 546/153, 175, 174, 171, 170, 159, 157, 156, 155, 176

[56] References Cited

U.S. PATENT DOCUMENTS

| | | | |
|---|---|---|---|
| 4,661,499 | 4/1987 | Young et al. | 514/311 |
| 4,769,461 | 9/1988 | Musser et al. | 546/152 |
| 4,794,188 | 12/1988 | Musser et al. | 546/152 |
| 4,851,409 | 7/1989 | Young et al. | 546/152 |
| 4,904,786 | 2/1990 | Musser et al. | 546/152 |
| 4,918,081 | 4/1990 | Huang et al. | 514/314 |
| 4,920,130 | 4/1990 | Huang et al. | 514/311 |
| 4,920,131 | 4/1990 | Huang et al. | 514/314 |
| 4,920,132 | 4/1990 | Huang et al. | 514/314 |
| 4,920,133 | 4/1990 | Huang et al. | 514/314 |
| 4,962,203 | 10/1990 | Young et al. | 546/152 |
| 5,070,881 | 12/1991 | Hughes et al. | 546/175 |
| 5,081,126 | 1/1992 | Oku et al. | 546/153 |
| 5,102,881 | 4/1992 | Zamboni et al. | 514/311 |
| 5,104,882 | 4/1992 | Young et al. | 514/311 |
| 5,112,837 | 5/1992 | Burrows et al. | 546/176 |
| 5,120,744 | 6/1992 | Raddatz et al. | 546/176 |
| 5,126,354 | 6/1992 | Mohrs et al. | 514/312 |

FOREIGN PATENT DOCUMENTS

| | | |
|---|---|---|
| 0181568 | 5/1986 | European Pat. Off. |
| 0206751 | 12/1986 | European Pat. Off. |
| 0223368 | 5/1987 | European Pat. Off. |
| 0233763 | 8/1987 | European Pat. Off. |
| 0271287 | 6/1988 | European Pat. Off. |
| 0318093 | 5/1989 | European Pat. Off. |
| WO87/05510 | 9/1987 | PCT Int'l Appl. |
| 89/04303 | 5/1989 | PCT Int'l Appl. |
| 89/04304 | 5/1989 | PCT Int'l Appl. |
| WO89/4304 | 5/1989 | PCT Int'l Appl. |
| 89/04305 | 5/1989 | World Int. Prop. O. |

Primary Examiner—Donald G. Daus
Attorney, Agent, or Firm—Gabriel Lopez; Joseph F. DiPrima

[57] ABSTRACT

Compounds having the formula:

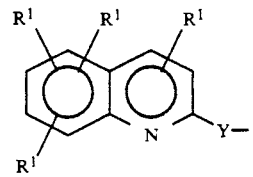
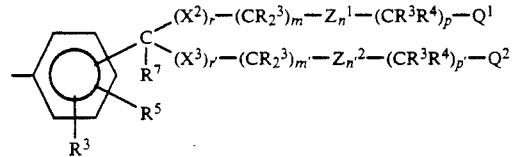

are leukotriene antagonists and inhibitors of leukotriene biosynthesis. These compounds are useful as anti-asthmatic, anti-allergic, anti-inflammatory, and cytoprotective agents.

8 Claims, No Drawings

HETARYL STYRYL QUINOLINES AS LEUKOTRIENE INHIBITORS

CROSS-REFERENCE

This is a division of Ser. No. 527,236, filed May 22, 1990, now U.S. Pat. No. 5,104,882, which is a continuation-in-part of Ser. No. 356,478, filed May 24, 1989, now abandoned, which is a continuation-in-part of Ser. No. 275,160, filed Nov. 22, 1988, now abandoned, which is a continuation-in-part of Ser. No. 125,050, filed Nov. 25, 1987, now abandoned.

BACKGROUND OF THE INVENTION

The leukotrienes and their biological activities, especially their roles in various disease states and conditions have been described. For example, see U.S. Pat. No. 4,683,325 (Jul. 28, 1987), which is incorporated herein by reference.

Several classes of compounds exhibit ability to antagonize the action of leukotrienes in mammals, especially humans. See for example: UK 2,058,785 and 2,094,301; and EP 56,172, 61,800, and 68,739.

EP 110,405 (Jun. 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors of the biosynthesis of the leukotrienes, to methods for their preparation, to intermediates useful in their preparation and to methods and pharmaceutical formulations for using these compounds in mammals (especially humans).

Because of their activity as leukotriene antagonists or biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

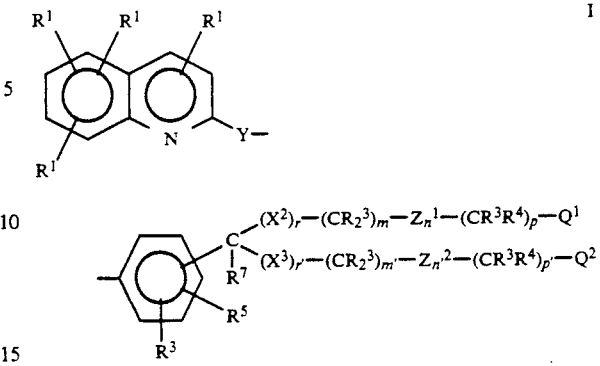

wherein
$R^1$ is H, halogen $C_1-C_8$ alkyl, $C_2-C_8$ alkenyl, $C_2-C_8$ alkynyl, $-CF_3$, $-SR^2$, $-S(O)R^2$, $-S(O)_2R^2$, $-NR^3R^3$, $-Or^3$, $-COOR^3$, $-(C=O)R^3$, $-C(OH)R^3R^3$, $-CN$, $-NO_2$, $-N_3$, substituted or unsubstituted phenyl, substituted or unsubstituted benzyl, substituted or unsubstituted 2-phenethyl, or substituted or unsubstituted pyridyl;

$R^2$ is $C_1$-$14$ $C_8$ alkyl, $C_2-C_8$ alkenyl, $C_2-C_8$ alkynyl, $-CF_3$, substituted or unsubstituted phenyl, substituted or unsubstituted benzyl, or substituted or unsubstituted 2-phenethyl;

$R^3$ is H or $R^2$;

$R^4$ is H, halogen, $-NO_2$, $-CN$, $-OR^3$, $-SR^3$, $NR^3R^3$, or $C_1-C_8$ alkyl;

$CR^3R^4$ may be the radical of a naturally occurring amino acid;

$R^5$ is H, halogen, $-NO_2$, $-N_3$, $-CN$, $-SR^2$, $-NR^3R^3$, $-OR^3$, $C_1-C_8$ alkyl, $-(C=O)R^3$, or $-S(O)_2R^2$;

$R^6$ is $-(CH_2)_s-C(R^7R^7)-(CH_2)_s-R^8$ or $-CH_2CONR^{12}R^{12}$;

$R^7$ is H or $C_1-C_4$ alkyl;

$R^8$ is
  A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
  B) the radical $W-R^9$;

$R^9$ contains up to 21 carbon atoms and is (1) a hydrocarbon radical or (2) an acyl radical of an organic acyclic or monocyclic carboxylic acid containing not more than 1 heteroatom in the ring;

$R^{10}$ is $-SR^{11}$, $-OR^{12}$, $-NR^{12}R^{12}$;

$R^{11}$ is $C_1-C_6$ alkyl, $-(C=O)R^{14}$, substituted or unsubstituted phenyl, or substituted or unsubstituted benzyl;

$R^{12}$ is H, $R^{11}$, adamantyl, naphthyl, halogen-substituted $C_1-C_6$alkyl, $C_1-C_6$ alkylene-$OR^3$, or two $R^{12}$ groups joined to the same N may form a ring of 5 or 6 members containing up to two heteroatoms chosen O, S or N;

$R^{13}$ is $C_1-C_8$ alkyl, $C_2-C_8$ alkenyl, $C_2-C_8$ alkynyl, $-CF_3$, or unsubstituted phenyl, benzyl, or 2-phenethyl;

$R^{14}$ is H or $R^{13}$;

$R^{15}$ is $R^3$ or halogen;

$R^{16}$ is H, $C_1-C_4$ alkyl, or OH;

$R^{17}$ is $C_1-C_8$ alkyl, $C_2-C_8$ alkenyl, $C_2-C_8$ alkynyl, or substituted or unsubstituted phenyl, benzyl, or 2-phenethyl;

$R^{18}$ is $C_1$-$C_8$ alkyl, $C_2$-$C_8$ alkenyl, $C_2$-$C_8$ alkynyl, —$CF_3$, or substituted or unsubstituted phenyl, benzyl, or 2-phenethyl;

$R^{19}$ is $C_4$-$C_8$ alkyl, $C_2$-$C_8$ alkenyl, $C_2$-$C_8$ alkynyl, —$CF_3$, substituted phenyl, or unsubstituted phenyl, benzyl, or 2-phenethyl;

$R^{20}$ is H or $R^{17}$;

m and m' are independently 0-8;

n and n' are independently 0 or 1 but not both 0;

p and p' are independently 0-8;

m+n+p is 1-10 when $X^2$ is O, S, S(O), or $S(O)_2$;

m+n+p is 0-10 when $X^2$ is $CR^3R^{16}$;

m'+n'+p' is 1-10 when $X^3$ is O, S, S(O), or $S(O)_2$;

m'+n'+p' is 0-10 when $X^3$ is $CR^3R^{16}$;

r is 0 or 1 when $Z^1$ is HET (—$R^3$, —$R^5$);

r is 1 when $Z^1$ is —$CONR^3$ or when n=0;

r' is 0 or 1 when $Z^2$ is HET(—$R^3$, —$R^5$);

r' is 1 when $Z^2$ is $CONR^3$ or when n'=0;

s is 0-3;

$Q^1$ and $Q^2$ are independently —$COOR^3$, tetrazole, methyltetrazole, —$COOR^6$, —$CONHS(0)_2R^{13}$, —CN, —$CONR^{12}R^{12}$, —CHO, —$CH_2OH$, —$COCH_2OH$, —$NR^7S(O)_2R^{13}$; —$C(O)R^{19}$, —$NR^{20}C(O)OR^{17}$, —$NR^{12}C(O)NR^{12}R^{12}$, —$NR^7C(O)R^{18}$, —OC(O)$NR^{12}R^{12}$, —$S(O)_2R^{18}$, —$S(O)R^{18}$, —$S(O)_2NR^{12}R^{12}$, —$NO_2$, S-substituted phenyl,

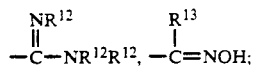

or if $Q^1$ or $Q^2$ is COOH and $R^4$ is —OH, —SH, or —$NHR^3$ then $Q^1$ or $Q^2$ and $R^4$ and the carbons through which they are attached may form a heterocyclic ring by loss of water;

W is O, S, or $NR^3$;

$X^1$ is O, S, —S(O)—, —$S(O)_2$—, —$NR^3$, or —$CR^3R^3$—;

$X^2$ and $X^3$ are independently O, S, S(O), $S(O)_2$, or $CR^3R^3$—;

$X^2$ and $X^3$ are independently O, S, S(O), $S(O)_2$, $X^2$ and $X^3$ are independently O, S, S(O), $S(O)_2$, or $CR^3R^{16}$;

Y is —$CR^3$=$CR^3$—, —C≡C—, —$CR^3R^3R^3$—$X^1$, —$X^1$—$CR^3R^3$—, —$CR^3R^3$—$X^1$—$CR^3R^3$—,

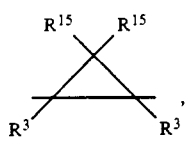

C=O, —$NR^3$—$\overset{O}{\overset{\|}{C}}$—, —$\overset{O}{\overset{\|}{C}}$—$NR^3$—, O, S, or $NR^3$;

$Z^1$ and $Z^2$ are independently —$CONR^3$— or —HET(—$R^3$—$R^5$)—, provided that at least one of them is —HET(—$R^3$, —$R^5$)—;

HET is

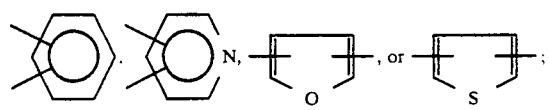

and the pharmaceutically acceptable salts thereof.

Alkyl, alkenyl, and alkynyl are intended to include linear, branched, and cyclic structures and combinations thereof.

As used herein, the term "alkyl" includes "loweralkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-ethyl-2,2-methyl-4-propylnonyl, cyclododecyl, adamantyl, and the like.

As used herein, the term "loweralkyl" includes those alkyl groups of from 1 to 7 carbon atoms. Examples of loweralkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

Alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" includes those alkoxy groups of from 1 to 3 carbon atoms of either a straight, branched, or cyclic configuration. Examples of alkoxy groups include methoxy, ethoxy, propoxy, isopropoxy, cyclopropyloxy, and the like.

Substituted phenyl, benzyl, 2-phenethyl and pyridyl include 1 or 2 substituents on the aromatic ring selected from $C_1$-$C_6$ alkyl, $R^{10}$, $NO_2$, $SCF_3$, halogen, —$COR^7$, —$COR^{10}$, CN, and $CF_3$.

Halogen includes F, Cl, Br and I.

The prodrug esters of Q (i.e., when Q=—$COOR^6$) are intended to include the esters such as are described by Saari et al., J. Med. Chem., 21, No. 8, 746-753 (1978), Sakamoto et al., Chem. Pharm. Bull., 32, No. 6, 2241-2248 (1984) and Bundgaard et al., J. Med. Chem., 30, No. 3, 451—454 (1987).

When Q and $R^4$ and the carbons through which they are attached form a ring, the rings thus formed include lactones, lactams, and thiolactones.

It is intended that the definitions of any substituent (e.g., $R^1$, $R^2$, m, Q, X, etc.) in a particular molecule be independent of its definitions elsewhere in the molecule. Thus, —$NR^3R^3$ represents —NHH, —$NHCH_3$, —$NHC_6H_5$, etc.

The heterocycles formed when two $R^{12}$ groups join through N include pyrrolidine, piperidine, morpholine, thiamorpholine, piperazine, and N-methylpiperazine.

The naturally occurring amino acids, the radicals of which may be $CR^3R^4$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:

$R^1$ is H, halogen, $C_1$-$C_8$ alkyl, —$CF_3$, —$SR^2$, —$S(O)R^2$, —$S(O)_2R^2$, —$OR^3$, or —CN;

$R^2$ is $C_1$-$C_8$ alkyl or —$CF_3$;

$R^3$ is H or $R^2$;
$R^4$ is H, $-OR^3$, $-SR^3$, $NR^3R^3$, or $C_1-C_8$ alkyl;
$CR^3R^4$ may be the radical of a naturally occurring amino acid;
$R^5$ is H, halogen, $-CN$, $-SR^2$, $-OR^3$, $C_1-C_8$ alkyl, or $-(C=O)R^3$;
$R^6$ is $-(CH_2)_s-C(R^7R^7)-(CH_2)_s-R^8$ or $-CH_2CONR^{12}R^{12}$;
$R^7$ is H or $C_1-C_4$ alkyl;
$R^8$ is
  A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
  B) the radical $W-R^9$;
$R^9$ contains up to 21 carbon atoms and is (1) a hydrocarbon radical or (2) an acyl radical of an organic acyclic or monocyclic carboxylic acid containing not more than 1 heteroatom in the ring;
$R^{10}$ is $-SR^{11}$, $-OR^{12}$, or $-NR^{12}R^{12}$;
$R^{11}$ is $C_1-C_6$ alkyl, $-(C=O)R^{14}$, unsubstituted phenyl, or unsubstituted benzyl;
$R^{12}$ is H, $R^{11}$, or two $R^{12}$ groups joined to the same N may form a ring of 5 or 6 members containing up to two heteroatoms chosen from O, S or N;
$R^{13}$ is $C_1-C_8$ alkyl, $-CF_3$, or unsubstituted phenyl, benzyl, or 2-phenethyl;
$R^{14}$ is H or $R^{13}$;
$R^{15}$ is $R^3$ or halogen;
$R^{16}$ is H, $C_1-C_4$ alkyl, or OH;

the carbons through which they are attached may form a heterocyclic ring by loss of water;
W is O, S, or NH;
$X^1$ is O, S, $-NR^3$, or $-CR^3R^3-$;
$X^2$ and $X^3$ are independently O, S, or $CR^3R^{16}$;
Y is $-CR^3=CR^3-$, $-C\equiv C-$, $-CR^3R^3-X^1-$, or $-X^1-CR^3R^3-$;
$Z^1$ and $Z^2$ are independently $-CONR^3-$ or $-HET(-R^3-R^5)-$ provided that at least one of them is $-HET(-R^3, -R^5)-$;
HET is

and the pharmaceutically acceptable salts thereof.
More-preferred compounds of Formula I are those wherein:
$CR^3R^4$ is not the radical of a naturally occurring amino acid;
$Q^1$ and $Q^2$ are independently $-COOR^3$, tetrazole or $-CONR^{12}R^{12}$;
Y is $-CH=CH-$;
$Z^1$ and $Z^2$ are $-HET(-R^3-R^5)-$;
and the remainder of the definitions are as in the above preferred embodiment.
Another more-preferred group of compounds of Formula I are those of Formula Ia:

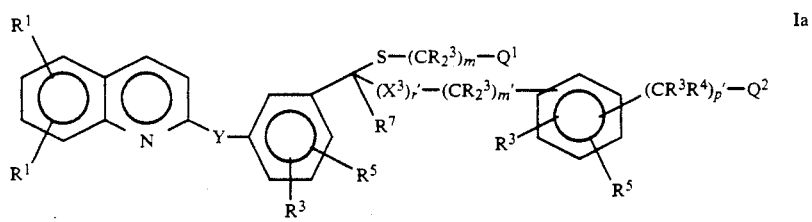

Ia m and m' are independently 0-4;
n and n' are independently 0 or 1 but not both 0;
p and p' are independently 0-4;
m+n+p is 1-10 when $X^2$ is O or S;
m+n+p is 0-10 when $X^2$ is $CR^3R^{16}$;
m'+n'+p' is 1-10 when $X^3$ is O or S;
m'+n'+p' is 0-10 when $X^3$ is $CR^3R^{16}$;
r is 0 or 1 when $Z^1$ is HET $(-R^3, -R^5)$;
r is 1 when $Z^1$ is $-CONR^3$;
r' is 0 or 1 when $Z^2$ is HET$(-R^3, -R^5)$;
r' is 1 when $Z^2$ is $CONR^3$;
s is 0-3;
$Q^1$ and $Q^2$ are independently $-COOR^3$, tetrazole, $-COOR^6$, $-CONHS(O)_2R^{13}$, $-CONR^{12}R^{12}$, $-NHS(O)_2R^{13}$; or if $Q^1$ or $Q^2$ is COOH and $R^4$ is $-OH$, $-SH$, or $-NHR^3$ then $Q^1$ or $Q^2$ and $R^4$ and wherein:
$R^4$ is H or $C_1-C_8$ alkyl;
$CR^3R^4$ is not the radical of a naturally occurring amino acid;
m is 1-4;
m' is 0-4;
p' is 0-4;
r' is 0 or 1;
$Q^1$ and $Q^2$ are independently $-COOR^3$, tetrazole, $-CONHS(O)_2R^{13}$, or $-CONR^{12}R^{12}$;
$X^3$ is S or $CR^3R^{16}$;
Y is $-CH=CH-$ or $-CH_2O-$;
and the remainder of the definitions are as in the above preferred embodiment.
Another preferred embodiment of the invention is compounds of Formula I of the Formula Ib:

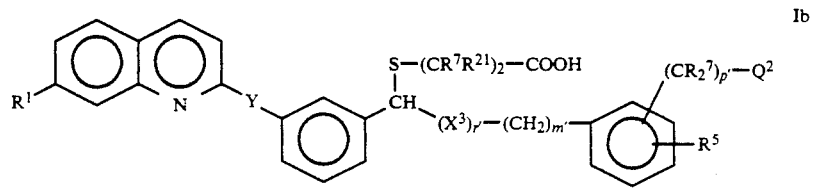

Ib wherein $R^1$ is halogen,
$R^5$ is H, halogen, —CN, —$SR^2$, —$S(O)_2R^2$, or —$OR^2$;
$R^7$ is $H_7$ or $C_1$-$C_4$ alkyl;
$R^{21}$ is $R^7$ or —O—$C_1$-$C_4$ alkyl;
r' 0 or 1;
m' is 0-2;
p' is 0 or 1;
$Q^2$ is as defined for Formula I;
$X^3$ is S or $CH_2$; and
Y is —$CH_2CH_2$—, —CH=CH— or —$CH_2O$—.

It will be understood that in the discussion of methods of treatment which follows, references to the compounds of Formula I are meant to also include the pharmaceutically acceptable salts and the lactone, lactam and thiolactone forms.

The compounds of Formula I are active as antagonists of SRS-A and especially of leukotriene $D_4$. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the biosynthesis of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. They are also effective in the treatment of inflammatory diseases of the eye.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cyto-protective ability. These assays are; (A) an ethanol-induced lesion assay and (B) an indomethacin-induced ulcer assay and are described in U.S. Pat. No. 4,683,325 Jul. 28, 1987).

The leukotriene antagonist properties of compounds of the present invention were evaluated using the following assays.

Guinea-Pig Ileum Preparation for Evaluation of Antagonists of Leukotriene $D_4$ and Other Mediators Tissue Sections of ileum were taken from male Hartley strain guinea pigs (Charles River, U.S.A.) 300 to 500 g which were sacrificed by a blow to the head and exsanguinated. Terminal ileum was removed, cleaned with warm Tyrode's solution and then divided into segments of approximately 1.5-2.0 cm in each. The segments of ileum were then mounted under 1 g tension in a 20 ml organ bath containing 10 ml of Tyrode's solution with the following composition (mM): NaCl, 137; KCl, 2.7; $MgSO_4 \cdot 7H_2O$, 0.8; $CaCl_2$, 1.8; $NaH_2PO_4$, 0.42; $NaHCO_3$, 11.9; Dextrose, 5.6. The bathing solution was continuously aerated with 95% $O_2$ and 5% $CO_2$ and bath temperature was maintained at 37° C. The beta-adrenoceptor blocker, timolol (0.5 µg/ml) and the antimuscarinic agent atropine (1.0 µM) were present in the Tyrode's solution. Isometric tension changes were recorded using Grass FT03 force displacement transducers (Grass Instrument G., Quincy, Mass.) connected to a Beckman Type R Dynograph. The output (analog) signals from all channels of the Beckman Dynograph were converted to digital signals (DL-12 Data Logger, Buxco Electronics). These signals were subsequently fed into an IBM-XT computer for storage and subsequent analysis (Buxco Electronics Custom Software). In order to wash the tissue, the bath solution was automatically aspirated and replaced with a constant volume (10 ml) of fresh solution by means of timer controlled solenoid valves.

Antagonist Testing

After the tissues were stable a standard dose of 0.3 ng/ml $LTD_4$ (100 µl) was repeatedly added (timer controlled Harvard Pump) to the bath every 4.5 minutes (1 minute contact, 30 second wash, 3 minute rest) until a consistent response was obtained (minimum of 4 responses). Addition of $LTD_4$ was performed automatically with two 4-channel Harvard Apparatus Syringe Pumps which delivered 100 µl (final bath concentration 0.3 ng/ml) of agonist simultaneously to all tissues every 4.5 minutes. Following each addition of $LTD_4$ the tissue was washed with Tyrode's solution until baseline tension was re-established. After consistent responses were obtained the tissues were used to screen compounds.

Usually, 10 µl of a 10 mg/ml solution of the compound to be tested was added to the bath 30 seconds prior to the addition of $LTD_4$. The compound and $LTD_4$ remained in contact with the tissue until the maximum tension was developed (1 minute) after which the tissue was washed repeatedly until the baseline was re-established. Percent inhibition relative to the immediately preceding control response was computed on an IBM-XT for each dose of test compound (Buxco Electronics Custom Software). If the compound was active (greater than 50% inhibition) then tests were performed with 10 fold serial dilutions until inhibition was less than 50%. Provided the response was inhibited by less than 20%, the tissue was used immediately to evaluate another compound. When the response was inhibited by greater than 20%, cycles of $LTD_4$ alone were added until a consistent response was re-established.

In order to determine the specificity of the active compounds, they were tested against contractions induced by a standard dose of histamine (50 ng/ml) using a similar protocol to that described above (½ minute contact time, 30 seconds wash and 2 minutes rest).

$LTD_4$ Binding

The results for $LTD_4$ binding were determined by the method of S. S. Pong and R. N. DeHaven, Proc. Nat. Acad. Sci. USA, 80, 7415-7419 (1983).

Compounds of Formula I were tested using the following assay to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350× g, 5 min), resuspended in buffer with vigorous shaking, filtered through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated c formation is calculated from the ratio of transmission change in the sample to the transmission change in the compound-free control.

The following assays can be used to evaluate compounds which are either leukotriene antagonists or inhibitors of leukotriene biosynthesis or which possess a combination of these two properties.

Antigen Challenge 'in vitro' Assay

Male guinea pigs weighing 300-350 g are sensitized by injecting (intraperitoneally) 0.5 ml of a suspension containing 0.4 mg of egg albumin (Ovalbumin, Grade V, Sigma Chemical Co.) and 4.0 g of aluminum hydroxide in 19.6 ml of saline. Two weeks are permitted for sensitization to occur.

Three sensitized guinea pigs are stunned and exanguinated: The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No. 7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine ($7\times10^{-6}M$), atropine ($1\times10^{-7}M$) and indomethacin ($1.4\times10^{-6}M$) are added to the buffer to block the response to released histamine, acetylcholine, and cyclooxygenase products. To record responses, one end of the tracheal chain is attached to a Gould-Statham UC-2 force displacement transducer which is connected to a Beckman Type R Dynograph. The preparations are allowed to equilibrate for one hour during which time the tissues are automatically washed (10 ml volume displacement) every 6 minutes.

[1]modified Krebs solution in grams/liter and (mM): NaCl—6.87 (120); glucose—2.1 (11); $NaHCO_3$—2.1 (25); KCl—0.32 (4.72); $CaCl_2$—0.28 (2.5); $MgSO_4.7H_2O$—0.11 (0.5); $KH_2PO_4$—0.16 (1.2); pH at bathing solution=7.35±0.05.

After the equilibration period the tissues are primed with methacholine (10 μg/ml), washed and allowed to recover to baseline. The tissues are treated again with a second dose of methacholine, washed, allowed to return to baseline and washed for an additional hour.

Two chains are used as a control. These are incubated in a concentration of egg albumin (0.1 μg/ml) sufficient to induce an average contraction of 50-80% of the methacholine response.

Each compound to be tested is added (at a final bath concentration of 10 μg/ml) 20 minutes prior to challenging the tissue with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph of the respiratory patterns. For challenge, 2 ml of a 3% solution of antigen in saline is placed into each nebulizer and the aerosol is generated with air from a small Potter diaphragm pump operating at 10 psi and flow of 8 liters/minute.

Rats are sensitized by injecting (subcutaneously) 1 ml of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 μg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intraveneously 2 minutes prior to challenge. They are either dissolved in saline or 1% methocel or suspended in 1% methocel. The volume injected is 1 ml/kg (intraveneously) or 10 ml/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acid, and the like. Particularly preferred are hydrobromic, hydrochloric, phosphoric, and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001–1% by weight solutions or suspensions of the compounds of Formula I in an acceptable opthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof. NSAIDs which are within the scope of this invention are those disclosed in U.S. Pat. No. 4,683,325 (Jul. 28, 1987).

Pharmaceutical compositions comprising the Formula I compounds may also contain inhibitors of the biosynthesis of the leukotrienes such as are disclosed in U.S. Pat. No. 4,666,907 (Apr. 19, 1987), U.S. Pat. No. 4,663,307 (May 5, 1987), U.S. Pat. No. 4,611,056 (Sept. 9, 1986), and U.S. Pat. No. 4,634,766 (Jan. 6, 1987), which are hereby incorporated herein by reference.

The compounds of the Formula I may also be used in combination with leukootriene antagonists such as those disclosed in EP 106,565 (Apr. 25, 1984) and EP 104,885 (Apr, 4, 1984) which are hereby incorporated herein by reference and others known in the art such as those disclosed in EP 56,172 (Jul. 21, 1982) and U.S. Pat. No. 4,424,231 (Jan. 3, 1984); and in U.K. Patent Specification No. 2,058,785, which are hereby incorporated herein by reference.

Pharmaceutical compositions comprising the Formula I compounds may also contain as the second active ingredient prostaglandin (including thromboxane) antagonists such as those disclosed in U.S. Pat. No. 4,536,507 (Aug. 20, 1985), U.S. Pat. No. 4,237,160 (Dec. 2, 1980), EP 166,597 (Jan. 1, 1986), and EP 234,708 (Sep. 2, 1987). They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in Nature, vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK 2,038,821 (e.g., UK-37248 and dazoxiben hydrochloride), U.S. Pat. No. 4,217,357 (e.g., UK-34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP 98,690 (e.g., CV-4151).

The combination compositions can be administered orally or or other than orally; e.g., parenterally, by insufflation, topically, rectally, etc.; using appropriate dosage forms; e.g., tablets, capsules, suspensions, solutions, and the like, for oral administration; suspension emulsions, and the like, for prenteral administration; solutions for intravenous administration; and ointments, transdermal patches, and the like, for topical administration. These compositions are formulated similarly to the compositions discussed above.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following compounds (formula I') are within the scope of the invention:

TABLE 1

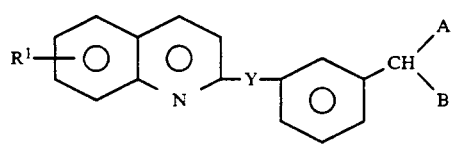

I'

| Example | R$^1$ | Y | A | B |
|---|---|---|---|---|
| 1 | 7-Cl | —CH=CH— | —S(CH$_2$)$_2$CO$_2$H | —CH$_2$CH$_2$(1,2-Phe)CO$_2$H* |
| 2 | 7-Cl | —CH=CH— | —S(CH$_2$)$_2$C(O)N(CH$_3$)$_2$ | —CH$_2$CH$_2$(1,2-Phe)CO$_2$H |
| 3 | 7-Cl | —CH$_2$CH$_2$— | —S(CH$_2$)$_2$C(O)N(CH$_3$)$_2$ | —(1,3-Phe)CO$_2$H |
| 4 | 7-Cl | —CH=CH— | —S(CH$_2$)$_2$C(O)N(CH$_3$)$_2$ | —(2,5-Thio)CO$_2$H |
| 5 | 7-Cl | —CH=CH— | —S(CH$_2$)$_2$C(O)N(CH$_3$)$_2$ | —(1,3-Phe)CO$_2$H |
| 6 | 7-Cl | —CH=CH— | —S(CH$_2$)$_2$C(O)N(CH$_3$)$_2$ | —(1,4-Phe)CO$_2$H |
| 7 | 7-Cl | —CH=CH— | —S(CH$_2$)$_2$CO$_2$H | —(1,3-Phe)CO$_2$H |
| 8 | 7-Cl | —CH=CH— | —S—(1,3-Phe)CO$_2$H | —(CH$_2$)$_2$CH(CH$_3$)CH$_2$CO$_2$H |
| 9 | 7-Cl | —CH$_2$O— | —S(CH$_2$)$_2$C(O)N(CH$_3$)$_2$ | —(1,3-Phe)CO$_2$H |
| 10 | 7-Cl | —CH=CH— | —S(1,3-Phe)CO$_2$H | —(1,3-Phe)CO$_2$H |
| 11 | 7-Cl | —CH$_2$O— | —S(CH$_2$)$_2$C(O)NH-t-Bu | —(1,3-Phe)CO$_2$H |
| 12 | 7-Cl | —CH$_2$O— | —S(CH$_2$)$_2$C(O)N(CH$_3$)$_2$ | —(3,5-Pye)CO$_2$H |
| 13 | 7-Cl | —CH=CH— | —S(CH$_2$)$_2$C(O)N(CH$_3$)$_2$ | —(3,5-Pye)CO$_2$H |
| 14 | 7-Cl | —CH$_2$O— | —S—(1,3-Phe)CO$_2$H | —S—(1,3-Phe)CO$_2$H |
| 15 | 7-Cl | —CH=CH— | —S—(1,3-Phe)CO$_2$H | —S—(1,3-Phe)CO$_2$H |
| 16 | 7-Cl | —CH=CH— | —S—(1,4-Phe)CO$_2$H | —S—(1,4-Phe)CO$_2$H |
| 17 | 7-Cl | —CH=CH— | —S—(1,4-Phe)CO$_2$H | —(2,6-Pye)CO$_2$H |
| 18 | 7-OCH$_3$ | —CH=CH— | —S(CH$_2$)$_2$CO$_2$H | —(1,3-Phe)CO$_2$H |
| 19 | 6-CF$_3$ | —CH=CH— | —S(CH$_2$)$_2$CO$_2$H | —(1,3-Phe)CO$_2$H |
| 20 | 7-CF$_3$ | —CH=CH— | —S(CH$_2$)$_2$CO$_2$H | —(1,4-Phe)CO$_2$H |
| 21 | 6-SO$_2$CH$_3$ | —CH=CH— | —S(CH$_2$)$_2$CO$_2$H | —(1,3-Phe)CO$_2$H |
| 22 | H | —CH=CH— | —S(CH$_2$)$_2$CO$_2$H | —(1,3-Phe)CO$_2$H |
| 23 | 7-Cl | —CH=CH— | —S(1,4-Phe)CO$_2$H | —(1,3-Phe)CO$_2$H |
| 24 | 7-Cl | —CH=CH— | —S(1,4-Phe)C(O)N)(CH$_3$)$_2$ | —(1,3-Phe)CO$_2$H |
| 25 | 7-Cl | —CH$_2$O— | —S(CH$_2$)$_2$CO$_2$H | —CH$_2$(1,3-Phe)CO$_2$H |
| 26 | 7-Cl | —CH=CH— | —S(4,2-Pye)CO$_2$H | —(1,3-Phe)CO$_2$H |
| 27 | 7-Cl | —CH=CH— | —S(1,2-Phe)CO$_2$H | —(1,3-Phe)CO$_2$H |
| 28 | 7-Cl | —CH$_2$O— | —S(CH$_2$)$_2$CO$_2$H | —(CH$_2$)$_2$(1,2-Phe)CO$_2$H |
| 29 | 7-Cl | —CH$_2$O— | —S(CH$_2$)$_2$C(O)NMe$_2$ | —(CH$_2$)$_2$(1,2-Phe)CO$_2$H |
| 30 | 7-Cl | —CH$_2$O— | —S(1,2-Phe)CO$_2$H | —S(1,2-Phe)CO$_2$H |
| 31 | 7-Cl | —CH$_2$O— | —(CH$_2$)$_2$C(O)N(CH$_3$)$_2$ | —(1,3-(4-Cl—Phe))CO$_2$H |
| 32 | 7-Cl | —CH$_2$O— | —SCH$_2$(1,2-Phe)CO$_2$H | —SCH$_2$(1,2-Phe)CO$_2$H |
| 33 | 7-Cl | —CH$_2$O— | —SCH$_2$(1,2-Phe)CO$_2$H | —S(CH$_2$)$_2$C(O)N(CH$_3$)$_2$ |
| 34 | 7-Cl | —CH=CH— | —S(CH$_2$)$_3$C(O)N(CH$_3$)$_2$ | —(1,3-Phe)CO$_2$H |
| 35 | 7-Cl | —CH$_2$O— | —S(CH$_2$)$_2$C(O)NH-t-Bu | —(CH$_2$)$_2$(1,2-Phe)CO$_2$H |
| 36 | 7-Cl | —CH$_2$CH$_2$— | —S(CH$_2$)$_2$C(O)NH-t-Bu | —(CH$_2$)$_2$(1,2-Phe)CO$_2$H |
| 37 | 7-Cl | —CH$_2$CH$_2$— | —S(CH$_2$)$_2$C(O)N(CH$_3$)$_2$ | —(CH$_2$)$_2$(1,3-Phe)CO$_2$H |
| 38 | 7-Cl | —CH$_2$O— | —S(CH$_2$)$_2$C(O)N(CH$_2$)$_2$ | —(1,2-Phe)CO$_2$H |
| 39 | 7-Cl | —CH$_2$O— | —S(CH$_2$)$_2$C(O)NH(1-adamantyl) | —(CH$_2$)$_2$(1,2-Phe)CO$_2$H |
| 40 | 7-Cl | —CH$_2$O— | —S(CH$_2$)$_2$C(O)N(CH$_3$)$_2$ | —(CH$_2$)$_2$(1,2-Phe)CN$_4$H* |
| 41 | 7-Cl | —CH$_2$O— | —S(CH$_2$)$_2$C(O)N(CH$_3$)$_2$ | —(CH$_2$)$_2$(1,2-Phe)CH$_2$CN$_4$H |
| 42 | 7-Cl | —CH$_2$O— | —S(CH$_2$)$_2$C(O)N(CH$_3$)$_2$ | —(CH$_2$)$_2$(1,2-Phe)CH$_2$CO$_2$H |
| 43 | 7-Cl | —CH$_2$O— | —S(CH$_2$)$_2$CO$_2$H | —(CH$_2$)$_2$(1,2-Phe)C(O)N(CH$_3$)$_2$ |
| 44 | 7-Cl | —CH$_2$O— | —S(CH$_2$)$_2$C(O)N(CH$_3$)$_2$ | —(1,3-Phe)CH$_2$CN$_4$H |
| 45 | 7-Cl | —CH$_2$O— | —S(1,3-Phe)CO$_2$H | —(1,3-Phe)CO$_2$H |
| 46 | 7-Cl | —CH$_2$O— | —S(CH$_2$)$_2$CO$_2$H | —(1,3-Phe)CH$_2$C(O)N(CH$_3$)$_2$ |
| 47 | 7-Cl | —CH$_2$O— | —S(CH$_2$)$_2$CO$_2$H | —(1,3-Phe)CH$_2$C(O)NH-t-Bu |
| 48 | 7-Cl | —CH$_2$O— | —S(CH$_2$)$_2$CN$_4$H | —(1,3-Phe)CH$_2$C(O)N(CH$_3$)$_2$ |
| 49 | 7-Cl | —CH$_2$O— | —S(CH$_2$)$_2$CN$_4$H | —(1,3-Phe)CH$_2$C(O)NH-t-Bu |
| 50 | 7-Cl | —CH$_2$O— | —SCH$_2$C(O)N(CH$_3$)$_2$ | —(1,3-Phe)CH$_2$CN$_4$H |
| 51 | 7-Cl | —CH$_2$O— | —SCH$_2$C(O)NH-t-Bu | —(1,3-Phe)CH$_2$CN$_4$H |
| 52 | 7-Cl | —CH$_2$O— | —S(CH$_2$)$_2$C(O)N(CH$_3$)$_2$ | —(1,2-Phe)CH$_2$CN$_4$H |
| 53 | 7-Cl | —CH$_2$O— | —S(CH$_2$)$_2$C(O)NH-t-Bu | —(1,2-Phe)CH$_2$CN$_4$H |
| 54 | 7-Cl | —CH$_2$O— | —SCH$_2$CO$_2$H | —(CH$_2$)$_2$(1,2-Phe)C(O)N(CH$_3$)$_2$ |
| 55 | 7-Cl | —CH$_2$O— | —SCH$_2$CO$_2$H | —(CH$_2$)$_2$(1,2-Phe)C(O)NH-t-Bu |

TABLE 1-continued

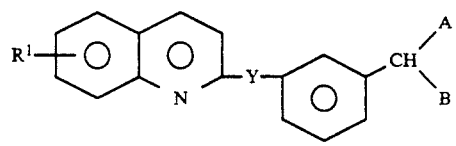

| Example | R¹ | Y | A | B |
|---|---|---|---|---|
| 56 | 7-Cl | —CH₂O— | —S(CH₂)₂CO₂H | —(CH₂)₂(1,3-Phe)C(O)N(CH₃)₂ |
| 57 | 7-Cl | —CH₂O— | —S(CH₂)₂CO₂H | —(CH₂)₂(1,3-Phe)C(O)NH-t-Bu |
| 58 | 7-Cl | —CH₂O— | —SCH₂CO₂H | —(CH₂)₂(1,3-Phe)C(O)N(CH₃)₂ |
| 59 | 7-Cl | —CH₂O— | —SCH₂CO₂H | —(CH₂)₂(1,3-Phe)C(O)NH-t-Bu |
| 60 | 7-Cl | —CH₂O— | —SCH₂CN₄H | —(CH₂)₂(1,3-Phe)C(O)N(CH₃)₂ |
| 61 | 7-Cl | —CH₂O— | —SCH₂CN₄H | —(CH₂)₂(1,3-Phe)C(O)NH-t-Bu |
| 62 | H | —CH₂O— | —S(CH₂)₂CO₂H | —(CH₂)₂(1,2-Phe)C(O)N(CH₃)₂ |
| 63 | 6,7-diCl | —CH₂O— | —S(CH₂)₂CO₂H | —(CH₂)₂(1,2-Phe)C(O)N(CH₃)₂ |
| 64 | 7-S(O)₂Me | —CH₂O— | —S(CH₂)₂CO₂H | —(CH₂)₂(1,2-Phe)C(O)N(CH₃)₂ |
| 65 | 6-OCH₃ | —CH₂O— | —S(CH₂)₂CO₂H | —(CH₂)₂(1,2-Phe)C(O)N(CH₃)₂ |
| 66 | 6-CH(CH₃)₂ | —CH₂O— | —S(CH₂)₂CO₂H | —(CH₂)₂(1,2-Phe)C(O)N(CH₃)₂ |
| 67 | 7-Cl | —CH₂O— | —S(CH₂)₂CO₂H | —(CH₂)₂(1,2-Phe)C(O)NH-t-Bu |
| 68 | 7-Cl | —CH₂O— | —S(CH₂)₂CO₂H | —(CH₂)₂(1,2-Phe)C(O)N(CH₂)₅* |
| 69 | 7-Cl | —CH₂O— | —S(CH₂)₂CO₂H | —(CH₂)₂(1,2-Phe)C(O)N((CH₂)₂O(CH₂)₂)* |
| 70 | 7-Cl | —CH₂O— | —S(CH₂)₂CO₂H | —(CH₂)₂(1,2-Phe)C(O)NH-1-adamantyl |
| 71 | 7-Cl | —CH₂O— | —S(CH₂)₂CO₂H | —(CH₂)₂(1,2-Phe)C(O)NHCH₂Ph* |
| 72 | 7-Cl | —CH₂O— | —S(CH₂)₂CO₂H | —(CH₂)₂(1,2-Phe)C(O)NH-1-naphthyl |
| 73 | 7-Cl | —CH₂O— | —S(CH₂)₂CN₄H | —(CH₂)₂(1,2-Phe)C(O)N(CH₃)₂ |
| 74 | 7-Cl | —CH₂O— | —S(CH₂)₂CN₄H | —(CH₂)₂(1,2-Phe)C(O)NH-t-Bu |
| 75 | 7-Cl | —CH₂O— | —SCH₂CH(CH₃)CO₂H | —(CH₂)₂(1,2-Phe)C(O)N(CH₃)₂ |
| 76 | 7-Cl | —CH₂O— | —SCH₂CH(CH₃)CO₂H | —(CH₂)₂(1,2-Phe)C(O)NH-t-Bu |
| 77 | 7-Cl | —CH₂O— | —S(CH₂)₂CO₂H | —(CH₂)₂(1,2-(4-Br—Phe))C(O)N(CH₃)₂ |
| 78 | 7-Cl | —CH₂O— | —S(CH₂)₂CO₂H | —(CH₂)₂(1,2-(4-SCH₃—Phe))C(O)N(CH₃)₂ |
| 79 | 7-Cl | —CH₂O— | —S(CH₂)₂CO₂H | —(CH₂)₂(1,2-(4-S(O)₂CH₃—Phe))C(O)N(CH₃)₂ |
| 80 | 7-Cl | —CH₂O— | —S(CH₂)₂CO₂H | —(CH₂)₂(1,2-(5-Br—Phe))C(O)N(CH₃)₂ |
| 81 | 7-Cl | —CH₂O— | —S(CH₂)₂CO₂H | —(CH₂)₂(1,2-(5-SCH₃—Phe))C(O)N(CH₃)₂ |
| 82 | 7-Cl | —CH₂O— | —S(CH₂)₂CO₂H | —(CH₂)₂(1,2-(5-S(O)₂CH₃—Phe))C(O)N(CH₃)₂ |
| 83 | 7-Cl | —CH₂O— | —S(CH₂)₂C(O)N(CH₃)₂ | —(CH₂)₂(1,2-Phe)C(O)NHS(O)₂CH₃ |
| 84 | 7-Cl | —CH₂O— | —S(CH₂)₂C(O)NHS(O)₂CF₃ | —(CH₂)₂(1,2-Phe)C(O)N(CH₃)₂ |
| 85 | 7-Cl | —CH₂O— | —S(CH₂)₂C(O)N(CH₃)₂ | —(1,3-Phe)CH₂C(O)NHS(O)₂Ph |
| 86 | 7-Cl | —CH₂O— | —OCH₂CN₄N | —(CH₂)₂(1,2-Phe)C(O)N(CH₃)₂ |
| 87 | 7-Cl | —CH₂O— | —OCH₂CO₂H | —(CH₂)₂(1,2-Phe)C(O)N(CH₃)₂ |
| 88 | 7-Cl | —CH₂O— | —OCH(CH₃)CO₂H | —(CH₂)₂(1,2 Phe)C(O)N(CH₃)₂ |
| 89 | 7-Cl | —CH₂O— | —O(CH₂)₂C(O)N(CH₃)₂ | —(1,3-Phe)CH₂CN₄H |
| 90 | 7-Cl | —CH₂O— | —O(CH₂)₂C(O)N(CH₃)₂ | —(1,3-Phe)CH(CH₃)CN₄H |
| 91 | 7-Cl | —CH₂CH₂— | —S(CH₂)₂CO₂H | —(CH₂)₂(1,2-Phe)C(O)N(CH₃)₂ |
| 92 | 7-Cl | —CH₂CH₂— | —SCH₂CH(CH₃)CO₂H | —(CH₂)₂(1,2-Phe)C(O)N(CH₃)₂ |
| 93 | 7-Cl | —CH₂CH₂— | —SCH₂CO₂H | —(CH₂)₂(1,2-Phe)C(O)N(CH₃)₂ |
| 94 | 7-Cl | —CH₂CH₂— | —SCH(CH₃)CO₂H | —(CH₂)₂(1,2-Phe)C(O)N(CH₃)₂ |
| 95 | 7-Cl | —CH₂O— | —S(CH₂)₂CO₂H | —(CH₂)₂(1,2-Phe)C(O)N(C₂H₅)₂ |

TABLE 1-continued

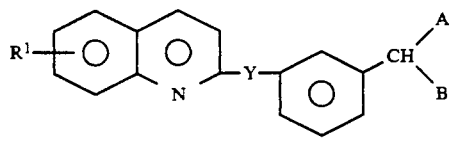

| Example | R¹ | Y | A | B |
|---------|------|--------|---------------|------------------------------|
| 96 | 7-Cl | —CH₂O— | —S(CH₂)₂CO₂H | —(CH₂)₂(1,2-Phe)C(O)NHCH₃ |

*Phe = [1,2-phenylene ring]

Thio = [thiophene ring, S]

Pye = [pyridine ring, N]

Ph = [phenyl ring]

N(CH₂)₅ = —N[piperidine ring]

N((CH₂)₂O(CH₂)₂) = —N[morpholine ring]O t-Bu = —C(CH₃)₃

CN₄H = —[tetrazole ring with N—N, N—N]—H

Compounds of the present invention can be prepared according to the following methods. Temperatures are in degrees Celcius.

METHOD A

Quinaldine derivative II is condensed with aldehyde IIa in the presence of a suitable catalyst like ZnCl₂ at temperatures greater than 120° or by heating with a dehydrating agent such as acetic anhydride to give adduct III. Bromo acid IV is treated with 2 equivalents of a base such as n-butyllithium in a suitable solvent such as THF at −100° then at −78° with III to afford alcohol V. Alcohol V is reacted with thiol VI in the presence of a suitable catalyst such as BF₃ or AlCl₃ to give adduct VII.

Method B

Alternatively adduct V can be transformed to VIII, where Z is a suitable leaving group such as Cl, using reaction conditions such as CCl₄/trioctylphosphine. VIII is reacted with thiol VI in the presence of a suitable base such as K₂CO₃ to give adduct VII.

METHOD C

Referring to Method C, a quinoline derivative of structure IX is prepared from II using a suitable reagent such as N-bromosuccinimide. IX is then reacted with a compound of formula X in the presence of a suitable base such as NAOH, NaH, K₂CO₃ or NaOMe in an inert solvent such as THF with warming if necessary to provide the adduct XI. Using the reactions described in Methods A or B Adduct XI is transformed to XII.

METHOD D

Referring to Method D, bromo derivative XIII can be treated with PPh₃ in a suitable solvent such as toluene or CH₃CN with warming if necessary to provide phosphonium salt XIV. The phosphonium salt XIV is treated with n-butyllithium then with lactol XV to afford styrene adduct XVI. Alcohol XVI in transformed to ester XVII using conventional methods such as CrO₃/pyridine followed by MnO₂/NaCN/AcOH/MeOH. Styrene adduct XVII is condensed with thiol VI in the presence of a suitable catalyst such as AlCl₃ to give thiol ether XVIII.

When A=CN, XVIII is reduced with a reagent such as SnCl₂/HCl to give aldehyde XIX. Quinaldine derivative IX is treated with PPh₃ in a suitable solvent such as toluene to give phosphonium salt XX. The phosphonium salt XX is treated with n-butyl lithium then with aldehyde XIX to give styryl quinoline XXI.

When A=OMe, XVIII is dimethylated using a suitable reagent such as BBr₃ to give phenol derivative XXII. Phenol XXII is condensed with quinaldine derivative IX using a suitable catalyst such as K₂CO₃ to afford adduct XXIII.

METHOD E

Referring to Method E, quinaldine derivative II is first treated with LDA and then with bromo derivative XXIV to afford adduct XXV. Cyano derivative XXV is reduced to aldehyde XXVI with a reagent such as $SnCl_2/HCl$. Using the methodology described in Method A or B XXVI is converted to XXVII.

METHOD F

Reaction of styrylaldehyde III with an alkanoic acid or tetrazole substituted with a thiol or hydroxy group in an inert solvent such as benzene in the presence of a suitable catalyst such as $BF_3.OEt$ affords the styrylquinoline derivative XXX.

The groups $Q^1$ and $Q^2$ may be modified by hydrolysis of an ester group, removal of a blocking group, or conversion of a nitrile to an amide or tetrazole by heating with tributyltin azide, thus providing additional examples of the leukotriene antagonists of the present invention. Compound XXX is representative of the structure I compounds.

METHOD G

Other compounds of Formula I can be prepared as indicated in Method G. Thus the ester derivative XXXI can be reduced to the alcohol XXXII by lithium aluminum hydride or other suitable reducing agents. Alcohol XXXII can then be oxidized to aldehyde XXXII by pyridinium chlorochromate or other suitable oxidizing agents. Carboxylic acids of Formula XXXIa can be converted to the acid chloride XXXIV (the acid bromide or a mixed carbonate anhydride could also be used) which when reacted with diazomethane yields the diazoketone XXXV. Compound XXXV, upon reaction with aqueous acid, preferably a nonnucleophilic acid such as sulfuric acid or p-toluenesulfonic acid, is converted to the hydroxymethyl ketone XXXVI.

Acid chloride XXXIV, upon reaction with a sulfonamide, $R^{13}SO_2NH_2$, in the presence of a weak base yields the acyl-sulfonamide XLII. Reaction of XXXIV with an amine, $R^{12}R^{12}NH$, yields amide XXXVII. Amide XXXVII can be sequentially reduced, to amine XXXVIII, with diborane or lithium aluminum hydride, and sulfonylated with $R^{13}SO_2Cl$ to produce sulfonamide XXXIX. Amide XXXVII (when both $R^{12}$ substituents are hydrogen) can be dehydrated by standard reagents to nitrile XL, which is converted to tetrazole XLI by reaction with sodium azide, tri-n-butyltin azide or other suitable methods.

METHOD H

Compound XI is converted to phosphonium salt XLII by the following sequence of reactions: 1) reduction of the carbonyl group to an alcohol by means of a suitable reducing agent such as $NaBH_4$ or $LiBH_4$; 2) conversion of the alcohol to a bromide with an appropriate reagent combination such as 1,2-bis(diphenylphosphino)ethane/$CBr_4$; 3) reaction of the bromide with triphenylphosphine. A Wittig olefination reaction between XV and XLII, using a base such as potassium hexamethyldisilazide (KHMDS), yields compound XLIII. Alcohol XLIII is converted to amide XLIV by the sequence: 1) oxidation to the aldehyde using $MnO_2$ in EtOAc; 2) oxidative conversion of the aldehyde to the methyl ester using $MnO_2/NaCN/AcOH/MeOH/THF$; 3) treatment of the resulting ester with an amine $HNR^{12}R^{12}$ or an aluminum amide such as $(CH_3)_2AlNR^{12}R^{12}$ yields amide XLIV. Reaction of XLIV and VI as described in Method D then yields compound XLV.

METHOD I

Compound XVII is converted to amide XLVI by one of the methods described in Methods G and H. Hydration of the double bond in XLVI is effected by sequential treatment with $Hg(OAc)_2$ and $NaBH_4$ to yield compound XLVII. Reaction of XLVII with alcohol XLIX, using a catalyst such as $ZnCl_2$ then yields compound L. An alternate synthesis of XLVII involves, first hydration of XVII to XLVIII, followed by amide formation. Compound L can also be prepared by acid-catalyzed addition of XLIX to the double bond in XLVI. Methods of hydration and of alcohol addition to double bonds are described in J. March, *Advanced Organic Chemistry*, 3rd. ed., John Wiley & Sons, New York, 1985, pp. 681–687.

It is to be noted that intermediate XLVIII may form a seven-membered ring lactone between the alcohol group and the ester group. Such a lactone can also be used to form amide XLVII.

Compound L is transformed to compounds LI or LII by the methodology described in Method D.

METHOD J

The functional groups, representative of $Q^1$ or $Q^2$, which are present in intermediates V, XVI, XVII, XVIII, XIX, XXII, XLIII, XLIV, XLVI, XLVII, XLVIII and L can be transformed to other representatives of $Q^1$ or $Q^2$ by the methodology described in Method G. These transformed intermediates can also be employed, according to the above methods, to prepare compounds of Formula I.

It will be evident to one skilled in the art that the above described methods must be compatible with the other functional groups present in the molecules. Where necessary, such compatibility is achieved by suitable protection and deprotection techniques (see for example, T. W. Greene, *Protective Groups in Organic Synthesis*, John Wiley & Sons, New York, 1981).

METHOD K

The enol acetate of LIII is obtained by heating LIII in isopropenyl acetate in the presence of an acid. Ozolysis of this enol ester yields the aldehyde LIV. Starting from a bromophenol, protection of the alcohol and addition of a reagent such as butyllithium, lithium or magnesium affords the organometallic LV, which is reacted with LIV to give the hydroxyacid LVI. At this point, the acid can be converted to an ester ($R^2I$/base), an amide (from the ester by treatment with $Me_2AlNR^{12}R^{12}$), a nitrile (formation of $RCONH_2$ and dehydration with trifluoroacetic anhydride/pyridine) or a ketone (addition of $R^2Li$ at 0° C. and quenching with TMSCl). Deprotection of the phenol is then done by using a reagent such as tetrabutylammonium fluoride in the case of silyl ether or pyridinium p-toluenesulfonate when P is a 2-tetrahydropyranyl group. Reaction of the phenol with a 2-(bromomethyl)quinoline (IX) derivative in the presence of $K_2CO_3$ yields the hydroxyketone LVII. The benzylic alcohol is then reacted with methanesulfonyl chloride in the presence of a base such as triethylamine and the mesylate so obtained is displaced by the sodium or the cesium thiolate of VI to afford LVIII. Alternatively, the benzylic alcohol LVII can be displaced by the thiol VI in the presence of a Lewis acid such as BF$_3$·Et$_2$O or AlCl$_3$ to give LVIII. Finally, the groups Q$^1$ and Q$^2$ of LVIII can be converted to other groups as in methods G or J as follows: an ester can be hydrolyzed to the acid; a nitrile can be reacted with tributyltin azide to afford a tetrazole; an oxime can be obtained from a ketone by treatment with hydroxylamine hydrochloride; an amide can be obtained from an acid as already described or from an ester by reaction with NR$^{12}$R$^{12}$AlMe$_2$; a nitrile can be obtained from an ester by treatment with Me$_2$AlNH$_2$ at ca. 80° C.; a carbamate can be obtained from a benzoic acid by reaction with diphenylphosphoryl azide and R$^{17}$OH; and an aniline amide or a sulfonamide can be obtained by first forming the aniline from a benzoic acid by reaction with diphenylphophoryl azide/Et$_3$N or isobutyl chloroformate/sodium azide and second, acylation or sulfonylation of this aniline derivative with R$^{18}$COCl or a sulfonic anhydride.

METHOD L

The hydroxyacid LVI is cyclized to the lactone LIX using a reagent such as 2-chloro-N-methylpyridinium iodide. Deprotection of the phenol and coupling with IX as in Method K affords lactone LIX. The lactone can be converted to an hydroxyacid (hydrolysis with NaOH), an hydroxyamide (reaction with Me$_2$AlNR$^{12}$R$^{12}$), an hydroxynitrile (reaction with Me$_2$AlNH$_2$ at ca. 80° C.) or an hydroxyester (reaction with R$^2$ONa). These benzylic alcohol derivatives are reacted with the thiol VI as in Method K to afford LVIII. Alternatively, the lactone LIX can be reacted with VI in the presence of a Lewis acid such as a combination of BF$_3$·Et$_2$O and trifluoroacetic acid to yield LVIII. The groups Q in LVIII can be transformed as described in Methods G, J and K.

METHOD M

The aldehyde LX (represented in compounds III, XI, and XXVI) is reacted with an organometallic reagent R$^7$CH$_2$M and the benzylic alcohol so obtained is oxidized to LXI with an oxidant like activated manganese dioxide. LXI is then reacted with the iodide LXII in the presence of a base such as lithium diisopropylamide to yield the addition product LXIII. Many iodides LXII are known in the art and may be prepared as described for iodides 1 and 2. Reduction with sodium borohydride or addition of an organometallic reagent affords the benzylic alcohol LXIV, which is then treated as in Method K to give the thioether LXV.

METHOD N

The enolate of the ketone LXVI, obtained by treatment of LXVI with a base such as KH or NaH, is reacted with dimethylcarbonate to yield the ketoester LXVII. LXVII is enolized with a base such as NaH and treated with the benzylic iodide LXII. The adduct so obtained is then decarboxylated using conditions such as heating with HCl in acetic acid to afford the ketone LXVIII. In cases where Q$^2$ is an ester, a mixture of ketoacid and ketoester is obtained; reesterification of the mixture with diazomethane or R$^2$I/K$_2$CO$_3$ afford LXVIII. Finally, LXVIII is treated as in Methods M or O to afford LXIX, its isomer or LXVa, all representatives of the structure I.

METHOD O

The hydroxyacid LVI is esterified using conditions such as heating with MeI and K$_2$CO$_3$ or reacting with diazomethane. Treatment of this hydroxyester with an oxidant such as pyridinium chlorochromate or activated manganese dioxide afford the ketoester LXXI. The ketone is then reduced using the chiral oxazaborolidine LXXII (see J. Am. Chem. Soc. 1987, 109, 7925-6) in the presence of borane.THF complex. Deprotection of the phenol and reaction with IX as in Method L gave the chiral benzylic alcohol LXXIII. The group Q$^2$ of LXXIII can be transformed to a nitrile, an amide or a ketone as described in Method K. The chiral center of LXXIII can be inverted to give LXXIV using conditions such as: 1) treatment with triphenylphosphine, diethyl azodicarboxylate and an acid such as R-(−)-α-methoxyphenylacetic acid (a chiral acid seems to improve the resolution); and 2) hydrolysis of the ester so obtained with a base such as NaOH. Formation of the mesylate, displacement by the thiol VI and transformation of the groups Q as in Method K yield LXXV and LXXVI, both representatives of the structure I.

METHOD P

Method P is complementary to Method F for the synthesis of dithioacetals. To the benzaldehyde LX is added one equivalent of each of thiolacetic acid and the thiol VI in the presence of a Lewis acid such as BF$_3$·Et$_2$O or trifluoroacetic acid. The mixed dithioacetal LXXVII thus formed is then treated with sodium methoxide in methanol at −20° C. and reacted with a bromide or an iodide to yield LXXVIII, which is an analog of structure XXX. Transformation of the groups Q can be done as in Method K to afford other derivatives, all of which are representatives of structure I.

METHOD Q

LXXIX is obtained from the addition of vinylmagnesium bromide to the benzaldehyde LX. LXXIX is then reacted with one equiv of an aryl compound containing a leaving group such as a triflate, an iodide or a bromide in the presence of 0.03 equiv. of Pd(OAc)$_2$, 0.09 equiv of triphenylphosphine and 1.25 equiv of NaHCO$_3$ in dimethylformamide at 100° C. to afford LXXX, which is then treated as in Method M or O to afford LXXXI as a chiral compound or as a mixture of isomers.

METHOD R

The benzaldehyde LX is treated as in Method H to afford the styrene LXXXII. The carbamate LXXXIII is then obtained by a Curtius rearrangement of the acid with diphenylphosphoryl azide and triethylamine in the presence of an alcohol. Alternatively, the aniline derivative can be formed first by treatment with diphenylphosphoryl azide/Et$_3$N/H$_2$O or with isobutyl chloroformate/NaN$_3$/H$_2$O. Then, alkylation of the aniline with a chloroformate in the presence of a base such as triethylamine affords the carbamate. LXXXIII is finally treated as in Method D or K of afford LXXXIV.

METHOD S

The compound LVIII in which the group Q$^2$ is a sulfone is obtained as follows. First, a thiophenol is obtained from the allylphenol LXXXV by reaction with sodium hydride and dimethylthiocarbamoyl chloride, rearrangement of the intermediate to the S-dimethylcarbamothioate by heating at reflux in 1,2,4-trichlorobenzene and hydrolysis with sodium methoxide. Alkylation of the thiophenol give LXXXVI, which is oxidized to the sulfone with an oxidant such as meta-chloroperbenzoic acid. Ozonolysis of the allyl group afford LXXXVII, which is transformed to LVIII as described in Method K for the conversion of LIV and LVIII.
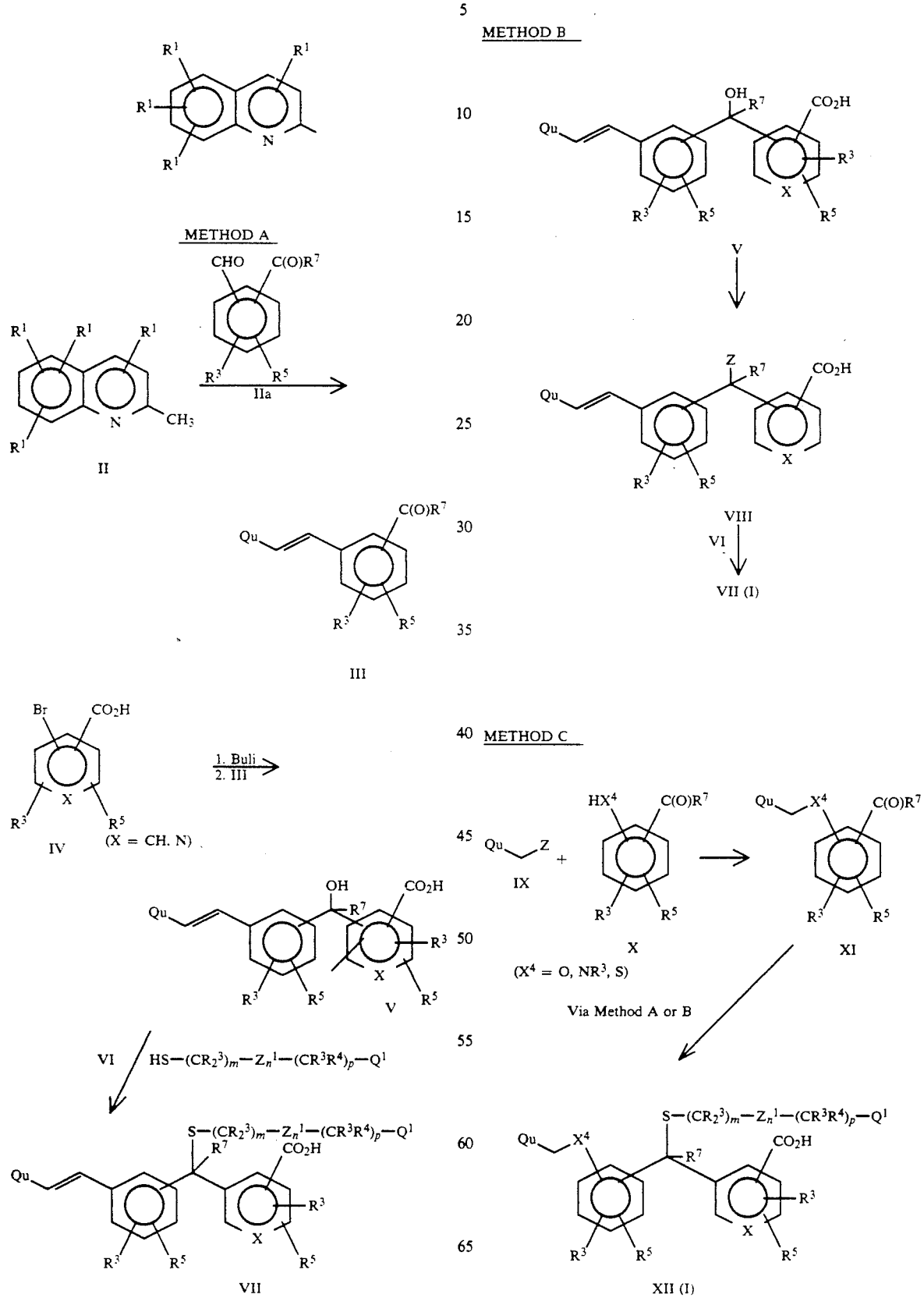

METHOD D
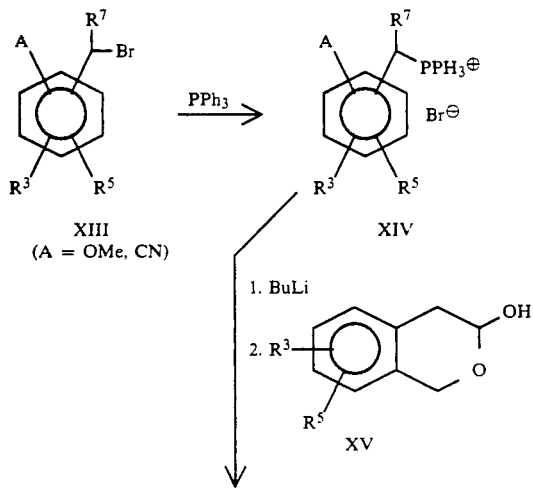
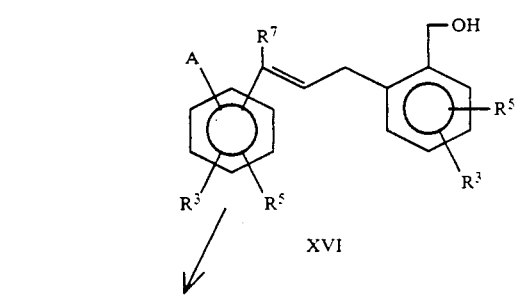
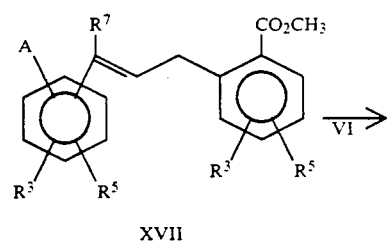
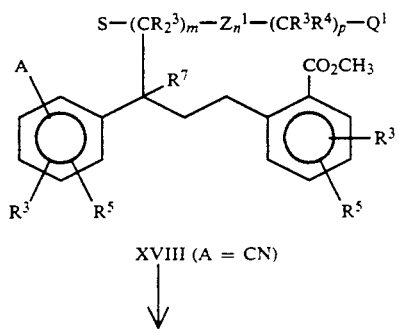
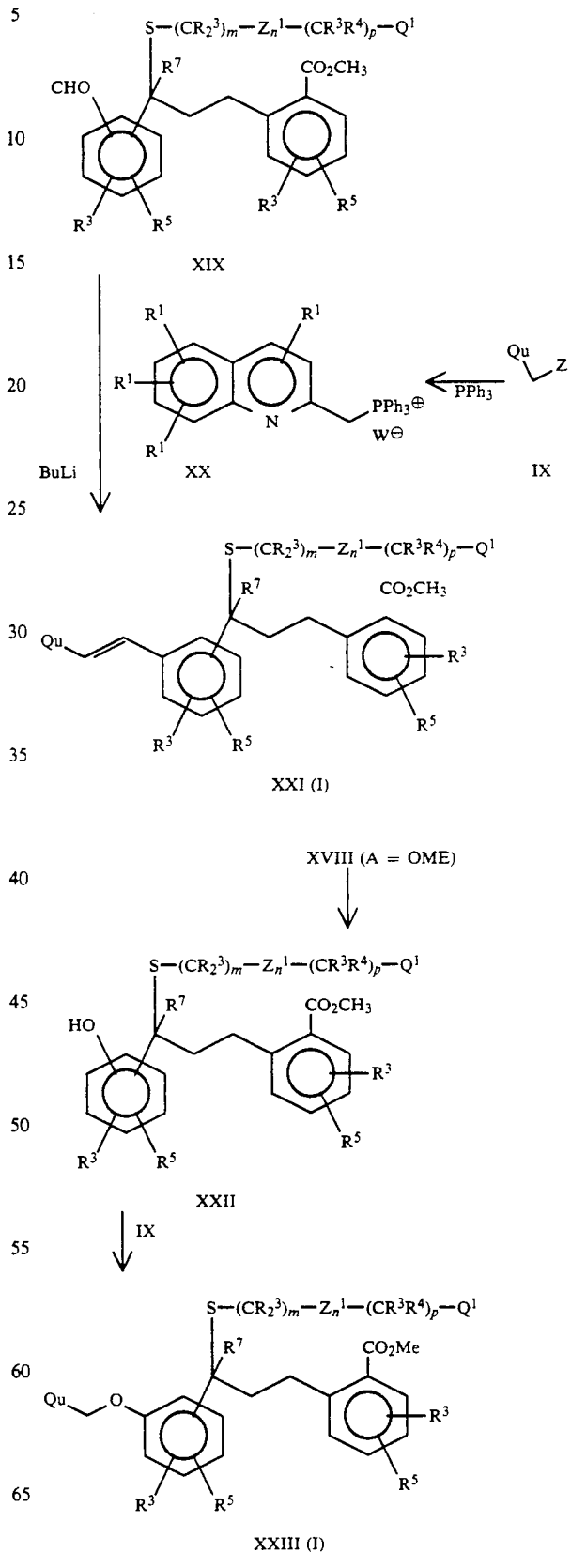

METHOD E
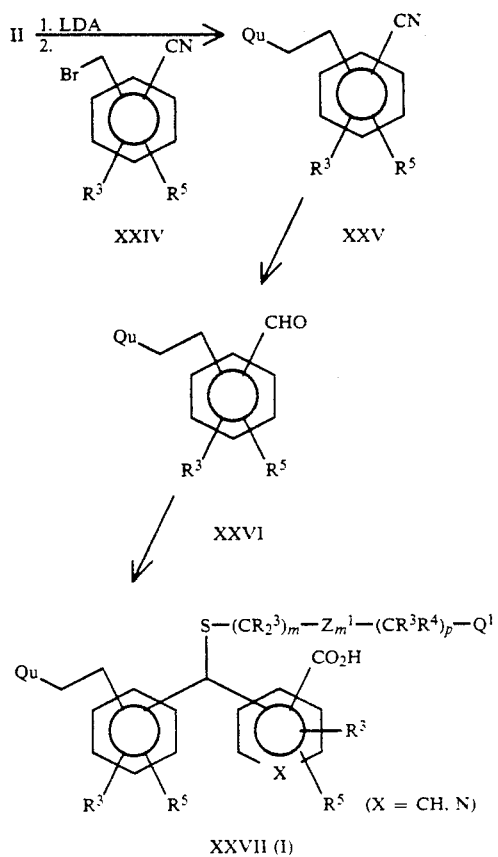
METHOD F
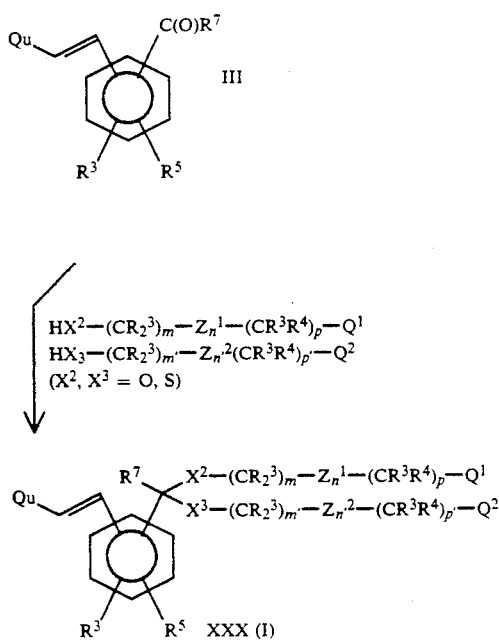
METHOD G
QP below represents the residual structure of VII. XII, XXI, XXIII, XXVII or XXX in which $Q^1$ or $Q^2$ was $CO_2R^3$ (XXXI)
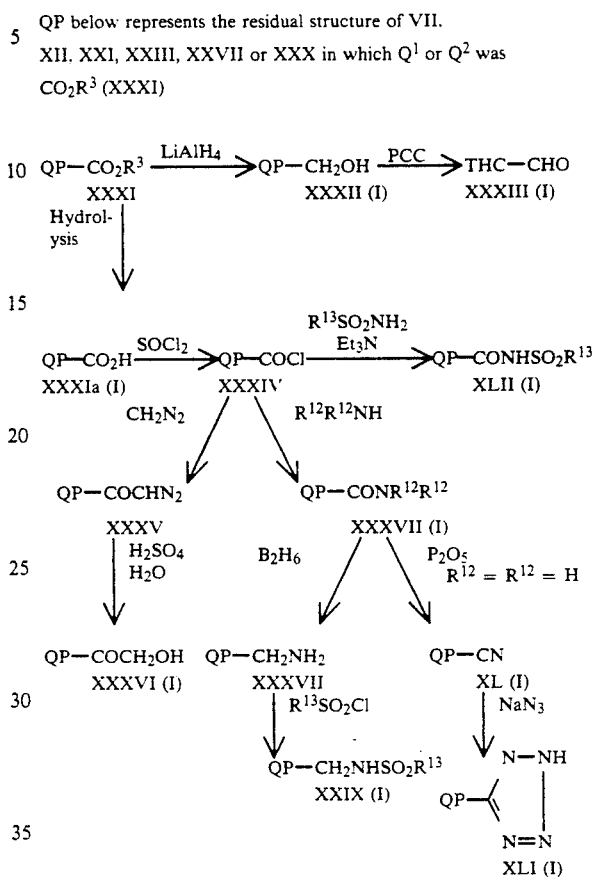
METHOD H
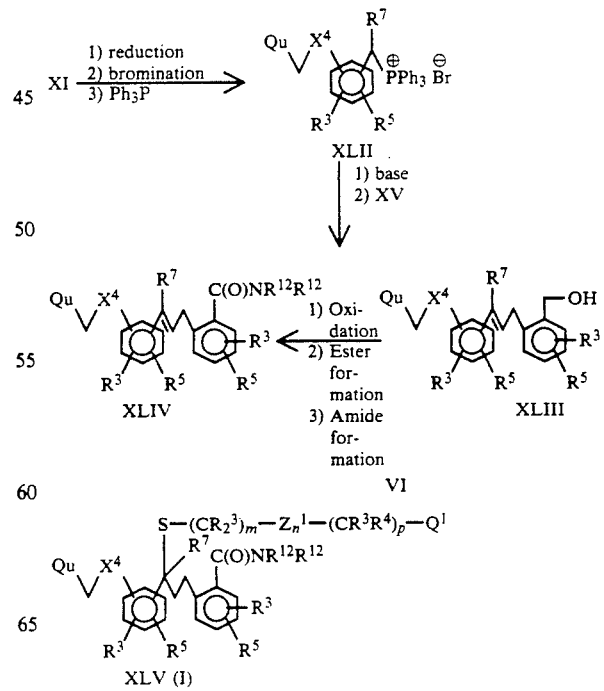

METHOD I
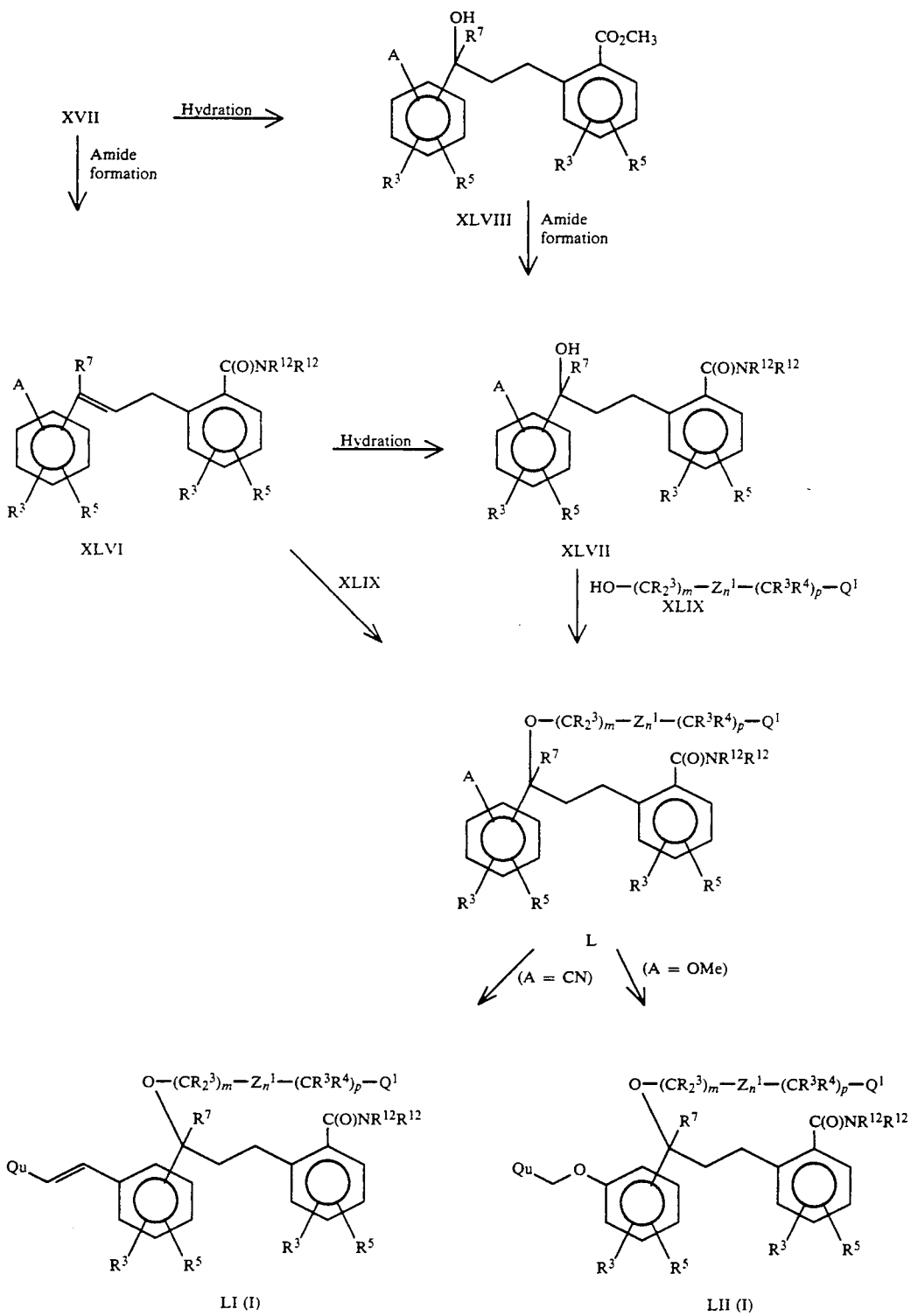

METHOD K
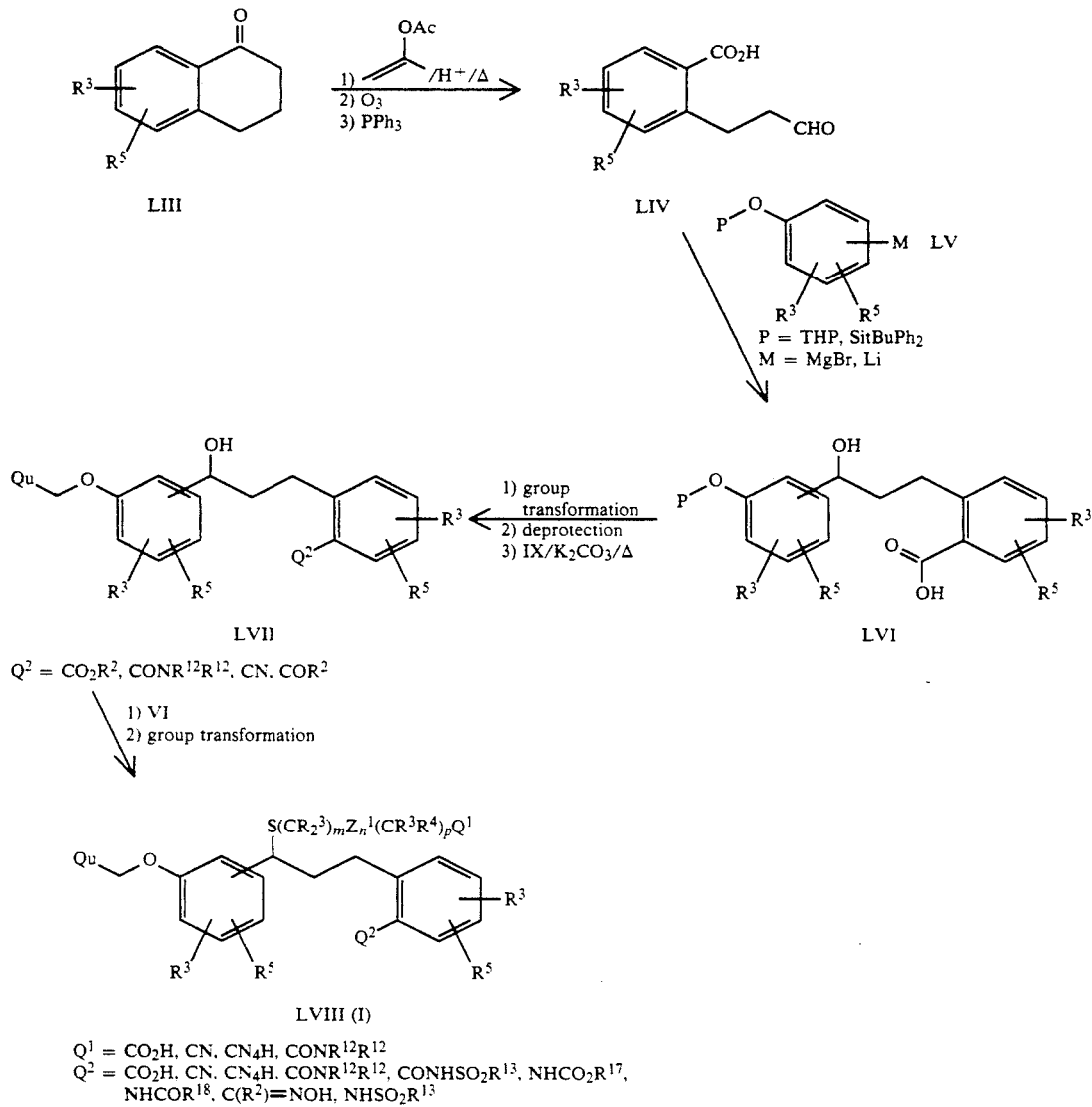
LVIII (I)
$Q^1 = CO_2H, CN, CN_4H, CONR^{12}R^{12}$
$Q^2 = CO_2H, CN, CN_4H, CONR^{12}R^{12}, CONHSO_2R^{13}, NHCO_2R^{17},$
$NHCOR^{18}, C(R^2)=NOH, NHSO_2R^{13}$
METHOD L
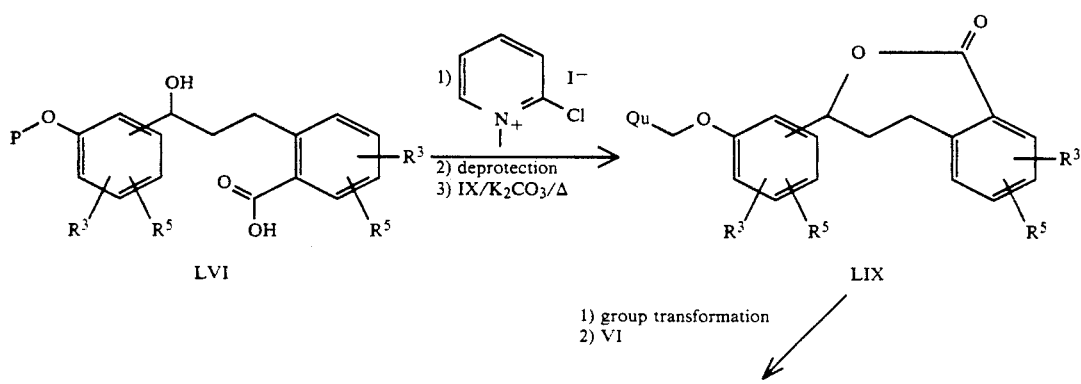

METHOD L
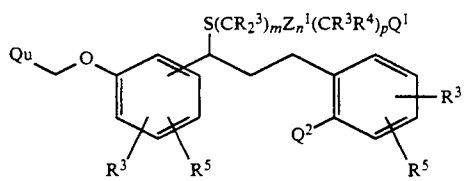
LVIII (I)
$Q^1$ = $CO_2H$, CN, $CN_4H$, $CONR^{12}R^{12}$
$Q^2$ = $CO_2H$, CN, $CN_4H$, $CONR^{12}R^{12}$, $CONHSO_2R^{13}$, $NHCO_2R^{17}$, $NHCOR^{18}$, $C(R^2)$=NOH, $NHSO_2R^{13}$
METHOD M
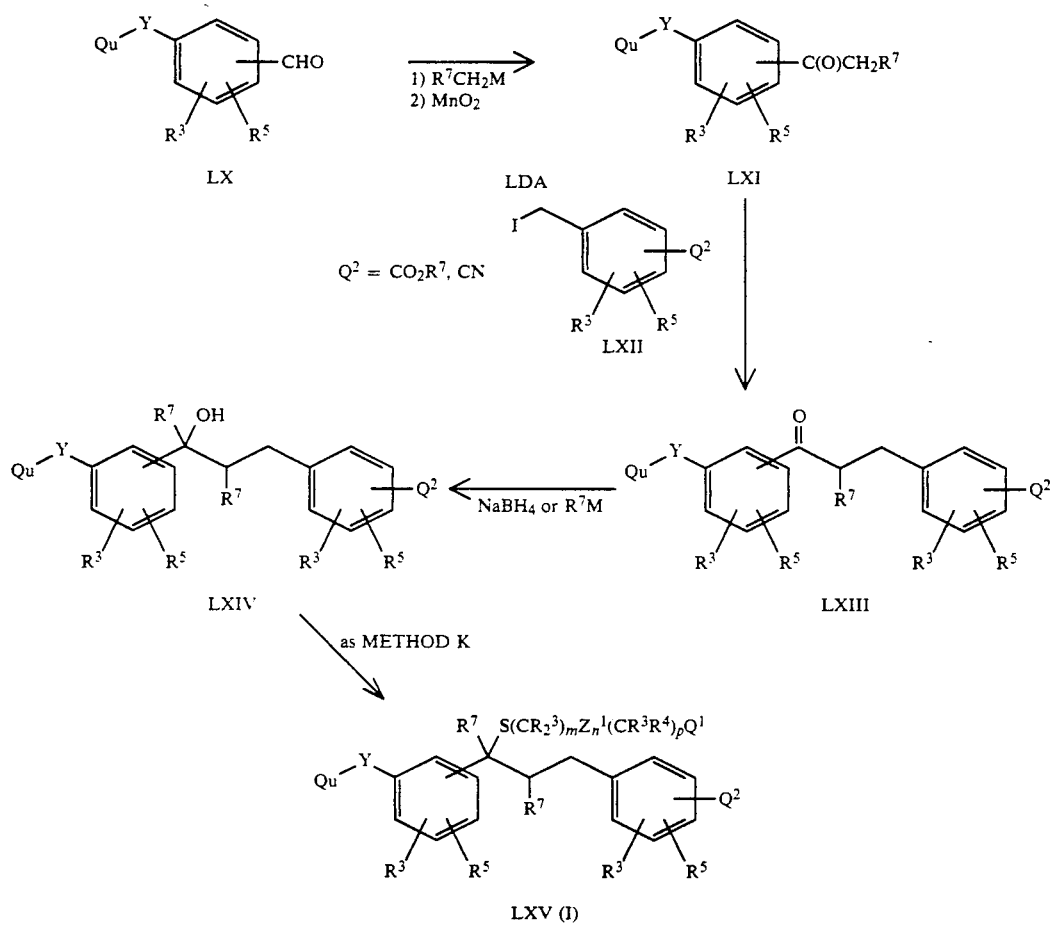
LXV (I)
$Q^1$ = $CO_2H$, CN, $CN_4H$, $CONR^{12}R^{12}$
$Q^2$ = $CO_2H$, CN, $CN_4H$, $CONR^{12}R^{12}$, $CONHSO_2R^{13}$, $NHCO_2R^{17}$, $NHCOR^{18}$, $C(R^2)$=NOH, $NHSO_2R^{13}$
METHOD N
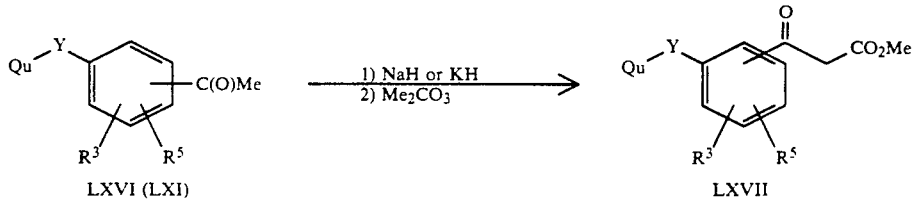

-continued
METHOD N
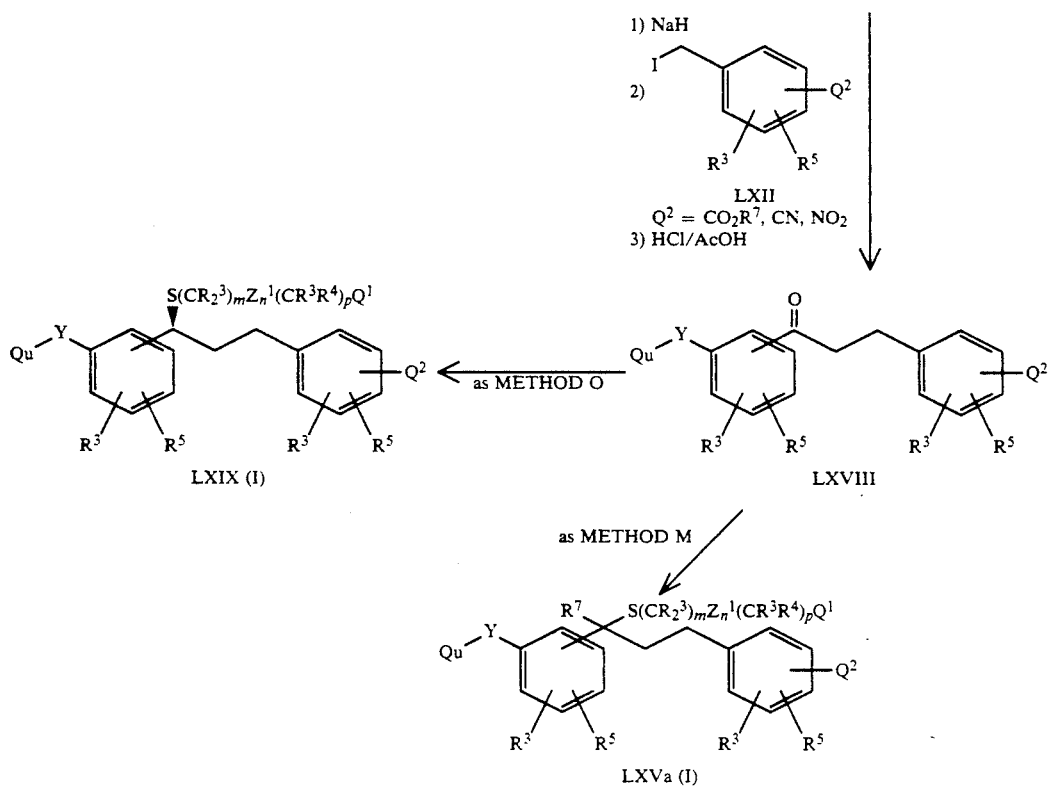
$Q^1 = CO_2H, CN, CN_4H, CONR^{12}R^{12}$
$Q^2 = CO_2H, CN, CN_4H, CONR^{12}R^{12}, CONHSO_2R^{13}, NHCO_2R^{17}, NHCOR^{18}, C(R^2)=NOH, NO_2, NHSO_2R^{13}$
METHOD O
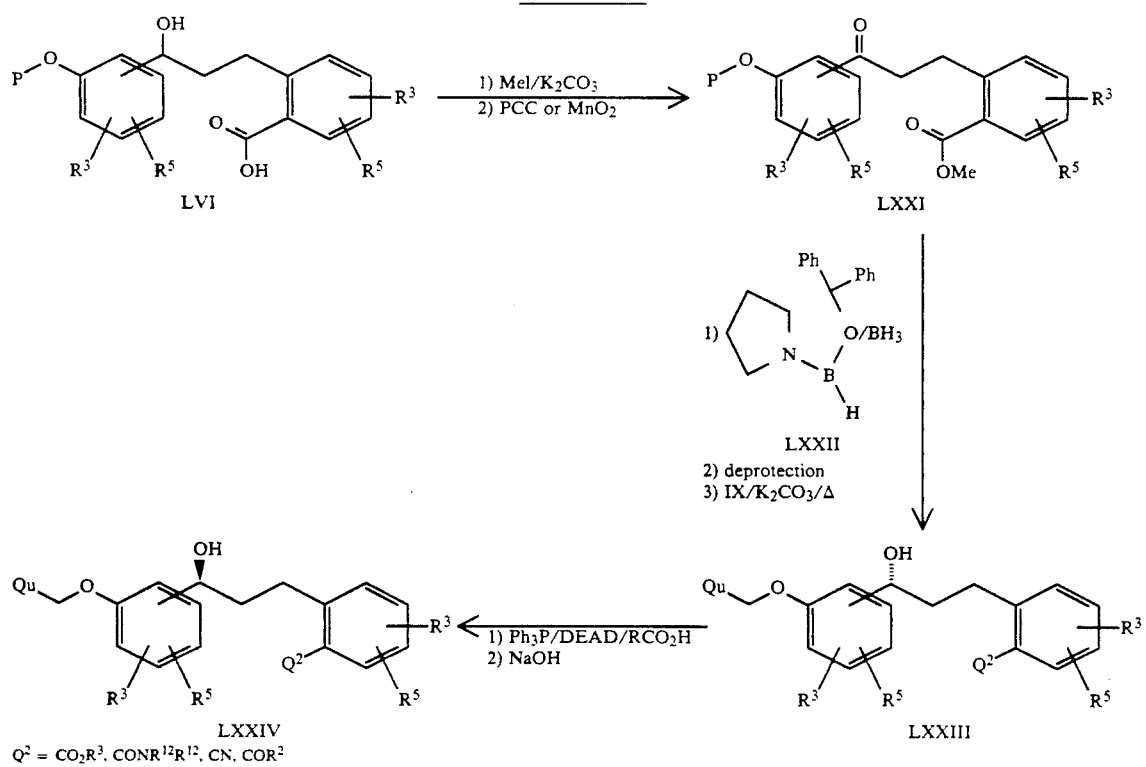
$Q^2 = CO_2R^3, CONR^{12}R^{12}, CN, COR^2$

-continued
METHOD O

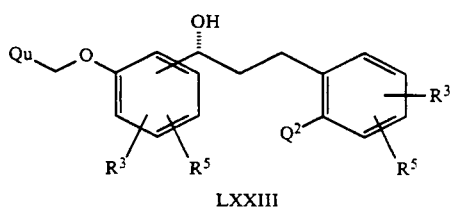

LXXIII

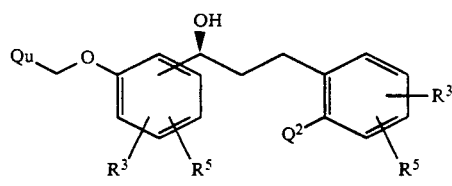

LXXIV

1) MsCl/Et₃N
2) IX/NaH or Cs₂CO₃
3) group transformation

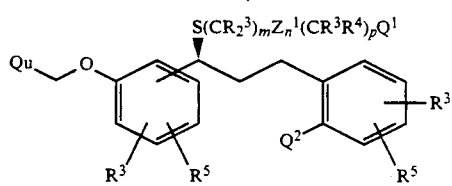

LXXV (I)

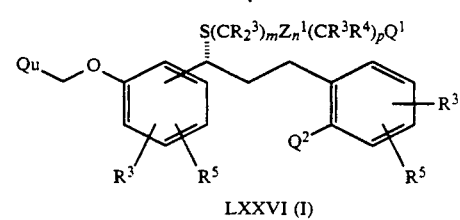

LXXVI (I)

$Q^1$ = CO₂H, CN, CN₄H, CONR¹²R¹²
$Q^2$ = CO₂H, CN, CN₄H, CONR¹²R¹², CONHSO₂R¹³, NHCO₂R¹⁷, NHCOR¹⁸, C(R²)=NOH, NHSO₂R¹³

METHOD P

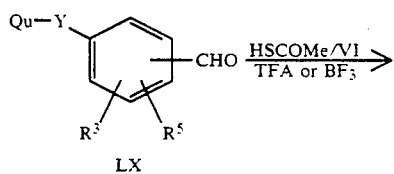

LX $\xrightarrow{\text{HSCOMe/VI}}_{\text{TFA or BF}_3}$

-continued
METHOD P

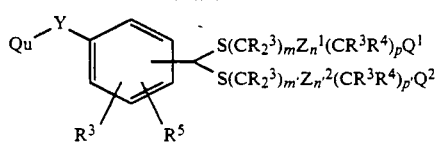

LXXVIII (XXX)

$Q^1$ and $Q^2$ = CO₂H, CN, CN₄H, CONR¹²R¹², CONHSO₂R¹³

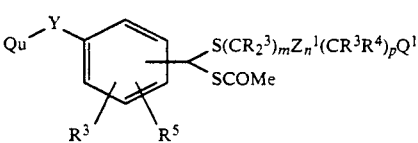

LXXVII

1) MeONa
2) L(CR₂³)ₘ'Zₙ'²(CR³R⁴)ₚ'Q²
   L = Br, I
3) group transformation

METHOD Q

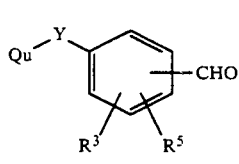

LX

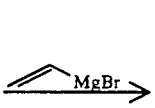

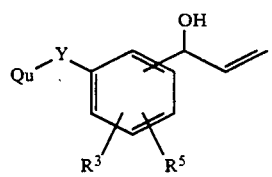

LXXIX

L—HET(—R³, —R⁵)(CR³R⁴)ₚ'Q²
Pd(OAc)₂/Ph₃P
100° C.
L = OSO₂CF₃, I, Br

METHOD Q
$Q^2$ = $CO_2R^3$, CN, $CONR^{12}R^{12}$, $CONHSO_2R^{13}$,
$NHCO_2R^{17}$, $NR^{17}CO_2R^{17}$, $NHCOR^{18}$, $NO_2$,
$NHSO_2R^{13}$, $COR^2$
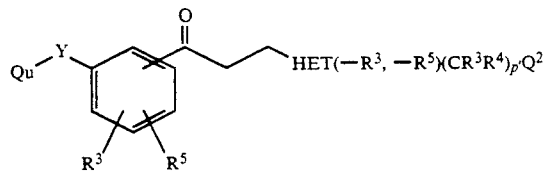
LXXX
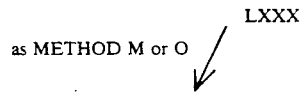
as METHOD M or O
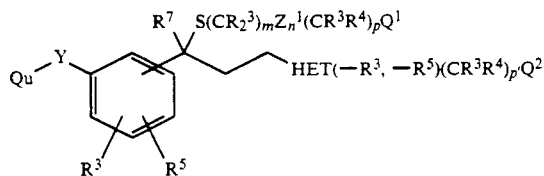
LXXXI (chiral or not) (I)
$Q^1$ = $CO_2H$, CN, $CN_4H$, $CONR^{12}R^{12}$
$Q^2$ = $CO_2H$, CN, $CN_4H$, $CONR^{12}R^{12}$, $CONHSO_2R^{13}$,
$NHCO_2R^{17}$, $NR^{17}CO_2R^{17}$, $NHCOR^{18}$, $NO_2$,
$NHSO_2R^{13}$, $C(R^2)$=NOH
METHOD R
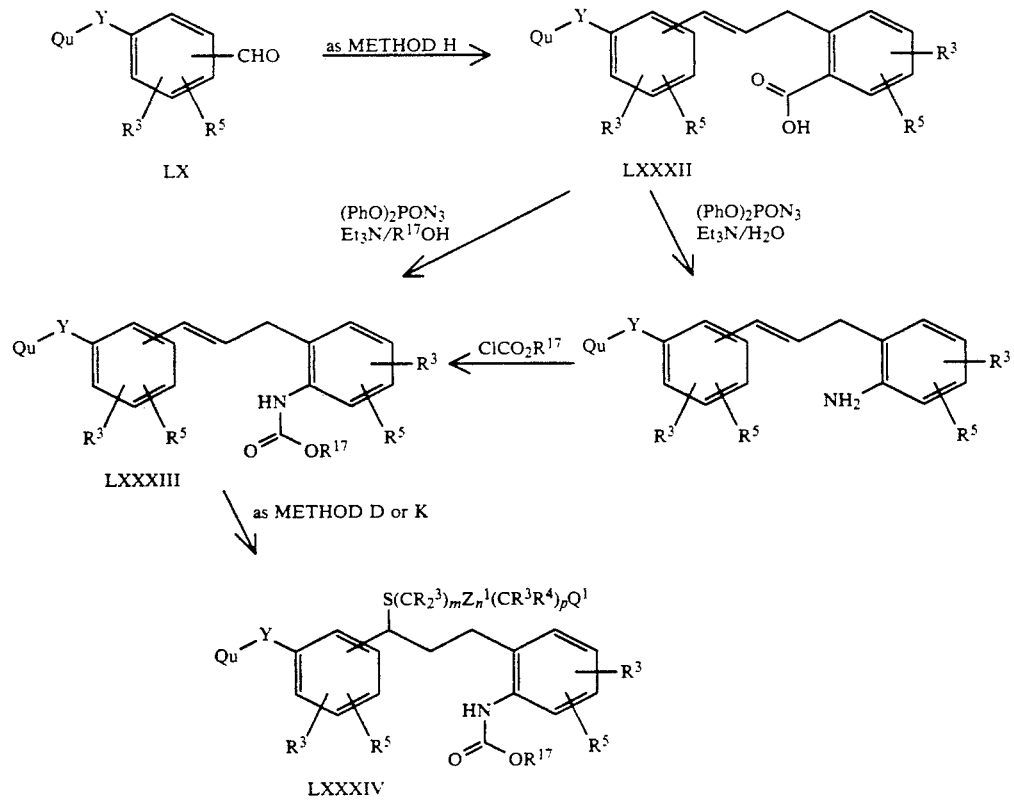
$Q^1$ = $CO_2H$, CN, $CN_4H$, $CONR^{12}R^{12}$

METHOD S

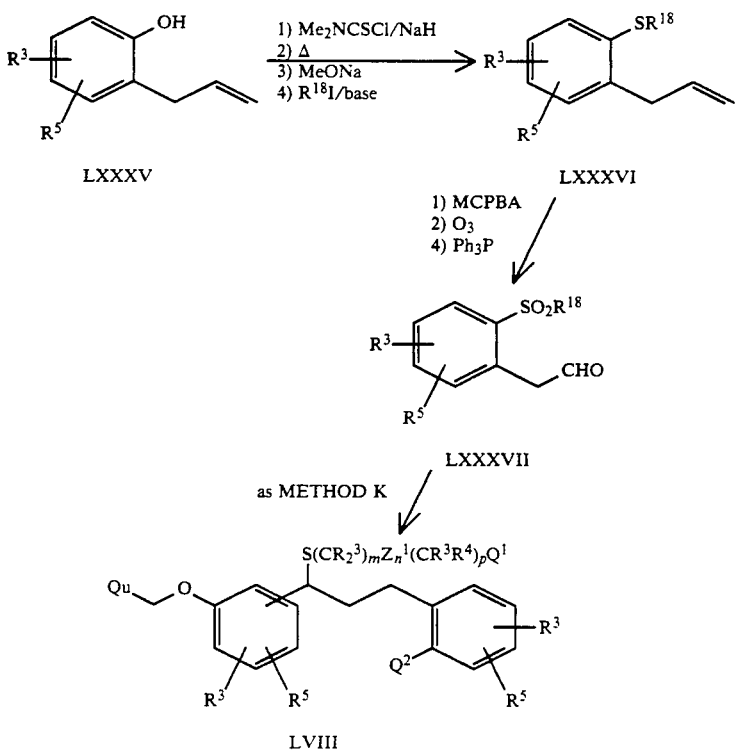

$Q^1 = CO_2H, CN, CN_4H, CONR^{12}R^{12}$
$Q^2 = SO_2R^{18}$

INTERMEDIATES

IODIDES

Iodide 1 Methyl 2-(iodomethyl)benzoate

Following the procedure in Tetrahedron, 22, 2107, (1966) phthalide was converted to 2-(bromomethyl)benzoic acid using HBr in HOAc. The methyl ester was prepared by well-known methodology.

A mixture of NaI (180 g) and methyl 2-(bromomethyl)benzoate (82.44 g, 360 mmol) in acetone (500 mL) was stirred at r.t. for 2 h. The acetone was evaporated and the product was redissolved in EtOAc. It was washed with 25% aq. NH$_4$OAc followed by 10% aq NaHCO$_3$, a sodium bisulfite solution and brine. Evaporation to dryness afforded 100 g (100% yield) of the title iodide.

$^1$H NMR (CDCl$_3$) δ: 3.95 (3H, s), 4.93 (2H, s), 7.32 (1H, m), 7.43 (2H, m), 7.94 (1H, d).

Iodide 2 Methyl 5-chloro-2-(iodomethyl)benzoate

Step 1

6-Chloro-3-hydroxyphthalide

In a 5 L 3-necked round-bottomed flask a solution of N,N,N'-trimethylethylenediamine (101.6 mL, 0.78 mol) in THF (1 L, dried over 3Å molecular sieves) was cooled to −20° C. Under a nitrogen atmosphere 10.0M n-butyllithium in hexanes (75 mL, 0.75 mol) was added over 15 min maintaining the temperature at −20° to −25° C. The mixture was aged at −20° C. for 15 min. A solution of 4-chlorobenzaldehyde (100 g, 0.71 mol) in THF (1 L) was added over 20 minutes to the lithium amide mixture maintaining the temperature at −25° to −20° C. The mixture was aged at −20° C. for 30 minutes. N,N,N', N'-Tetramethylethylenediamine (118 mL, 0.824 mol) was added, followed by the addition of n-butyllithium (78.4 mL of 10.0M in hexanes, 0.78 mol) maintaining the temperature at −25° to −20° C. The mixture was stirred at −20° C. for 2 h.

In another 5 L 3-necked flask equipped with a thermometer, mechanical stirrer, gas inlet tube, and outlet for release of the pressure, a solution of 1,3-dimethylimidazolidinone (100 mL) and THF (1 L) was cooled to −30° C. The slurry of the anion was added via cannula over 45–60 min maintaining the temperature between −30° and −20° C. Simultaneously, dry CO$_2$ was added from a tank at a flow rate sufficient to deliver 15–20 equiv of carbon dioxide (CO$_2$) over the time of the addition. The CO$_2$ addition was continued for 5 min after the addition of the aryl lithium mixture was complete. The mixture was stirred at −20° C. for 30–60 min and was quenched with 6 N aqueous HCl (860 mL). The temperature was allowed to rise to 5°–10° C. during the addition. The mixture was stirred at this temperature for 30 min. Water (860 mL) was added and the product was extracted with isopropyl acetate (1×2 L; 1×1 L). The product was extracted from the combined isopropyl acetate layers with 5% aqueous NaHCO$_3$ (1×2 L; 2×1 L). The combined aqueous layers were acidified with 6N aqueous HCl (400 mL). The aqueous layer was extracted with isopropyl acetate (1×1 L; 3×400 mL). The combined layers were washed with brine (400 mL) and dried (Na$_2$SO$_4$). The filtered solution was concentrated to 1 L, whereupon crystals began to form. Cyclohexane (1 L) was added, and the slurry was concentrated to 800 mL; this procedure was repeated once again. To the resultant slurry was added cyclohexane (500 mL) and the mixture was cooled at 10° C. for 1 h. The light-yellow solid was filtered, washed with cold cyclohexane (500 mL), and vacuum dried (117.4 g, 89% yield). An analytical sample of the compound was obtained by recrystallization from cyclohexane/EtOAc: m.p. 135.5°–37° C.

$^1$H NMR (CD$_3$SOCD$_3$) δ: 8.3 (br s, 1H), 7.90 (d, J=1.85 Hz), 7.85 (dd, J=1.85 and 7.86 Hz, 1H), 7.71 (d, J=7.86 Hz, 2H), 6.7 (br s, 1H).

Anal. calcd for C$_8$H$_5$O$_3$Cl: C, 52.05; H, 2.73. Found: C, 52.12, H, 2.75.

Step 2

6-Chlorophthalide (or 6-chloro-1-(3H)-isobenzofuranone)

To a solution of NaBH$_4$ (1.9 g) in DMF (10 mL) at 0° C. was added dropwise a solution of the 3-hydroxyphthalide of Step 1 (9.2 g) in DMF (100 mL). After complete addition, the mixture was stirred at room temperature for 1 h. To the reaction mixture was added dropwise 6N HCl (20 mL) over a period of 15 min. A white solid was formed and the mixture was heated at 70° C. for 1 h. The mixture was cooled to room temperature, diluted with H$_2$O (100 mL) and extracted with EtOAc. The organic layers were washed with H$_2$O (3×100 mL), dried over Na$_2$SO$_4$ and evaporated to dryness to give the title product (8.2 g, 97% yield); m.p. 108°–109° C.

Step 3

Using the procedure described for Iodide 1 and the reference therein, 6-chlorophthalide was converted to the title compound.

$^1$H NMR (CDCl$_3$) δ: 3.95 (3H, s), 4.89 (2H, s), 7.37 (1H, s), 7.4 (1H, d, J=2 Hz), 7.92 (1H, d, J=2 Hz).

IR (KBr) 1725 cm$^{-1}$.

Iodide 3

Methyl 3,4-dichloro-6-(iodomethyl)benzoate

This iodide was obtained using the procedure of Iodide 1, from 5,6-dichlorophthalide.

KETOESTERS

Ketoester 1

Methyl 3-(3-(2-(7-chloro-2-quinolinyl)-ethenyl)phenyl)-3-oxopropanoate

The ketoester was prepared as in Example 402, Step 2.

Ketoester 2

Methyl 3-(3-((7-chloro-2-quinolinyl)-methoxy)phenyl)-3-oxopropanoate

A suspension of 60% NaH in oil (11.2 g, 0.28 mol) was washed with two 50 mL portions of hexane. It was then suspended in 58 mL of THF and 19.6 mL (0.23 mol) of dimethyl carbonate. Methanol (3.75 mL, 0.092 mol) was then added slowly (CAUTION) and the mixture was heated to a gentle reflux. The ketone described in Example 379, Step 1, (28.8 g, 0.092 mol) in solution in 87 mL of THF was added to the NaH suspension dropwise, over 50 min, after which the mixture was refluxed for a further 15 min. The mixture was cooled to 0° C. and carefully quenched with 82 mL of 3M HOAc, followed by 110 mL of brine. The slurry was extracted 4 times with CHCl$_3$, the organic phase was dried and evaporated. The residue was purified by flash chromatography on a 100 mm diameter×200 mm height silica gel column eluted with 1 L of each 7%, 8%, 9% and 10% EtOAc in toluene. The pooled fractions were evaporated to give a black solid which was crystallized twice from toluene:hexane 2:1 to yield 24.3 g (72%) of a beige solid. The NMR data suggest a keto-enol mixture.

$^1$H NMR (CDCOCD$_3$)δ:3.68 (2.4H, s), 3.80 (0.6H, s), 4.12 (1.6H, s), 4.96 (2H, br s), 5.86 (0.2H, s), 7.2–7.7 (5H, m), 7.77 (1H, d), 8.05 (2H, m), 8.43 (1H, d).

Ketoester 3

Methyl 3-(3-(2-(7-chloro-2-quinolinyl)ethyl)phenyl)-3-oxopropanoate

Step 1

1-(3-(2-(7-Chloro-2-quinolinyl)ethyl)phenyl)ethanone

To a cooled suspension of the nitrile of Example 3, Step 1 (44 g, 0.15 mol) in 300 mL of toluene at −78° C. was added 225 mL of Me$_3$Al in toluene slowly via a syringe. During addition of Me$_3$Al, the nitrile was partially dissolved in the solution. The reaction was stirred at −78° C. for 15 min and then warmed up to r.t. After 10 min, the reaction mixture was heated up to reflux for 16 h. It was then cooled down to r.t., and poured into a mixture of 600 mL of H$_2$O, 150 mL of concentrated HCl and excess ice. The mixture was stirred at r.t. for 1.5 h and the yellow solid was collected by filtration, washed with toluene and then with H$_2$O. The solid was partitioned between EtOAc and a NaK tartrate solution. The organic phase was separated and washed once with brine. After removal of the solvent, the residue was crystallized from EtOAc:hexane 4:1 to give 29 g (62%) of the title ketone.

Step 2

Using the procedure described for the formation of the Ketoester 2, Ketoester 3 was obtained from the ketone of Step 1.

QUINOLINES

Quinoline 1

2-(Bromomethyl)-6,7-dichloroquinoline

Step 1

6,7-Dichloro-2-methylquinoline

Using the procedure of Leir (J. Org. Chem, 42, 911 (1977)), but starting from 3,4-dichloroaniline, there was obtained the title compound.

$^1$H NMR (CD$_3$COCD$_3$)δ:2.5 (3H, s), 7.45 (1H, d), 8.14 (1H, s), 8.24 (1H, s), 8.35 (1H, d).

Step 2

Using the same procedure as described for Quinoline 3, Step 2, but starting with the product of Step 1, there was obtained the title compound.

$^1$H NMR (CD$_3$COCD$_3$)δ:4.80 (2H, s), 7.75 (1H, d), 8.18 (1H, s), 8.25 (1H, s), 8.4 (1H, d).

Quinoline 2

2-(Chloromethyl)quinoline

This quinoline is commercially available.

Quinoline 3

2-(Bromomethyl)-7-(methylsulfonyl)-quinoline

Step 1

2-Methyl-7-(methylsulfonyl)quinoline

To a suspension of 60% NaH in oil (32.0 g, 0.800 mol) in THF (1 L) was added 3-mercaptoaniline (100 g) in THF (200 mL) and the mixture was stirred at r.t. for 1 h. MeI (140 g) was then added and the reaction mixture was stirred overnight at 60°. The mixture was filtered and distilled to give a crude methyl thioether, b.p. 80°–100° C./0.5 mm Hg. To the crude thioether in 6N HCl (500 mL) at 100° was added dropwise crotonaldehyde (35 g) over 30 min. The reaction mixture was cooled, neutralized with NH$_4$OH and extracted with ethyl acetate. Flash chromatography of the extract using EtOAc:toluene 15:85 afforded the quinaldine (85% pure, 15% of the 5-isomer).

To this quinaldine (14 g) in CH$_2$Cl$_2$ (200 mL) at 0° C. was added MCPBA (meta-chloroperbenzoic acid) (22 g) in CH$_2$Cl$_2$ (100 mL). After 2 hrs, more MCPBA (5 g) was added. The reaction mixture was stirred 1 hr at r.t., cooled to 0° C. and Ca(OH)$_2$ (30 g) was added. Thirty min. later the mixture was filtered and evaporated. Flash chromatography using 30–40% EtOAc/toluene afforded the title sulfone.

$^1$H NMR (CD$_3$COCD$_3$) δ: 2.75 (3H, s), 3.25 (3H, s), 7.7 (2H, s), 7.95 (1H, dd), 8.15 (1H, d), 8.35 (1H, d), 8.5 (1H, br d).

Step 2

To the sulfone of Step 1 (6.5 g) in CCl$_4$ (200 mL) was added NBS (N-bromosuccinimide) (6.5 g) and benzoyl peroxide (0.2 g). The reaction mixture was heated for 6 hrs, cooled and evaporated. Flash column chromatography using 10–20% EtOAc/toluene afforded the title compound.

$^1$H NMR (CD$_3$COCD$_3$) δ: 3.4 (3H, s), 4.95 (2H, s), 7.9 (1H, d), 8.1 (1H, dd), 8.3 (1H, d), 8.52 (1H, d), 8.6 (1H, d).

Quinoline 4

2-(Bromomethyl)-6-methoxyquinoline

Step 1

2-(Hydroxymethyl)-6-methoxyquinoline

To 6-methoxy-2-methylquinoline (8.5 g, prepared according to the general procedure of Leir, (J. Org. Chem., 42, 911 (1977)) in THF at 0° C. was added LDA (lithium diisopropylamide) (50 mmol). The reaction mixture was stirred 30 min. This solution was added via a cannula to a solution of N-(phenylsulfonyl)-3-phenyloxaziridine) in THF (30 mL) at 0° C. over 15 min. After stirring 15 min at 0° C., pH 7 phosphate buffer was added. The mixture was extracted with EtOAc, dried and evaporated. Flash chromatography using 20–40% EtOAc/toluene afforded the title compound.

$^1$H NMR (CD$_3$COCD$_3$) δ: 3.9 (3H, s), 4.65 (1H, br t), 4.80 (2H, br d), 7.25 (1H, d), 7.3 (1H, d), 7.55 (1H, dd), 7.9 (1H, d), 8.2 (1H, d).

Step 2

To the alcohol from Step 1 (2.5 g) and CBr$_4$ (5.6 g) in CH$_2$Cl$_2$ (50 mL) at 0° C. was added a solution of DIPHOS (1,2-bis(diphenylphosphino)ethane) (3.4 g) in CH$_2$Cl$_2$ (20 mL) over 10 min. The reaction mixture was stirred 1 hr at r.t. and quenched with hexane (50 mL). The reaction mixture was passed through a pad of SiO$_2$ eluting with 30% EtOAc/hexane. The eluant was evaporated and chromatographed using 20% EtOAc/hexane to afford the title bromide (2.5 g).

$^1$H NMR (CD$_3$COCD$_3$) δ: 3.9 (3H, s), 4.75 (2H, s), 7.25 (1H, d), 7.35 (1H, d), 7.6 (1H, dd), 7.85 (1H, d), 8.2 (1H, d).

STYRENES

Styrene 1

Methyl 2-(3-(3-((7-chloro-2-quinolinyl)methoxy)phenyl)-2-propenyl)benzoate

The styrene was prepared as in Example 29, Method B, Step 6.

Styrene 2

Methyl 2-(3-(3-(2-(7-chloro-2-quinolinyl)ethyl)phenyl)-2-propenyl)benzoate

The styrene was prepared as in Example 36, Step 1.

Styrene 3

Methyl 2-(3-(3-(2-(7-chloro-2-quinolinyl)ethenyl)phenyl)-2-propenyl)benzoate Using the procedures of Example 29, Method B, Steps 1–6, 3-(2-(7-chloro-2-quinolinyl)ethenyl)benzaldehyde (see EP 233,763, Example 24, Step 1) was converted to Styrene 3.

Styrene 4

Methyl 2-(3-(3-(2-(7-chloro-2-quinolinyl)cyclopropyl)phenyl)-2-propenyl)benzoate The aldehyde of 3-(2-(7-chloro-2-quinolinyl)ethenyl)-benzaldehyde (see EP 233,763, Example 24, Step 1) was protected as an acetal by heating it at reflux in benzene for 18 h, using a Dean-Stark apparatus, with 1.2 equiv. of ethylene glycol and 0.5 equiv. of p-toluenesulfonic acid. Aqueous work up and extraction with EtOAc gave the pure acetal. The cyclopropanation was done with 1.9 equiv. of the anion obtained from trimethylsulfoxonium iodide and NaH in DMSO (dimethylsulfoxide) as described in J. Am. Chem. Soc., 87, 1353 (1965). Then, the acetal was deblocked by heating at reflux in THF:HOAc:H$_2$O 6:2:1 for 5 h to yield 3-(2-(7-chloro-2-quinolinyl)cyclopropyl)benzaldehyde, which was converted to Styrene 4 using the procedure of Example 29, Method B, Steps 1–6.

Styrene 5

7-Chloro-2-((3-(3-(2-(methylsulfonyl)phenyl)-1-propenyl)phenoxy)methyl)quinoline

Step 1

S-(2-(2-Propen-1-yl)phenyl)dimethylcarbamothioate

2-Allylphenol was treated with dimethylthiocarbomoyl chloride and NaH, then heated in 1,2,4-trichlorobenzene at reflux as in Example 8, Steps 5–6, to afford the title compound.

Step 2

2-(2-Propen-1-yl)thiophenol

A solution of the product of Step 1 (2.00 g, 9.04 mmol) in MeOH (50 mL) was added to a solution of MeONa (832 mg of Na, 36 mmol) in MeOH (60 mL) containing BHT (2,6-di-tert-butyl-4-methylphenol, 100 mg). The resulting mixture was then heated at 50° C. for 18 h and cooled to r.t. The mixture was poured on cold 10% HCl under $N_2$ and extracted with $Et_2O$. The organic phase was dried over $Na_2SO_4$, filtered and evaporated at reduced pressure. The desired compound was purified by flash chromatography on silicic acid with hexane to provide 1.00 g (75%) of the title compound as a colorless oil.

$^1H$ NMR ($CD_3COCD_3$) δ: 3.42 (2H, d), 4.08 (1H, s), 5.05 (2H, m), 5.93 (1H, m), 7.00–7.41 (4H, m).

Step 3

1-(Methylthio)-2-(2-propen-1-yl)benzene

To a solution of the thiol of Step 2 (1.00 g, 6.71 mmol) in DMF (22 mL) containing BHT (10 mg) and MeI (209 mg, 8.72 mmol) at 0° C. was added NaH (20.9 mg, 8.7 mmol). After 1 h at r.t., the reaction mixture was quenched by the addition of 25% aq $NH_4OAc$ and extracted with EtOAc in the usual manner. The title thioether was isolated (770 mg, 80%) by flash chromatography on silica with hexane.

$^1H$ NMR ($CD_3COCD_3$) δ: 2.41 (3H, s), 3.41 (2H, d), 5.01 (2H, m), 5.95 (1H, m), 6.95–7.33 (4H, m).

Step 4

1-(Methylsulfonyl)-2-(2-propen-1-yl)benzene

To a solution of the thioether of Step 3 (110 mg, 0.674 mmol) in MeOH (2.2 mL) at 0° C. was added a suspension of oxone (1.24 g, 2.01 mmol) in $H_2O$. After 0.5 h at r.t., water was added until obtention of a homogenous solution. After a few minutes, the desired product was extracted with EtOAc, dried over $Na_2SO_4$, filtered and evaporated. The title compound was purified by flash chromatography to give 56 mg (42%) of material.

$^1H$ NMR ($CD_3COCD_3$) δ: 3.16 (3H, s), 3.91 (2H, d), 5.12 (2H, m), 6.08 (1H, m), 7.50 (2H, m), 7.66 (1H, m), 8.01 (1H, m).

Step 5

2-(Methylsulfonyl)phenylacetaldehyde was obtained from the ozonolysis (Example 366, Step 2) of the sulfone of Step 4. It was then transformed to the title styrene using the procedures of Example 29, Method B, Step 4.

Styrene 6

Ethyl ((2-(3-(3-((7-chloro-2-quinolinyl)methoxy)phenyl)-2-propenyl)phenyl)amino)carboxylate Using the procedure of Example 29, Method A, Step 3, the styrene 1 was hydrolyzed to the acid, which was then transformed to the title carbamate as in Example 178, Step 1.

Styrene 7

Ethyl ((2-(3-(3-(2-(7-chloro-2-quinolinyl)ethyl)phenyl)-2-propenyl)phenyl)amino)carboxylate This styrene was obtained from Styrene 2 as described for Styrene 6.

Styrene 8

7-Chloro-2-(2-(3-(3-(2-(((trifluoromethyl)sulfonyl)amino)phenyl)-1-propenyl)phenyl)ethyl)quinoline

Step 1

2-(3-(2-(7-Chloro-2-quinolinyl)ethyl)-2-propenyl)aniline

Using the procedure of Example 29, Method A, Step 3, Styrene 2 was hydrolyzed to the acid. This acid (1.65 g, 3.9 mmol), triethylamine (1.1 mL, 7.7 mmol) and diphenylphosphoryl azide (1.7 g, 6.2 mmol) were mixed together in dioxane (75 mL) and the solution was stirred 2 h at r.t. followed by 10 min. at 60° C. Water (2 mL) was added and the mixture was heated at 90° C. for 2 h. Evaporation of the solvent gave a crude oil which was subjected to flash chromatography (EtOAc:Hexane:Toluene) to give the desired product (875 mg).

Step 2

The product of Step 1 (415 mg, 1.0 mmol) was dissolved in $CH_2Cl_2$ (40 mL) containing triethylamine (304 μL, 2.2 mmol) at −78° C. Trifluoromethanesulfonic anhydride (193 μL, 1.1 mmol) was added dropwise and the reaction mixture was stirred 3 h with slow warming to 0° C. followed by an additional 2 h at this temperature. Water (15 mL) was added, the organic phase was decanted and the aqueous one was extracted with EtOAc and $CH_2Cl_2$. The combined organic extracts were washed with brine, dried over $MgSO_4$, and evaporated in vacuo. Flash chromatography of the residue (10% to 30% EtOAc in hexane with 0.05% of formic acid) gave the title product (370 mg) along with some bis(trifluoromethylsulfonamide) (136 mg) which could be hydrolyzed to the desired mono trifluoromethylsulfonamide with aqueous KOH in a mixture of MeOH and THF.

Styrene 9

1-((2-(3-(3-(2-(7-Chloro-2-quinolinyl)ethyl)phenyl)-2-propenyl)phenyl)amino)2,2-dimethyl-1-propanone Using the procedure of Example 381, but using trimethylacetyl chloride instead of acetyl chloride, the aniline precursor of Styrene 8 (Step 1) was transformed to the title styrene.

THIOLS

Thiol 1

Methyl 3-mercaptopropanoate

The thiol is commercially available.

Thiol 2

3-Mercaptopropanoic acid

The thiol is commercially available.

Thiol 3

N,N-Dimethyl 3-mercaptopropanamide

The thiol was prepared as in U.S. Pat. No. 4,851,409, Example 27, Step 4.

Thiol 4

Ethyl 3-mercapto-2-methylpropanoate

The thiol was prepared as in Example 372, Step 1.

Thiol 5

3-Mercapto-2-methylpropanoic acid

The thiol was prepared as in Example 372, Step 1.

Thiol 6

Ethyl 2-ethyl-3-mercaptopropanoate

The thiol was prepared as in Example 113, Step 2.

Thiol 7

2,2-Dimethyl-3-mercaptopropanoic acid

Using the procedure described in Chem. Abstr., 58, 11490b, c, (1963) this thiol was obtained from 3-bromo-2,2-dimethylpropanoic acid (J. Am. Chem. Soc. 3016 (1955)) by substitution of the bromide by KSH.

Thiol 8

2,2-Diethyl-3-mercaptopropanoic acid

Using the procedure described for Thiol 7 and the references therein, 2-ethylbutyraldehyde was converted to the title thiol.

Thiol 9

Ethyl 1-(mercaptomethyl)cyclopropanecarboxylate

Step 1

1,1-Cyclopropanedimethanol

To a suspension of LiAlH$_4$ (15.0 g, 395 mmol) in THF (500 mL) at 0° C. was added dropwise, to maintain the temperature below 55° C., a solution of diethyl 1,1-cyclopropanedicarboxylate (50.0 g, 268 mmol) in THF (250 mL). When the reaction was completed, H$_2$O (15 mL), 15% NaOH (15 mL) and H$_2$O (45 mL) were added successively. The mixture was then filtered on celite and washed with THF. The filtrate was evaporated to dryness and the resulting oil was distilled at 110° C./5 mm Hg to give 17.7 g (66%) of the title diol.

$^1$H NMR (CDCl$_3$) δ: 0.41 (4H, s), 2.30 (2H, t), 2.58 (4H, d).

Step 2

Methyl 1-(bromomethyl)cyclopropanecarboxylate

The diol of Step 1 was oxidized with KMnO$_4$ (as described in Chem. Ber., 2254 (1973)) to give 1-(hydroxymethyl)cyclopropanecarboxylic acid, which was esterified with diazomethane. Using CBr$_4$/DIPHOS (Example 29, Method B, Step 2), the alcohol was converted to the title bromide.

Step 3

To a solution of the bromide of Step 2 (460 mg, 2.39 mmol) in EtOH:H$_2$O 3:1 (5.5 mL) at 0° C. were added, under a flow of nitrogen, K$_2$CO$_3$ (182 mg) and NaSH (282 mg, 5.03 mmol). After 10 h at r.t., the reaction was quenched by the addition of 10% HCl and the resulting mixture was extracted with EtOAc, dried with Na$_2$SO$_4$ and evaporated. The thiol was purified by flash chromatography (20% EtOAc/Hexane) to give 150 mg (43%) of the title compound.

$^1$H NMR (CD$_3$COCD$_3$) δ: 0.88 (2H, m), 1.16 (2H, m), 2.70 (2H, d), 3.58 (3H, s).

Thiol 10

Ethyl 4-mercaptobutanoate

The thiol was prepared as in Chem. Abstr., 58, 11490b, c (1963).

Thiol 11

Methyl 4-mercapto-2-methylbutanoate

Using the procedure described in Chem. Abstr., 58, 11490b, c (1963) this thiol was obtained from methyl 4-bromo-2-methylbutanoate (Helv. Chem. Acta, 63, 2508 (1980)).

Thiol 12

Ethyl 3-mercapto-2-propylpropanoate

Starting from diethyl 2-propylpropanedioate and following the procedure of Arch. Pharm., 313, 846 (1980) and Example 113, Steps 1 and 2, the title compound was prepared.

Thiol 13

2-Ethyl-3-mercaptopropanoic acid

Hydrolysis of Thiol 6 as in Example 1, Step 8 gave the title compound.

Thiol 14

Ethyl alpha-(mercaptomethyl)-cyclopropaneacetate

Step 1

Cyclopropaneacetonitrile

A solution of 16.7 g (0.34 mol) of NaCN in 200 mL of DMSO was heated to 70° C., and 40 g (0.296 mol) of (bromomethyl)cyclopropane were added. After 2 h at this temperature, a heavy solid stopped the stirring. The mixture was cooled to r.t. and the solid was loosened with water. The mixture was partitioned between 1 L of water and 400 mL of Et$_2$O, and the aqueous layer was reextracted twice with Et$_2$O. The combined organic phases were dried over MgSO$_4$ and evaporated. Distillation afforded 20.75 g (87%) of the title compound as a colorless liquid; b.p. 34.5°–36.5° C./15 mm Hg.

$^1$H NMR (CDCl$_3$) δ: 0.34 (2H, m), 0.67 (2H, m), 1.1 (1H, m), 2.38 (2H, d).

Step 2

Ethyl alpha-cyanocyclopropaneacetate

To a suspension of 13 g (0.54 mol) of NaH in 150 mL of THF was added 76 mL (0.625 mol) of diethylcarbonate. This mixture was heated to gentle reflux, and 0.5 mL (9 mmol) of ethanol was added carefully. This was followed by the addition of a solution of 14.6 g of the nitrile from Step 1 in 40 mL of THF, over a period of 2 h. After addition, the mixture was refluxed an additional 45 min before cooling in ice. Careful addition of 200 mL of 3M HOAc, followed by 250 mL of brine loosened any solid. This mixture was extracted twice with CH$_2$Cl$_2$, the organic phase was dried over Na$_2$SO$_4$ and evaporated. Distillation afforded 21.26 g (77%) of the title compound as a colorless oil; b.p. 57° C./0.2 mm Hg.

$^1$H NMR (CDCl$_3$) δ: 0.57 (2H, m) 0.77 (2H, m), 1.35 (4H, m), 3.24 (1H, d), 4.28 (2H, q)

Step 3

Diethyl cyclopropylpropanedioate

At 10° C., 100 mL of EtOH was saturated with gaseous HCl. A solution of 25.03 g (0.164 mol) of the cyanoester from Step 2 in 100 mL of EtOH was then added, and this solution was heated to 60° C. in a rubber septum stoppered flask for 15 h. The mixture was then poured onto 600 mL of ice and stirred until it reached r.t. Ether extraction, Na$_2$SO$_4$ drying and evaporation afforded an oil which was distilled to give a 28.7 g (88%) of the title compound as a colorless oil; b.p. 55° C./0.05 mm Hg.

$^1$H NMR (CDCl$_3$) δ: 0.33 (2H, br q), 0.68 (2H, br q), 1.30 (6H, t), 1.35 (1H, m), 2.61 (1H, d), 4.24 (4H, q).

Step 4

Ethyl 2-cyclopropyl-2-propenoate

Using the procedure described in Arch. Pharm. 313, 846 (1980), the title compound was obtained from the malonate of Step 3.

Step 5

Ethyl alpha-((acetylthio)methyl) cyclopropaneacetate

A solution of 14.1 g (0.100 mol) of the acrylate from Step 4 in 57 mL (0.40 mol) of triethylamine was diluted with 21.5 mL (0.30 mol) of thiolacetic acid. This solution was heated at 70° C. for 8 h and left at r.t. for 15 h. Addition of a volume of Et$_2$O gave two phases, which were separated. The bottom phase was reextracted with Et$_2$O. The organic phases were washed twice with 25% aq NH$_4$OAc, once with 10% aq NH$_4$OAC, dried over MgSO$_4$ and evaporated. Kugelrohr distillation at 120° C./0.25 mm Hg gave 14.89 g (69%) of the title compound as an orange oil.

$^1$H NMR (CDCl$_3$) δ: 0.38 (2H, m), 0.57 (2H, m), 0.96 (1H, m), 1.28 (3H, t), 1.85 (1H, m), 2.33 (3H, s), 3.21 (2H, m), 4.18 (2H, m).

Step 6

Hydrolysis of the thioester of Step 5 using the procedure of Example 113, Step 2, afforded the title thiol.

Thiol 15

Methyl 3-mercapto-2-hydroxy-2-methylpropanoate

Step 1

Ethyl 2-methyl-2-oxiranecarboxylate

To a solution of 85% m-CPBA (meta-chloroperbenzoic acid, 42.0 g, 244 mmol) in 1,2-dichloroethane (500 mL) containing BHT (500 mg) was added in one portion ethyl methacrylate (10 g, 174 mmol). After 2 h at 70° C., the reaction mixture was filtered and the solid washed with CH$_2$Cl$_2$. The filtrate was then partially evaporated and diluted with CH$_2$Cl$_2$. The organic phase was successively washed with sat. NaHCO$_3$, aq KI, Na$_2$S$_2$O$_3$ and NaHCO$_3$. The organic phase was then dried over Na$_2$SO$_4$, filtered and evaporated. The desired epoxide was distilled at 72° C./16 mm Hg to give 16.0 g (70%) of title material.

$^1$H NMR (CD$_3$COCD$_3$) δ: 1.35 (3H, t), 1.61 (3H, s), 2.91 (1H, d), 3.16 (1H, d), 4.33 (2H, q).

Step 2

Ethyl 3-(benzylthio)-2-hydroxy-2-methylpropanoate

To a solution of the epoxide of Step 1 (5.0 g, 38 mmol), in EtOH (22 mL) at 0° C. was added an EtOH solution containing NaOH (1.55 g) and benzyl mercaptan (4.2 g, 38 mmol). After 1 h, the reaction mixture was quenched by the addition of 25% aq NH$_4$OAc and the thioether extracted with EtOAc. After drying over NaSO$_4$, evaporation and flask chromatography, 8.8 g (70%) of title material were obtained.

$^1$H NMR (CD$_3$COCD$_3$) δ: 1.25 (3H, t), 1.38 (3H, s), 2.70 (2H, AB), 3.41 (1H, s), 3.58 (2H, AB), 4.15 (2H, q), 7.13–7.33 (5H, m).

Step 3

Using the procedure of Example 229, Steps 3–5, the compound of Step 2 was converted to the title thiol.

Thiol 16

2-(Mercaptomethyl)benzoic acid 2-(iodomethyl)benzoic acid, a precursor of Iodide 1, was substituted with thiolacetic acid (1.2 equiv) in the presence of K$_2$CO$_3$ in DMF at 60° C. for an hour to give the thioacetate, which was hydrolyzed with NaOH to give the title thiol.

Thiol 17

5-Chloro-2-(mercaptomethyl)benzoic acid

This thiol was obtained from Iodide 2 as described for Thiol 16.

Thiol 18

Methyl 3-mercapto-2-methoxypropanoate

The thiol was obtained as in Example 229, Step 5.

The invention is further defined by reference to the following examples, which are intended to be illustrative and not limiting.

All temperatures are in degrees Celsius.

EXAMPLE 1

2-(3-(3-(2-(7-chloroquinolin-2-yl)ethyl)phenyl)-3-(2-carboxyethylthio)propyl)benzoic acid, disodium salt Step 1

Preparation of (3-cyanophenylmethyl)triphenylphosphonium bromide

To a solution of 3-bromomethylbenzonitrile (19.6 g) in CH$_3$CN (500 ml) triphenylphosphine (Ph$_3$P) was added (30 g). The reaction mixture was stirred at 60° cooled and filtered. The title product thus obtained was dried and used as such for the next step.

Step 2

Preparation of 2-(1-(3-cyanophenyl)propen-3-yl)benzyl alcohol

To phosphonium salt (step 1) (13.4 g) in tetrahydrofuran (THF) (100 mL) at −78° was added potassium hexamethyldisilazide (KHMDS) (0.6M in toluene) (50 mL). The reaction mixture was warmed to 0° for 1 hr. After cooling to −78°, 1H-3-hydroxy-3,4-dihydrobenzo(c)pyran (2 g) in THF (10 mL) was added. The mixture was warmed to room temperature (RT) for 1 hr, poured onto pH 7 buffer, extracted with ethyl acetate, dried and evaporated. Flash chromatography using 20% ethyl acetate in toluene afforded the title compound.

p.m.r. (CDCl$_3$) δ (ppm): 1.8 (m, 1H), 3.7 (m, 2H), 5.64 (d, 1H), 5.84 (d, 1H), 5.9–6.6 (m, 2H), 7.1–7.7 (m, 8H).

Step 3

Preparation of 2-(1-(3-cyanophenyl)propen-3-yl))benzaldehyde

To a suspension of pyridinium chlorochromate (PCC) (10 g) and 4A powdered molecular sieves in CH$_2$Cl$_2$ (200 mL) was added the alcohol from step 2. The mixture was stirred 1 hr at room temperature, ether was added and the mixture was filtered through a pad of SiO$_2$ using 30% ethyl acetate-hexane as eluant. The filtrate was evaporated to afford the title compound which was used as such for the next step.

Step 4

Preparation of methyl-2-(1-(3-cyanophenyl)propen-3-yl)benzoate

To a solution of aldehyde (step 3) in MeOH (200 mL), AcOH (1.2 mL) and NaCN (4 g) was added MnO$_2$ (20 g). The mixture was stirred for 2 hrs and poured onto H$_2$O (1 L). The aqueous phase was extracted with ethyl acetate (2×500 mL) and the combined organic phases were dried and evaporated. Flash chromatography of the residue using 5% ethyl acetate in toluene afforded the title compound as a mixture of cis and trans isomers.

p.m.r. (CDCl$_3$) δ (ppm): 3.4 and 3.6 (s, 3H), 3.7 and 3.9 (dd, 2H), 6.2–6.8 (m, 2H), 7.4–7.8 (m, 7H), 8.1 (m, 1H).

Step 5

Preparation of methyl 2-(3-(2-(methoxycarbonyl)ethylthio)-3-(3-cyanophenyl)propyl)benzoate To a solution of olefin (step 4) (367 mg) in CH$_2$Cl$_2$ (10 mL) was added methyl 3-mercaptopropionate (200 mg) and AlCl$_3$ (0.7 g). The mixture was stirred for 3 hrs. at room temperature, quenched with 25% aq. NH$_4$OAc and extracted with ethyl acetate. The organic phase was dried and evaporated. Flash chromatography of the residue using 10% ethyl acetate in toluene afforded the title compound.

p.m.r. (CDCl$_3$) δ (ppm): 2.0–2.3 (m, 2H), 2.4–2.7 (m, 4H), 2.8–3.1 (m, 2H), 3.7 (s, 3H), 3.9 (s, 3H), 3.9 (t, 1H), 7.1–7.7 (m, 7H), 7.9 (d, 1H).

Step 6

Preparation of methyl 2-(3-(2-(methoxycarbonyl)ethylthio)-3-(3-formylphenyl)propyl)benzoate HCl (gas) was bubbled into a suspension of SnCl$_2$ (1.2 g) in ether until 2 layers were formed. The cyano compound (350 mg) (step 5) was then added. The mixture was stirred 3 hours at room temperature and carefully quenched with H$_2$O at 0°. The reaction mixture was poured onto pH 7 buffer (300 mL), extracted with ethyl acetate (200 mL), and the organic phase was dried and evaporated. Flash chromatography of the residue using 25% ethyl acetate in hexane afforded the title compound.

p.m.r. (CDCl$_3$) δ (ppm): 2.2–2.3 (m, 2H), 2.5–2.7 (m, 4H), 2.85–3.2 (m, 2H), 3.75 (s, 3H), 3.95 (s, 3H), 4.0 (s, 1H), 7.2–8.0 (m, 8H), 10.1 (2, 1H).

Step 7

Preparation of methyl 2-(3-(3-(2-(7-chloroquinolin-2-yl)ethenyl)phenyl)-3-(2-(methoxycarbonyl)ethylthio)propyl)benzoate To a suspension of ((7-chloroquinolin-2-yl)methyl)triphenylphosphonium bromide (EP 233,763, Example 4, step 2) (489 mg) in THF (5 ml) at −78° was added butyllithium (0.51 ml of 1.6N). The reaction mixture was stirred at −78° 1 hr and aldehyde (350 mg) (step 6) in THF (2 ml) was added. The mixture was warmed to RT, poured onto buffer (pH 7), extracted with ethyl acetate, and the organic phase was dried and evaporated. Flash chromatography using 25% ethyl acetate/hexane afforded the title compound.

p.m.r. (CD$_3$COCD$_3$) δ (ppm): 2.3–2.4 (m, 2H), 2.5–2.7 (m, 4H), 2.85–3.15 (m, 2H), 3.65 (s, 3H), 3.85 (s, 3H), 4.05 (t, 1H), 7.3–8.0 (m, 13H), 8.05 (d, 1H), 8.3 (d, 1H).

Step 8

To the diester (step 7) in THF (5 mL) and MeOH (5 mL) was added LiOH (5 mL of 1N). The solution was stirred 3 days at RT, partitioned between EtOAc/H$_2$O (acidified with AcOH), and the organic phase was dried and evaporated to give the diacid. To the diacid was added 2 eq. of NaOH and the solution was freeze dried to give the title compound.

Anal. Calcd. for C$_{30}$H$_{24}$NO$_4$SNa$_2$Cl·3H$_2$O: C 57.18; H 4.79; N 2.22; Na 7.28. Found: C 57.70; H 4.63; N 2.13; Na 7.52.

EXAMPLE 2

2-(3-(3-(2-(7-chloroquinolin-2-yl)ethenyl)phenyl)-3-(2-(dimethylcarbamoyl)ethylthio)propyl)benzoic acid, sodium salt Using the procedure of Example 1 but replacing methyl 3-mercaptopropionate with 3-mercapto-N,N-dimethylpropionamide in step 5 and using 1 eq. of NaOH in step 8 instead of 2 eq. NaOH there was obtained the title compound.

p.m.r. (CD$_3$COCD$_3$) δ (ppm): 2.2–2.3 (m, 2H), 2.4–2.7 (m, 4H), 2.8 (s, 3H), 2.9 (s, 3H), 2.85–3.2 (m, 2H), 4.05 (t, 1H), 7.0–8.0 (m, 13H), 8.0 (d, 1H), 8.3 (d, 1H).

EXAMPLE 3

3-(3-(2-(7-chloroquinolin-2-yl)ethenyl)phenyl)-(2-(dimethylcarbamoyl)ethylthio)methyl)benzoic acid, sodium salt

Step 1

Preparation of 3-(2-(7-chloroquinolin-2-yl)ethyl)benzonitrile

To 7-chloroquinaldine (18 g) in THF (200 mL) at −78° was added lithium diisopropylamide (LDA) (0.1M). The reaction mixture was stirred for 30 min at −78° and added dropwise to a solution of 3-(bromomethyl)benzonitrile (19.6 g) in THF (200 mL) at 0°. The mixture was stirred 2 hrs at 0°, quenched with 25% aq. NH$_4$OAc, extracted with ethyl acetate (500 mL) and the organic phase was dried and evaporated. Flash chromatography using 20% ethyl acetate/hexane afforded the title compound.

p.m.r. (CDCl$_3$) δ (ppm): 3.3–3.4 (m, 4H), 7.0–8.2 (m, 9H).

Step 2

Preparation of
3-(2-(7-chloquinolin-2-yl)ethyl)benzaldehyde

To a solution of nitrile (step 1) (10 g) in formic acid (150 mL) and H₂O (50 mL) was added Ni-Al alloy (6 g). The reaction mixture was heated at 130° for 2 days, filtered and evaporated. The residue was partitioned between ethyl acetate (500 mL) and aqueous NaHCO₃, and the organic phase was dried and evaporated. Flash chromatography using 25% ethyl acetate hexane afforded the title aldehyde which was used as such for the next step.

Step 3

Preparation of
3-((3-(2-(7-chloroquinolin-2-yl)ethyl)phenyl)hydroxymethyl)benzoic acid To a solution of 3-bromobenzoic acid (0.8 g) at −100° in THF (20 mL) was added dropwise 2 eq. of n-butyllithium in hexane. The mixture was warmed to −78° and aldehyde (1 g) (step 2) in THF (5 mL) was added dropwise over 15 min. After stirring 2 hrs at −78° the reaction mixture was quenched with buffer (25% aq. NH₄OAc), extracted with ethyl acetate, and the organic phase was dried and evaporated. Flash chromatography of the residue using 15% to 25% acetone/toluene/acetic acid 0.1% afforded the title compound.

p.m.r. (CDCl₃) δ (ppm): 3.1 (m, 2H), 3.3 (m, 2H), 5.8 (s, 1H), 6.0–7.0 (bs, 1H), 7.05–7.60 (m, 8H), 7.70 (d, 1H), 8.0 (m, 2H), 8.1–8.2 (m, 2H).

Step 4

To a solution of alcohol (step 3) (0.4 g) in CH₂Cl₂ (25 mL) was added 3-mercapto-N,N-dimethylpropionamide (0.2 mL) and AlCl₃ (800 mg). The reaction mixture was stirred 1 hr at RT, and quenched with 25% NH₄OAc (100 mL)/AcOH (2 mL)/THF (50 mL) and EtOAc (200 mL). The organic phase was separated dried and evaporated. Flash chromatography of the residue using 25% to 40% acetone/toluene/acetic acid (0.1%) afforded the acid of the title compound.

p.m.r. (CD₃COCD₃) δ (ppm): 2.2–2.4 (m, 4H), 2.55 (s, 3H), 2.65 (s, 3H), 2.8–3.0 (m, 4H), 5.15 (s, 1H), 7.0–8.0 (m, 13H).

Step 5

The acid was treated with NaOH (1 eq.) in H₂O/EtOH, evaporated and freeze dried to give the title compound.

Anal. Calcd. for C₃₀H₂₈N₂SO₃ClNa·H₂O: C 62.75; H 5.45; N 4.86; Na 4.00. Found: C 62.35; H 5.38; N 5.30; Na 3.53.

EXAMPLE 4

5-((3-(2-(7-chloroquinolin-2-yl)ethenyl)phenyl)(2-(dimethylcarbamoyl)ethylthio)methyl)thiophene-2-carboxylic acid

Step 1

Preparation of
5-((3-(2-(7-chloroquinolin-2-yl)ethenyl)phenyl)hydroxymethyl)thiophene-2-carboxylic acid At −78° C., BuLi, 1.6M in hexanes (7.5 mL, 2.3 equiv.) was added dropwise to a solution of thiophene-2-carboxylic acid (0.784 g, 1.2 equiv.) in THF (20 mL) and the mixture was stirred at −78° C. for 30 minutes. Then a solution of 3-(2-(7-chloro-2-quinolinyl)ethenyl) benzaldehyde (EP 233,763, Example 24, step 1) (1.515 g, 5.15 mmoles) in THF (25 mL) was added dropwise. Stirring was continued for an hour at −78° C. and the reaction was quenched with 25% aqueous NH₄OAc. The mixture was acidified to pH 5 with acetic acid and extracted with EtOAc. The organic fraction was dried over Na₂SO₄ and evaporated. Flash chromatography on silica using EtOAc:toluene:AcOH 30:70:1 and 40:60:1 yielded the title compound.

¹H NMR (CD₃COCD₃) δ (ppm): 6.80 (s, 1H), 7.32–7.65 (m, 6H), 7.70 (d, 1H), 7.82–8.04 (m, 5H), 8.33 (d, 1H).

Step 2

At −10° C., AlCl₃ (2.323 g, 8 equiv.) was added to a solution of the hydroxyacid of step 1 (915 mg, 2.17 mmoles) and 3-mercapto-N,N-dimethylpropionamide (587 mg, 2 equiv.) in CH₂Cl₂ (45 mL) and the mixture was stirred at 0° C. for 1.5 hours. An oil separated, which was collected with a spatula and quenched with THF: 25% aqueous NH₄OAc ∼1:1. The remaining reaction mixture was stirred 30 minutes at room temperature and quenched at 0° C. with 25% aqueous NH₄OAc. The solutions were combined, acidified with acetic acid and extracted with EtOAc. Drying the organic phase over Na₂SO₄ and flash chromatography of the residue using acetone:toluene:AcOH 20:80:1 and 30:70:1 afforded the title acid.

¹H NMR (CD₃COCD₃) δ (ppm): 2.60 (m, 2H), 2.70 (m, 2H), 2.84 (s, 3H), 2.96 (s, 3H), 6.60 (s, 1H), 7.37–7.58 (m, 5H), 7.63 (d, 1H), 7.77 (d, 1H), 7.82–8.03 (m, 5H), 8.33 (d, 1H).

EXAMPLE 5

3-((3-(2-(7-chloroquinolin-2-yl)ethenyl)phenyl) (2-(dimethylcarbamoyl)ethylthio)methyl)benzoic acid

Step 1

Preparation of
3-((3-(3-(7-chloroquinolin-2-yl)ethenyl)phenyl)hydroxymethyl)benzoic acid To the dilithium salt (5.92 mmoles) obtained from 3-bromobenzoic acid (W. E. Parham and Y. A. Sayed, J. Org. Chem., 39, 2051 (1974)), a solution of 3-(2-(7-chloro-2-quinolinyl)ethenyl)benzaldehyde (1.503 g, 5.16 mmoles) in THF (25 mL) was added dropwise at −78° C. The mixture was stirred 2 hours at −78° C. and was quenched with 25% aqueous NH₄OAc. The mixture was acidified to pH 5 with AcOH and extracted with EtOAc. The organic fractions were dried over Na₂SO₄ and evaporated. Flash chromatography on silica using EtOAc:toluene:AcOH 30:70:1 yielded the title compound.

¹H NMR (CD₃COCD₃·DMSO-d6) δ (ppm): 5.90 (s, 1H), 6.00 (s, 1H, OH), 7.36–7.58 (m, 5H), 7.62 (d, 1H), 7.73 (d, 1H), 7.82–8.02 (m, 6H), 8.13 (s, 1H), 8.37 (d, 1H).

Step 2

At 0° C., AlCl₃ (1.182 g, 7.5 equiv.) was added to a suspension of the hydroxyacid of step 1 (492 mg, 1.183 mmoles) and 3-mercapto-N,N-dimethylpropionamide (327 mg, 2 equiv.) in CH₂Cl₂ (12 mL). The mixture was stirred at 0° C. for 1.5 hours and was quenched with THF:25% aqueous NH₄OAc. Acidification to pH 5 with AcOH, extraction with EtOAc, drying the organic phase over Na₂SO₄ and flash chromatography on silica using acetone:toluene:AcOH 20:80:1 afforded the title acid.

¹H NMR (CD₃COCD₃) δ (ppm): 2.63 (m, 2H), 2.73 (m, 2H), 2.83 (s, 3H), 2.95 (s, 3H), 5.62 (s, 1H), 7.40–7.56 (m, 5H), 7.65 (d, 1H), 7.79–8.03 (m, 7H), 8.22 (s, 1H), 8.34 (d, 1H).

EXAMPLE 6

4-((3-(2-(7-chloroquinolin-2-yl)ethenyl)phenyl)(2-(dimethylcarbamoyl)ethylthio)methyl)benzoic acid Using the same procedure as for Example 5, but substituting 3-bromobenzoic acid by 4-bromobenzoic acid in step 1, the title compound was prepared.

¹H NMR (CD₃COCD₃) δ (ppm): 2.62 (m, 2H), 2.72 (m, 2H), 2.84 (s, 3H), 2.95 (s, 3H), 5.59 (s, 1H), 7.38–7.57 (m, 4H), 7.60–7.73 (m, 3H), 7.82–8.07 (m, 7H), 8.33 (d, 1H).

EXAMPLE 7

3((2-carboxyethylthio)(3-(2-(7-chloroquinolin-2-yl)ethenyl)phenyl)methyl)benzoic acid To a suspension of the hydroxyacid of Example 5, step 1, (193 mg, 464 μmoles) in CH₂Cl₂ (5 mL), 3-mercaptopropionic acid (45 μL, 1.1 equiv.) was added, followed by AlCl₃ (254 mg, 4 equiv.) and 2,6-di-tert-butyl-4-methylphenol (23 mg, 0.2 equiv.). The reaction mixture was stirred at room temperature 6.7 hours. Then, at 0° C., THF was added, followed by 25% aqueous NH₄OAc. The mixture was acidified to pH 5 with AcOH and was extracted with EtOAc. Drying of the organic phase over Na₂SO₄ and flash chromatography of the residue on silica using acetone:toluene:AcOH 10:90:1 afforded the title diacid.

¹H NMR (CD₃COCD₃·DMSO) δ (ppm): 2.57 (m, 2H), 2.69 (m, 2H), 5.62 (s, 1H), 7.40–7.58 (m, 5H), 7.66 (d, 1H), 7.81 (d, 1H), 7.85–8.04 (m, 6H), 8.20 (s, 1H), 8.35 (d, 1H).

EXAMPLE 8

6-(3-carboxyphenylthio)-6-(3-(2-(7-chloroquinolin-2-yl)ethenyl)phenyl)-3-methylhexanoic acid

Step 1

Preparation of methyl 3-methyl-5-(methylsulfonyloxy)pentanoate

To methyl 5-hydroxy-3-methylpentanoate (B. Lythgoe, J. Chem. Soc., Perkin Trans. I, 834 (1978)) (9.63 g, 65.9 mmoles) in 200 mL CH₂Cl₂ at −78° C., Et₃N (14 mL, 1.5 equiv.) and methanesulfonyl chloride (5.6 mL, 1.1 equiv.) were added. After one hour of stirring at room temperature, 25% NH₄OAc was added. Extraction with CH₂Cl₂, filtration of the organic phase through silica and evaporation afforded the title compound, which was used as such in the next step.

Step 2

Preparation of methyl 5-iodo-3-methylpentanoate

The mesylate (step 1, 14.4 g, 6.42 mmoles) and NaI (48 g, 5 equiv.) were heated to reflux in 200 mL acetone for 3 hours. The mixture was then filtered through celite and the solvent evaporated. The residue was partionned between water and Et₂O, the ether extract washed with 5% Na₂S₂O₃ and brine, dried and evaporated. Flash chromatography of the residue on silica with EtOAc:hexane 2.5:97.5 afforded the title compound.

¹H NMR (90 MHz, CDCl₃) δ (ppm): 1.00 (d, 3H), 1.70–2.43 (m, 5H), 3.20 (t, 2H), 3.67 (s, 3H).

Step 3

Preparation of (5-methoxy-3-methyl-5-oxopentyl)triphenylphosphonium iodide

Triphenylphosphine (14.6 g, 2 equiv.) and the iodide (step 2, 7.85 g, 27.6 mmoles) were heated to 80° C. in 50 mL of toluene for 24 hours and at 100° C. 6 hours. The mixture was allowed to cool to room temperature, the toluene layer was discarded and the remaining oil heated in toluene for another hour. After cooling to room temperature, the toluene layer was removed. The remaining oil was heated for one hour in ether, the ether was removed at room temperature and the remaining oil dried under vacuum.

¹H NMR (CDCl₃) δ (ppm): 1.09 (d, 3H), 1.50–2.00 (m, 3H), 2.26–2.45 (m, 2H), 3.59 (s, 3H), 3.50–3.85 (m, 2H), 7.69–7.90 (m, 15H).

Step 4

Preparation of methyl 6-(3-cyanophenyl)-3-methyl-5-hexenoate

Under a continuous flow of N₂ at −78° C., KHMDS (0.684M in toluene, 110 mL, 1.3 equiv.) was added dropwise to a solution of the phosphonium salt (step 3, 0.133M in THF:HMPA 10:1, 620 mL, 1.4 equiv.) and 3-cyanobenzaldehyde (7.702 g, 58.7 mmoles) over a period of 30 minutes. The mixture was then allowed to warm to room temperature and was stirred for a further 2 hours. 25% aqueous NH₄OAc was added and the aqueous layer was extracted with EtOAc. The organic layer was washed twice with brine, dried over Na₂SO₄ and evaporated. The residue was purified by flash chromatography on silica using EtOAc:hexane 7.5:92.5 and 10:90 to afford the title product.

¹H NMR (CDCl₃) δ0.98 (d, 3H), 2.07–2.42 (m, 5H), 3.66 (s, 3H), 5.79 (td, 1H), 6.48 (d, 1H), 7.40–7.59 (m, 4H) p.p.m.

Step 5

Preparation of O-(3-(methoxycarbonyl)phenyl)dimethylcarbamothioate

At 0° C., NaH (59.6% in oil, 2.975 g, 1.1 equiv.) was added portionwise to a solution of methyl 3-hydroxybenzoate (10.22 g, 67.2 mmoles) in dimethylformamide (70 mL) and the mixture was stirred 30 minutes at room temperature. Then, dimethylthiocarbamoyl chloride (11.95 g, 1.4 equiv.) was added and stirring was continued for 3 hours. The reaction mixture was poured into buffer (700 mL) and extracted with EtOAc. The organic layer was dried over Na₂SO₄ and evaporated. Flash chromatography of the residue on silica using EtOAc:toluene 2.5:97.5 afforded the title compound.

¹H NMR (CDCl₃) δ (ppm): 3.37 (s, 3H), 3.48 (s, 3H), 3.93 (s, 3H), 7.29 (d, 1H), 7.48 (dd, 1H), 7.75 (broad s, 1H), 7.95 (d, 1H).

Step 6

Preparation of S-(3-methoxycarbonyl)phenyl)dimethylcarbamothioate

The product of step 5 (8.452 g, 35.3 mmoles) was heated to reflux for 5 days in dichlorobenzene (50 mL). Flash chromatography of the reaction mixture on silica using EtOAc:toluene 5:95 and 10:90 yielded the title product.

$^1$H NMR (CDCl$_3$) δ (ppm): 3.05 (broad s, 3H), 3.12 (broad s, 3H), 3.91 (s, 3H), 7.48 (dd, 1H), 7.70 (d, 1H), 8.08 (d, 1H), 8.18 (broad s, 1H).

Step 7

Preparation of methyl 3-mercaptobenzoate

To the product of step 6 (6.767 g, 28.3 mmoles) in MeOH (23 mL), MeONa (1.74M in MeOH, 33 mL, 2 equiv.) was added and the solution was stirred at room temperature 8 hours and kept at 5° C. for 3 days. NH$_4$OAc (600 mL) was added, followed by HCl (1N, 60 mL). Extraction with EtOAc, drying of the organic phase over Na$_2$SO$_4$ and flash chromatography of the residue on silica with EtOAc:hexane:AcOH 4:96:1 yielded the title thiol.

$^1$H NMR (CDCl$_3$) δ (ppm): 3.55 (s, 1H), 3.92 (s, 3H), 7.31 (d, 1H), 7.46 (d, 1H), 7.82 (d, 1H), 7.95 (broad s, 1H).

Step 8

Preparation of methyl 6-(3-cyanophenyl)-6-(3-(methoxycarbonyl)phenylthio)-3-methylhexanoate The cyanostyrene of step 4 (506 mg, 2.08 mmoles) and the thiol of step 7 (449 mg, 1.3 equiv.) were mixed together in CH$_2$Cl$_2$ (20 mL). AlCl$_3$ (1.16 g, 4.2 equiv.) was added and the mixture was stirred at room temperature 1.5 hours. At 0° C., 25% aqueous NH$_4$OAc was added. Extraction with EtOAc and flash chromatography of the residue from the dried organic phase on silica with EtOAc:hexane 15:85 and 20:80 afforded the title compound.

$^1$H NMR (CDCl$_3$) δ (ppm): 0.93 (2d, 3H), 1.02–1.55 (m, 2H), 1.78–2.36 (m, 5H), 3.66 (2s, 3H), 3.94 (s, 3H), 4.13 (dd, 1H), 7.22–7.53 (m, 6H), 7.88 (broad s, 2H).

Step 9

Preparation of methyl 6-(3-formylphenyl)-6-(3-(methoxycarbonyl)phenylthio)-3-methylhexanoate HCl gas was bubbled into a suspension of SnCl$_2$ (2.769 g, 9 equiv.) in ether (16 mL) until obtention of 2 liquid phases. The nitrile of step 8 (670 mg, 1.628 mmoles) in toluene (3 mL) was then added. HCl was bubbled into the mixture for 30 minutes and occasionally during a further 5 hours. At 0° C., water (~20 mL) was added to the flask and the mixture was stirred at room temperature until obtention of a clear reaction mixture (~5–10 minutes). The reaction mixture was then poured into EtOAc:25% aqueous NH$_4$OAc 1:1 (~500 mL) and the resulting suspension was stirred overnight, filtered through celite and extracted with EtOAc. The organic layer was dried over Na$_2$SO$_4$ and evaporated. Flash chromatography of the residue on silica using EtOAc:hexane 15:85 and 20:80 yielded the title aldehyde.

$^1$H NMR (CDCl$_3$) δ (ppm): 0.92 (2d, 3H), 1.04–1.55 (m, 2H), 1.84–2.34 (m, 5H), 3.62 (2s, 3H), 3.90 (s, 3H), 4.21 (t, 1H), 7.20–7.54 (m, 4H), 7.72 (broad s, 2H), 7.84 (d, 1H), 7.89 (s, 1H).

Step 10

Preparation of methyl 6-(3-(2-(7-chloroquinolin-2-yl)ethenyl)phenyl)-6-(3-(methoxycarbonyl)phenylthio)-3-methylhexanoate At −78° C., BuLi (1.6M in hexanes, 1.0 mL, 1.2 equiv.) was added dropwise to a suspension of ((7-chloroquinolin-2-yl)methyl)triphenylphosphonium bromide (EP 233,763, Example 4, step 2) (926 mg, 1.3 equiv.) in THF (9 mL) and the suspension was stirred at this temperature for 1 hour. The benzaldehyde of step 9 (566 mg, 1.364 mmoles) in THF (5 mL) was then added dropwise. The mixture was stirred at −78° C. for 15 minutes and at room temperature for 2 hours. It was quenched with 25% aqueous NH$_4$OAc and extracted with EtOAc. The organic layer was dried over Na$_2$SO$_4$, filtered through silica and evaporated. Flash chromatography of the residue using EtOAc:hexane 15:85 and 20:80 yielded the title diester.

$^1$H NMR (CD$_3$COCD$_3$) δ (ppm): 0.85 (2d, 3H), 1.07–1.56 (m, 2H), 1.83–2.30 (m, 5H), 3.53 (2s, 3H), 3.80 (s, 3H), 4.45 (t, 1H), 7.30–7.58 (m, 7H), 7.67–7.98 (m, 7H), 8.32 (d, 1H).

Step 11

To the diester of step 10 (722 mg, 1.26 mmoles) in THF:MeOH 1:1 (12 mL), LiOH 1.0N (3.8 mL, 3 equiv.) was added and the mixture was stirred for 28 hours. 25% aqueous NH$_4$OAc was then added and the mixture was acidified to pH 5 with HCl. Extraction with EtOAc, drying of the organic layer over Na$_2$SO$_4$ and flash chromatography of the residue on silica using EtOAc:toluene:AcOH 30:70:1 yielded the title diacid.

$^1$H NMR (CD$_3$COCD$_3$) δ (ppm): 0.92 (2d, 3H), 1.14–1.65 (m, 2H), 1.88–2.16 (m, 4H), 2.21–2.38 (m, 1H), 4.50 (t, 1H), 7.30–7.62 (m, 7H), 7.70–8.03 (m, 7H), 8.32 (d, 1H).

EXAMPLE 9

3-((3-((7-chloroquinolin-2-ylmethyl)oxy)phenyl)(2-(dimethylcarbamoyl)ethylthio)methyl)benzoic acid, sodium salt

Step 1

Preparation of methyl 3-[(3-((7-chloroquinolin-2-ylmethyl)oxy)phenyl)hydroxymethyl]benzoate To a suspension of 3-bromobenzoic acid (905 mg) in THF (25 cc) at −78° C. was added 1.6M BuLi (6.25 cc) and the mixture was stirred for ½ hr at −78° C. A solution of 3-((7-chloroquinolin-2-ylmethyl)oxy)benzaldehyde (EP 233,763, Example 16, step 1) (1.49 g) in THF (25 cc) was added dropwise and allowed to react for 1 hr at −78°. 25% aqueous NH$_4$OAc (25 cc) and acetic acid (3 cc) were added at −78° and the mixture allowed to warm to 25° C., at which temperature it was extracted with ethyl acetate (3×25 cc). The organic layer was washed with brine and the solvents were removed in vacuo. The residue was taken up in dry 10% HCl in MeOH for 16 hrs at room temperature. Most of the MeOH was removed in vacuo and the residue partitioned between 25% aqueous NH$_4$OAc (10 cc) and ethyl acetate (3×10 cc). The organic layer was washed with brine and the solvents removed in vacuo. The residue was purified by chromatography to afford the title compound.

p.m.r. (CD$_3$COCD$_3$) δ (ppm): 8.3–8.4 (d, 1H), 6.9–8.1 (m, 12H), 5.85–5.9 (d, 1H), 5.35 (s, 2H), 5.1 (d, 1H), 3.85 (s, 3H).

Step 2

Preparation of methyl 3-((3-((7-chloroquinolin-2-ylmethyl)oxy)phenyl)(2-(dimethycarbamoyl)ethylthio)methyl)benzoate To a solution of the alcohol (step 1) (70 mg) at 25° C. and 3-mercapto-N,N-dimethylpropionamide (66 mg) in dichloroethane (2 cc) was added AlCl$_3$ (212 mg) and the gummy suspension stirred for ½ hr after which time 25% aqueous NH$_4$OAc (5 cc) was added. Organic materials were extracted with ethyl acetate and the organic layer washed with brine and the solvents removed in vacuo. The residue was purified by chromatography to afford the title compound which was used as such in the next step.

Step 3

To a solution of the ester (step 2) (244 mg) in MeOH (1 cc) and THF (3 cc) was added 2N NaOH (750 μL) and the mixture stirred 3 hrs at 25° C. after which the solvents were removed in vacuo. The residue was partitioned between 25% aqueous NH$_4$OAc (10 cc) containing AcOH (2 cc) and ethyl acetate (25 cc). The organic layer was washed with brine and the solvent removed to give a residue which was purified by chromatography. To the acid obtained was added 1 equivalent of NaOH and the mixture freeze dried to afford the title compound.

p.m.r. (CD$_3$COCD$_3$) δ (ppm): 6.9–8.4 (m, 13H), 5.5 (s, 1H), 5.35 (s, 2H), 2.9 (s, 3H), 2.8 (s, 3H), 2.5–2.7 (m, 4H).

EXAMPLE 10

3-((3-carboxyphenylthio)(3-(2-(7-chloroquinolin-2-yl)-ethenyl)phenyl)methyl)benzoic acid

Step 1

Preparation of 3-((3-(2-(7-chloroquinolin-2-yl)ethenyl)phenyl)(3-methoxycarbonylphenylthio)methyl)benzoic acid To a suspension of the hydroxyacid of Example 5, step 1 (1.032 g, 2.48 mmoles) in CH$_2$Cl$_2$ (25 mL), methyl 3-mercaptobenzoate (Example 8, step 7, 545 mg, 1.3 equiv.) and 2,6-di-tert-butyl-4-methylphenol (106 mg, 0.2 equiv.) were added. At 0° C., AlCl$_3$ (1.290 g, 3.9 equiv.) was added and the reaction mixture was stirred at 0° C. 1.3 hours. THF and 25% aqueous NH$_4$OAc were then added and the mixture was stirred at room temperature for 3 hours. The mixture was acidified to pH 5 with acetic acid and was extracted with EtOAc. The organic layer was dried over Na$_2$SO$_4$ and evaporated. Flash chromatography of the residue on silica using EtOAc:toluene:AcOH 10:90:1 yielded the title compound (contaminated by a diaddition product), which was used as such in the next step.

Step 2

To the mixture of step 1 (400 mg containing 460 μmoles of monoaddition product and 153 μmoles of diaddition product) in THF:MeOH 1:1 (6 mL), LiOH 1.0N (2 mL) was added and the reaction mixture was stirred for 2 days. 25% aqueous NH$_4$OAc was then added and the mixture was acidified with AcOH and extracted with EtOAc. Drying the organic phase over Na$_2$SO$_4$ and flash chromatography of the residue on silica using EtOAc:toluene:AcOH 20:80:1 and 30:70:1 yielded the title compound.

$^1$H NMR (CD$_3$COCD$_3$) δ (ppm): 6.17 (s, 1H), 7.32–7.68 (m, 8H), 7.78–8.08 (m, 9H), 8.27 (s, 1H), 8.31 (d, 1H).

EXAMPLE 11

3-((3-((7-chloroquinolin-2-ylmethyl)oxy)phenyl)(2-(t-butylcarbamoyl)ethylthio)methyl)benzoic acid sodium salt

Step 1

Preparation of methyl 3-((3-((7-chloroquinolin-2-ylmethyl)oxy)phenyl)(2-carboxyethylthio)methyl)benzoate To a 0° C. solution of the alcohol (Example 9, step 1) (475 mg) and 3-mercaptopropionoic acid (160 mg) in dichloroethane (15 cc), AlCl$_3$ (532 mg), was added portion-wise and the suspension was stirred for ½ hr at 0° C. after which time 25% aqueous NH$_4$OAc (10 cc) was added. The organic materials were extracted with ethyl acetate (3×10 cc), the organic layer washed with brine and the solvents removed in vacuo to yield a residue which was purified by chromatography to afford the title compound.

p.m.r. (CD$_3$COCD$_3$) δ (ppm): 6.9–8.4 (m, 13H), 5.5 (s, 1H), 5.35 (s, 2H), 3.85 (s, 3H), 2.5–2.7 (m, 4H).

Step 2

Preparation of methyl 3-((3-((7-chloroquinolin-2-ylmethyl)oxy)phenyl)(2-(t-butylcarbamoyl)ethylthio)methyl)benzoate To a 0° solution of the acid (step 1) (522 mg) in dichloromethane (25 cc), acetonitrile (7 cc) and triethylamine (202 mg) was added 2-chloro-1-methylpyridinium iodide (511 mg) and the mixture left to react for 1.5 hrs at 0° C. Then t-butylamine (366 mg) was added and the mixture stirred at 25° C. for 16 hrs. 25% aqueous NH$_4$OAc (25 cc) was added and the mixture extracted with ethyl acetate (3×25 cc). The combined organic layers were washed with brine and the solvents removed in vacuo. The residue was purified by chromatography to afford the title compound.

p.m.r. (CD$_3$COCD$_3$) δ (ppm): 6.9–8.4 (m, 13H), 6.75 (bs, 1H), 5.45 (s, 1H), 5.35 (s, 2H), 3.85 (s, 3H), 2.3–2.65 (m, 4H), 1.3 (s, 9H).

Step 3

To a solution of the ester (step 2) (327 mg) in MeOH (1 cc) and THF (3 cc) was added 2N NaOH (850 μL) and the reaction stirred for 16 hrs at 25° C. 25% aqueous NH$_4$OAc (10 cc) and acetic acid (1 cc) were added and the organic material extracted with ethyl acetate (3×10 cc). The organic layer was washed with brine and the solvents removed in vacuo to give the acid which was treated with one equivalent of NaOH and freeze dried to afford the title compound.

p.m.r. (CD$_3$COCD$_3$) δ (ppm): 6.8–8.3 (m, 14H), 5.25 (s, 2H), 5.2 (s, 1H), 2.2–2.6 (m, 4H), 1.25 (s, 9H).

EXAMPLE 12

5-((3-((7-chloro-2-quinolinyl)methoxy)phenyl)((3-dimethylamino-3-oxopropyl)thio)methyl)-3-pyridine-carboxylic acid, sodium salt

Step 1

Preparation of methyl 5-((3-((7-chloro-2-quinolinyl)methoxy)phenyl)-hydroxymethyl)-3-pyridinecarboxylate To a −100° C. suspension of 3-bromonicotinic acid (1.21 g) in THF (25 c.c.) was added BuLi (1.6M in hexanes, 12 mmoles); after 45 min there was added a solution of the aldehyde from EP 233,763, Example 16, Step 1 (1.48 g), in THF (25 c.c.) and the mixture was stirred 1.5 hr at −78° C. It was then poured onto 25% aqueous NH$_4$OAc and 1 c.c. of conc. AcOH was added; the product was extracted with ethyl acetate, washed with brine, dried with MgSO$_4$ and the solvents removed in vacuo. The residue was purified by chromatography to yield the carboxylic acid which was esterified with 10% HCl in MeOH at r.t. After removal of most of the MeOH, 25% aqueous NH$_4$OAc was added and the product extracted with ethyl acetate, washed with brine and the solvents removed in vacuo to yield the title compound.

$^1$H NMR (CD$_3$COCD$_3$) δ (ppm): 3.90 (s, 3H), 5.30 (s, 2H), 5.45 (d, 1H), 6.00 (bs, 1H), 6.90–9.00 (m, 12H).

Step 2

Preparation of methyl 5-((3-((7-chloro-2-quinolinyl)-methoxy)phenyl)-chloromethyl)-3-pyridinecarboxylate To a r.t. solution of the alcohol (Step 1) (217 mg) in dichloromethane (10 c.c.) and carbon tetrachloride (5 c.c.) was added tri-n-octyl phosphine (650 mg) and the reaction was stirred for 1.5 hr. The reaction products were preabsorbed on SiO$_2$ and the title compound purified by chromatography.

$^1$H NMR (CD$_3$COCD$_3$) δ (ppm): 3.90 (s, 3H), 5.40 (s, 2H), 6.55 (s, 1H), 7.05–9.10 (m, 12H).

Step 3

Preparation of methyl 5-((3-((7-chloro-2-quinolinyl)-methoxy)phenyl)((3-dimethylamino-3-oxopropyl)thio)-methyl)-3-pyridinecarboxylate To a solution of the chloride (Step 2) (122 mg) and N,N-dimethyl 3-mercaptopropionamide (45 mg) in acetonitrile (10 c.c.) was added cesium carbonate (440 mg) and the mixture was heated to 80° C. for 3 hrs. The reaction products were pre-absorbed on SiO$_2$ and the title compound purified by chromatography.

$^1$H NMR (CD$_3$COCD$_3$) δ (ppm) 2.50–2.70 (m, 4H), 2.80 (s, 3H), 2.90 (s, 3H), 3.90 (s, 3H), 5.40 (s, 2H), 5.60 (s, 2H), 6.95–9.00 (m, 12H).

Step 4

To a 0° C. solution of the ester (Step 3) (85 mg) in THF (3 c.c.) and MeOH (1 c.c.) was added 2N NaOH (0.25 c.c.) and the mixture was stirred at r.t. for 3 hrs. 25% aqueous NH$_4$OAc was added followed by conc. AcOH (3 drops) and the mixture was extracted with ethyl acetate; the organic layer was washed with brine, dried with MgSO$_4$ and the solvents removed in vacuo. To the residue in ethanol (1 c.c.) was added 2N NaOH (77 μL) and the solution freeze dried to yield the title compound.

$^1$H NMR (CD$_3$COCD$_3$·DMSO) δ (ppm): 2.40–2.70 (m, 4H), 2.80 (s, 3H), 2.90 (s, 3H), 5.40 (s, 2H), 6.90–9.00 (m, 12H).

EXAMPLE 14

3,3'-(((3-((7-Chloro-2-quinolinyl)methoxy)phenyl)methylene)bis(thio))bis(benzoic acid), disodium salt

Step 1

Preparation of dimethyl 3,3'-(((3-((7-chloro-2-quinolinyl)methoxy)phenyl)methylene)bis(thio))bis(benzoate)

At room temperature (r.t.), BF$_3$·Et$_2$O (270 μL, 3.2 equiv.) was slowly added to a mixture of methyl 3-mercaptobenzoate (Example 8, Step 7; 269 mg, 2.2 equiv.) and 3-((7-chloro-2-quinolinyl)methoxy)benzaldehyde (EP 233,763, Example 16, Step 1; 204 mg) in CH$_2$Cl$_2$ (3.5 mL). The reaction mixture was stirred 2.5 hours and was quenched at 0° C. with 25% aq. NH$_4$OAc. Extraction with EtOAc, drying over Na$_2$SO$_4$ and flash chromatography of the residue using EtOAc: toluene 5:95 yielded the title compound.

$^1$H NMR (CD$_3$COCD$_3$) δ (ppm): 3.87 (s, 6H), 5.33 (s, 2H), 6.05 (s, 1H), 6.99 (d, 1H), 7.10–7.30 (m, 3H), 7.40 (t, 2H), 7.55–7.70 (m, 4H), 7.85 (d, 2H), 7.95–8.05 (m, 4H), 9.37 (d, 1H).

Step 2

Using the procedure of Example 8, Step 11, the diester of Step 1 was hydrolyzed to the diacid. The diacid was dissolved in ethanol and 2 equiv. of NaOH 1.000N were added. The solvents were removed in vacuo and the residue was taken up in water and freeze-dried.

Anal. calc'd for C$_{31}$H$_{20}$ClNO$_5$S$_2$Na$_2$·H$_2$O: C, 57.28; H, 3.41; N, 2.15; S, 9.86; Cl, 5.45; Na, 7.07. Found: C, 57.18; H, 3.31; N, 2.00; S, 11.01; Cl, 5.34; Na, 6.35.

EXAMPLE 23

3-(((4-Carboxyphenyl)thio)(3-(2-(7-chloro-2-quinolinyl)ethenyl)phenyl)methyl)benzoic acid, disodium salt

Step 1

Preparation of methyl 4-mercaptobenzoate

4-Mercaptobenzoic acid (J. Org. Chem., 1962, 27, 2835; 1.72 g) and 98% H$_2$SO$_4$ (0.7 mL) were mixed together in MeOH (55 mL) for 4 days. At 0° C., 25% aq. NH$_4$OAc (500 mL) was then added and the ester was extracted with EtOAc, dried over Na$_2$SO$_4$ and the residue was purified by filtration through silica using EtOAc:toluene 10:90.

$^1$H NMR (CDCl$_3$) δ (ppm): 3.62 (s, 1H), 3.90 (s, 3H), 7.28 (d, 2H), 7.89 (d, 2H).

Step 2

Using the procedure of Example 10, but substituting methyl 3-mercaptobenzoate by methyl 4-mercaptobenzoate from Step 1, the title compound (free diacid) was obtained. It was then converted to the disodium salt using the procedure of Example 14, Step 2.

Anal. calc'd for C$_{32}$H$_{20}$ClNO$_4$SNa$_2$·2.8 H$_2$O: C, 59.46; H, 3.99; N, 2.17; S, 4.96; Cl, 5.48; Na, 7.11. Found: C, 59.40; H, 4.21; N, 2.10; S, 5.03; Cl, 5.59; Na, 6.37.

EXAMPLE 24

3-((3-(2-(7-Chloro-2-quinolinyl)ethenyl)phenyl)((4-(dimethylaminocarbonyl)phenyl)thio)methyl)benzoic acid, sodium salt

Step 1

Preparation of N,N-dimethyl 4-mercaptobenzamide

To $P_2O_5$ (411 mg, 0.5 equiv.) in DMF (4 mL), 4-mercaptobenzoic acid (J. Org. Chem., 1962, 27, 2835; 883 mg) was added and the mixture was heated at reflux for 10 hours (see Monatsh Chem., 1968, 99, 1799). Water and EtOAc were added and the resulting mixture was stirred until complete decomposition of polyphosphoric acid. The organic layer was separated, dried over $Na_2SO_4$ and concentrated. The benzamide was purified by flash chromatography using EtOAc:toluene:AcOH 15:85:1 and 25:75:1.

$^1$H NMR (CDCl$_3$) δ (ppm): 3.00 (br s, 3H), 3.10 (br s, 3H), 3.54 (br s, 1H), 7.22–7.38 (m, 4H).

Step 2

Using the procedure of Example 5, but substituting N,N-dimethyl 3-mercaptopropanamide by the thiol of Step 1, the title compound (free acid) was obtained (the reaction conditions for the alcohol substitution by the thiol were 0° C. 4 hours, then r.t. 30 min). It was then converted to the sodium salt as in Example 14, Step 2 (only one equiv. of NaOH was used).

Anal calc'd for $C_{34}H_{26}ClN_2O_3SNa \cdot 1.5H_2O$: C, 65.02; H, 4.65; N, 4.46; S, 5.10; Cl, 5.64; Na, 3.66. Found: C, 65.03; H, 4.61; N, 4.28; S, 5.56; Cl, 5.93; Na, 3.37.

EXAMPLE 25

3-(2-((2-Carboxyethyl)thio)-2-(3-((7-chloro-2-quinolinyl)methoxy)phenyl)ethyl)benzoic acid

Step 1

Preparation of 1-methoxy-3-vinylbenzene

At $-78°$ C., BuLi 1.6N (29.8 mL, 1.3 equiv.) was added dropwise to a suspension of methyltriphenylphosphonium bromide (18.4 g, 1.4 equiv.) in THF (130 mL) and the mixture was stirred at r.t. 30 min. At $-78°$ C., 3-methoxybenzaldehyde (4.5 mL) was then added and the mixture was stirred at r.t. 2 hours. After quenching with 25% aq. NH$_4$OAc, the title compound was extracted with EtOAc, dried over Na$_2$SO$_4$ and purified by filtration through silica using EtOAc:hexane 10:90.

Step 2

Preparation of (3-methoxyphenyl)oxirane

At 0° C., m-chloroperbenzoic acid (82%, 10.6 g, ~1.4 equiv.) was added to the product of Step 1 in CH$_2$Cl$_2$ (185 mL). The mixture was stirred at 0° C. for 30 min. and at r.t. for 2 hours. 10% Aq. Na$_2$CO$_3$ was then added, the phases were separated and the aqueous was layer extracted with ether. The combined organic phases were dried over Na$_2$SO$_4$ and concentrated. The title compound was purified by distillation: B.P. 130°–136° C./16 mm Hg.

Step 3

Preparation of 1-bromo-3-((diphenyl(2-methyl-2-propyl)silyloxy)methyl)benzene

3-Bromobenzyl alcohol (15.00 g, 80.2 mmoles), tert-butylchlorodiphenylsilane (25 mL, 1.2 equiv.), 4-(dimethylamino)pyridine (1.06 g, 0.1 equiv.) and triethylamine (22 mL, 2 equiv.) were mixed together in CH$_2$Cl$_2$ (200 mL). After 20 hours of stirring, 25% Aq. NH$_4$OAc was added and the phases were separated. The aqueous layer was extracted with EtOAc and the organic phases were combined, dried over Na$_2$SO$_4$ and concentrated. The title compound was purified by filtration through silica using ether:hexane 5:95.

$^1$H NMR (CDCl$_3$) δ (ppm): 1.10 (s, 9H), 4.73 (s, 2H), 7.14–7.30 (m, 2H), 7.32–7.53 (m, 8H), 7.67 (dd, 4H).

Step 4

Preparation of 1-(3-methoxyphenyl)-2-(3-((diphenyl(2-methyl-2-propyl)silyloxy)methyl)phenyl)ethanol At $-78°$ C., BuLi 1.6M (47 mL) was added dropwise to the bromide of Step 3 (31.77 g, 75 mmoles) in THF (100 mL). The mixture was stirred at $-20°$ C. for 10 min. and was added, via a cannula, to a cooled ($-20°$ C.) suspension of CuCN (3.68 g) in THF (25 mL); a solution was obtained. (3-Methoxyphenyl)oxirane from Step 2 (1.8 g, 12 mmoles) was dissolved in THF (20 mL) and cooled to $-78°$ C. It was then added, via a cannula, to the cooled ($-20°$ C.) solution of cuprate. The mixture was stirred at $-20°$ C. for 1 hour and at r.t. for 3 hours. Saturated NH$_4$Cl containing 10% NH$_4$OH was added and stirring was continued for 30 min. Water was then added and the desired compound was extracted with EtOAc, dried over Na$_2$SO$_4$ and purified by flash chromatography on silica using EtOAc:hexane 10:90, 15:85 and 25:75. (See also J. Am. Chem. Soc., 1982, 104, 2305 for the cuprate addition to epoxides.)

$^1$H NMR (CDCl$_3$) δ (ppm): 1.10 (s, 9H), 1.94 (d, 1H, OH), 2.94 (dd, 1H), 3.04 (dd, 1H), 3.80 (s, 3H), 4.76 (s, 2H), 4.87 (m, 1H), 6.82 (br d, 1H), 6.90–6.98 (m, 2H), 7.12 (m, 1H), 7.17 (s, 1H), 7.25–7.30 (m, 3H), 7.33–7.47 (m, 6H), 7.70 (dd, 4H).

Step 5

Preparation of 1-chloro-1-(3-methoxyphenyl)-2-(3-((diphenyl(2-methyl-2-propyl)silyloxy)methyl)phenyl)ethane To the benzyl alcohol of Step 4 (1.116 g, 2.25 mmoles) in CH$_2$Cl$_2$:CCl$_4$ 1:2 (10 mL) cooled to 0° C., trioctylphosphine (2.508 g, 3 equiv.) was added and the mixture was stirred at r.t. for 4 hours. Silica gel was added and the mixture was stirred 5 min. It was then poured onto a flash chromatography column and eluted with EtOAc:hexane 5:95. The title compound thus obtained was used as such for the next step.

Step 6

Preparation of methyl 3-((1-(3-methoxyphenyl)-2-(3-((diphenyl(2-methyl-2-propyl)silyloxy)methyl)phenyl)ethyl)thio)propanoate The chloride of Step 5 was dissolved in CH$_3$CN (15 mL). CsCO$_3$ (2.221 g) and methyl 3-mercaptopropanoate (340 μL) were added and the resulting mixture was stirred at 65° C. for 2 hours and at reflux for 2 hours. EtOAc was added and the suspension was filtered through celite. Flash chromatography of the residue (after evaporation) on silica using EtOAc:hexane 7.5:92.5 and 10:90 yielded 1-(3-methoxyphenyl)-2-(3-((diphenyl(2-methyl-2-propyl)silyloxy)methyl)-phenyl)ethene (the elimination product), followed by the title compound.

$^1$H NMR (CDCl$_3$) δ (ppm): 1.10 (s, 9H), 2.41 (t, 2H), 2.56 (t, 2H), 3.11 (d, 2H), 3.63 (s, 3H), 3.77 (s, 3H), 4.01 (t, 1H), 4.70 (s, 2H), 6.74 (dd, 1H), 6.83 (m, 2H), 6.94 (m, 1H), 7.04 (br s, 1H), 7.13–7.21 (m, 3H), 7.34–7.47 (m, 6H), 7.68 (d, 4H).

Step 7

Preparation of methyl 3-((1-(3-methoxyphenyl)-2-(3-(hydroxymethyl)phenyl)ethyl)thio)propanoate The silyl ether of Step 6 (469 mg, 783 μmoles), Bu$_4$NF (1.0M in THF, 1.6 mL) and acetic acid (160 μL) were mixed together in THF (4 mL) for 8 hours. 25% Aq. NH$_4$OAc was added and the title compound was extracted with EtOAc, dried over Na$_2$SO$_4$ and purified by flash chromatography on silica using EtOAc:toluene 20:80.

$^1$H NMR (CDCl$_3$) δ (ppm): 1.83 (br s, 1H, OH), 2.43 (t, 2H), 2.53 (t, 2H), 3.12 (d, 2H), 3.65 (s, 3H), 3.80 (s, 3H), 4.02 (t, 1H), 4.62 (s, 2H), 6.78 (d, 1H), 6.80–6.90 (m, 2H), 7.00 (d, 1H), 7.08 (s, 1H), 7.12–7.25 (m, 3H).

Step 8

Preparation of methyl 3-(2-((2-(methoxycarbonyl)ethyl)thio)-2-(3-methoxyphenyl)ethyl)benzoate Using the procedure of Example 1, Steps 3 and 4, the benzyl alcohol of Step 7 was oxidized to the title ester.

$^1$H NMR (CDCl$_3$) δ (ppm): 2.43 (t, 2H), 2.56 (t, 2H), 3.14 (m, 2H), 3.63 (s, 3H), 3.79 (s, 3H), 3.90 (s, 3H), 4.03 (t, 1H), 6.78 (d, 1H), 6.80–6.88 (m, 2H), 7.17–7.30 (m, 3H), 7.80 (s, 1H), 7.85 (d, 1H).

Step 9

Preparation of methyl 3-(2-(3-hydroxyphenyl)-2-((2-(methoxycarbonyl)ethyl)thio)ethyl)benzoate At −78° C., BBr$_3$ (1.0M in CH$_2$Cl$_2$, 2 mL, 4 equiv.) was added dropwise to a solution of the methyl ether of Step 8 (193 mg, 497 μmoles) and Et$_3$N (14 μL, 0.2 equiv.) in CH$_2$Cl$_2$ (2 mL). The reaction mixture was stirred 1.5 hours at −20° C. and quenched with 25% aq. NH$_4$OAc.. Extraction with EtOAc, drying over Na$_2$SO$_4$ and flash chromatography of the residue on silica using EtOAc:toluene 7.5:92.5 and 12.5:87.5 yielded the title phenol.

$^1$H NMR (CDCl$_3$) δ (ppm): 2.43 (t, 2H), 2.56 (t, 2H), 3.14 (m, 2H), 3.65 (s, 3H), 3.91 (s, 3H), 4.00 (t, 1H), 5.50 (br s, 1H, OH), 6.72 (d, 1H), 6.75–6.83 (m, 2H), 7.10–7.30 (m, 3H), 7.80 (s, 1H), 7.85 (d, 1H).

Step 10

Preparation of methyl 3-(2-(3-((7-chloro-2-quinolinyl)methoxy)phenyl)-2-((2-(methoxycarbonyl)ethyl)thio)ethyl)benzoate The phenol of Step 9 (142 mg, 379 μmoles), 2-(bromomethyl)-7-chloroquinoline (143 mg, 1.5 equiv.) and K$_2$CO$_3$ (milled, 105 mg, 2 equiv.) were mixed together in acetone (4 mL) and heated at reflux 8 hours. EtOAc was then added and the mixture was filtered through a small pad of silica gel. Flash chromatography of the residue using EtOAc:toluene 5:95 and 7.5:92.5 afforded the title compound.

$^1$H NMR (CD$_3$COCD$_3$) δ (ppm): 2.42 (m, 2H), 2.53 (m, 2H), 3.20 (m, 2H), 3.58 (s, 3H), 3.85 (s, 3H), 4.27 (t, 1H), 5.37 (s, 2H), 6.90–7.00 (m, 2H), 7.13 (br s, 1H), 7.21 (t, 1H), 7.27–7.37 (m, 2H), 7.60 (dd, 1H), 7.70 (d, 1H), 7.74–7.80 (m, 2H), 8.02 (d, 1H), 8.05 (br s, 1H), 8.40 (d, 1H).

Step 11

Using the procedure of Example 8, Step 11, the diester of Step 10 was hydrolyzed to the title diacid.

$^1$H NMR (CD$_3$COCD$_3$) δ (ppm): 2.42 (m, 2H), 2.55 (m, 2H), 3.22 (m, 2H), 4.30 (t, 1H), 5.37 (s, 2H), 6.92 (dd, 1H), 6.98 (d, 1H), 7.15–7.35 (m, 4H), 7.60 (dd, 1H), 7.70 (d, 1H), 7.80 (m, 2H), 8.01 (d, 1H), 8.05 (br s, 1H), 8.40 (d, 1H).

EXAMPLE 26

3-(1-(3-(2-(7-chloro-2-quinolinyl)ethenyl)phenyl)-1-((2-carboxy-4-pyridinyl)thio)methyl)benzoic acid

Step 1

Preparation of methyl 3-((3-(2-(7-chloro-2-quinolinyl)ethenyl)phenyl)hydroxymethyl)benzoate At 0° C., AcCl (10 mL) was added to MeOH (80 mL) and the solution was stirred ≈30 min. at r.t. The hydroxyacid of Example 5, Step 1 (1.96 g, 4.7 mmoles) was then added and the mixture was stirred at r.t. 4 days. It was then poured into 25% aq. NH$_4$OAc (400 mL), THF (100 mL) and EtOAc (150 mL). The phases were separated and the aqueous layer was extracted twice with EtOAc:THF 2:1. The combined extracts were dried over Na$_2$SO$_4$. Flash chromatography of the residue using EtOAc:toluene 10:90 and 20:80 yielded the title ester.

Step 2

Preparation of methyl 3-((3-(2-(7-chloro-2-quinolinyl)ethenyl)phenyl)chloromethyl)benzoate To the hydroxyester of Step 1 (307 mg, 714 μmoles) in CH$_2$Cl$_2$:CCl$_4$ 3:2 (5 mL) was added dropwise trioctylphosphine (815 mg, 3 equiv.) and the resulting solution was stirred at r.t. 5 hours. 25% Aq. NH$_4$OAc was then added and the title compound was extracted with EtOAc, dried over Na$_2$SO$_4$ and purified by flash chromatography on silica using EtOAc:toluene 2.5:97.5.

$^1$H NMR (CD$_3$COCD$_3$) δ (ppm): 3.88 (s, 3H), 6.58 (s, 1H), 7.43–7.60 (m, 5H), 7.73 (d, 1H), 7.80–8.01 (m, 7H), 8.20 (s, 1H), 8.33 (d, 1H).

Step 3

Preparation of methyl 3-(1-(3-(2-(7-chloro-2-quinolinyl)ethenyl)phenyl)-1-((2-carboxy-4-pyridinyl)thio)methyl)benzoate A mixture containing the chloride of Step 2 (166 mg, 370 μmoles), Cs$_2$CO$_3$ (61 mg, 5 equiv.), 2-carboxy-4-mercaptopyridine (84 mg, 2 equiv.) and 2,6-di-tert-butyl-4-methylphenol (53 mg, 0.5 equiv.) in CH$_3$CN (4 mL) is stirred in the dark 20 hours. 25% Aq. NH$_4$OAc was added and the product was extracted with EtOAc after acidification to pH 2, and purified by flash chromatography.

Step 4

Using the procedure of Example 8, Step 11, the ester of Step 3 is hydrolyzed to the title acid.

EXAMPLE 27

3-(1-((2-carboxyphenyl)thio)-1-(3-(2-(7-chloro-2-quinolinyl)ethenyl)phenyl)methyl)benzoic acid, disodium salt

Step 1

Preparation of methyl 2-mercaptobenzoate

A solution of HCl/MeOH was formed by the reaction of AcCl (35 mL) with MeOH (200 mL) at 0° C. Thiosalicylic acid (9.91 g, 64.3 mmoles) was added to this solution and the mixture was stirred at r.t. 7 days. It was then poured into 25% aq. NH$_4$OAc (2.5 ). Extraction with EtOAc, drying over Na$_2$SO$_4$ and flash chromatography of the residue on silica using EtOAc:hexane 2.5:97.5 and 5:95 yielded the title ester.

$^1$H NMR (CDCl$_3$) δ (ppm): 3.93 (s, 3H), 4.70 (s, 1H), 7.17 (m, 1H), 7.32 (m, 2H), 8.02 (d, 1H).

Step 2

Using the procedure of Example 10, but substituting methyl 3-mercaptobenzoate for methyl 2-mercaptobenzoate from Step 1 and doing the hydrolysis Step 2 with NaOH at 50° C. 8 hours instead of with LiOH at r.t. 2 days, the title acid was obtained. The disodium salt was then prepared using the procedure of Example 14, Step 2.

Anal. calc'd for C$_{32}$H$_{20}$ClNO$_4$SNa$_2$·3H$_2$O: C, 59.13; H, 4.03; N, 2.15; S, 4.93; Cl, 5.45; Na, 7.07 Found: C, 59.11; H, 3.97; N, 2.21; S, 5.18; Cl, 5.54; Na, 6.15

EXAMPLE 28

2-(3-(3-((7-chloro-2-quinolinyl)methoxy)phenyl)-3-((2-carboxyethyl)thio)propyl)benzoic acid

Step 1

Preparation of methyl 2-(3-(3-methoxyphenyl)-2-propenyl)benzoate

Using the procedure of Example 1, Steps 1–4, with the modifications below, the title compound (cis:trans mixture) was prepared. In Step 1, 3-methoxybenzyl chloride was used in place of 3-(bromomethyl)benzonitrile and the phosphonium salt was formed at reflux of CH$_3$CN for 19 hours.

$^1$H NMR (CDCl$_3$) δ (ppm): 3.80–4.10 (m, 8H), 5.80, 6.40 and 6.55 (m, 2H, cis:trans mixture), 6.70–6.97 (m, 3H), 7.15–7.50 (m, 4H), 7.90 (d, 1H).

Step 2

Preparation of methyl 2-(3-((2-(methoxycarbonyl)ethyl)thio)-3-(3-methoxyphenyl)propyl)benzoate Using the procedure of Example 1, Step 5, but doing the reaction at −10° C. for 20 minutes, the compound of Step 1 was converted to the title product.

$^1$H NMR (CDCl$_3$) δ (ppm): 2.12 (m, 2H), 2.46 (m, 2H), 2.59 (m, 2H), 2.88 (m, 1H), 3.04 (m, 1H), 3.67 (s, 3H), 3.84 (m, 7H), 6.80 (d, 1H), 6.90 (m, 2H), 7.17–7.28 (m, 3H), 7.40 (t, 1H), 7.87 (d, 1H).

Step 3

Using the procedure of Example 25, Steps 9–11, the preceding compound was converted to the title diacid.

$^1$H NMR (CD$_3$COCD$_3$) δ (ppm): 2.12 (m, 2H), 2.42 (m, 2H), 2.51 (m, 2H), 2.87 (m, 1H), 3.03 (m, 1H), 3.93 (t, 1H), 5.40 (s, 2H), 6.97 (d, 1H), 7.03 (d, 1H), 7.15–7.33 (m, 4H), 7.43 (t, 1H), 7.60 (d, 1H), 7.76 (d, 1H), 7.90 (d, 1H), 8.00 (d, 1H), 8.06 (s, 1H), 8.41 (d, 1H).

EXAMPLE 29

2-(3-(3-((7-chloro-2-quinolinyl)methoxy)phenyl)-3-((3-dimethylamino-3-oxopropyl)thio)propyl)benzoic acid, sodium salt

Method A

Step 1

Preparation of methyl 2-(3-((3-dimethylamino-3-oxopropyl)thio)-3-(3-methoxyphenyl)propyl)benzoate At −10° C., AlCl$_3$ (879 mg, 5.5 equiv.) was added to a solution containing N,N-dimethyl 3-mercaptopropanamide (191 mg, 1.2 equiv.), the styrene of Example 28, Step 1 (333 mg, 1.18 mmoles) and 2,6-di-tert-butyl-4-methylphenol (53 mg, 0.2 equiv.) in CH$_2$Cl$_2$ (12 mL). The resulting mixture was stirred in the dark at 0° C. for 3 hours and was quenched with 25% aq. NH$_4$OAc. Extraction with EtOAc, drying over Na$_2$SO$_4$ and flash chromatography of the residue with acetone:toluene 10:90 and 15:85 yielded the title product, which was used as such for the next step.

Step 2

Preparation of methyl 2-(3-(3-((7-chloro-2-quinolinyl)methoxy)phenyl)-3-((3-dimethylamino-3-oxopropyl)thio)propyl)benzoate Using the procedures of Example 25, Steps 9 and 10, but avoiding the use of Et$_3$N in Step 9, the product of Step 1 was converted to the title compound.

$^1$H NMR (CD$_3$COCD$_3$) δ (ppm): 2.08 (m, 2H), 2.40 (m, 2H), 2.52 (m, 2H), 2.75 (m, 1H), 2.80 (s, 3H), 2.90 (s, 3H), 2.94 (m, 1H), 3.80 (s, 3H), 3.93 (t, 1H), 5.48 (s, 2H), 6.98 (d, 1H), 7.02 (d, 1H), 7.15–7.33 (m, 4H), 7.43 (t, 1H), 7.60 (dd, 1H), 7.80 (m, 2H), 8.03 (d, 1H), 8.14 (br s, 1H), 8.50 (d, 1H).

Step 3

The ester of Step 2 (620 mg, 1.07 mmoles) was hydrolyzed with 3.3N NaOH (3.3 mL, 10 equiv.) in THF:MeOH 1:1 (11 mL) at r.t. for 24 hours. 25% Aqueous NH$_4$OAc was added and the solution was acidified with AcOH. Extraction with EtOAc, drying over Na$_2$SO$_4$ and flash chromatography of the residue on silica with acetone:toluene:AcOH 10:90:1 and 15:85:1 yielded the title acid. It was then converted to the sodium salt as in Example 14, Step 2, but only one equiv. of NaOH was used.

Anal calc'd for C$_{31}$H$_{30}$ClN$_2$O$_4$SNa·0.5H$_2$O: C, 62.67; H, 5.26; N, 4.72; S, 5.40; Cl, 5.97; Na, 3.87. Found: C, 62.86; H, 5.21; N, 4.53; S, 5.12; Cl, 5.87; Na, 3.62.

Method B

Step 1

Preparation of 3-((7-chloro-2-quinolinyl)methoxy)benzenemethanol 3-((7-Chloro-2-quinolinyl)methoxy)benzaldehyde (EP 233,763, Example 16, Step 1; 9.60 g, 32.24 mmoles) was dissolved in EtOH:THF 3:1 (215 mL). At 0° C., NaBH$_4$ (1.21 g, 1 equiv.) was added and the mixture was stirred at r.t. 20 min. It was then poured into 25% aq. NH$_4$OAc (500 mL) and EtOAc. Extractions with EtOAc, drying over Na$_2$SO$_4$ and filtration through silica yielded the benzyl alcohol, which was used as such in the next step.

Step 2

Preparation of 2-((3-(bromomethyl)phenoxy)methyl)-7-chloroquinoline

To the product of Step 1 and CBr$_4$ (13.90 g, 1.3 equiv.) in CH$_2$Cl$_2$ (160 mL) at 0° C., a solution of 1,2-bis(diphenylphosphino)ethane (DIPHOS, 8.37 g, 0.65 equiv.) in CH$_2$Cl$_2$ (75 mL) was added and the resulting mixture was stirred at 0° C. for 45 min. and at r.t. for 30 min. Ether was then added and the mixture was filtered through a pad of silica and the silica was washed with EtOAc:toluene 20:80 to yield the pure benzylic bromide.

$^1$H NMR (CD$_3$COCD$_3$) δ (ppm): 4.62 (s, 2H), 5.40 (s, 2H), 7.04 (d, 1H), 7.08 (d, 1H), 7.21 (s, 1H), 7.30 (t, 1H), 7.60 (dd, 1H), 7.76 (d, 1H), 8.02 (d, 1H), 8.05 (s, 1H), 8.42 (d, 1H).

Step 3

Formation of ((3-((7-chloro-2-quinolinyl)methoxy)phenyl)methyl)-triphenyl-phosphonium bromide The bromide of Step 2 (7.20 g, 22.3 mmoles) and triphenylphosphine (8.82 g, 1.5 equiv.) were heated at reflux in CH$_3$CN (75 mL) for 8 hours. At r.t., ether was added and an oil separated, which crystallized on trituration. The solid was filtered and was swished with ether for 20 hours to yield the phosphonium salt.

$^1$H NMR (CD$_3$COCD$_3$/CD$_3$SOCD$_3$) δ 5.15 (s, 2H), 5.23 (d, 2H), 6.69 (d, 1H), 6.77 (s, 1H), 7.02 (d, 1H), 7.19 (t, 1H), 7.56 (d, 1H), 7.62–7.80 (m, 13H), 7.85–7.95 (m, 3H), 8.04 (s, 1H), 8.08 (d, 1H), 8.48 (d, 1H).

Step 4

Formation of 2-(3-(3-((7-chloro-2-quinolinyl)methoxy)phenyl)-2-propenyl)benzenemethanol At −10° C., potassium hexamethyldisilazide 0.65M in toluene (21 mL, 1.8 equiv.) was added dropwise to a suspension of the phosphonium salt of Step 3 (8.457 g, 13.53 mmoles, 1.8 equiv.) in THF (70 mL) and the mixture was stirred at 0° C. for 30 min. At −78° C., 1H-3-hydroxy-3,4-dihydrobenzo(c)pyran (1.141 g, 7.60 mmoles) in THF (14 mL) was added slowly. The mixture was allowed to warm to r.t. and was stirred for a further 3 hours. 25% Aqueous NH$_4$OAc was added and the products were extracted with EtOAc, dried over Na$_2$SO$_4$ and purified by flash chromatography on silica using EtOAc:toluene 10:90 and 15:85. The title compound was obtained as a cis:trans mixture and was used as such for the next step.

$^1$H NMR (CD$_3$COCD$_3$) δ (ppm): 3.60 (d, 2H), 4.55 and 4.72 (s, 2H), 5.37 (s, 2H), 5.75 and 6.35–6.57 (m, 2H), 6.91 (d, 1H), 6.99 (d, 1H), 7.12–7.30 (m, 5H), 7.43 (m, 1H), 7.60 (d, 1H), 7.73 (d, 1H), 8.00 (m, 2H), 8.40 (d, 1H).

Step 5

Preparation of 2-(3-(3-((7-chloro-2-quinolinyl)-methoxy)phenyl)-2-propenyl)benzaldehyde To a solution of the benzylic alcohol of Step 4 (2.899 g, 6.20 mmoles) in EtOAc (120 mL) was added portionwise activated MnO$_2$ (10.15 g, approx. 18 equiv.) and the reaction was followed by TLC (EtOAc:toluene 7.5:92.5). When the reaction was completed (approx. 2 hours), the mixture was filtered through silica, concentrated, and the title product was purified by flash chromatography on silica using EtOAc:toluene 2.5:97.5.

$^1$H NMR (CD$_3$COCD$_3$) δ (ppm): 4.00 (d, 2H), 5.35 (s, 2H), 5.72 and 6.30–6.60 (m, 2H), cis:trans mixture), 6.90–8.10 (m, 12H), 8.39 (d, 1H), 10.33 (s, 1H).

Step 6

Preparation of methyl 2-(3-(3-((7-chloro-2-quinolinyl)methoxy)phenyl)-2-propenyl)benzoate Using the procedures of Example 1, Step 4, but dissolving the aldehyde of Step 5 in hot THF before doing the reaction, the title compound was obtained.

$^1$H NMR (CD$_3$COCD$_3$) δ (ppm): 3.70 and 3.82–3.95 (m, 5H, cis:trans mixture), 5.38 (2s, 2H), 5.70 and 6.47 (2m, 2H), 6.87–8.05 (m, 12H), 8.38 (2d, 1H).

Step 7

Using the procedure of Example 29, Method A, Steps 1 and 3, the product of Step 6 was converted to the title compound.

EXAMPLE 30

2,2′-(((3-((7-chloro-2-quinolinyl)methoxy)phenyl)methylene)bis(thio))bis(benzoic acid), disodium salt

Step 1

Preparation of dimethyl 2,2′-(((3-((7-chloro-2-quinolinyl)methoxy)phenyl)methylene)bis(thio))bis(benzoate)

Using the procedure of Example 14, Step 1 but using methyl 2-mercaptobenzoate (Example 27, Step 1) instead of methyl 3-mercaptobenzoate, the title diester was obtained. It was used as such in the next step.

Step 2

The diester of Step 1 (603 mg, 980 μmoles) was stirred in MeOH:THF:H$_2$O 7:5:3 (15 mL) with NaOH (1 mL of 10 N) at 50° C. for 5 hours and at r.t. 20 hours. The work up of the reaction and the formation of the title compound was the same as Example 14, Step 2.

Anal. calc'd for C$_{31}$H$_{20}$ClNO$_5$S$_2$Na$_2$·0.7: H$_2$O: C, 57.75; H, 3.35; N, 2.17; S, 9.95; Cl, 5.50; Na, 7.13. Found: C, 57.55; H, 3.39; N, 2.04; S, 9.78; Cl, 5.67; Na, 6.67.

EXAMPLE 31

2-chloro-5-((3-((7-chloro-2-quinolinyl)methoxy)-phenyl)-((3-dimethylamino-3-oxopropyl)thio)methyl)-benzoic acid, sodium salt

Step 1

Preparation of 2-chloro-5-((3-((7-chloro-2-quinolinyl)methoxy)-phenyl)hydroxymethyl)benzoic acid To a suspension of 5-bromo-2-chlorobenzoic acid (1.004 g, 4.26 mmoles) in THF (20 mL) at −100° C., n-BuLi (5.3 mL of 1.6M, 2 equiv.) was added dropwise and the mixture was stirred at −78° C. for 1.2 hours. At −100° C., a solution of 3-((7-chloro-2-quinolinyl)methoxy)benzaldehyde (EP 233,763, Example 16, Step 1; 1.253 g, 4.21 mmoles) in THF (15 mL) was added dropwise and the mixture was stirred 2 hours at −78°

C. AcOH (2 mL) was then added, followed by 25% aq. NH₄OAc. The product was extracted with EtOAc:THF 1:1, dried over Na₂SO₄ and purified by flash chromatography on silica with EtOAc:-toluene:AcOH 30:70:1.

¹H NMR (CD₃COCD₃) δ (ppm): 5.34 (s, 2H), 5.87 (s, 1H), 6.95 (dd, 1H), 7.05 (d, 1H), 7.18 (s, 1H), 7.26 (t, 1H), 7.38 (d, 1H), 7.52 (dd, 1H), 7.62 (dd, 1H), 7.72 (d, 1H), 7.94 (d, 1H), 8.01 (d, 1H), 8.03 (s, 1H), 8.38 (d, 1H).

Step 2

To a suspension of the alcohol of Step 1 (279 mg, 614 μmoles) in CH₂Cl₂ (6 mL) at 0° C., N,N-dimethyl 3-mercaptopropanamide (97 mg, 1.15 equiv.) was added, followed by AlCl₃ (580 mg, 7 equiv.). The mixture was stirred 2 hours at 0° C. and was quenched with 25% aq. NH₄OAc, THF and AcOH. The product was extracted with EtOAc:THF 1:1, dried over Na₂SO₄ and purified by flash chromatography on silica using acetone:-toluene:AcOH 10:90:1, 20:80:1 and 30:70:1 sequentially. The sodium salt was formed as in Example 14, Step 2, but only one equiv. of NaOH was used.

Anal. calc'd for C₂₉H₂₅Cl₂N₂O₄SNa·0.5 H₂O: C, 58.01; H, 4.36; N, 4,67; S, 5.34; Cl, 11.81; Na, 3.83. Found: C, 57.90; H, 4.62; N, 4.40; S, 5.56Cl, 11.91; Na, 3.68.

EXAMPLE 32

2,2'-(((3-((7-chloro-2-quinolinyl)methoxy)phenyl)-methylene)bis(thiomethyl))bis(benzoic acid), disodium salt Step 1

Preparation of ethyl 2-(mercaptomethyl)benzoate

H₂S was bubbled through a solution of KOH (290 mg, 1.2 equiv.) in MeOH (4 mL) at 0° C. until saturation. A solution of ethyl 2-(chloromethyl)-benzoate and ethyl 2-(bromomethyl)benzoate (Tetrahedron, 1966, 22, 2107; 1.006 g of a 1:2 mixture, 4.28 mmoles) in MeOH (3 mL) was then added dropwise at −20° C. The mixture was warmed to 0° C. for 1 hour and to r.t. for 2 hours. H₂S was occasionally bubbled into the reaction mixture during all this process. Addition of 25% aq. NH₄OAc, extraction with EtOAc, drying over Na₂SO₄ and distillation of the residue (80°-86° C./0.15 mm) yielded the title compound, which was used as such for the next step.

Step 2

Using the procedure of Example 14, Step 1, but replacing methyl 3-mercaptobenzoate by the thiol of Step 1, the diester of the title compound was obtained. It was then hydrolyzed using the procedure of Example 30, Step 2 to yield the title compound.

Anal calc'd for C₃₃H₂₄ClNO₅S₂Na₂·0.5 H₂O: C, 59.24; H, 3.77; N, 2.09; S, 9.58; Cl, 5.30; Na, 6.87. Found: C, 59.34; H, 3.70; N, 2.09; S, 10.13; Cl, 5.04; Na, 6.64.

EXAMPLE 33

2-((((3-((7-chloro-2-quinolinyl)methoxy)phenyl)((3-dimethylamino-3-oxopropyl)thio)methyl)thio)methyl)-benzoic acid Step 1

Preparation of N,N-dimethyl-3-(((acetylthio)(3-((7-chloro-2-quinolinyl)methoxy)phenyl)methyl)thio)propanamide Using the procedure of Example 14, Step 1, but using 1.1 equiv. of thiolacetic acid and 1.1 equiv. of N,N-dimethyl 3-mercaptopropanamide instead of 2.2 equiv. of methyl 3-mercaptobenzoate, and adding BF₃·Et₂O at 0° C. instead of at r.t., the title compound was obtained. It was used as such for the next step.

Step 2

Preparation of ethyl 2-((((3-((7-chloro-2-quinolinyl)-methoxy)phenyl)((3-dimethylamino-3-oxopropyl)thio)-methyl)thio)methyl)-benzoate At −78° C., 1.26M MeONa (410 μL, 1.1 equiv.) was added dropwise to a solution of the mixed dithioketal of Step 1 (230 mg, 470 μmoles) in THF (5 mL) and the mixture was stirred at −78° C. for 15 min. Then, a solution of ethyl 2-(chloromethyl)-benzoate and ethyl 2-(bromomethyl)benzoate (Tetrahedron, 1966, 22, 2107; 222 mg of a 1:2 mixture, 2.13 equiv.) in THF (1 mL) was added. The mixture was stirred at −78° C. for 2.2 hours, then at −20° C. for 0.8 hour and at 0° C. for 0.5 hour. Addition of 25% aq. NH₄OAc, extraction with EtOAc, drying over Na₂SO₄ and flash chromatography of the residue on silica with EtOAc:toluene 40:60 yielded the title dithioketal.

¹H NMR (CD₃COCD₃) δ (ppm): 1.33 (t, 3H), 2.45 (t, 2H), 2.60–2.80 (m, 2H), 2.82 (s, 3H), 2.89 (s, 3H), 4.07 (d, 1H), 4.15 (d, 1H), 4.30 (q, 2H), 4.90 (s, 1H), 5.37 (s, 2H), 6.98 (dd, 1H), 7.03 (d, 1H), 7.16 (m, 1H), 7.20–7.50 (m, 4H), 7.59 (d, 1H), 7.73 (d, 1H), 7.86 (d, 1H), 8.00 (d, 1H), 8.03 (s, 1H), 8.40 (d, 1H).

Step 3

Using the procedures of Example 8, Step 11, the title acid was prepared.

¹H NMR (CD₃COCD₃) δ (ppm): 2.58 (t, 2H), 2.70 (m, 1H), 2.80–2.95 (m, 1H), 2.88 (s, 3H), 2.94 (s, 3H), 4.11 (AB system, 2H), 4.98 (s, 1H), 5.40 (s, 2H), 6.99 (dd, 1H), 7.06 (d, 1H), 7.15–7.47 (m, 5H), 7.58 (d, 1H), 7.75 (d, 1H), 7.90 (d, 1H), 8.00 (d, 1H), 8.06 (s, 1H), 8.42 (d, 1H).

EXAMPLE 34

3-((3-(2-(7-Chloro-2-quinolinyl)ethenyl)phenyl)((4-(dimethylamino)-4-oxopropyl)thio)methyl)benzoic acid Step 1

Preparation of methyl 3-((acetylthio)(3-(2-(7-chloro-2-quinolinyl)ethenyl)-phenyl)methyl)benzoate Using the procedure of Example 26, Step 3, but replacing 4-mercaptopyridine by thiolacetic acid (1.2 equiv.) and using 1 equiv. of 2,6-di-tert-butyl-4-methylphenol and 1.3 equiv. of CsCO₃, the title thiolester was prepared.

¹H NMR (CD₃COCD₃) δ (ppm): 2.38 (s, 3H), 3.87 (s, 3H), 6.08 (s, 1H), 7.45–7.55 (m, 5H), 7.64 (d, 1H), 7.70 (d, 1H), 7.75–8.00 (m, 6H), 8.09 (s, 1H), 8.30 (d, 1H).

Step 2

Preparation of methyl 3-((3-(2-(7-chloro-2-quinolinyl)ethenyl)phenyl)((4-(dimethylamino)-4-oxopropyl)-thio)methyl)benzoate At −78° C., 1.26M MeONa (970 μL, 4 equiv.) is added to a mixture of the thiolester of Step 1 (147 mg, 301 μmoles) and N,N-dimethyl 4-chlorobutanamide (2.9 equiv.) in THF (3 mL). The mixture is stirred at 0° C. for 45 min., at r.t. for 15 min and then at 50° C. for 3 hours. Addition of 25% aq. NH₄OAc, extraction with EtOAc:THF 1:1, drying over Na₂SO₄ and flash chromatography of the residue on silica yields the title compound.

Step 3

The ester of Step 2 is hydrolyzed in THF:MeOH:H₂O 2:4:1 (1 mL) with 3 equiv. of 10N NaOH at r.t. for 23 hours. 25% aq. NH₄OAc is added and the product is extracted with EtOAc, dried over Na₂SO₄ and purified by flash chromatography on silica.

EXAMPLE 35

2-(3-(3-((7-chloro-2-quinolinyl)methoxy)phenyl)-3-((3-((2-methyl-2-propyl)amino)-3-oxopropyl)thio)propyl)-benzoic acid, sodium salt Step 1

Preparation of 3-((1-(3-((7-chloro-2-quinolinyl)-methoxy)phenyl)-3-(2-(methylycarbonyl)phenyl)propyl)-thio)propanoic acid To methyl 2-(3-(3-((7-chloro-2-quinolinyl)-methoxy)-phenyl)-2-propenyl)benzoate (Example 29, Method B, Step 6), 3-mercaptopropionic acid was added using the procedure of Example 29, Method A, Step 1 , to yield the title compound.

¹H NMR (CD₃COCD₃) δ (ppm): 2.10 (m, 2H), 2.43 (m, 2H), 2.52 (m, 2H), 2.70–3.00 (m, 2H), 3.80 (s, 3H), 3.95 (t, 1H), 5.42 (s, 2H), 7.00 (m, 2H), 7.15–7.33 (m, 4H), 7.43 (t, 1H), 7.58 (d, 1H), 7.77 (d, 1H), 7.80 (d, 1H), 7.97 (d, 1H), 8.04 (s, 1H), 8.39 (d, 1H).

Step 2

Preparation of methyl 2-(3-(3-((7-chloro-2-quinolinyl)methoxy)phenyl)-3-((3-((2-methyl-2-propyl)amino)-3-oxopropyl)thio)propyl)-benzoate To a solution of the acid of Step 1 (385 mg, 700 μmoles) in CH₂Cl₂:CH₃CN 4:1 (20 mL) at 0° C., Et₃N (290 μL, 2 equiv.) was added, followed by 2-chloro-1-methylpyridinium iodide (535 mg, 2 equiv.) and the reaction mixture was stirred at 0° C. for 1.8 hours. Then, tert-butylamine was added and stirring was continued at r.t. 3 hours. Addition of 25% aq. NH₄OAc, extraction with EtOAc, drying over Na₂SO₄ and flash chromatography of the residue on silica, using EtOAc:toluene 20:80 and 25:75 sequentially yielded the title compound.

¹H NMR (CD₃COCD₃) δ (ppm): 1.30 (s, 9H), 2.07 (m, 2H), 2.25 (t, 2H), 2.50 (t, 2H), 2.70–3.00 (m, 2H), 3.80 (s, 3H), 3.90 (t, 1H), 5.32 (s, 2H), 6.70 (br, s, 1H, NH), 7.00 (m, 2H), 7.10–7.35 (m, 4), 7.44 (t, 1H), 7.58 (d, 1H), 7.76 (d, 1H), 7.80 (d, 1H), 7.98 (d, 1H), 8.04 (s, 1H), 8.40 (d, 1H).

Step 3

Using the procedure of Example 29, Method A, Step 3, the ester of Step 2 was converted to the title sodium salt Anal. calc'd for C₃₃H₃₄ClN₂O₄SNa·0.5H₂O: C, 63.70; H, 5.67; N, 4.50; S, 5.15; Cl, 5.70; Na, 3.70. Found: C, 63.51; H, 5.78; N, 4.07; S, 5.61; Cl, 5.48; Na, 3.60.

EXAMPLE 36

2-(3-(3-(2-(7-chloro-2-quinolinyl)ethyl)phenyl)-3-((3-((2-methyl-2-propyl)amino)-3-oxopropyl)thio)propyl)-benzoic acid Step 1

Preparation of methyl 2-(3-(3-(2-(7-chloro-2-quinolinyl)ethyl)phenyl)-2propenyl)benzoate Using the procedure of Example 29, Method B, Steps 1–6, the aldehyde of Example 3, Step 2, was converted to the title product.

¹H NMR (CD₃COCD₃) δ (ppm): 3.10–3.35 (m, 4H), 3.72 and 3.88 (m, 5H; cis:trans mixture), 5.70 and 6.42 (m, 2H), 7.05–7.60 (m, 10H), 7.80–8.02 (m, 2H), 8.20 (m, 1H).

Step 2

The styrene of Step 1 was converted to the title acid using the procedure of Example 35.

¹H NMR (CD₃COCD₃) δ (ppm): 1.28 (s, 9H), 2.10 (td, 2H), 2.25 (t, 2H), 2.50 (m, 2H), 2.90 (m, 2H), 3.15 (t, 2H), 3.32 (t, 2H), 3.86 (t, 1H), 6.80 (br s, 1H, NH), 7.00 (m, 1H), 7.10–7.35 (m, 5H), 7.40–7.53 (m, 3H), 7.90 (d, 2H), 8.02 (s, 1H), 8.25 (d, 1H).

EXAMPLE 37

3-(3-(3-(2-(7-chloro-2-quinolinyl)ethyl)phenyl)-3-((3-dimethylamino)-3-oxopropyl)thio)propyl)benzoic acid Step 1

Preparation of 3-(1,3-dioxolan-2-yl)benzaldehyde

Ethylene glycol (4.5 mL, 1.05 equiv.), isophthalaldehyde (10.201 g, 76 mmoles) and p-toluenesulfonic acid (560 mg) were heated at reflux in benzene (100 mL) for 8.5 hours. Water was continuously removed from the reaction mixture with a Dean-Stark apparatus. The solvent was then evaporated and the title compound was purified by flash chromatography on silica using EtOAc:toluene 2.5:92.5 and 5.95.

¹H NMR (CDCl₃) δ (ppm): 4.13 (m, 4H), 5.90 (s, 1H), 7.57 (t, 1H), 7.77 (d, 1H), 7.91 (d, 1H), 8.03 (s, 1H), 10.05 (s, 1H) ppm.

Step 2

Preparation of methyl 3-(1,3-dioxolan-2-yl)benzoate

Using the procedure of Example 1, Step 4, the aldehyde of Step 1 was oxidized to the title ester, which was used as such for the next step.

Step 3

Preparation of methyl 3-formylbenzoate

To the ketal of Step 2 (10.046 g, 45.7 mmoles) in THF:MeOH 3:2 (100 mL), 10N aqueous HCl (80 mL) was added and the mixture was stirred for 1 hour. Addition of 25% aq. NH₄OAc, extraction with EtOAc, drying over MgSO$_4$ and flash chromatography of the residue on silica using EtOAc:toluene 2.5:97.5 yielded the title aldehyde.

$^1$H NMR (CDCl$_3$) δ (ppm): 4.00 (s, 3H), 7.67 (t, 1H), 8.10 (d, 1H), 8.32 (d, 1H), 8.54 (s, 1H), 10.08 (s, 1H).

Step 4

Preparation of methyl 3-(2-(trimethylsilyl)oxiranyl)benzoate

Using the procedure described in J. Am. Chem. Soc., 1977, 99, 4536, the product of Step 3 was converted to the title epoxysilane. In order to improve the yield, the anion of chloromethyltrimethylsilane was formed at −78° C. for 1.2 hours and the aldehyde, dissolved in THF and cooled to −78° C., was added to this anion at −100° C.

$^1$H NMR (CD$_2$Cl$_2$) δ (ppm): −0.17 and 0.15 (2s, 9H, mixture of cis:trans epoxyde), 2.32 and 2.55 (2d, 1H), 3.75 and 4.28 (2d, 1H), 3.90 (s, 3H), 7.37–7.60 (m, 2H), 7.90–8.05 (m, 2H).

Step 5

Preparation of methyl 3-(formylmethyl)benzoate

At 0° C., formic acid (6 mL) was added to a solution of the epoxysilane of Step 4 (605 mg, 2.42 mmoles) in THF:H$_2$O 10:1 (6.6 mL) and the mixture was stirred at r.t. for 4 hours. The solvents were evaporated and the product was purified by flash chromatography on silica using EtOAc:hexane 15:85 and 20:80 sequentially.

$^1$H NMR (CDCl$_3$) δ (ppm): 3.80 (s, 2H), 3.93 (s, 3H), 7.45 (m, 2H), 7.90 (s, 1H), 8.00 (d, 1H), 9.80 (s, 1H).

Step 6

Preparation of methyl 3-(3-(3-(2-(7-chloro-2-quinolinyl)ethyl)phenyl)-2-propenyl)benzoate The title compound was obtained using the procedure of Example 29, Method B, Steps 4–6, with the following modifications to Step 4: 1.2 equiv. of phosphonium salt and 1.0 equiv. of KHMDS were used, and the aldehyde used was that of Example 37, Step 5.

$^1$H NMR (CDCl$_3$) δ (ppm): 3.15 (m, 2H), 3.27 (m, 2H), 3.60 (d, 2H), 3.91 (s, 3H), 5.78 and 6.22–6.63 (2m, 2H, cis:trans mixture), 7.05–7.30 (m, 5H), 7.30–7.50 (m, 3H), 7.70 (2 d, 1H), 7.83–8.10 (m, 4H).

Step 7

Using the procedure of Example 29, Method A, Step 1 and Step 3, the product of Step 6 was converted to the title compound.

$^1$H NMR (CD$_3$COCD$_3$) δ (ppm): 2.10 (m, 2H), 2.37 (m, 2H), 2.48 (t, 2H), 2.60 (t, 2H), 2.80 (s, 3H), 2.86 (s, 3H), 3.18 (m, 2H), 3.32 (m, 2H), 3.80 (t, 1H), 7.15–7.30 (m, 4H), 7.40 (m, 3H), 7.50 (d, 1H), 7.80–7.92 (m, 3H), 8.04 (s, 1H), 8.22 (d, 1H).

EXAMPLE 38

2-((3-((7-chloro-2-quinolinyl)methoxy)phenyl)((3-dimethylamino-3-oxopropyl)thio)methyl)benzoic acid

Step 1

Preparation of 3-(3-((7-chloro-2-quinolinyl)methoxy)phenyl)-1-(3H)isobenzofuranone At −100° C., 1.6M BuLi (2.7 mL, 4.32 mmoles) was added dropwise to a suspension of 2-bromobenzoic acid (421 mg, 2.09 mmoles) in THF (8.5 mL) and the mixture was stirred at −78° C. for 2.5 hours. At −100° C., a solution of 3-((7-chloro-2-quinolinyl)methoxy)benzaldehyde (EP 233,763, Example 16, Step 1; 498 mg, 1.67 mmoles) in THF (6 mL) was added and the mixture was stirred at −78° C. for 45 min., then at 0° C. for 15 min. AcOH was added at 0° C. and the reaction mixture was poured into 1N HCl and stirred overnight. 25% aq. NH$_4$OAc was then added and the pH was adjusted to 5 by addition of 8N KOH. Extraction with EtOAc:THF 1:1, drying over Na$_2$SO$_4$ and flash chromatography of the residue using EtOAc:toluene 5:95 afforded the title lactone.

$^1$H NMR (CD$_3$COCD$_3$) δ (ppm): 5.38 (AB system, 2H), 6.58 (s, 1H), 7.00 (d, 1H), 7.10 (m, 2H), 7.30–7.45 (m, 2H), 7.55–7.75 (m, 4H), 7.88 (d, 1H), 8.02 (m, 2H), 8.38 (d, 1H).

Step 2

Preparation of 2-((3-((7-chloro-2-quinolinyl)methoxy)phenyl)hydroxymethyl)benzoic acid To the lactone of Step 1 (188 mg, 468 μmoles) in THF:MeOH 1:1 (6 mL), 3.3N NaOH (2 mL) was added. The mixture was stirred at r.t. for 3 days. A saturated solution of NH$_4$Cl was added and the product was extracted with EtOAc, dried over Na$_2$SO$_4$ and concentrated. It was used as such for the next step.

Step 3

Using the procedure of Example 31, Step 2, the hydroxyacid of Step 2 was converted to the title compound.

$^1$H NMR (CD$_3$COCD$_3$) δ (ppm): 2.52 (m, 2H), 2.62 (m, 2H), 2.80 (s, 3H), 2.90 (s, 3H), 5.37 (s, 2H) 6.62 (s, 1H), 6.94 (d, 1H), 7.10 (d, 1H), 7.20–7.35 (m, 3H), 7.43 (t, 1H), 7.60 (dd, 1H), 7.68 (m, 2H), 7.89 (d, 1H), 8.00 (d, 1H), 8.05 (s, 1H), 8.38 (d, 1H).

EXAMPLE 39

2-(3-(3-((7-chloro-2-quinolinyl)methoxy)phenyl)-3-((3-oxo-3-(1-(tricyclo[3.3.1.1$^{3,7}$]decyl)amino)propyl)thio)propyl)benzoic acid, sodium salt Using the procedure of Example 35, with the modifications below, the title compound was synthesized. The modifications were only in Step 2, where 1) 1-adamantanamine hydrochloride (3 equiv.) was used instead of tert-butylamine, 2) 3 equiv. of Et$_3$N were added with the adamantanamine and 3) 3 equiv. of each Et$_3$N and 2-chloro-1-methylpyridinium iodide were used for the formation of the activated ester.

Anal. calc'd for: C$_{39}$H$_{40}$ClN$_2$O$_4$SNa·1.5 H$_2$O: C, 65.21; H, 6.03; N, 3.90; Cl, 4.94; Na, 3.20. Found: C, 65.24; H, 6.16; N, 3.70; Cl, 4.49; Na, 2.94.

EXAMPLE 40

N,N-dimethyl 3-((1-(3-((7-chloro-2-quinolinyl)methoxy)phenyl)-3-(2-(1H-tetrazol-5-yl)phenyl)propyl)thio)propanamide, sodium salt

Step 1

Preparation of 2-(3-(3-((7-chloro-2-quinolinyl)methoxy)phenyl)-2-propenyl)benzonitrile To the aldehyde (Example 29, Method B, Step 5) (700 mg) were added formic acid (5 mL), sodium formate (360 mg, 1.8 equiv.) and hydroxylamine hydrochloride (230 mg, 1.15 equiv.). The resulting mixture was warmed at 95° C. for 1 hr and then allowed to cool to room temperature. The reaction was quenched by the addition of saturated aqueous sodium bicarbonate, extracted with ether and dried with $Na_2SO_4$. The residue was purified by flash chromatography using 15% ethyl acetate in toluene to afford the title product.

$^1$H NMR (CD$_3$COCD$_3$) δ (ppm): 3.75 (m, 2H), 5.38 and 5.43 (2s, 2H), 5.76 and 6.41 to 6.70 (m, 2H, cis:trans mixture), 6.90 to 7.46 (m, 13H).

Step 2

Preparation of N,N-dimethyl 3-((1-(3-((7-chloro-2-quinolinyl)methoxy)phenyl)-3-(2-cyanophenyl)propyl)thio)propanamide Using the procedure of Example 29, Method A, Step 1, the cyanostyrene of Step 1 was converted to the title compound.

$^1$H NMR (CD$_3$COCD$_3$) δ (ppm): 2.04 (q, 2H), 2.41 (m, 2H), 2.55 (m, 2H), 2.75 (m, 2H), 2.80 and 2.86 (2s, 6H), 3.96 (t, 1H), 5.40 (s, 2H), 6.95 to 8.06 (m, 12H), 8.40 (d, 1H).

Step 3

To the nitrile (Step 2) (300 mg) dissolved in CH$_2$Cl$_2$ (0.1 mL) was added tributyltin azide (122 mg). The CH$_2$Cl$_2$ was removed by a flow of nitrogen and the mixture warmed at 120° C. After 8 hrs, additional tributyltin azide was added (100 mg). After warming 4 hrs, the reaction mixture was purified by flash chromatography (20% acetone in toluene with 1% of acetic acid) to give the corresponding tetrazole.

To the tetrazole (278 mg) dissolved in ethanol (10 mL) was added sodium hydroxide 1M (473 μL, 1 equiv.) and the solution was freeze dried to give the title compound.

$^1$H NMR (CD$_3$COCD$_3$) δ (ppm): 2.15 (m, 2H), 2.41 (m, 2H), 2.53 (m, 2H), 2.83 and 2.91 (2s, 6H), 3.15 (m, 2H), 3.86 (t, 1H), 5.38 (s, 2H), 6.88 to 8.05 (m, 12H), 8.36 (d, 1H).

Anal. calc'd for C$_{31}$H$_{30}$ClN$_6$O$_2$SNa·2.5H$_2$O: C, 56.92; H, 5.39; Cl, 5.42; N, 12.84; S, 4.90; Na, 3.51. Found: C, 56.80; H, 5.43; Cl, 5.33; N, 12.70;, S, 5.42; Na, 3.55.

EXAMPLE 41

N,N-dimethyl 3-((1-(3-((7-chloro-2-quinolinyl)methoxy)phenyl)-3-(2-((1H-tetrazol-5-yl)methyl)phenyl)propyl)thio)propanamide, sodium salt Step 1

Preparation of 2-((3-(3-(2-(bromomethyl)phenyl)-1-propenyl)phenoxy)methyl)-7-chloroquinoline Using the procedure of Example 29, Method B, Step 2, the benzyl alcohol of Example 29, Method B, Step 4 was converted to the title compound.

$^1$H NMR (CD$_3$COCD$_3$) δ (ppm): 3.75 (m, 2H), 4.66 (s, 2H), 5.36 (s, 2H), 5.80 and 6.46 to 6.63 (m, 2H, cis:-trans mixture) 6.91 to 8.05 (m, 12H), 8.36 (d, 1H).

Step 2

Preparation of 7-chloro-2-((3-(3-(2-(cyanomethyl)phenyl)-1-propenyl)-phenoxy)methyl)quinoline To the benzyl bromide (Step 1) (930 mg) dissolved in ethanol (13.5 mL) and water (2.7 mL) was added NaCN (611 mg, 6.5 equiv.). The resulting suspension was stirred at 60° C. for 1 hr and acetone (4 mL) was added. The mixture was warmed at 80° C. for 2 hr then cooled to 40° C. for 18 hr. The resulting solution was then poured in an ethyl acetate/25% aqueous ammonium acetate mixture, extracted with ethyl acetate and dried. The residue was purified by flash chromatography using 3% ethyl acetate in toluene to give the title compound.

$^1$H NMR (CD$_3$COCD$_3$) δ (ppm): 3.63 (m, 2H), 3.96 (m, 2H), 5.35 (m, 2H), 5.70 and 6.41 to 6.61 (m, 2H, cis:trans mixture), 6.86 to 8.05 (m, 12H), 8.50 (2d, 1H).

Step 3

Preparation of N,N-dimethyl 3-((1-(3-((7-chloro-2-quinolinyl)methoxy)phenyl)-3-(2-(cyanomethyl)phenyl)propyl)thio)propanamide Using the procedure of Example 29, Method A, Step 1, the benzyl nitrile of Step 2 was converted to the title compound.

$^1$H NMR (CD$_3$COCD$_3$) δ (ppm): 2.11 (m, 2H), 2.41 (m, 2H), 2.55 (m, 2H), 2.75 (m, 2H), 2.83 and 2.90 (2s, 6H), 3.83 (s, 2H), 3.96 (t, 1H), 5.41 (s, 2H), 6.96 to 8.06 (m, 12H), 8.41 (d, 1H).

Step 4

Using the procedure of Example 40, Step 3, the benzyl nitrile of Step 3 was converted to the title compound (except that the formation of the tetrazole was completed within 4 hrs).

$^1$H NMR (CD$_3$COCD$_3$) δ (ppm): 2.10 (m, 2H), 2.45 (m, 2H), 2.60 (m, 2H), 2.76 (m, 2H), 2.85 and 2.93 (2s, 6H), 3.95 (t, 1H), 4.08 (s, 2H), 6.91 to 8.08 (m, 12H), 8.41 (d, 1H).

Anal. calc'd for C$_{32}$H$_{32}$ClN$_6$O$_2$SNa·3H$_2$O: C, 56.76; H, 5.66; Cl, 5.24; N, 12.41; S, 4.73; Na, 3.39. Found: C, 56.54; H, 5.63; Cl, 5.74; N, 12.14; S, 5.45; Na, 3.38.

EXAMPLE 42

2-(3-(3-((7-Chloro-2-quinolinyl)methoxy)phenyl)-3-((3-dimethylamino-3-oxopropyl)thio)propyl)benzeneacetic acid, sodium salt Step 1

Preparation of methyl 2-(3-(3-((7-chloro-2-quinolinyl)methoxy)phenyl)-3-((3-dimethylamino-3-oxopropyl)thio)propyl)benzeneacetate A solution of benzyl nitrile (Example 41, Step 3) (400 mg) dissolved in methanol (6 mL) saturated with HCl gas was stirred at 60° C. for 5 hrs. The solvent was removed under reduced pressure and flash chromatography (40% ethyl acetate in toluene) of the resulting residue gave the title compound.

$^1$H NMR (CD$_3$COCD$_3$) δ (ppm): 2.10 (m, 2H), 2.41 (m, 2H), 2.55 (m, 2H), 2.66 (m, 2H), 2.83 and 2.91 (2s, 6H), 3.58 (2s, 5H), 3.96 (t, 1H), 5.36 (s, 2H), 6.95 to 8.08 (m, 12H), 8.41 (d, 1H).

Step 2

To the ester (Step 1) (360 mg) dissolved in methanol (20 mL) and water (5 mL) was added $K_2CO_3$ (200 mg). After 2 hr at room temperature NaOH 10N (500 μL) was added. After a period of 18 hrs the methanol was removed at reduced pressure and the resulting residue was partitioned between ethyl acetate and water (pH ~5 with acetic acid). The organic phase was collected, dried and evaporated to give the acid.

The acid (280 mg) was dissolved in ethanol and treated with NaOH 1M (484 μL, 1 equiv.). The solution was then freeze dried to give the title compound.

$^1$H NMR (CD$_3$COCD$_3$) δ (ppm): 2.21 (m, 2H), 2.36 (m, 2H), 2.50 (m, 2H), 2.61 (m, 2H), 2.83 and 2.90 (2s, 6H), 3.45 (s, 2H), 2.93 (t, 1H), 5.43 (s, 2H), 6.91 to 8.16 (m, 12H), 8.38 (d, 1H).

Anal. calc'd for $C_{32}H_{32}ClN_2O_4SNa \cdot 2.3H_2O$: C, 60.00; H, 5.76; Cl, 5.53; N, 4.37; S, 5.00. Found: C, 60.02; H, 5.83; Cl, 5.92; N, 4.17; S, 5.05.

EXAMPLE 43

3-((1-(3-((7-Chloro-2-quinolinyl)methoxy)phenyl)-3-(2-(dimethylaminocarbonyl)phenyl)propyl)thio)propanoic acid, sodium salt

Step 1

Preparation of N,N-dimethyl 2-(3-(3-((7-chloro-2-quinolinyl)methoxy)phenyl)-2propenyl)benzamide To the ester (Example 29, Method B, Step 6) (500 mg) dissolved in CH$_2$Cl$_2$ (5 mL) was added a solution of dimethylaluminum dimethylamide (0.8M, 7 mL, 5 equiv.) in toluene. The solution was stirred in a sealed tube at 60° C. After 36 hrs the reaction mixture was poured in ethyl acetate (50 mL), and HCl (10%, 20 mL) was then added at 0° C. After extraction with ethyl acetate, drying (Na$_2$SO$_4$) and evaporation, the resulting mixture was purified by flash chromatography with 25% ethyl acetate in toluene to give the title compound.

$^1$H NMR (CD$_3$COCD$_3$) δ (ppm): 2.75 and 2.86 (4s, 6H), 3.38 to 3.66 (m, 2H), 5.38 (2d, 2H), 5.78 and 6.30 to 6.55 (m, 2H, cis:trans mixture), 6.86 to 8.08 (m, 12H), 8.40 (d, 1H).

Step 2

Using the procedure of Example 29, Method A, Step 1, but using methyl 3-mercaptopropanoate instead of N,N-dimethyl 3-mercaptopropanamide, the styrene amide of Step 1 was converted the thioether.

The ester was hydrolyzed using the procedure of Example 42, Step 2 to give the title compound.

$^1$H NMR (CD$_3$COCD$_3$) δ (ppm): 2.10 (m, 2H), 2.20 (m, 2H), 2.36 (m, 2H), 2.45 (m, 2H), 2.50 and 2.86 (2s, 6H), 3.76 (t, 1H), 5.33 (s, 2H), 6.83 to 7.83 (m, 12H), 8.25 (d, 1H).

Anal. calc'd for $C_{31}H_{30}ClN_2O_4SNa \cdot 2.5H_2O$: C, 59.09; H, 5.60; Cl, 5.62; N, 4.44; S, 5.08; Na, 3.65. Found: C, 59.54; H, 5.32; Cl, 5.84; N, 4.58; S, 5.93; Na, 3.89.

EXAMPLE 44

N,N-dimethyl 3-((1-(3-((7-chloro-2-quinolinyl)methoxy)phenyl)-1-(3-((1H-tetrazol-5-yl)methyl)phenyl)methyl)thio)propanamide, sodium salt

Step 1

Preparation of 1-(3-((7-chloro-2-quinolinyl)methoxy)phenyl)-1-(3-(((2-methyl-2-propyl)diphenylsilyloxy)methyl)phenyl)methanol To the bromide from Example 25, Step 3 (2 g) dissolved in THF (9.7 mL) was added magnesium (128 mg, 1.1 equiv.) followed by few drops of 1,2-dibromoethane. The mixture was warmed to 60° C. until most of the magnesium has been consumed. The solution (5.7 mL) was then added to a solution of 3-((7-chloro-2-quinolinyl)methoxy)benzaldehyde (EP 233,763, Example 16, Step 1) (500 mg) in THF (9.7 mL) at 0° C. After 1 hr 25% aqueous ammonium acetate solution was added and the mixture extracted with ethyl acetate, dried and evaporated. The residue was purified by flash chromatography with 3% ethyl acetate in toluene to yield the title compound.

$^1$H NMR (CD$_3$COCD$_3$) δ (ppm): 1.04 (s, 9H), 4.75 (s, 2H), 4.86 (d, 1H), 5.80 (s, 1H), 6.78 to 8.08 (m, 22H), 8.36 (d, 1H).

Step 2

Preparation of 7-chloro-2-((3-((3-(((2-methyl-2-propyl)diphenylsilyloxy)methyl)phenyl)chloromethyl)phenoxy)methyl)quinoline Using the procedure of Example 26, Step 2, the benzyl alcohol of Step 1 was converted to the title compound, which was used as such for the next step.

Step 3

Preparation of N,N-dimethyl 3-((1-(3-((7-chloro-2-quinolinyl)methoxy)phenyl)-1-(3-(((2-methyl-2-propyl)diphenylsilyloxy)methyl)phenyl)-methyl)thio)propanamide To the benzyl chloride of Step 2 (1.6 g) dissolved in CH$_3$CN (10 mL) were added N,N-dimethyl 3-mercaptopropanamide (500 mL, 1.5 equiv.) and Cs$_2$CO$_3$ (1.6 g). The reaction mixture was stirred at 65° C. for 4 hrs then diluted with ethyl acetate and water, and the organic phase was dried and evaporated. The crude mixture was purified by flash chromatography with 25% ethyl acetate in toluene to afford the title compound.

$^1$H NMR (CD$_3$COCD$_3$) δ (ppm): 0.95 (s, 9H), 2.46 (m, 2H), 2.56 (m, 2H), 2.78 and 2.86 (2s, 6H), 3.91 (s, 2H), 5.33 (s, 1H), 5.38 (s, 2H), 6.90 to 8.08 (m, 22H), 8.36 (d, 1H).

Step 4

Preparation of N,N-dimethyl 3-((1-(3-((7-chloro-2-quinolinyl)methoxy)phenyl)-1-(3-(hydroxymethyl)phenyl)methyl)thio)propanamide To the silyl ether (Step 3) (1.4 g) in THF (9 mL) at 0° C. was added a solution of n-tetrabutyl-ammonium fluoride 1M in THF (3.6 mL, 2. equiv.). The resulting solution was allowed to warm to room temperature for a few hours. Then 25% aqueous ammonium acetate was added and the product was extracted with ethyl acetate, dried and evaporated. The residue was purified by flash chromatography (50% ethyl acetate in toluene followed by pure acetone) to give the title compound.

$^1$H NMR (CD$_3$COCD$_3$) δ (ppm): 2.50 (m, 2H), 2.60 (m, 2H), 2.83 and 2.91 (2s, 6H), 4.16 (t, 1H), 4.56 (d, 2H), 5.35 (s, 1H), 5.43 (s, 2H), 6.91 to 8.08 (m, 12H), 8.40 (d, 1H).

Step 5

Preparation of N,N-dimethyl 3-((1-(3-((7-chloro-2-quinolinyl)methoxy)phenyl)-1-(3-(cyanomethyl)phenyl)methyl)thio)propanamide To the alcohol (Step 4) (549 mg) in CH$_2$Cl$_2$ (6 mL) at −78° C. were added triethylamine (293 μL, 2 equiv.) and methanesulfonyl chloride (122 μL, 1.5 equiv.). Then the mixture was allowed to warm to −10° C. and 25% ammonium acetate was added, the mixture was extracted with ethyl acetate, dried and evaporated. The crude mixture was purified by flash chromatography (20% acetone in ethyl acetate) to give the mesylate.

To the mesylate (600 mg) dissolved in DMSO (2.4 mL) at r.t. was added NaCN (240 mg). Then after 4 hr the DMSO was evaporated and the crude mixture was purified by flash chromatography (50% ethyl acetate in toluene) to afford the title compound.

$^1$H NMR (CD$_3$COCD$_3$) δ (ppm): 2.55 (m, 2H), 2.61 (m, 2H), 2.83 and 2.91 (2s, 6H), 3.93 (s, 2H), 5.41 (s, 2H), 5.43 (s, 1H), 6.91 to 8.05 (m, 12H), 8.38 (d, 1H).

Step 6

Using the procedure of Example 40, Step 3, the benzyl nitrile of Step 5 was converted to the title compound (except that the formation of the tetrazole was completed within 4 hrs).

$^1$H NMR (CD$_3$COCD$_3$) δ (ppm): 2.46 (m, 2H), 2.55 (m, 2H), 2.76 and 2.80 (2s, 6H), 4.05 (s, 2H), 5.25 (s, 1H), 5.28 (s, 2H), 6.83 to 8.00 (m, 12H), 8.33 (d, 1H).

Anal. calc'd for C$_{30}$H$_{28}$ClN$_6$OSNa·6H$_2$O: C, 52.44; H, 5.87; Cl, 5.16; N, 12.23; S, 4.67; Na, 3.35 Found: C, 52.52; H, 5.53; Cl, 5.33; N, 12.14; S, 5.20; Na, 3.71

EXAMPLE 45

3-(((3-Carboxyphenyl)thio)(3-((7-chloro-2-quinolinyl)methoxy)phenyl)methyl)benzoic acid, disodium salt

Step 1

Preparation of methyl13-(((3-(methoxycarbonyl)phenyl)thio)(3-((7-chloro-2-quinolinyl)methoxy)phenyl)methyl)benzoate To a r.t. solution of the alcohol of Example 9, Step 1 (445 mg) in CCl$_4$ (10 c.c.) and CH$_2$Cl$_2$ (30 c.c.) was added tri-n-octylphosphine (1.3 g) and the mixture reacted for 1.5 hr. The reaction mixture was filtered through a plug of SiO$_2$ and the intermediate chloride isolated after removal of the solvent. This chloride (155 mg) was taken in CH$_3$CN (5 c.c.), methyl 3-mercaptobenzoate (84 mg) was added followed by dry cesium carbonate (163 mg) and the mixture was heated at 75° C. for 0.5 hr. After cooling, ethyl acetate (10 c.c.) was added and the organic layer was washed with 25% NH$_4$OAc (5 c.c), brine, dried with MgSO$_4$ and the solvent removed in vacuo to yield the title compound after purification by chromatography.

$^1$H NMR (CDCl$_3$) δ (ppm): 3.70–3.90 (2s, 6H), 5.20 (s, 2H), 5.45 (s, 1H), 6.70–8.05 (m, 17H).

Step 2

To a 0° C. solution of the ester of Step 1 (144 mg) in tetrahydrofuran (4 c.c.) and methanol (1 c.c.) was added 2N NaOH (370 μL) and the mixture was kept at 0° C. for 2 days. 25% NH$_4$OAc (5 c.c.) and acetic acid (3 drops) were added and the product was extracted in ethyl acetate (3×5 c.c). The organic layer was washed with brine and the solvents were removed in vacuo. The residue (126 mg) was taken in H$_2$O (2 c.c.) containing 2N NaOH (228 μL) and the solution was freeze dried to yield the title compound.

$^1$H NMR (DMSO-d$_6$ containing 10% CD$_3$COCD$_3$) δ (ppm): 5.30 (s, 2H), 5.80 (s, 1H), 6.85–8.50 (m, 17H).

EXAMPLE 46

3-(((3-((7-Chloro-2-quinolinyl)methoxy)phenyl)(3-(2-dimethylamino-2-oxoethyl)phenyl)methyl)thio)propanoic acid, sodium salt

Step 1

Methyl 3-((3-((7-chloro-2-quinolinyl)methoxy)phenyl)formyl)phenylacetate

The secondary alcohol of the product of Example 44, Step 1, was oxidized to the ketone as in Example 29, Method B, Step 5. The benzylic alcohol was then deprotected (Example 44, Step 4) and the nitrile was formed (Example 44, Step 5). Treatment of this nitrile with HCl in MeOH in a sealed tube for 6 h at 65° C. yielded the title methyl ester.

Step 2

The ester was reacted with Me$_2$NAlMe$_2$ (Example 366, Step 10) to afford the dimethylamide. Reduction of the ketone with NaBH$_4$ (Example 29, Method B, Step 1) gave a benzylic alcohol, which was reacted with methanesulfonyl chloride and triethylamine in dichloromethane at −40° C., then at r.t. by 3 h to yield the chloride. The chloride was then substituted by methyl 3-mercaptopropanoate in the presence of Cs$_2$CO$_3$ (Example 44, Step 3). Finally, hydrolysis of the ester using the procedure of Example 42, Step 2 afforded the title compound.

Anal. calcd for C$_{30}$H$_{28}$ClN$_2$SO$_4$Na·H$_2$O: C, 61.12; H, 5.09; N, 4.75. Found: C, 60.99; H, 4.96; N, 4.73.

Example 109

3-((1-(3-((7-Chloro-2-quinolinyl)methoxy)phenyl)-3-(4-chloro-2-(dimethylaminocarbonyl)phenyl)propyl)thio)propanoic acid

Step 1

1-Acetoxy-7-chloro-3,4-dihydronaphthalene

To a solution of 7-chlorotetralone (Can. Pat. 974997) (100 g) in isopropenyl acetate (400 mL) was added conc. H$_2$SO$_4$ (1 mL) and the mixture was refluxed for 16 hrs then cooled to room temperature and evaporated to dryness under reduced pressure. The residue was passed through a plug made of celite (100 g) and NaHCO$_3$ (100 g) using EtOAc; the filtrate was concentrated in vacuo and passed through a plug of SiO$_2$ (12 cm × 12 cm) using 30% EtOAc in hexanes, and the fractions containing the product combined and evaporated to dryness to yield the title compound as an oil (114 g, 93%), homogeneous by $^1$H NMR.

¹H NMR (CD₃COCD₃)δ: 2.30 (3H, s), 2.35–2.45 (2H, m), 2.75–2.85 (2H, m), 5.80 (1H, t), 7.1 (1h, br s*), 7.2 (2H, br s). *br s≈broad singlet

Step 2

2-(3-Oxopropyl)-5-chlorobenzoic acid

To a cold solution (−78° C.) of the crude enol acetate from Step 1 (57 g) in CH₂Cl₂ (250 mL) was added MeOH (50 mL) and the solution treated with an ozone/oxygen mixture from a Welsbach T-23 ozonator at −78° until a light blue color persisted (or until TLC showed no more starting material). Excess ozone was then blown away with N₂ and a CH₂Cl₂ (200 mL) solution of PPh₃ (80 g) was added at −78° and kept at −78° for 2 hrs; the mixture was then allowed to warm to r.t. and the solvents were removed on a rotavap. The residue was divided in two and each portion dissolved in THF (500 mL)-MeOH (150 mL) and then treated at 0° C. with 1N HCl (150 mL) for 4 hrs. An acid/base workup using 10% NaHCO₃ and Et₂O yielded, after acidification (6N HCl) at 0° C. and extraction into EtOAc, the title compound as a semi-solid residue (39.3 g, 67% combined yield).

¹H NMR (CD₃COCD₃)δ: 2.80–2.90 (2H, t), 3.25–3.35 (2H, t), 7.45–7.65 (2H, m), 7.95 (1H, d), 9.80 (1H, CHO, s).

Step 3

3-(t-Butyldiphenylsiloxy)bromobenzene

To a solution of 3-bromophenol (377 g) in CH₂Cl₂ (2.6 L) was added Et₃N (424 mL) and t-butyldiphenylsilyl chloride (611 g). The reaction was stirred at r.t. for 3 days, poured onto 4 L of aqueous NH₄OAc (25%), extracted with Et₂O, dried and evaporated. Flash chromatography of the residue using 5% EtOAc/hexane afforded 716 g (80%) of the title compound.

¹H NMR (CDCl₃)δ: 1.09 (9H, s), 6.59 (1H, d), 6.90 (1H, t), 7.00 (2H, m), 7.33–7.48 (6H, m), 7.71 (4H, m).

Step 4

5-Chloro-2-(3-hydroxy-3-(3-t-butyldiphenylsiloxy)-phenyl)propyl)benzoic acid

To a suspension of Mg (19.9 g, 0.77 mol) in THF (800 mL) was added the bromide from Step 3 (26 g, 64 mmol) and 1,2-dibromoethane (1 mL). The mixture was warmed to initiate the reaction. The remaining bromide (239 g, 0.58 mol) in THF (250 mL) was added dropwise over 1 h. The reaction was stirred overnight at r.t. The Grignard solution was decanted, using a canula, from the remaining Mg and used as such.

To the Grignard solution at 0°–5° was added dropwise the aldehyde from Step 2 (45 g, 0.26 mol) in THF (250 mL). After 1 hour the reaction was poured into NH₄Cl(250 g in 2 L H₂O) and extracted with EtOAc, dried (Na₂SO₄) and evaporated. Flash chromatography of the residue, using 20% EtOAc in hexane to 40% EtOAc-5% HOAc in hexane, afforded 120 g (92%) of the title compound.

¹H NMR (CD₃COCD₃)δ: 1.05 (9H, s), 1.80 (2H, q), 2.95 (2H, m), 4.95 (1H, t), 6.60 (1H, dd), 6.90 (2H, m), 7.05 (1H, t), 7.20–7.40 (1H, m), 7.35–7.50 (7H, m), 7.70–7.80 (4H, m), 7.90 (1H, d).

Step 5

8-Chloro-4,5-dihydro-3-(3-(t-butyldiphenylsiloxy))phenyl-2-benzoxepin-1(3H)-one

To the hydroxyacid of Step 4 (28 g, 51.4 mmol) and triethylamine (14 mL, 100 mmol) in 250 mL of CH₂Cl₂:CH₃CN 4:1 at 0° C., 2-chloro-1-methyl-pyridinium iodide (26.0 g, 100 mmol) was added and the resulting mixture was stirred at 0° C. for 2.5 h. 25% aq NH₄OAc was then added and the title lactone was extracted with EtOAc, dried over Na₂SO₄ and purified to yield 24.00 g (89%) by flash chromatography on silica with EtOAc:hexane 15:85.

Step 6

8-Chloro-4,5-dihydro-3-(3-hydroxyphenyl)-2-benzoxepin-1(3H)-one

At 0° C., 1.0M Bu₄NF (tetrabutylammonium fluoride, 55 mL) was added to a solution of the lactone of Step 5 (24.00 g, 45.5 mmol) and HOAc (7.0 mL, 122 mmol) in 250 mL of anhydrous THF and the resulting mixture was stirred at 0° C. for 2 h. 25% aq NH₄OAc was then added and the title phenol was extracted with EtOAc, dried over Na₂SO₄ and purified to yield 10.5 g, (80%) by flash chromatography on silica with EtOAc:-hexanes 3:10.

Step 7

8-Chloro-3-(3-((7-chloro-quinolinyl)methoxy)phenyl)-4,5-dihydro-2-benzoxepin-1-(3H)-one Using the procedure of Example 25, Step 10, the product of Step 6 was converted to the title compound. Yield: 90%.

¹H NMR (CD₃COCD₃) δ: 2.35 (2H, m), 3.00 (2H, m), 5.15 (1H, dd), 5.47 (2H, s), 7.00 (2H, m), 7.23 (1H, d), 7.29 (1H, t), 7.40 (1H, d), 7.60 (3H, m), 7.75 (1H, d), 8.00 (2H, m), 8.40 (1H, d).

Step 8

N,N-Dimethyl 5-chloro-2-(3-hydroxy-3-(3-((7-chloro-2-quinolinyl)methoxy)phenyl)propyl)benzamide To a solution of the lactone (46.4 g, 100 mmol) from Step 7 in toluene (250 mL) at 0° C. was added 0.95M Me₂AlNMe₂ in toluene (210 mL, 200 mmol) and the mixture was warmed up to 60° C. for 1 h. It was then cooled, poured slowly onto HCl (800 mL). EtOAc (300 mL) was added and the mixture was stirred until a clean separation of the layers was obtained. The pH of the aq phase was adjusted to 6 with NaOH and the aq layer was extracted twice again with EtOAc. The organic layer was washed with brine and the solvents removed to yield the pure title compound which was used as such in the next step.

¹H NMR (CD₃COCD₃) δ: 1.8–2.0 (2H, m), 2.5–2.75 (2H, m), 2.8 (3H, s), 3.0 (3H, s), 4.55 (1H, bt), 5.35–5.45 (2H, bs), 6.9–8.9 (12H, m).

Step 9

N,N-Dimethyl-5-chloro-2-(3-methanesulfonyloxy-3-((7-chloro-2-quinolinyl)methoxy)phenyl)propyl)benzamide To a solution of 11.2 g (22 mmol) of amide from Step 8 and 5.1 mL (37 mmol) of triethylamine in 200 mL of CH₂Cl₂ was added dropwise 2.2 mL (28 mmol) of methanesulfonyl chloride at −40°. The reaction was stirred at this temperature for 15 min., warmed up to −10° within 30 min. and stirred at −10° for 1 h. The reaction was quenched by pouring into ice-aq. NaHCO$_3$ and extracted twice with CH$_2$Cl$_2$. After removal of the solvent the crude title compound was used as such for the next step.

Step 10

Methyl 3-((1-(3-((7-chloro-2-quinolinyl)methoxy)phenyl)-3-(4-chloro-2-(dimethylaminocarbonyl)phenyl)propyl)thio)-propanoate The crude mesylate (ca. 22 mmol) from Step 9 was dissolved in 300 mL of acetonitrile. To the solution, which was degassed by bubbling argon through for a few min., was added 6.1 mL (55 mmol) of methyl 3-mercaptopropanoate, followed by 24.3 g (75 mmol) of Cs$_2$CO$_3$. The mixture was stirred at r.t. for 1 h. The solid was filtered, the reaction was diluted with CH$_2$Cl$_2$ and washed twice with sat. NH$_4$Cl solution. Chromatographic purification with toluene:EtOAc 4:1 afforded 9.7 of the title compound (72%).

$^1$H NMR (CD$_3$COCD$_3$) δ: 2.0–2.2 (2H, m), 2.3–3.0 (12H, m), 3.55 (3H, s), 3.8–3.95 (1H, t), 5.5 (2H, s), 6.9–8.4 (12H, m).

Step 11

To a solution of 9.0 g of ester from Step 10 in 200 mL of MeOH, 50 mL of aq K$_2$CO$_3$ solution (1M) was added. The mixture was stirred under nitrogen at r.t. for 15 hrs. The MeOH was partially evaporated, and the reaction was neutralized by addition of 5 mL of HOAc. The product was then partitioned between aq NH$_4$Cl and EtOAc containing 2% HOAc. The crude product was purified on silica gel to give 7.6 g of the title acid (87%).

$^1$H NMR (CD$_3$COCD$_3$) δ: 2.0–3.0 (8H, m), 2.75 (3H, s), 2.95 (3H, s), 3.95 (1H, t), 5.45 (2H, s), 6.95–8.05 (11H, m), 8.4 (1H, d).

Anal. calcd for C$_{31}$H$_{29}$Cl$_2$N$_2$O$_4$SNa·H$_2$O: C, 58.40; H, 4.90; N, 4.39. Found: C, 58.40; H, 4.95; N, 4.41.

Step 12

To a solution of the free acid in EtOH, 1 equiv. of NaOH was added. The mixture was evaporated and the residue was dissolved in H$_2$O and freeze dried to yield the sodium salt of the title compound.

EXAMPLE 110

N,N-Dimethyl 2-(3-(3-((7-chloro-2-quinolinyl)methoxy)phenyl)-3-((2-(1H-tetrazol-5-yl)ethyl)thio)propyl)benzamide, sodium salt Using the method of Example 29, Method A, Step 1,3-mercaptopropanoic acid was added to Styrene 1. The acid was converted to the amide using the procedure of Example 35, Step 2, but replacing tert-butylamine by ammonia. This amide was dehydrated to the nitrile with trifluoroacetic anhydride (1.1 equiv) and pyridine (6 equiv) in THF (concentration 0.1M) at −10° C. for 30 min. Finally, the title compound was obtained by treatment with Bu$_3$SnN$_3$ as in Example 40, Step 3.

Anal. calcd for C$_{31}$H$_{30}$ClN$_6$O$_2$SNa·2.2H$_2$O: C, 57.39; H, 5.30; N, 12.93. Found: C, 57.45; H, 4.92; N, 12.60.

EXAMPLE 111

N,N-Dimethyl 2-(3-(3-(2-(7-chloro-2-quinolinyl)ethyl)phenyl)-3-((2-(1H-tetrazol-5-yl)propyl)thio)propyl)benzamide, sodium salt Using the procedure of Example 110, but replacing 3-mercaptopropanoic acid by Thiol 5 and starting from Styrene 2, the title product was obtained.

Anal. Calcd for C$_{33}$H$_{34}$ClN$_6$O$_2$SNa·2.5H$_2$O: C, 59.49; H, 5.90; N, 12.61. Found: C, 59.22; H, 5.55; N, 12.56.

EXAMPLE 113

3-((1-(3-((7-Chloro-2-quinolinyl)methoxy)phenyl)-3-(2-(dimethylaminocarbonyl)phenyl)propyl)thio)-2-ethyl-propanoic acid, sodium salt Step 1

Ethyl 3-(acetylthio)-2-ethylpropanoate

Ethyl 2-ethyl-2-propenoate (Arch. Pharm., 313, 846 (1980)) (5 g, 39 mmol) was diluted with 5.6 mL (78 mmol) of thiolacetic acid and stirred at 65° C. for 36 h. The mixture was then diluted with Et$_2$O, washed with water, and the organic phase was dried with Na$_2$SO$_4$. Evaporation to dryness yielded the title material as an orange oil which was used as such for the next step.

$^1$H NMR (CDCl$_3$) δ: 0.96 (3H, t), 1.28 (3H, t), 1.70 (3H, m), 2.35 (3H, s), 3.10 (2H, m), 4.18 (2H, q).

Step 2

Ethyl 2-ethyl-3-mercaptopropanoate

To a solution of the thioester of Step 1 (5.00 g, 24.5 mmol) in MeOH (15 mL) at 0° C., under nitrogen, was added K$_2$CO$_3$ (9.67 g, 73.5 mmol). The resulting mixture was stirred at 0° C. for a half hour, and then HOAc (8.82 g, 147 mmol) and 25% aq NH$_4$OAc were added. The title thiol was extracted with EtOAc, dried over Na$_2$SO$_4$ and purified by distillation on a Kugelrohr apparatus (200° C./760 mm Hg). Yield: 1.700 g (45%).

$^1$H NMR (CD$_3$COCD$_3$) δ: 0.86 (3H, t), 1.25 (3H, t), 1.65 (2H, quintet), 1.78 (1H, t), 2.45 (1H, quintet) 2.68 (2H, m), 4.15 (2H, q).

Step 3

Using the procedure of Example 43, but replacing methyl 3-mercaptopropanoate by the thiol of Step 2 in Step 2, the title compound was prepared.

Anal. calcd for C$_{33}$H$_{34}$ClN$_2$O$_4$SNa: C, 64.63; H, 5.58; N, 4.56. Found: C, 64.48; H, 5.45; N, 4.39.

EXAMPLE 151

3-((1-(3-(2-(7-Chloro-2-quinolinyl)ethyl)phenyl)-3-(2-(1H-tetrazol-5-yl)phenyl)propyl)thio)-2-ethyl-propanoic, disodium salt The title compound was obtained from the acid of Example 343 using the procedure of Example 40, Step 3.

Anal. calcd for C$_{32}$H$_{32}$ClN$_5$O$_2$SNa$_2$: C, 57.80; H, 5.04; N, 10.37. Found: C, 57.86; H, 4.86; N, 10.54.

EXAMPLE 152

3-((1-(3-(2-(7-Chloro-2-quinolinyl)ethyl)phenyl)-3-(2-((4-methylphenylsulfonylaminocarbonyl)phenyl)-propyl)thio)-2-ethylpropanoic acid, monosodium salt

Step 1

2-(3-(3-(2-(7-Chloro-2-quinolinyl)ethyl)phenyl)-3-((3-ethoxy-2-ethyl-3-oxopropyl)thio)-propyl)benzoic acid The ester of Example 36, Step 1, was hydrolyzed to the acid using the procedure of Example 29, Method A, Step 3. Ethyl 2-ethyl-3-mercaptopropanoate (Example 113, Step 2) was then added to this styrene using the procedure of Example 29, Method A, Step 1, to yield the title compound.

$^1$H NMR (CD$_3$COCD$_3$) δ: 0.78 (3H, 2q, mixture of diastereoisomers), 1.20 (3H, q), 1.52 (2H, m), 2.14 (2H, m), 2.2–2.6 (3H, m), 2.92 (2H, m), 3.2 (2H, m), 3.35 (2H, m), 3.87 (1H, q), 4.10 (2H, 2q), 7.0–7.55 (9H, m), 7.91 (2H, d), 8.03 (1H, s), 8.28 (1H, d).

Step 2

Ethyl 3-((1-(3-(2-(7-chloro-2-quinolinyl)ethyl)phenyl)-3-(2-((4-methylphenylsulfonyl)aminocarbonyl)phenyl)-propyl)thio)-2-ethylpropanoate The acid of Step 1 (645 mg, 1.4 mmol) was dissolved in CH$_2$Cl$_2$ (50 mL) under a nitrogen atmosphere and 1-(3-(dimethylamino)propyl)-3-ethylcarbodiimide hydrochloride (340 mg, 1.8 mmol), p-toluenesulfonamide (260 mg, 1.5 mmol) and 4-dimethylaminopyridine (220 mg, 1.8 mmol) were added. The reaction mixture was stirred for 4 h at room temperature before pouring it into 1N HCl. Extraction with EtOAc and CH$_2$Cl$_2$, drying over anhydrous MgSO$_4$ and evaporation in vacuo gave the crude title product (900 mg), which was used as such for the next step (hydrolysis).

When the reaction was performed on a smaller scale, the title compound was purified by preparative thin layer chromatography eluting with an EtOAc:hexane:MeOH:HOAc (20:70:10:1) mixture.

$^1$H NMR (CD$_3$COCD$_3$) δ: 0.78 (3H, 2t, a mixture of diastereoisomers) 1.20 (3H, 2t), 1.48 (2H, m), 1.86 (2H, m), 2.2–2.6 (5H, m), 2.46 (3H, s), 2.90 (1H, NH, br s), 3.15–3.35 (4H, m), 3.6 (1H, q), 4.1 (2H, dq), 7.0–7.55 (13H, m), 7.88 (1H, d), 7.96 (1H, d), 7.98 (1H, s), 8.20 (1H, d).

Step 3

Using the procedure of Example 29, Method A, Step 3, but using 2 equivalents of KOH instead of 10 equiv. of NaOH, the ester of Step 2 was hydrolyzed to the acid which was purified by flash chromatography (toluene:acetone:methanol) followed by reversed phase chromatography (Delta prep column, 65% methanol in aqueous phosphate buffer at pH:7.0). It was then converted to the title compound using the procedure of example 14, Step 2, except that only on equiv. of NaOH was used.

$^1$H NMR of the acid (CD$_3$COCD$_3$) δ: 0.82 (3H, dt), 1.53 (2H, m), 1.87 (2H, m), 2.25–2.60 (5H, m), 2.43 (3H, s), 2.90 (1H, NH, br s), 3.15–3.35 (4H, m) 3.61 (1H, m), 7.05–7.55 (13H, m), 7.90 (1H, d), 7.96 (1H, d), 7.98 (1H, s), 8.21 (1H, d).

EXAMPLE 155

3-((1-(3-(2-(7-Chloro-2-quinolinyl)ethyl)phenyl)-3-(2-(N-methyl*-1H-tetrazol-5-yl)phenyl)propyl)thio)-2-ethylpropanoic acid, disodium salt The acid-tetrazole of Example 151 was treated with diazomethane in methanol to afford an ester-N-methyltetrazole. Then, the ester was hydrolyzed, as in Example 152, Step 3, to yield the title sodium salt.

$^1$H NMR of the acid (CD$_3$COCD$_3$) δ: 0.7–0.9 (3H, m), 1.4–1.6 (2H, m), 1.9–2.1 (2H, m), 2.2–2.7 (3H, m), 2.8 (1H, m), 2.95 (1H, m), 3.2–3.45 (4H, m), 3.9 (1H, t), 4.4 (3H, s), 7.2–7.5 (9H, m), 7.8 (1H, d), 7.9 (1H, d), 8.0 (1H, d), 8.15 (1H, d).

*mixture of 2 and 3-isomers

EXAMPLES 160 AND 354

Using the procedure of Example 35, but replacing 3-mercaptopropanoic acid by Thiol 13 and tertbutylamine by dimethylamine and ammonia respectively, the following compounds were obtained.

EXAMPLE 160

2-(3-(3-((7-Chloro-2-quinolinyl)methoxy)phenyl)-3-((2-ethyl-3-(dimethylamino)-3-oxopropyl)thio)propyl)benzoic acid, sodium salt Anal. calcd for C$_{33}$H$_{34}$ClN$_2$O$_4$SNa·3.7H$_2$O: C, 58.30; H, 6.14; N, 4.12. Found: C, 58.30; H, 6.10; N, 4.07.

EXAMPLE 354

2-(3-(3-((7-Chloro-2-quinolinyl)methoxy)phenyl)-3-((3-amino-2-ethyl-3-oxopropyl)thio)propyl)benzoic acid, sodium salt Anal. calcd for C$_{31}$H$_{30}$ClN$_2$O$_4$SNa·0.5H$_2$O: C, 62.67; H, 5.26; N, 4.72. Found: C, 62.97; H, 5.41; N, 4.66.

EXAMPLE 178

3-((1-(3-(2-(7-Chloro-2-quinolinyl)ethyl)phenyl)-3-(2-((ethoxycarbonyl)amino)phenyl)propyl)thio)-2-ethylpropanoic acid, sodium salt

Step 1

Ethyl 3-((1-(3-(2-(7-Chloro-2-quinolinyl)ethyl)phenyl)-3-(2-((ethoxycarbonyl)amino)phenyl)propyl)thio)-2-ethylpropanoate To the acid of Example 152, Step 1, (650 mg, 1.1 mmol) dissolved in toluene (30 mL) were added triethylamine (173 µl, 1.24 mmol) and diphenylphosphoryl azide (372 mg, 1.35 mmol). The reaction mixture was heated 30 minutes at 95° C. before adding EtOH (300 µl). After 14 h of heating, the solution was concentrated in vacuo. Et$_2$O and EtOAc were added and the organic phase was washed successively with saturated aqueous NH$_4$Cl, NaHCO$_3$ and with brine. Drying over MgSO$_4$ followed by evaporation of the solvents in vacuo gave the crude product which was purified by flash chromatography (8 to 15% acetone in toluene) to give 391 mg of the title compound.

$^1$H NMR (CD$_3$COCD$_3$) δ: 0.78 (3H, 2t, a mixture of diastereoisomers) 1.22 (3H, t), 1.24 (3H, t), 1.50 (2H, m), 2.0–2.75 (8H, m), 3.20 (2H, m), 3.30 (2H, m), 3.81 (1H, m), 4.10 (4H, 2q), 7.05–7.30 (6H, m), 7.41 (1H, d), 7.52 (2H, m), 7.72 (1H, br s), 7.88 (1H, d), 7.96 (1H, s), 8.20 (1H, d).

Step 2

Using the procedure of Example 152, Step 3, the title sodium salt was obtained.

Anal. calcd for $C_{34}H_{36}ClN_2O_4SNa \cdot H_2O$: C, 63.30; H, 5.94; N, 4.34. Found: C, 63.30; H, 5.84; N, 4.24.

EXAMPLE 228

3-(((3-((7-Chloro-2-quinolinyl)methoxy)phenyl)(((2-(dimethylaminocarbonyl)phenyl)methyl)thio)methyl)-thio)propanoic acid, sodium salt Using the procedure of Example 14, Step 1, but replacing methyl 3-mercaptobenzoate by a 1:1 mixture of methyl 3-mercaptopropanoate and 2-(mercaptomethyl) benzoic acid, a mixed dithioacetal was formed. The acid was then reacted with 1.1 equiv. of 1,1'-carbonyldiimidazole at r.t. in $CH_2Cl_2$ or THF for an hour, then with dimethylamine at r.t. for an hour to give the dimethylamide. Finally, hydrolysis of the ester as in Example 14, Step 2, afforded the title compound.

Anal. calcd for $C_{30}H_{28}ClN_2O_4S_2Na \cdot H_2O$: C, 58.01; H, 4.87; N, 4.51. Found: C, 57.73; H, 4.82; N, 4.73.

EXAMPLE 229

3-((3-(2-(Aminocarbonyl)phenyl)-1-(3-((7-chloro-2-quinolinyl)methoxy)phenyl)propyl)thio)-2-methoxypropanoic acid, sodium salt

Step 1

Methyl 2-methoxy-2-propenoate

The dimethyl acetal of methyl pyruvate was prepared using methyl pyruvate, trimethyl orthoformate, methanol and p-toluenesulfonic acid according to the method of Wermuth (Bull. Chem. Soc. Jp., 2987 (1970)). Methyl pyruvate dimethylacetal (50 g) p-toluenesulfonic acid (1.34 g) and hydroquinone (1.90 g) were heated in an oil bath ($\approx 150°$ C.) and methanol was allowed to distill off slowly ($\approx 10$ mL). The residue was then distilled to afford 32 g (81%) of the title ester; bp $\approx 50°$ C./20 mm Hg.

$^1$H NMR $(CDCl_3)\delta$: 3.67 (3H, s), 3.82 (3H, s), 4.65 (1H, d, J=2 Hz), 5.48 (1H, d, J=2 Hz).

Step 2

Methyl 3-(benzylthio)-2-methyoxypropanoate

To a solution of the propenoate of Step 1 (26.93 g, 0.23 mol) in THF (20 mL) at 0° C. was added benzyl mercaptan (23.0 mL, 0.23 mol) followed by 1M THF solution of Bu$_4$NF (20 mL). The mixture was stirred at r.t. for 1 h. The reaction was poured into $H_2O$ and extracted with EtOAc, washed with brine, dried and concentrated to yield 24.89 g (48%) of the title compound; b.p. 115°-130° C./1 mm Hg.

$^1$H NMR $(CDCl_3)\delta$: 2.76 (2H, m), 3.43 (3H, s), 3.78 (3H, s), 3.82 (2H, s), 3.96 (1H, dd), 7.34 (5H, m).

Step 3

3-(Benzylthio)-2-methoxypropanoic acid

To a solution of the ester (210 mg, 0.875 mmol) of Step 2 in MeOH:$H_2O$ 5:1 (6 mL) was added $K_2CO_3$ (210 mg). After 18 h, the reaction was quenched by the addition of 25% aq NH$_4$OAc. After acidification to pH 4 with 10% HCl, the product was extracted with EtOAc. The organic phase was dried over Na$_2$SO$_4$ and evaporated to provide 180 mg, (91%) of the title compound.

$^1$H NMR $(CD_3COCD_3)\delta$: 2.73 (2H, m), 3.36 (3H, s), 3.80 (2H, s), 3.95 (1H, q), 7.16–7.36 (5H, m).

Step 4

3-Mercapto-2-methoxypropanoic acid

The acid of Step 3 (1.3 g, 5.7 mmol) was dissolved in liquid ammonia at $-30°$ C. and small pieces of Na (469 mg, 20.4 mmol) were added until obtention of a persistant blue coloration. After 20 min, the ammonia was removed by a flow of $N_2$ and $H_2O$ (20 mL) and 10% HCl were added until obtention of pH $\approx 3.5$. The thiol was then extracted with EtOAc, dried over Na$_2$SO$_4$ and evaporated to provide 700 mg (89%) of title material.

$^1$H NMR $(CD_3COCD_3)\delta$: 1.88 (1H, t), 2.80 (2H, m), 3.36 (3H, s), 3.86 (1H, t).

Step 5

Methyl 3-mercapto-2-methoxypropanoate

To an ethereal solution of the acid of Step 4 was added $CH_2N_2$ at 0° C. The organic solvent was removed under reduced pressure to give the title compound.

$^1$H NMR $(CD_3COCD_3)\delta$: 1.93 (1H, t), 2.83 (2H, m), 3.40 (3H, s), 3.73 (3H, s), 3.91 (1H, t).

Step 6

4,5-Dihydro-3-(3-(diphenyl(2-methyl-2-propyl)siloxy)-phenyl-2-benzoxepin-1(3H)-one To 2-(3-hydroxy-3-(3-(tert-butyldiphenylsiloxy)-phenyl)propyl)benzoic acid (prepared from α-tetralone as in Example 366, Step 1–4) (25.58 g, 50.09 mmol) and triethylamine (22 mL, 158 mmol) in 250 mL of $CH_2Cl_2$:$CH_3CN$ 4:1 at 0° C., 2-chloro-1-methylpyridinium iodide (20.35 g, 79.7 mmol) was added and the resulting mixture was stirred at 0° C. for 2.5 h. 25% aq NH$_4$OAc was then added and the title lactone was extracted with EtOAc, dried over Na$_2$SO$_4$ and purified by flash chromatography on silica with EtOAc:hexane 10:90 and 15:85. Yield: 23.00 g, 93%.

Step 7

4,5-Dihydro-3-(3-hydroxyphenyl)-2-benzoxepin-1(3H)-one

At 0° C., 1.0M Bu$_4$NF (tetrabutylammonium fluoride, 60 mL) was added to a solution of the lactone of Step 6 (23.00 g, 46.7 mmol) and HOAc (7.0 mL, 122 mmol) in 250 mL of anhydrous THF and the resulting mixture was stirred at 0° C. for 2 h. 25% aq NH$_4$OAc was then added and the title phenol was extracted with EtOAc, dried over Na$_2$SO$_4$ and purified by flash chromatography on silica with EtOAc:toluene 10:90 and 15:85. Yield: 11.45 g, (96%).

Step 8

3-(3-((7-Chloro-2-quinolinyl)methoxy)phenyl)-4,5-dihydro-2-benzoxepin-1(3H)-one Using the procedure of Example 25, Step 10, the product of Step 7 was converted to the title compound. Yield: 90%.

$^1$H NMR $(CD_3COCD_3\text{-}CD_3SOCD_3)\delta$: 2.16–2.45 (2H, m), 2.86–3.10 (2H, m), 5.11 (1H, dd), 5.38 (2H, s), 7.01–7.12 (2H, m), 7.24 (1H, br s), 7.30 (1H, dd), 7.39–7.50 (2H, m), 7.57–7.70 (3H, m), 7.74 (1H, d), 8.04 (1H, s), 8.07 (1H, d), 8.47 (1H, d).

Step 9

2-(3-(3-((7-Chloro-2-quinolinyl)methoxy)phenyl)-3-((2,3-dimethoxy-3-oxopropyl)thio)propyl)benzoic acid To the lactone of Step 8 (500 mg, 1.20 mmol) and the thiol of Step 5 (270 mg, 1.80 mmol) in 1,2-dichloroethane (12 mL) at 0° C. was added $BF_3 \cdot Et_2O$ (920 mL, 7.20 mmol). The temperature was allowed to warm to room temperature to give a suspension. The mixture was then cooled to 0° C. followed by the addition of trifluoroacetic acid (1 mL). After 15 min, the ice bath was removed and the mixture was stirred until TLC showed completion (EtOAc:Hexane 1:1). At that time, the reaction was quenched by the addition of 25% aq $NH_4OAc$ at 0° C. The desired product was extracted with EtOAc, dried over $Na_2SO_4$ and purified by flash chromatography on silica using acetone:toluene 20:80 to yield 630 mg (84%) of title material.

$^1$H NMR ($CD_3COCD_3$)$\delta$: 2.11 (2H, quintet), 2.56 (2H, m), 2.75–3.06 (2H, m), 3.23 and 3.28 (3H, 2s, mixture of diasteromers), 3.64 (3H, 2s), 3.73 (1H, m), 3.94 (1H, m), 5.38 (2H, s), 6.94 (1H, m), 7.11–7.28 (6H, m), 7.39 (1H, m), 7.56 (1H, dd), 7.73 (1H, d), 7.83–8.04 (2H, m), 8.30 (1H, d).

Step 10

Using the procedure of Example 35, Step 2, but replacing tert-butylamine by ammonia, the acid of Step 9 was converted to the amide. The ester function was then hydrolyzed, using the procedure of Example 42, Step 2, to give the title sodium salt.

Anal. calcd for $C_{30}H_{28}ClN_2O_5SNa \cdot 1.5H_2O$: C, 58.68; H, 5.09; N, 4.56. Found: C, 58.34, H; 4.94; N, 4.47.

EXAMPLE 343

3-((1-(3-(2-(7-Chloro-2-quinolinyl)ethyl)phenyl)-3-(2-cyanophenyl)propyl)thio)-2-ethylpropanoic acid, sodium salt Using the procedure of Example 40, Steps 1-2, but substituting N,N-dimethyl 3-mercaptopropanamide by Thiol 13 and starting from 2-(3-(3-(2-(7-chloro-2-quinolinyl)ethyl)phenyl)-2-propenyl)benzaldehyde (a precursor of Styrene 2), the title compound was obtained.

$^1$H NMR ($CD_3COCD_3$) $\delta$: 0.87 (3H, 2t, mixture of diastereomers), 1.61 (2H, m), 2.19 (2H, m), 2.30–2.52 (2H, m), 2.52–2.93 (3H, m), 3.20 (2H, t), 3.33 (2H, t), 3.95 (1H, 2t), 7.12–7.45 (7H, m), 7.49 (1H, d), 7.58 (1H, dd), 7.69 (1H, d), 7.87 (1H, d), 8.06 (1H, br s), 8.21 (1H, d).

EXAMPLE 356

3((3-(4-Chloro-2-(methylaminocarbonyl)phenyl)-1-(3-((7-chloro-2-quinolinyl)methoxy)phenyl)propyl)thio)propanoic acid Using the procedure of Example 229, Step 9, but substituting the thiol of Step 5 by methyl 3-mercaptopropanoate, the thioether was obtained from the lactone of Example 377, Step 3. The methyl amide was then obtained as in Example 35, Step 2, and the ester was hydrolyzed as in Example 42, Step 2 to yield the title compound.

$^1$H NMR ($CD_3COCD_3$-$CD_3SOCD_3$) $\delta$: 2:00–2.80 (11H, m), 3.80 (1H, t), 5.40 (2H, s), 6.90 (2H, d), 7.05–7.30 (4H, m), 7.55 (1H, dd), 7.70 (1H, d), 8.00 (2H, m), 8.10 (1H, m), 8.40 (1H, d).

EXAMPLE 362

5-Chloro-2-(3-((2-carboxyethyl)thio)-3-(3-((7-chloro-2-quinolinyl)methoxy)phenyl)propyl)benzoic acid

Step 1

Methyl 5-chloro-2-(3-(3-((7-chloro-2-quinolinyl)methoxy)-phenyl)-3-hydroxy propyl) benzoate Sodium methoxide (243 mg, 4.5 mmol) was added to a cold (−5° C.) suspension of the lactone of Example 377, Step 3, (1.4 g, 3 mmol) in MeOH (7 mL) and THF (7 mL). After 15 min. the reaction mixture was warmed to r.t. and a solution was obtained. After 1 h the mixture was poured onto aq. saturated $NH_4Cl$ and the product was extracted with EtOAc, dried over $Na_2SO_4$, and the solvents were removed in vacuo to yield 1.48 g (100%) of the title compound.

$^1$H NMR ($CD_3COCD_3$) $\delta$: 1.95 (2H, m), 2.90 (2H, m), 3.80 (3H, s), 4.4 (1H, OH), 5.70 (1H, t), 5.40 (2H, s), 6.95–8.05 (11H, m), 8.30 (1H, d).

Step 2

Using the procedure of Example 366, Steps 11–12 and Example 14, Step 2, the ester of Step 1 was converted to the title diacid.

$^1$H NMR ($CD_3COCD_3$) $\delta$: 2.0–2.2 (2H, m), 2.4–2.6 (4H, m), 2.70–3.1 (2H, m), 3.9–4.0 (1H, t), 5.4 (2H, s), 6.9–8.05 (11H, m), 8.4 (1H, d).

EXAMPLE 364

3-((1-(3-((7-Chloro-2-quinolinyl)methoxy)phenyl)-3-(2-(1-(hydroxyimino)ethyl)phenyl)propyl)thio)-2-methyl-propanoic acid, sodium salt

Step 1

3-(2-Acetylphenyl)-1-(3-((7-chloro-2-quinolinyl)methoxy)phenyl)propanol

Using the procedure described in J. Org. Chem., 48, 1550, (1983), MeLi was added to 2-(3-hydroxy-3-(3-(tert-butyldiphenylsiloxy)phenyl)propyl)benzoic acid (Example 229, Step 6) at 0° C. in THF and the mixture was stirred at 0° C. for ≈2 hrs and was quenched with chlorotrimethylsilane to afford the methyl ketone. The silyl ether was then hydrolyzed and the 2-quinolinyl-methyl ether formed as in Example 229, Step 7-8, to yield the title compound.

Step 2

Using the procedure of Example 229, Step 9, the benzylic alcohol of Step 1 was reacted with Thiol 4. The ester was then hydrolyzed (Example 42, Step 2) and the oxime was formed by treatment with hydroxylamine hydrochloride (3 equiv) in pyridine at 60° C. for 2 hrs. Formation of the sodium salt yielded the title material.

Anal. calcd for $C_{31}H_{30}ClN_2O_4SNa \cdot 0.2H_2O$: C, 63.25; H, 5.21; N, 4.76. Found: C, 63.25; H, 5.20; N, 4.69.

EXAMPLE 365

(+)-3-((1-(3-((7-chloro-2-quinolinyl)methoxy)phenyl)-3-(4-chloro-2-dimethylaminocarbonyl)phenyl)propyl)-thio)propanoic acid, sodium salt The ester from Example 366, Step 7 was converted to the corresponding amide by the methodology of Example 366, Step 10. The secondary alcohol in the amide was then inverted by a Mitsunobu reaction (see Synthesis, 1–28 (1981)) and hydrolysis. Using the procedures of Example 366, Steps 8, 9, 11, 12 and 13 on the inverted alcohol, the title compound was obtained as the free acid; [α]$_D$= +74.9° (EtOH, c=3.30).

The title compound was prepared following the procedure of Example 366, Step 14.

EXAMPLE 366

(−)3-((1-(3-((7-Chloro-2-quinolinyl)methoxy)phenyl)-3-(4-chloro-2-(dimethylaminocarbonyl)phenyl)propyl)-thio)-propanoic acid, sodium salt

Step 1

1-acetoxy-7-chloro-3,4-dihydronaphthalene

To a solution of 7-chlorotetralone (Canadian Patent 974997, Sep. 23, 1975) (100 g) in isopropenyl acetate (400 mL) was added conc. H$_2$SO$_4$ (1 mL) and the mixture was refluxed for 16 hours then cooled to room temperature (r.t.) and evaporated to dryness under reduced pressure. The residue was passed through a plug made of celite (100 g) and NaHCO$_3$ (100 g) using ethyl acetate; the filtrate was concentrated in vacuo and passed through a plug of SiO$_2$ (12 cm×12 cm) using 30% EtOAc in hexanes, and the fractions containing the product combined and evaporated to dryness to yield the title compound as an oil (114 g, 93%), homogeneous by $^1$H NMR.

$^1$H NMR (CD$_3$COCD$_3$) δ (ppm): 2.30 (s, 3H, CH$_3$), 2.35–2.45 (m, 2H, CH$_2$), 2.75–2.85 (m, 2H, CH$_2$), 5.80 (t, 1H, CH), 7.1 (brs*, 1H, Ar), 7.2 (brs, 2H, Ar)
*brs=broad singlet

Step 2

2-(3-Oxopropyl)-5-chlorobenzoic acid

To a cold solution (−78° C.) of the crude enol acetate from Step 1 (57 g) in CH$_2$Cl$_2$ (250 mL) was added MeOH (50 mL) and the solution treated with an ozone/oxygen mixture from a Welsbach T-23 ozonator at −78° until a light blue color persisted. Excess ozone was then blown away with N$_2$ and a CH$_2$Cl$_2$ (200 mL) solution of PPh$_3$ (80 g) was added at −78° and kept at −78° for 2 hrs; the mixture was then allowed to warm to r.t. and the solvents were removed on a rotavap. The residue was divided in two and each portion dissolved in THF (500 mL)-MeOH (150 mL) and then treated at 0° C. with 1N HCl (150 mL) for 4 hrs. An acid/base work-up using 10% NaHCO$_3$ and Et$_2$O yielded, after acidification (6N HCl) at 0° C. and extraction into EtOAc, the title compound as a semi-solid residue (39.3 g, 67% combined yield).

$^1$H NMR (CD$_3$COCD$_3$) δ (ppm): 2.80–2.90 (t, 2H, CH$_2$), 3.25–3.35 (t, 2H, CH$_2$), 7.45–7.65 (m, 2H, Ar), 7.95 (d, 1H, Ar), 9.80 (s, 1H, CHO).

Step 3

3-(t-Butyldiphenylsiloxy)bromobenzene

To a solution of 3-bromophenol (377 g) in CH$_2$Cl$_2$ (2.6 L) was added Et$_3$N (424 mL) and t-butyldiphenylsilyl chloride (611 g). The reaction was stirred at r.t. for 3 days, poured onto 4 L of aqueous NH$_4$OAc (25%), extracted with Et$_2$O, dried and evaporated. Flash chromatography of the residue using 5% EtOAc/hexane afforded 716 g (80%) of the title compound.

$^1$H NMR (CDCl$_3$) δ (ppm): 1.09 (s, 9H), 6.59 (d, 1H), 6.90 (t, 1H) 7.00 (m, 2H), 7.33–7.48 (m, 6H), 7.71 (m, 4H).

Step 4

5-Chloro-2-(3-hydroxy-3-(3-(t-butyldiphenylsiloxy)-phenyl)propyl)benzoic acid

To a suspension of Mg (19.9 g, 0.77 mol) in THF (800 ml) was added the bromide from Step 3 (26 g, 64 mmol) and 1,2-dibromoethane (1 mL). The mixture was warmed to initiate the reaction. The remaining bromide (239 g, 0.58 mol) in THF (250 mL) was added dropwise over 1 hr. The reaction was stirred overnight at room temperature. The Grignard solution was decanted, using a canula, from the remaining magnesium and used as such.

To the Grignard solution at 0°–5° was added dropwise the aldehyde from Step 2 (45 g, 0.26 mol) in THF (250 mL). After 1 hour the reaction was poured into NH$_4$Cl (250 g in 2 L H$_2$O) and extracted with EtOAc, dried (Na$_2$SO$_4$) and evaporated. Flash chromatography of the residue, using 20% EtOAc in hexane to 40% EtOAc-5% HOAc in hexane, afforded 120 g (92%) of the title compound.

$^1$H NMR (CD$_3$COCD$_3$) δ (ppm): 1.05 (s, 9H), 1.80 (q, 2H), 2.95 (m, 2H) 4.95 (t, 1H), 6.60 (dd, 1H), 6.90 (m, 2H), 7.05 (t, 1H), 7.20–7.40 (m, 1H), 7.35–7.50 (m, 7H), 7.70–7.80 (m, 4H), 7.90 (d, 1H)

Step 5

Methyl 5-chloro-2-(3-hydroxy-3-(3-(t-butyldiphenylsiloxy)-phenyl)propyl)benzoate To a suspension of the hydroxy acid (Step 4) (95 g) in acetone (1 L) and K$_2$CO$_3$ (55 g, 2 eq) was added CH$_3$I (129 mL 2 eq.) and the mixture heated to reflux for 16 hr. The reaction mixture was cooled, EtOAc (1 L) was added, and the reaction filtered. Evaporation of the solvents afforded the title compound (93 g).

$^1$H NMR (CD$_3$COCD$_3$) δ (ppm): 1.10 (s, 9H), 1.80 (m, 2H), 2.80–3.00 (m, 2H), 3.80 (s, 3H), 4.20 (d, 1H), 4.50 (m, 1H), 6.65 (d, 1H), 6.80 (m, 2H), 7.05 (t, 1H), 7.23 (m, 1H), 7.30–7.50 (m, 7H), 7.70–7.90 (m, 5H).

Step 6

Methyl 5-chloro-2-(3-oxo-3-(3-t-butyldiphenylsiloxy)phenyl)-propyl)benzoate

A solution of the alcohol from Step 5 (93 g, 0.18 mol) in CH$_2$Cl$_2$ (0.3 L) was added dropwise to a suspension of pyridinium chlorochromate (PCC) (69 g, 0.3 mol) and 4 Å powdered molecular sieves (94 g) in CH$_2$Cl$_2$ (1 L) at approx. 10° C. The reaction mixture was stirred for 2 hrs. Ether (1 L) was then added and the mixture was passed through a 500 g pad of SiO$_2$. The pad was washed with Et$_2$O (2 L) and EtOAc:hexane 1:1 (2 L). The combined filtrates were combined and evaporated. Flash chromatography of the residue using 10% EtOAc in hexane afforded 81 g (87%) of the title compound.

$^1$H NMR (CD$_3$COCD$_3$) δ (ppm): 1.15 (s, 9H), 3.10–3.30 (m, 4H) 3.90 (s, 3H), 6.90 (s, 1H), 7.30 (t, 1H), 7.40–7.50 (m, 9H), 7.55 (s, 1H), 7.70–7.85 (m, 4H), 7.95 (s, 1H).

Step 7

(+) Methyl 5-chloro-2-(3-hydroxy-3-(3-(t-butyldiphenylsiloxy)-phenyl)propyl)benzoate To a solution of 44 g (82 mmol) of ketone from Step 6 in 180 mL of THF was added 1 g of (S)-tetrahydro-1-methyl-3,3-diphenyl-1H,3H-pyrrolo[1,2c]-[1,3,2]oxazaborole (J. Am. Chem. Soc. 109, 7925–6 (1987) at r.t. The solution was cooled to −20°, and 60 ml of borane-THF (1M) solution was added dropwise. The addition was completed in ca. 20 min., and the solution was stirred at −20° for 10 min. after addition. The reaction was then quenched by slow addition of 120 ml of 1N HCl and then partitioned between EtOAc and aq. NaCl. Drying, evaporation and chromatography of the residue on SiO2 with hexane:EtOAc 4:1 afforded 39 g of the title compound (89%). $[\alpha]_D = +9.4°$ (THF, c=4.4).

$^1$H NMR (CDCl$_3$) δ (ppm): 1.10 (s, 9H), 1.87 (m, 2H, CH$_2$), 2.60 (d, 1H, OH), 2.91 (t, 2H, CH$_2$), 3.86 (s, 3H, CH$_3$), 4.53 (t, 1H, CH) 6.63 (d, 1H, arom), 6.78 (s, 1H, arom), 6.88 (d, 1H, arom), 7.00–7.12 (m, 2H, arom), 7.38 (m, 7H, arom), 7.72 (d, 4H, arom), 7.90 (d, 1H, arom).

Step 8

Resolved Methyl 5-chloro-2-(3-hydroxy-3-(3-hydroxyphenyl)propyl)-benzoate

To a solution of 39 g (71 mmol) of the ester from Step 7, and 8 mL of HOAc in 600 mL of acetonitrile was added slowly 100 mL of tetrabutylammonium fluoride in THF (1M) at r.t. The reaction was stirred for 2 hr at r.t. and then partitioned between EtOAc and brine. Chromatographic purification on Si$_2$O with CH$_2$Cl$_2$:EtOAc 2:1 gave 22 g of crystalline title compound (93%). Recrystallization from hexane:EtOAc=2:1 gave 15.7 g of needle-like colorless crystals. From the mother liquor 5.5 g more of product were recovered by concentration of the solvent.

$^1$H NMR (CDCl$_3$) δ (ppm): 2.02 (m, 2H, CH$_2$), 3.00 (s, 1H, OH), 3.02 (t, 2H, CH$_2$), 3.88 (s, 3H, CH$_3$), 4.65 (t, 1H, CH), 5.51 (s, 1H, OH), 6.74 (dd, 1H, arom), 6.78 (m, 2H, arom), 7.20 (m, 2H, arom), 7.40 (dd, 1H, arom), 7.38 (d, 1H, arom).

Step 9

(+)-Methyl 5-chloro-2-(3-hydroxy-3-(3((7-chloro-2-quinolinyl)methoxy)phenyl)propyl)benzoate To a solution of 14.5 g (45 mmol) of phenol from Step 8 and 14 g (54 mmol) of 2-(bromomethyl)-7-chloroquinoline in 600 ml of acetonitrile was added 30 g of K$_2$CO$_3$ at r.t. The mixture was then heated at 70° for 3 hr. After cooling, the solid was filtered, the acetonitrile was partially evaporated and the reaction was partitioned between EtOAc and aq. NH$_4$Cl. Drying, evaporation and crystallization from toluene afforded 14.2 g of the title compound. The mother liquid was purified on SiO$_2$ with toluene:EtOAc 4:1 to give another 7.5 g of the title compound. Yield: 21.7 g (97%). $[\alpha]_D = +3.47°$ (THF, c=1.76).

$^1$H NMR (CDCl$_3$) δ (ppm): 2.00 (m, 2H, CH$_2$), 2.74 (d, 1H, OH), 2.98 (t, 2H, CH$_2$), 3.89 (s, 3H, CH$_2$), 4.68 (m, 1H, CH), 5.38 (s, 2H, CH$_2$), 6.90 (dd, 1H), 6.96 (d, 1H), 7.05 (s, 1H), 7.15 (d, 1H), 7.26 (t, 1H), 7.38 (dd, 1H), 7.48 (dd, 1H), 7.68 (d, 1H), 7.75 (d, 1H), 7.87 (d, 1H), 8.06 (s, 1H), 8.15 (d, 1H).

Step 10

(+)N,N-Dimethyl-5-chloro-2-(3-hydroxy-3-(3-((7-chloro-2-quinolinyl)methoxy)phenyl)-propyl)benzamide In 100 mL of toluene and 30 mL of 1,2-dichloroethane was dissolved 14 g (28.2 mmol) of ester from Step 9 by warming. To this solution was added 110 mL of Me$_2$NAlMe$_2$ in toluene (ca. 0.4M) at 30°. The reaction was stirred at 70° for 2 hr. and poured into ice cold aq. NH$_4$Cl. The product was extracted with EtOAc. After chromatographic purification on silica gel with toluene:EtOAc 1:1, 13.9 g (96%) of the title compound was isolated. $[\alpha]_D = +15.4°$ (THF, c=0.91).

$^1$H NMR (CDCl$_3$) δ (ppm): 2.10 (m, 2H, CH$_2$), 2.71 (t, 2H, CH$_2$), 2.89 (s, 3H, CH$_3$), 3.15 (s, 3H, CH$_3$), 4.53 (bt, 1H, CH), 5.38 (s, 2H, CH$_2$), 6.90 (dd, 1H), 6.95 (d, 1H), 7.05 (s, 1H), 7.18–7.38 (m, 4H), 7.53 (dd, 1H), 7.71 (d, 1H), 7.78 (d, 1h), 8.09 (s, 1H), 8.18 (d, 1H).

Step 11

Resolved N,N-dimethyl-5-chloro-2-(3-methane-sulfonyloxy-3-(3-((7-chloro-2-quinolinyl)-methoxy)phenyl)propyl)benzamide To a solution of 10 g (20 mmol) of amide from Step 10 and 8 ml (56 mmol) of triethylamine in 260 ml of CH$_2$Cl$_2$ was added dropwise 2.2 ml (28 mmol) of methanesulfonyl chloride at −40°. The reaction was stirred at this temperature for 15 min., warmed up to −10° within 30 min. and stirred at −10° for 1 hr. The reaction was quenched by pouring into ice-aq. NaHCO$_3$ and extracted twice with CH$_2$Cl$_2$. After removal of the solvent the crude title compound was used as such for the next step.

Step 12

(+) Methyl-3-((1-(3((7-chloro-2-quinolinyl)-methoxy)-phenyl)-3-(4-chloro-2-(dimethyl-aminocarbonyl)-phenyl)propyl)thio)propanoate The crude mesylate (ca. 20 mmol) from Step 11 was dissolved in 200 ml of acetonitrile. To the solution, which was degassed by bubbling argon through for a few min., was added 7.2 ml (60 mmol) of methyl 3-mercaptopropanoate, followed by 13.7 g (42 mmol) of Cs$_2$CO$_3$. The mixture was stirred at r.t. for 1 hr. The solid was filtered, the reaction was diluted with CH$_2$Cl$_2$ and washed twice with sat. NH$_4$Cl solution. Chromatographic purification with toluene:EtOAc 4:1 afforded 11 g (90%) of the title compound. $[\alpha]_D = 73°$ (THF, c=3.5).

$^1$H NMR (CDCl$_3$) δ (ppm): 2.06 (b, 2H, CH$_2$), 2.36–2.57 (m, 6H, 3CH$_2$), 2.74 (s, 3H, CH$_3$), 3.00 (s, 3H, CH$_3$), 3.66 (s, 3H, CH$_3$), 3.75 (t, 1H, CH), 5.38 (s, 2H, CH$_2$), 6.92 (d, 1H), 7.01 (s, 1H), 7.03–7.30 (m, 5H), 7.51 (dd, 1H), 7.71 (d, 1H), 7.77 (d, 1H), 8.07 (s, 1H), 8.18 (d, 1H).

Step 13

To a solution of 15.9 g of ester from Step 12 in 300 mL of methanol, 80 mL of aq. K$_2$CO$_3$ solution (1M) was added. The mixture was stirred under nitrogen at r.t. for 15 hr. The methanol was partially evaporated, and the reaction was neutralized by addition of 5 ml of HOAc. The product was then partitioned between aq. NH₄Cl and EtOAc containing 2% HOAc. The crude product was purified on silica gel with toluene:isopropanol 10:1 and then with toluene:isopropanol:acetic acid 10:1:0.1 to give 14.8 g (94%) of the title acid. $[\alpha]_D = -75.1°$ (THF, c=4.41)

$^1$H NMR (CDCl₃) δ: (ppm): 2.07 (b, 2H, CH₂), 2.42–2.60 (m, 6H, 3CH₂), 2.75 (s, 3H, CH₃), 3.03 (s, 3H, CH₃), 3.77 (t, 1H, CH), 5.39 (s, 2H, CH₂), 6.90 (d, 1H), 7.03 (s, 1H), 7.06–7.27 (m, 5H), 7.50 (dd, 1H), 7.70 (d, 1H), 7.77 (d, 1H), 8.09 (s, 1H), 8.18 (d, 1H).

Step 14

To a solution of the free acid in ethanol, 1 eq. of NaOH was added. The mixture was evaporated and the residue was dissolved in H₂O and freeze dried to yield the title compound.

EXAMPLE 367

3-((3-(4-Chloro-2-((ethoxycarbonyl)amino)phenyl)-1-(3-((7-chloro-2-quinolinylmethoxy)phenyl)propyl)thio)-propanoic acid, sodium salt Methyl 3-mercaptopropanoate was added to the lactone of Example 377, Step 3 (as in Example 229, Step 9), to yield a benzylic thioether. The acid function was then converted to the amine as described in the preparation of styrene 8, Step 1. Then, the carbamate was obtained by reaction with ethyl chloroformate and N-methylmorpholine in CH₂Cl₂ at r.t. in the presence of a catalytic amount of 4-(dimethylamino)pyridine. Finally, the ester was hydrolyzed as in Example 42, Step 2, to yield the title sodium salt.

Anal. calcd for C₃₁H₂₉Cl₂N₂O₅SNa·0.5H₂O: C, 57.77; H, 4.69; N, 4.35. Found: C, 57.93; H, 4.58; N, 4.15.

EXAMPLE 368

3-((3-(2-Chloro-6-(dimethylaminocarbonyl)phenyl)-1-(3-((7chloro-2-quinolinyl)methoxy)phenyl)propyl)thio)-propanoic acid Starting from 5-chloro-1-tetralone (Can. Pat. 048,579) and using the procedure of Example 366, Steps 1–5 and 8–13, the title compound was obtained.

$^1$H NMR (CD₃COCD₃) δ: 1.90–3.10 (15H, m), 4.00 (1H, t), 5.35–5.55 (2H, AB), 6.95–8.05 (11H, m), 8.40 (1H, d).

EXAMPLE 369

3-((3-(4-Chloro-2-(dimethylaminocarbonyl)phenyl)-1-(3-((7-chloro-2-quinolinyl)methoxy)phenyl)propyl)sulfinyl)propanoic acid, sodium salt To a solution of the title compound of Example 109 (300 mg, 0.502 mmol) in CH₂Cl₂ (2.5 mL) at 0° C. was added a solution of 85% m-CPBA (meta-chloroperbenzoic acid) (96 mg, 0.555 mmol) in CH₂Cl₂ (1 mL). When the reaction was completed (as shown by TLC with 40% acetone in toluene), 25% aq NH₄OAc was added. The product was extracted with EtOAc, dried over Na₂SO₄, filtered and evaporated at reduced pressure. The resulting mixture was purified by flash chromatography to provide 220 mg (73%) of the title acid, which was converted to its sodium salt (Example 366, Step 13).

$^1$H NMR (CD₃SOCD₃) δ: 1.9–2.6 (8H, m), 2.63, 2.65, 2.85 and 2.90 (6H, 4s), 3.80 (1H, m), 5.40 (2H, s), 6.90 (1H, m), 7.15 (2H, m), 7.20–7.40 (4H, m), 7.65 (1H, dd), 7.75 (1H, d), 8.05 (2H, m), 8.50 (1H, d).

EXAMPLE 370

3-((3-(3-Chloro-2-(dimethylaminocarbonyl)phenyl)-1-(3-((7-chloro-2-quinolinyl)methoxy)phenyl)thio)-propanoic acid, sodium salt

Step 1

N,N-Dimethyl 2-chloro-6-(3-(3-((7-chloro-2-quinolinyl)methoxy)phenyl)-3-oxo-1-propenyl)benzamide Using the procedure of Example 366, Step 10, Me₂AlNMe₂ was added to 7-chloro-3-hydroxy-1-(3H)-isobenzofuranone (J. Org. Chem., 49, 1078 (1984)) to give N,N-dimethyl 2-chloro-6-formylbenzamide. This aldehyde was then reacted with the ylid of Example 379, Step 3 as in Example 379, Step 5 to afford the title compound.

Step 2

N,N-Dimethyl 2-chloro-6-(3-(3-((7-chloro-2-quinolinyl)methoxy)phenyl)-3-oxopropyl)benzamide To a r.t. solution of the olefin of Step 1 (1.37 g, 2.71 mmol) in MeOH (10 mL) was added tris(triphenylphosphine)rhodium (I) chloride (200 mg) and the reaction was put under an H₂ atmosphere for 16 h. The reaction was filtered through celite, the solvent removed in vacuo and the residue passed over a plug of SiO₂ with EtOAc:hexanes 1:1. The whole operation was repeated to yield 700 mg of the title compound.

$^1$H NMR (C₆D₆) δ: 2.25 (3H, s), 2.70 (3H, s), 2.80–3.20 (3H, m), 3.35–3.75 (1H, m), 5.10 (2H, s), 6.70–7.50 (10H, m), 7.85 (1H, br d), 8.30 (1H, br d).

Step 3

Using the procedures of Example 29, Method B, Step 1 and of Example 366, Steps 11–13, the title compound was obtained.

Anal. calcd for C₃₁H₂₉Cl₂N₂O₄SNa·1.5H₂O: C, 57.59; H, 4.99; N, 4.33. Found: C, 57.47; H, 5.03; N, 4.40.

EXAMPLE 372

3-((1-(3-((7-Chloro-2-quinolinyl)methoxy)phenyl)-3-(2-(1H-tetrazol-5-yl)phenyl)propyl)thio)-2-methyl-propanoic acid, disodium salt

Step 1

3-Mercapto-2-methylpropanoic acid

Using the procedure of Example 113, Steps 1–2, ethyl 3-mercapto-2-methylpropanoate was obtained from ethyl methacrylate. The ester was then hydrolyzed as in Example 1, Step 8, to give the title thiol, which was purified by distillation; b.p. ≈ 100° C/0.5 mm Hg.

Step 2

Using the procedure of Example 40, but substituting N,N-dimethyl 3-mercapto-propanamide by 3-mercapto-2-methylpropanoic acid in Step 2 and using 2 equivalents of NaOH for the formation of the sodium salt in Step 3, the title compound was prepared.

Anal. calcd for C₃₀H₂₆ClN₅O₃SNa₂·6H₂O: C, 49.62; H, 5.27; N, 9.64. Found: C, 49.48; H, 5.29; N, 9.51.

EXAMPLE 373

3-((1-(3-((7-Chloro-2-quinolinyl)methoxy)phenyl)-3-(2-(aminocarbonyl)phenyl)propyl)thio)-2-methyl-propanoic acid, sodium salt Methyl 2-(3-(3-((7-chloro-2-quinolinyl)methoxy)-phenyl)-2-propenyl)benzoate (Example 29, Method B, Step 6) was hydrolyzed to the acid using the procedure of Example 29, Method A, Step 3. Using the procedure of Example 35, Step 2, but replacing tert-butylamine by ammonia, the amide was obtained. Then, 3-mercapto-2-methylpropanoic acid (Example 372, Step 1) was added as in Example 29, Method A, Step 1. The title sodium salt was finally obtained with one equivalent of NaOH as in Example 14, Step 2.

Anal. calcd for $C_{30}H_{28}ClN_2O_4SNa \cdot H_2O$: C, 61.17; H, 5.13; N, 4.76; Cl, 6.02. Found: C, 61.27; H, 4.94; N, 4.93; Cl, 6.28.

EXAMPLE 374

(+)
3-((1-(3-((7-Chloro-2-quinolinyl)methoxy)phenyl)-3-(2-(dimethylaminocarbonyl)phenyl)propyl)thio)propanoic acid, sodium salt

Step 1

(+) N,N-Dimethyl 2-(3-hydroxy-3-(3-tert-butyldiphenylsiloxy)phenyl)-propyl)benzamide Starting from α-tetralone and using the procedure of Example 366, Steps 1-6, methyl 2-(3-oxo-3-(3-(tert-butyldiphenylsiloxy)phenyl)propyl) benzoate was prepared. The ketone was reduced as in Example 366, Step 7, to afford the chiral alcohol. Finally, the ester was reacted with $Me_2AlNMe_2$ as in Example 366, Step 10, to give the title compound. $[\alpha]_D + 16.9$ (c=0.75, THF)

$^1$H NMR (CDCl$_3$)δ: 1.1 (9H, s), 1.9 (2H, m), 2.65 (2H, t), 2.8 (3H, s), 3.1 (3H, s), 4.35 (1H, m), 6.55 (1H, d), 6.75 (1H, s), 6.8 (1H, d), 7.0 (1H, t), 7.2 (4H, m), 7.4 (6H, m), 7.7 (4H, m).

Step 2

The secondary alcohol of Step 1 was inverted using a Mitsunobu reaction (see Synthesis, 1 (1981)) and hydrolysis as in Example 1, Step 8 to afford (−) N,N-dimethyl 2-(3-(3-hydroxyphenyl)-3-hydroxypropyl)-benzamide $[\alpha]_D - 34.1$ (c=1.10, THF). Finally, using the procedure of Example 366, Steps 9, 11-13, the phenol was converted to the title acid. $[\alpha]_D + 72.9$ (c=1.5, EtOH).

$^1$H NMR (CDCl$_3$) δ: 2.1 (2H, m), 2.45-2.6 (6H, m), 2.75 (3H, s), 3,1 (3H, s), 3.8 (1H, t), 5.38 (2H, s), 6.91 (2H, m), 7.05 (1H, s), 7.1-7.3 (5H, m), 7.5 (1H, dd), 7.7 (1H, d), 7.8 (1H, d), 8.1 (1H, s), 8.2 (1H, d).

For the title sodium salt:
Anal. calcd for $C_{31}H_{30}ClN_2O_4SNa \cdot 0.3H_2O$: C, 63.06; H, 5.22; N, 4.74. Found: C, 63.03; H, 5.15; N, 4.66.

EXAMPLE 375

(−)
3-((1-(3-((7-Chloro-2-quinolinyl)methoxy)phenyl)-3-(2-(dimethylaminocarbonyl)phenyl)propyl)thio)propanoic acid, sodium salt Using the procedure of Example 374, but omitting the inversion of the chiral benzylic alcohol, the title compound was obtained. $[\alpha]_D$ of the acid −68° (c=1.10, EtOH).

Anal. calcd for $C_{31}H_{30}ClN_2O_4SNa \cdot H_2O$: C, 62.78; H, 5.27; N, 4.72. Found: C, 62.55; H, 5.25; N, 4.62.

EXAMPLE 376

5-Bromo-2-(3-((2-carboxyethyl)thio)-3-(3-((7-chloro-2-quinolinyl)methoxy)phenylpropyl)benzoic acid. disodium salt Using the procedures of Example 366, Steps 1-5, 8, 9, 11, 12 and Example 14, Step 2, 7-bromo-1-tetralone was converted to the title compound.

Anal. calcd for $C_{29}H_{23}NO_5SClBrNa_2 \cdot 1H_2O$: C, 51.46; H, 3.72; N, 2.07, Br, 11.8. Found: C, 51.02; H, 3.47; N, 1.98; Br, 11.35.

EXAMPLE 377

3-((1-(3-((7-Chloro-2-quinolinyl)methoxy)phenyl)-3-(4-chloro-2-(dimethylaminocarbonyl)phenyl)propyl)thio)-butanoic acid, sodium salt

Step 1

Methyl 3-(acetylthio)butanoate

A mixture of thiolacetic acid (15.2 g, 199 mmol) and methyl crotonate (10.0 g, 100 mmol) was heated at 70° C. After 2 days, the reaction mixture was allowed to cool to r.t. 25% aq NH$_4$OAc was added and the product was extracted with EtOAc, dried over Na$_2$SO$_4$ and evaporated under reduced pressure. The title compound was distilled (75° C./0.5 mm Hg) as a yellow oil (14.8 g, 90.0%).

$^1$H NMR (CD$_3$COCD$_3$) δ: 1.35 (3H, d), 2.26 (3H, s), 2.63 (2H, m), 3.65 (3H, s), 3.85 (1H, m).

Step 2

Methyl 3-mercaptobutanoate

To a solution of the ester of Step 1 (5.0 g, 28.4) in MeOH (140 mL) at 0° C. was added K$_2$CO$_3$ (32.0 g, 231 mmol). After 15 min, the reaction was quenched by the addition of 25% aq. NH$_4$OAc and the title compound was extracted with EtOAc, dried with Na$_2$SO$_4$ and evaporated. The title thiol was obtained at a colorless oil (3.00 g, 79%).

$^1$H NMR (CD$_3$COCD$_3$) δ: 1.30 (3H, d), 2.13 (1H, d), 2.55 (2H, m), 3.30 (1H, m), 3.62 (3H, s).

Step 3

8-Chloro-3-(3-((7-chloro-2-quinolinyl)methoxy)-phenyl)-4,5-dihydro-2-benzoxepin-1(3H)-one Using the procedure of Example 229, Steps 6-8, the hydroxyacid of Example 366, Step 4, was converted to the title lactone.

$^1$H NMR (CD$_3$COCD$_3$) δ: 2.35 (2H, m), 3.00 (2H, m), 5.15 (1H, dd), 5.47 (2H, s), 7.00 (2H, m), 7.23 (1H, d), 7.29 (1H, t), 7.40 (1H, d), 7.60 (3H, m), 7.75 (1H, d), 8.00 (2H, m), 8.40 (1H, d).

Step 4

Using the procedure of Example 229, Step 9, the thiol of Step 2 was added to the lactone of Step 3. Then using the procedure of Example 229, Step 10, but replacing ammonia for dimethylamine, the title compound was obtained.

Anal. calcd for $C_{32}H_{31}Cl_2N_2O_4SNa \cdot H_2O$: C, 59.03; H, 5.06; N, 4.30. Found: C, 59.38; H, 5.05; N, 4.33.

EXAMPLE 379

3-((1-(3-((7-Chloro-2-quinolinyl)methoxy)phenyl)-3-(5-(dimethylaminocarbonyl)-2-furanyl)propyl)thio)-propanoic acid, sodium salt

Step 1

1-(3-((7-Chloro-2-quinolinyl)methoxy)phenyl)ethanone

To 3-((7-chloro-2-quinolinyl)methoxy)benzaldehyde, MeMgBr was added (in THF at 0° C.) to give an ethanol derivative, which was oxidized to the title compound as in Example 29, Method B, Step 5.

$^1$H NMR (CD$_3$COCD$_3$) δ: 2.56 (s, 3H, CH$_3$CO), 5.44 (s, 2H, OCH$_2$) 7.34 (m, 1H), 7.44 (m, 1H), 7.5–7.7 (m, 3H), 7.72 (d, 1H, J=8.6 Hz), 7.95–8.10 (m, 2H), 8.41 (d, 1H, J=8.6 Hz)

Step 2

2-Bromo-1-(3-((7-chloro-2-quinolinyl)methoxy)phenyl)ethanone

A solution of the ketone of Step 1 (10.9 g, 35 mmol) in HOAc (210 mL) was treated with NaBrO$_3$ (1.75 g, 11.7 mmol) in H$_2$O (35 mL), and then 48% HBr (35 mL) was added dropwise. The yellow suspension was stirred for 5 min. and then the flask was transferred to an oil-bath preheated to 105° C. In 11 min, the solid had dissolved. After stirring at 105° C. for a further 5 min, the reaction mixture was cooled in an ice-bath before collecting the hydrobromide of the product.

The free base was isolated by basification with NaHCO$_3$ and extraction with EtOAc. The solid was slurried with diisopropyl ether, filtered off and dried to give 9.08 g (66%) of the title compound, m.p. 110°–112° C.

Step 3

1-(3-((7-Chloro-2-quinolinyl)methoxy)phenyl)-2-(triphenylphosphoranylidine)ethanone A solution of the bromoketone of Step 2 (8.78 g, 22.5 mmol) and triphenylphosphine (5.90 g, 22.5 mmol) in CH$_2$Cl$_2$ (45 mL) was allowed to stand at room temperature for 2 h. 1N NaOH (66 mL) was added, and the mixture was stirred vigorously for 2 hours. Addition of toluene and evaporation of the CH$_2$Cl$_2$ gave 11.44 g (89%) of the title product as a solid, m.p. 187°–188° C.

Anal. calcd for C$_{36}$H$_{27}$ClNO$_2$P: C, 75.59; H, 4.76; N, 2.45; P, 5.41. Found: C, 75.42; H, 4.75; N, 2.61; P, 5.03.

Step 4

N,N-Dimethyl-5-formyl-2-furan-carboxamide

N,N-Dimethyl-2-(2-Furanyl)imidazoline (A. J. Carpenters and D. J. Christwick, Tetrahedron, 41, 3803 (1985)) (8.25 g, 50 mmol) in dry THF (125 mL) was lithiated with 1.6M n-butyl lithium (33 mL). After 2 h at −78° C., the solution was transferred by a cannula to a stirred solution of dimethylcarbamoyl chloride (5.0 mL, 54.5 mmol) in THF (10 mL) at −100° C. Stirring at −100° C. was continued for 15 min, and then the mixture was allowed to attain room temperature. After another 2 h, 1M H$_2$SO$_4$ (150 mL) was added and the mixture was stirred for an hour. Extraction with EtOAc (5×100 mL) gave a crude product which was purified by column chromatography (200 g of silica gel eluted with 1:2 EtOAc:hexane containing 10% of tert-butanol) to give 5.45 (65%) of title product, m.p. 75°–76° C.

Anal. calcd for C$_8$H$_9$NO$_3$: C, 57.48; H, 5.43; N, 8.38. Found: C, 57.57; H, 5.18; N, 8.07.

Step 5

N,N-Dimethyl 5-(3-(3-((7-chloro-2-quinolinyl)methoxy)phenyl)-3-oxo-1-propenyl)-2-furancarboxamide A mixture of the furancarboxaldehyde of Step 4 (1.25 g, 7.5 mmol), the phosphoranylidene of Step 3 (4.29 g, 7.5 mmol) and toluene (43 mL) was heated at 80° C. for 4 h. When cool, a small amount of insoluble material was filtered off, and the solution was evaporated onto silica gel (30 g). The solid was placed on top of a column of silica gel (300 g), and eluted with 1:10:100:100 formic acid:tert-butanol:ethyl acetate:toluene to yield 4.78 g of a mixture. Recrystallization of this solid from acetonitrile (25 mL) gave the title product 2.52 g (73%), m.p. 141°–142° C.

Anal. calcd for C$_{26}$H$_{21}$ClN$_2$O$_4$: C, 67.75; H, 4.59; Cl, 7.69; N, 6.08. Found: C, 67.49; H, 4.49; Cl, 7.88; N, 6.13.

Step 6

N,N-Dimethyl 5-(3-(3-((7-chloro-2-quinolinyl)methoxy)phenyl)-3-oxopropyl)-2-furancarboxamide Tellurium (650 mg, 5 mmol) was dissolved in EtOH (20 mL) containing NaBH$_4$ (450 mg, 11.8 mmol). Reaction started spontaneously, and was completed by heating at reflux for 30 min. The unsaturated ketone of Step 5 (920 mg, 2 mmol) was added, and the mixture was stirred at room temperature for 7 hours. Methanol (20 mL) was added, and the solution was filtered through celite. After evaporation, the product was isolated by partitioning between a mixture of Et$_2$O, EtOAc and H$_2$O, followed by column chromatography (silica gel eluted with 1:2 EtOAc:hexane containing 10% of tert-butanol) to yield 246 g (27%), mp 129°–131° C.

Step 7

Using the procedures of Example 29, Method B, Steps 1 and 2, the ketone of Step 6 was converted to the benzylic bromide, which was reacted with methyl 3-mercaptopropanoate in the presence of Cs$_2$CO$_3$ in acetonitrile. Finally, hydrolysis of the ester as in Example 29, Method A, Step 3 with 2 equiv of NaOH afforded the title product.

Anal. calcd for C$_{29}$H$_{28}$ClN$_2$O$_5$Na·2H$_2$O: C, 57.00; H, 5.28;, N, 4.54. Found: C, 57.37; H, 4.93; N, 4.28.

EXAMPLE 381

3-((3-(2-(Acetylamino)-4-chlorophenyl)-1-(3-((7-chloro-2-quinolinyl)methoxy)phenyl)propyl)thio)-propanoic acid To the aniline prepared as an intermediate in Example 367 (440 mg, 0.8 mmol), dissolved in CH$_2$Cl$_2$ at room temperature were added triethylamine (660 μL, 4.8 mmol), acetyl chloride (170 μL, 2.4 mmol) and 4-dimethylaminopyridine (10 mg, 0.08 mmol). The solution was stirred 5 hours before adding a saturated aqueous solution of NH$_4$Cl. Extraction with CH$_2$Cl$_2$ followed by drying over MgSO$_4$ and evaporation of the solvent in vacuo gave the crude product as a solid. The pure amide (267 mg) was obtained along with an impure fraction (217 mg) simply by swishing it in Et$_2$OAc 95:5 followed by filtration and drying. The ester was then hydrolyzed as in Example 42, Step 2 to give the title acid.

$^1$H NMR (CD$_3$COCD$_3$) δ: 2.02 (3H, s), 2.10 (2H, m), 2.35–2.80 (6H, m), 3.88 (1H, dd), 5.40 (2H, s), 6.95–7.35 (6H, m), 7.60 (1H, dd), 7.75 (2H, br d), 8.0 (1H, d), 8.05 (1H, d), 8.40 (1H, d), 8.55 (1H, br s, NH).

EXAMPLE 382

3-((1-(3-((7-Chloro-2-quinolinyl)methoxy)phenyl)-3-(4-chloro-2-(((methylsulfonyl)amino)carbonyl)phenyl)-propyl)thio)propanoic acid, disodium salt Methyl 3-mercaptopropanoate was added to the lactone of Example 377, Step 3 (as in Example 229, Step 9) to yield a benzylic thioether. Using the procedure of Example 152, Steps 2–3, but substituting p-toluenesulfonamide in Step 2 for methylsulfonamide, the title compound was obtained.

Anal. calcd for C$_{30}$H$_{26}$Cl$_2$N$_2$O$_6$S$_2$Na$_2$: C, 52.10; H, 3.79; N, 4.05. Found: C, 52.20; H, 3.69; N, 4.77.

EXAMPLES 383, 384 AND 388

Using the procedure of Example 229, Step 9 and Example 42, Step 2, the lactone of Example 377, Step 3, was converted to the following compounds. For Examples 383 and 384, Thiols 5 and 13 were used in place of methyl 3-mercapto-2-methoxypropanoate.

EXAMPLE 383

5-Chloro-2-(3-((2-carboxybutyl)thio)-3-(3-((7-chloro-2-quinolinyl)methoxy)phenyl)propyl)benzoic acid, disodium salt.

Anal. calcd for C$_{31}$H$_{27}$Cl$_2$NO$_5$SNa$_2$·0.5H$_2$O: C, 57.15; H, 4.33; N, 2.15. Found: C, 57.00; H, 4.32; N, 2.11.

EXAMPLE 384

5-Chloro-2-(3-((2-carboxypropyl)thio)-3-(3-((7-chloro-2-quinolinyl)methoxy)phenyl)propyl)benzoic acid, disodium salt.

Anal. calcd for C$_{30}$H$_{25}$Cl$_2$NO$_5$SNa$_2$·0.5H$_2$O: C, 56.52; H, 4.11; N, 2.20. Found: C, 56.73; H, 4.13; N, 2.18.

EXAMPLE 388

5-Chloro-2-(3-(3-((7-chloro-2-quinolinyl)methoxy)-phenyl)-3-(2-carboxy-2-methoxyethyl)thio)propyl)benzoic acid, disodium salt.

Anal. calcd for C$_{30}$H$_{25}$Cl$_2$NO$_6$SNa$_2$·0.5H$_2$O: C, 55.14; H, 4.01; N, 2.14. Found: C, 54.71; H, 3.72; N, 2.05.

EXAMPLE 395

2-(3-((2-Carboxyethyl)thio)-3-(3-((7-chloro-2-quinolinyl)methoxy)phenyl)propyl)-5-phenylbenzoic acid The diacid of Example 376 (380 mg, 0.6 mmol) and phenylboronic acid (295 mg, 2.4 mmol) were placed in a 2 neck flask which was purged 5 minutes with nitrogen. Toluene (6 mL) and 2M aqueous Na$_2$CO$_3$ (1.2 mL) were introduced and the flask was purged again by 3 cycles of vacuum and nitrogen flushing. Tetrakis(triphenylphosphine)palladium (0) (45 mg, 0.06 mmol) was added and the resulting mixture was refluxed for 4 hours with careful exclusion of air. The mixture was then cooled to room temperature, 1M HCl was added and the aqueous phase was extracted with EtOAc. The combined organic phases were dried over MgSO$_4$ and concentrated in vacuo. The residue was purified by flash chromatography on SiO$_2$ (17:80:3 EtOAc:toluene:acetone) to give the title compound (340 mg).

$^1$H NMR of the diacid (CD$_3$COCD$_3$) δ: 2.18 (2H, m), 2.43 (2H, m), 2.55 (2H, m), 2.88 (1H, m), 3.05 (1H, m), 3.98 (1H, dd), 5.42 (2H, s), 7.0 (2H, m), 7.15–7.8 (11H, m), 7.98 (1H, d), 8.05 (1H, d), 8.18 (1H, d), 8.40 (1H, d).

EXAMPLE 400

3-((1-(3-((7-Chloro-2-quinolinyl)methoxy)phenyl)-3-(2-(dimethylaminocarbonyl)-3-pyridinyl)propyl)thio)-propanoic acid, sodium salt Ketoester 2 was reacted with 2-propyl 3-(bromomethyl)-2-pyridinecarboxylate (J. Med. Chem., 1989, 32, 827) as in Example 402, Step 3, except that the treatment with MeI/K$_2$CO$_3$ was avoided, to give a ketoester. The ketone was reduced with NaBH$_4$ (Example 402, Step 4), the ester was hydrolyzed with NaOH, and the hydroxyacid was lactonized (Example 229, Step 6). The title product was obtained from the lactone as in Example 366, Steps 10–13.

Anal. calcd for C$_{30}$H$_{29}$ClN$_3$O$_4$SNa: C, 61.48; H, 4.99; N, 7.17. Found: C, 61.62; H, 5.18; N, 7.06.

EXAMPLE 402

3-((3-(4-Chloro-2-(dimethylaminocarbonyl)phenyl)-1-(3-(2-(7-chloro-2-quinolinyl)ethenyl)phenyl)propyl)thio)propanoic acid

Step 1

1-(3-(2-(7-Chloro-2-quinolinyl)ethenyl)phenyl)ethanone

To 3-(2-(7-chloro-2-quinolinyl)ethenyl)benzaldehyde, MeMgBr was added (in THF at 0° C.) to give an ethanol derivative, which was oxidized to the title compound as in Example 29, Method B, Step 5.

$^1$H NMR (CD$_3$COCD$_3$) δ: 2.68 (3H, s), 7.55–7.68 (3H, m), 7.89–8.05 (6H, m), 8.36 (2H, m).

Step 2

Methyl 3-(3-(2-(7-chloro-2-quinolinyl)ethenyl)phenyl)-3-oxopropanoate

In a 500 mL flask fitted with a condenser were suspended the ketone of Step 1 (57.05 g, 185 mmol) and dimethylcarbonate (13.70 mL, 2.5 equiv.) in THF (230 mL). 80% NaH (16.70 g, 3 equiv.) was added portionwise over a few minutes and the reaction was initiated through the addition of MeOH (370/l). The mixture was stirred at r.t. The solids gradually dissolved and when the evolution of hydrogen has subsided, the mixture was heated at 70° C. for 1 h. After cooling to r.t., it was poured onto cold 25% aq NH$_4$OAc. The solid was collected and air dried and swished in EtOH (600 mL) containing EtOAc (50 mL) for 18 h. The title compound was collected as a pale beige solid, 60.3 g, 89%.

$^1$H NMR (CD$_3$COCD$_3$) δ: 3.70 (s, 3H); 3.73 (small peak, OCH$_3$ of enol form); 7.45–7.70 (m, 6H); 7.80–8.10 (m, 3H), 8.36 (d, 2H).

Step 3

Methyl 2-(3-(3-(2-(7-chloro-2-quinolinyl)ethenyl)phenyl)-3-oxopropyl)benzoate

To a solution of the β-ketoester of Step 2 (50.0 g, 0.136 mol) and the iodide 1 (41.5 g, 1.1 equiv.) in DMF at 0° C. was added 80% NaH (4.51 g, 1.1 equiv.). The ice bath was removed and the mixture was stirred at r.t. After 2 h, when no starting material remained, the reaction mixture was poured onto cold 25% aq NH₄OAc. The solid collected was swished in EtOH (60 mL) overnight to afford 60.0 g (97%) of the pure adduct.

The above material was suspended in EtOAc/conc. HCl mixture (1.2 L/240 mL) and heated at 90° C. for 4 h. After it was cooled to r.t., it was poured onto cold aq NH₄Cl. The solid was collected and air dried.

The above mixture (containing the title ester and its acid) was suspended in acetone (500 mL) containing MeI (4.25 mL) and powdered K₂CO₃ (18 g). The mixture was heated at 50° C. for 3 h until the methylation was complete. The reaction mixture was partitioned between EtOAc and H₂O. The aqueous phase was extracted with EtOAc (x2) and the combined organic phase was washed with brine, dried and concentrated. The resulting residue was recrystallized from EtOAc:- hexane 1:1 to afford 37.7 g (53%) of the title compound.

Step 4

Methyl 2-(3-(3-(2-(7-chloro-2-quinolinyl)ethenyl)phenyl)-3-hydroxypropyl)benzoate To a solution of the ketone of Step 3 (4.24 g, 9.31 mmol) in THF (60 mL) and MeOH (20 mL) at 0° C. was added in one portion NaBH₄ (460 mg, 1.3 equiv.). The mixture was stirred for 30 min at r.t. and the reaction was quenched by the addition of acetone ($\approx$1 mL). The solvent was removed and the residue was partitioned between EtOAc and H₂O. Conventional work-up of the organic phase gave a residue which was purified by flash chromatography (EtOAc:hexane 1:3 and 1:2) to give 3.84 g (90%) of the title compound as a foam.

Step 5

Using the procedure of Example 366, Steps 10–13, the title compound was obtained.

¹H NMR (CD₃COCD₃) δ: 2.20 (2H, m), 2.45–2.75 (6H, m), 2.78 (3H, s), 2.97 (3H, s), 4.03 (1H, t), 7.19 (1H, s), 7.33 (2H, s), 7.39–7.55 (4H, m), 7.65 (1H, m), 7.77 (1H, s), 7.85–8.02 (4H, m), 8.33 (1H, d).

EXAMPLE 403

3-((1-(3-((7-Chloro-2-quinolinyl)methoxy)phenyl)-3-(4-chloro-2-(1H-tetrazol-5-yl)phenyl)propyl)thio)-propanoic acid, disodium salt Using the procedure of Example 366, Step 10, but using Me₂AlNH₂ at 75° C., the lactone of Example 377, Step 3, was opened to the hydroxynitrile. Then, using the procedures of Examples 366, Steps 11–12, Example 41, Step 4 and Example 366, Step 13, the title tetrazole was obtained.

¹H NMR (disodium salt) (CD₃COCD₃:CD₃SOCD₃) δ: 1.95–2.30 (4H, m), 2.40–2.60 (2H, t), 2.75–2.90 (1H, m), 3.10–3.30 (1H, m), 3.85–3.95 (1H, t), 5.40 (2H, s), 6.90–7.30 (7H, m), 7.60–8.10 (4H, m), 8.5 (1H, d).

Anal. calcd for C₂₉H₂₃Cl₂N₅O₃SNa₂·3H₂O: C, 50.30; H, 4.22; N, 10.11. Found: C, 50.54; H, 4.24; N, 10.12.

EXAMPLE 404

3-((1-(3-((7-Chloro-2-quinolinyl)methoxy)phenyl)-3-(2-cyanophenyl)propyl)thio)-2-methylpropanoic acid, sodium salt The acid of the title compound was obtained as the last intermediate in the synthesis of the product of Example 372 (before the treatment with Bu₃SnN₃). The sodium salt was obtained as in Example 372 except that one equiv. of NaOH was used.

Anal. calcd for C₃₀H₂₆ClN₂O₃SNa·0.7H₂O: C, 63.70; H, 4.88; N, 4.95. Found: C, 63.71; H, 4.83; N, 4.74.

EXAMPLE OF TABLE 2

Using the procedure of Examples 43, 113, 373 and 29, Method B, the compounds of Table 2 were obtained from Styrenes 1–9 and methyl 2-(3-(3((6-methoxy-2-quinolinyl)methoxy)phenyl)-2-propenyl)benzoate (obtained from Quinoline 4 and 3-hydroxybenzaldehyde, using the procedures of Example 366, Step 9 and Example 29, Method B, Steps 1–6), Thiols 1–12 and the following amines: ammonia, methylamine, dimethylamine, ethylamine, diethylamine, tert-butylamine, iso-butylamine, piperidine, pyrolidine and morpholine.

TABLE 2

| Ex. | Formula | Calculated | | | Found | | |
|---|---|---|---|---|---|---|---|
| | | C | H | N | C | H | N |
| 54 | C₃₀H₂₈ClN₂O₄SNa·1.5H₂O | 60.24 | 5.22 | 4.68 | 60.56 | 5.31 | 4.53 |
| 65 | C₃₂H₃₄N₂O₄S | NMR data below | | | | | |
| 68 | C₃₄H₃₂ClN₂O₄SNa·0.5H₂O | 64.40 | 5.56 | 4.42 | 64.19 | 5.46 | 4.35 |
| 69 | C₃₃H₃₂ClN₂O₅SNa·H₂O | 61.42 | 5.23 | 4.34 | 61.22 | 5.25 | 4.23 |
| 75 | C₃₂H₃₂ClN₂O₄SNa·1.7H₂O | 61.03 | 5.67 | 4.45 | 60.90 | 5.41 | 4.35 |
| 91 | C₃₂H₃₂ClN₂O₃SNa·1.5H₂O | 62.99 | 5.78 | 4.59 | 62.99 | 5.58 | 4.48 |
| 92 | C₃₃H₃₄ClN₂O₃SNa·0.5H₂O | 65.39 | 5.82 | 4.62 | 65.96 | 6.45 | 4.39 |
| 95 | C₃₃H₃₄ClN₂O₄SNa·0.3H₂O | 64.08 | 5.64 | 4.53 | 64.16 | 5.68 | 3.94 |
| 97 | C₃₂H₃₀ClN₂O₃SNa | NMR data below | | | | | |
| 99 | C₃₁H₂₉ClN₂O₃S | NMR data below | | | | | |
| 100 | C₃₃H₃₄ClN₂O₄SNa·H₂O | 62.75 | 5.78 | 4.43 | 62.90 | 5.64 | 4.30 |
| 103 | C₃₄H₃₆ClN₂O₃SNa·0.5H₂O | 65.75 | 6.15 | 4.67 | 65.85 | 6.01 | 4.52 |
| 104 | C₃₃H₃₄ClN₂O₄SNa·0.5H₂O | 63.70 | 5.67 | 4.5 | 0.30 | | |
| 106 | C₃₃H₃₂ClN₂O₄SNa·0.5H₂O | 63.90 | 5.32 | 4.51 | 64.02 | 5.42 | 4.39 |
| 107 | C₃₃H₃₂ClN₂O₄SNa·0.5H₂O | 63.91 | 5.36 | 4.52 | 63.65 | 5.40 | 4.40 |
| 108 | C₃₄H₃₄ClN₂O₃SNa·H₂O | 65.11 | 5.79 | 4.47 | 64.77 | 5.92 | 4.12 |
| 112 | C₃₃H₃₂ClN₂O₃SNa·0.5H₂O | 65.60 | 5.51 | 4.64 | 65.70 | 5.59 | 4.42 |
| 114 | C₃₁H₃₀ClN₂O₃SNa·H₂O | 63.41 | 5.49 | 4.77 | 63.50 | 5.21 | 4.68 |
| 115 | C₃₂H₃₂ClN₂O₃SNa·2H₂O | 62.08 | 5.86 | 4.52 | 62.50 | 5.79 | 4.36 |
| 116 | C₃₁H₂₈ClNO₄SNa₂·1.5H₂O | 60.14 | 5.05 | 2.26 | 60.17 | 4.89 | 2.22 |
| 118 | C₃₂H₃₂ClN₂O₄SNa·1.5H₂O | 61.38 | 5.63 | 4.47 | 61.58 | 5.55 | 4.27 |
| 119 | C₃₃H₃₄ClN₂O₄SNa·0.6H₂O | 63.51 | 5.68 | 4.48 | 63.40 | 5.76 | 4.29 |
| 120 | C₃₁H₃₀ClN₂O₄SNa·1.2H₂O | 61.36 | 5.34 | 4.61 | 61.33 | 5.33 | 4.39 |
| 121 | C₃₄H₃₆ClN₂O₄SNa·0.6H₂O | 64.00 | 5.83 | 4.34 | 64.12 | 5.91 | 4.23 |
| 122 | C₃₂H₃₂ClN₂O₄SNa·0.5H₂O | 63.20 | 5.47 | 4.61 | 63.08 | 5.53 | 4.38 |
| 126 | C₃₂H₃₂ClN₂SO₃Na·1.5H₂O | 63.04 | 5.65 | 4.58 | 63.38 | 5.66 | 4.52 |
| 154 | C₃₁H₃₀ClN₂O₄SNa·0.7H₂O | 62.30 | 5.30 | 4.69 | 62.32 | 5.17 | 4.63 |

TABLE 2-continued

| Ex. | Formula | Calculated | | | Found | | |
|---|---|---|---|---|---|---|---|
| | | C | H | N | C | H | N |
| 157 | $C_{32}H_{32}ClN_2O_4SNa.5H_2O$ | 55.77 | 6.14 | 4.06 | 55.33 | 6.11 | 4.53 |
| 159 | $C_{36}H_{36}ClN_2O_4SNa.4H_2O$ | 58.40 | 6.34 | 4.01 | 58.31 | 6.26 | 3.81 |
| 174 | $C_{32}H_{32}ClN_2O_5SNa.0.5H_2O$ | 61.58 | 5.33 | 4.49 | 61.83 | 5.27 | 4.39 |
| 176 | $C_{33}H_{34}ClN_2O_4SNa.0.5H_2O$ | 63.71 | 5.67 | 4.50 | 63.89 | 5.62 | 4.46 |
| 180 | $C_{33}H_{35}ClN_2O_5S$ | NMR data below | | | | | |
| 231 | $C_{32}H_{30}ClF_3N_2O_4S_2Na_2.6H_2O$ | 47.03 | 5.18 | 3.43 | 47.32 | 5.07 | 3.64 |
| 255 | $C_{31}H_{31}ClNO_5S_2Na$ | NMR data below | | | | | |
| 309 | $C_{36}H_{40}ClN_2O_3SNa.4H_2O$ | 60.79 | 6.80 | 3.94 | 60.65 | 6.86 | 4.12 |
| 344 | $C_{31}H_{28}ClNO_2SNa.1.5H_2O$ | 58.62 | 4.88 | 2.20 | 58.75 | 5.09 | 2.15 |
| 355 | $C_{33}H_{32}ClN_2O_3SNa.1.5H_2O$ | 63.70 | 5.67 | 4.50 | 63.80 | 5.66 | 4.35 |
| 361 | $C_{29}H_{27}ClNO_5S_2Na.H_2O$ | 57.09 | 4.79 | 2.30 | 57.12 | 4.71 | 2.25 |
| 363 | $C_{32}H_{31}Cl_2N_2O_3SNa.2.5H_2O$ | 58.01 | 5.48 | 4.23 | 57.92 | 5.31 | 3.98 |
| 378 | $C_{34}H_{37}ClN_2O_3S$ | NMR data below | | | | | |

EXAMPLE 65 (ACID)

$^1$H NMR ($CD_3COCD_3$) δ: 2.10 (2H, m), 2.30–2.60 (6H, m), 2.70 (3H, s), 2.90 (3H, s), 3.90 (1H, t), 3.90 (3H, s), 5.30 (2H, s), 6.90 (1H, dd), 7.00–7.40 (9H, m), 7.65 (1H, d), 7.85 (1H, d), 8.20 (1H, d).

EXAMPLE 97 (SODIUM SALT)

$^1$H NMR ($CD_3COCD_3$:$CD_3SOCD_3$) δ: 2.1–2.3 (4H, m), 2.4–2.7 (4H, m), 2.75 (3H, s), 2.9 (3H, s), 3.95 (1H, t), 7.0–8.0 (14H, m), 8.38 (1H, d).

EXAMPLE 99 (ACID)

$^1$H NMR ($CD_3COCD_3$) δ: 2.2–2.4 (2H, m), 2.5–2.7 (4H, m), 2.7–3.0 (2H, m), 2.9 (3H, d), 4.0 (1H, t), 7.20–7.95 (14H, m), 8.05 (1H, br d), 8.35 (1H, d).

EXAMPLE 180 (ACID)

$^1$H NMR ($CD_3COCD_3$) δ: 0.8 (3H, 2t, a mixture of diastereoisomers), 1.20 (3H, t), 1.50 (2H, m), 2.05–3.0 (7H, m), 3.88 (1H, q), 4.10 (2H, 2q), 5.40 (2H, s), 6.95–7.35 (6H, m), 7.52 (1H, br d), 7.59 (1H, dd), 7.75 (2H, d), 8.00 (1H, d), 8.03 (1H, d), 8.40 (1H, d).

EXAMPLE 255 (SODIUM SALT)

$^1$H NMR ($CD_3COCD_3$) δ: 0.71 (3H, m, mixture of diastereomers), 1.46 (2H, m), 2.05–3.16 (10H, m), 3.91 (1H, 2t), 5.33 (2H, s), 6.83–7.05 (2H, m), 7.16 (2H, m), 7.33 (2H, m), 7.53 (2H, m), 7.70 (1H, d), 7.91 (2H, t), 8.00 (1H, br s), 8.33 (1H, d).

EXAMPLE 378 (ACID)

$^1$H NMR ($CD_3COCD_3$) δ: 0.82 (3H, m, mixture of diasteromers), 1.5 (2H, m), 2.06 (1H, m), 2.3–2.7 (6H, m), 2.85 (3H, 2s), 2.97 (3H, 2s), 3.14 (2H, m), 3.78 (2H, m), 3.84 (1H, m), 7.1–7.3 (8H, m), 7.41 (1H, d), 7.48 (1H, dd), 7.87 (1H, d), 8.0 (1H, s), 8.20 (1H, d).

EXAMPLES OF TABLE 3

The styrene-ester of Example 28, Step 1, was transformed to an amide using $Me_2AlNMe_2$ or $Me_2AlNH$-tBu as in Example 366, Step 10. It was then converted to the final product as in Example 28, Steps 2 and 3. In some cases, Quinolines 1–3 were used instead of 2-(bromomethyl)-7-chloroquinoline.

TABLE 3

| Ex. | Formula | Calculated | | | Found | | |
|---|---|---|---|---|---|---|---|
| | | C | H | N | C | H | N |
| 62 | $C_{31}H_{31}N_2O_4SNa.1.5H_2O$ | 64.46 | 5.93 | 4.85 | 64.40 | 6.04 | 4.78 |
| 63 | $C_{31}H_{29}Cl_2N_2O_4SNa.H_2O$ | 58.40 | 4.90 | 4.39 | 58.94 | 4.71 | 4.36 |
| 64 | $C_{32}H_{33}N_2O_6S_2Na.2.3H_2O$ | 57.35 | 5.66 | 4.18 | 57.20 | 5.77 | 4.01 |
| 67 | $C_{33}H_{34}ClN_2O_4SNa.3.2H_2O$ | 59.09 | 6.07 | 4.18 | 58.99 | 6.11 | 3.96 |

EXAMPLES OF TABLE 4

Starting with the lactones of Example 377, Step 3 and Example 229, Step 8, and using the procedures of Example 366, Steps 10–13, the compounds of Table 4 were obtained. Thiols 1, 4, 6, 14 and 15 and $Me_2AlNMe_2$ and $Me_2AlNH_2$ (at 65° C.) were used in their syntheses.

TABLE 4

| Ex. | Formula | Calculated | | | Found | | |
|---|---|---|---|---|---|---|---|
| | | C | H | N | C | H | N |
| 123 | $C_{31}H_{29}Cl_2N_2O_4SNa$ 1.5$H_2O$ | 57.58 | 4.94 | 4.33 | 57.37 | 4.97 | 4.21 |
| 124 | $C_{29}H_{25}Cl_2N_2O_4SNa$ 3$H_2O$ | 53.95 | 4.84 | 4.34 | 53.61 | 4.80 | 4.59 |
| 230 | $C_{30}H_{28}ClN_2O_5SNa$ 1.5$H_2O$ | 58.69 | 5.05 | 4.56 | 58.67 | 4.99 | 4.55 |
| 358 | $C_{33}H_{33}Cl_2N_2O_4SNa$ 4$H_2O$ | 55.07 | 5.74 | 3.84 | 55.32 | 5.73 | 3.88 |
| 359 | $C_{34}H_{34}Cl_2O_4SNa$ 2$H_2O$ | 61.76 | 5.79 | 4.24 | 61.85 | 5.85 | 4.11 |
| 360 | $C_{32}H_{32}Cl_2N_2O_4SNa$ 3$H_2O$ | 55.81 | 5.56 | 4.07 | 55.80 | 5.47 | 4.03 |
| 380 | $C_{30}H_{27}Cl_2N_2O_4SNa$ 3$H_2O$ | 54.63 | 5.04 | 4.25 | 54.85 | 4.94 | 4.33 |

EXAMPLES OF TABLE 5

General procedure for mixed dithioacetal formation

N,N-Dimethyl 3-((acetylthio(3-(2-(7-chloro-2-quinolinyl)ethenyl)-phenyl)methyl)thio)propanamide To a solution of 3-(2-(7-chloro-2-quinolinyl)-ethenyl)-benzaldehyde (10.74 g, 36.6 mmol) in 35 mL of TFA (trifluoroacetic acid) at r.t. was added thiolacetic acid (3.34 g, 3.14 mL, 43.9 mmol) followed by N,N-dimethyl-3-mercaptopropanamide (5.84 g, 43.9 mmol) in 5 mL of TFA. The mixture was stirred for 5 min, then poured into ice cold NH₄OAc buffer (500 mL). The aq layer was extracted with EtOAc (4×250 mL). The combined organic layers were washed with NH₄OAc buffer (250 mL), brine (250 mL) and dried over MgSO₄. Plug filtration using EtOAc:hexane:MeOH 10:10:1 gave 10.6 g (60% yield) of the title product.

Using the general procedure described above, the procedures of Examples 14, 33 and 228, Thiols 1, 3, 16 and 17, Iodides 1 and 2, and 2-(bromomethyl)benzonitrile, the compounds of Table 5 were synthesized. The tetrazoles (Examples 405 and 406) are obtained from the nitrile derivatives using the procedure of Example 40, Step 3.

TABLE 5

| Ex. | Formula | Calculated | | | Found | | |
|---|---|---|---|---|---|---|---|
| | | C | H | N | C | H | N |
| 386 | $C_{29}H_{22}ClNO_4S_2Na_2$ 1.5$H_2O$ | 56.08 | 4.06 | 2.26 | 55.98 | 4.10 | 2.20 |
| 387 | $C_{29}H_{21}Cl_2NO_4S_2Na_2$ 1.5$H_2O$ | 53.14 | 3.69 | 2.14 | 52.92 | 3.95 | 2.42 |
| 390 | $C_{31}H_{29}ClN_2O_3S_2Na$ $H_2O$ | 60.33 | 4.90 | 4.54 | 60.18 | 4.97 | 4.58 |
| 391 | $C_{31}H_{28}Cl_2N_2O_3S_2$ | NMR data below | | | | | |
| 405 | $C_{29}H_{24}ClN_5O_2S_2$ | | | | | | |
| 406 | $C_{31}H_{29}ClN_6OS_2$ | | | | | | |
| 407 | $C_{34}H_{26}ClNO_4S_2$ | NMR data below | | | | | |
| 408 | $C_{34}H_{24}Cl_3NO_4S_2$ | NMR data below | | | | | |
| 409 | $C_{31}H_{29}ClN_2O_3S_2$ | | | | | | |
| 410 | $C_{31}H_{28}Cl_2N_2O_3S_2$ | NMR data below | | | | | |

EXAMPLE 391 (ACID)

¹H NMR (CDCl₃) δ: 2.60–3.15, (4H, m), 2.91 (3H, s), 3.03 (3H, s), 4.10–4.35 (2H, m), 5.09 (1H, s), 7.30–8.05 (13H, m), 8.35 (1H, d).

EXAMPLE 407 (DIACID)

¹H NMR (CDCl₃) δ: 4.10 (4H, m), 4.68 (1H, s), 6.95–8.10 (18H, m), 8.43 (1H, d), 12.95 (2H, br s).

EXAMPLE 408 (DIACID)

¹H NMR (CD₃COCD₃) δ: 4.20 (4H, m), 4.74 (1H, s), 7.10–8.15 (16H, m), 8.38 (1H, d).

EXAMPLE 410 (ACID)

¹H NMR CDCl₃) δ: 2.56–2.95 (4H, m), (2.85 (3H, s), 3.10 (3H, s), 3.70–3.96 (2H, m), 4.89 (1H, s), 7.10–7.75 (12H, m), 8.05–8.18 (2H, m).

EXAMPLES OF TABLE 6

Using the general procedure of Example 402, the compounds of Table 6 were synthesized. Ketoesters 1–3, Thiols 1, 3 and 18, Iodides 1–3, 2-(bromomethyl)nitrobenzene, and 2-propyl-3-bromomethyl-2-pyridinecarboxylate (J. Med. Chem., 32, 827(1989)) were used. In some cases the formation of the amide with Me₂AlNR₂ was avoided; in other cases, Me₂AlNHtBu, Me₂AlNH₂ )at 65° C.) were used. For Example 426, the nitrile was obtained with Me₂AlNH₂ at 80° C. and was transformed to the tetrazole (as in Example 40, Step 3).

TABLE 6

| Ex. | Formula | Calculated | | | Found | | |
|---|---|---|---|---|---|---|---|
| | | C | H | N | C | H | N |
| 385 | $C_{29}H_{22}Cl_3NO_5SNa_2$ 1.5$H_2O$ | 51.53 | 3.73 | — | 51.24 | 3.95 | — |
| 389 | $C_{30}H_{27}Cl_2NO_4S$ | NMR data below | | | | | |
| 392 | $C_{28}H_{33}ClN_2O_5SNa_2$ 1.5$H_2O$ | 53.72 | 4.51 | 4.47 | 53.51 | 4.32 | 4.54 |
| 393 | $C_{30}H_{27}ClNO_2S$ | NMR data below | | | | | |
| 394 | $C_{34}H_{35}ClNO_2S$ | NMR data below | | | | | |
| 396 | $C_{30}H_{23}Cl_2NO_4SNa_2$ 2.5$H_2O$ | 54.97 | 4.31 | 2.14 | 55.08 | 3.89 | 1.95 |
| 397 | $C_{32}H_{29}Cl_2N_2O_3SNa$ $H_2O$ | 60.66 | 4.93 | 4.42 | 60.50 | 4.51 | 4.16 |
| 398 | $C_{30}H_{25}Cl_2N_2O_3SNa$ 1.5$H_2O$ | 58.64 | 4.59 | 4.56 | 58.22 | 4.03 | 4.32 |
| 399 | $C_{30}H_{25}Cl_2N_5O_2S$ | NMR data below | | | | | |
| 401 | $C_{34}H_{34}Cl_2N_2O_3S$ | NMR data below | | | | | |
| 411 | $C_{29}H_{27}ClN_2O_5S$ | NMR data below | | | | | |
| 412 | $C_{31}H_{28}ClNO_5S$ | NMR data below | | | | | |

EXAMPLE 389 (diacid)

¹H NMR (CDCl₃) δ: 2.12 (2H, q), 2.42–2.58 (4H, m), 2.70–2.82 (1H, m), 2.90–3.23 (3H, m), 3.32–3.50 (2H, m), 3.80 (1H, t), 6.55 (1H, d), 6.94–7.17 (2H, m), 7.18 (1H, m), 7.32–7.48 (4H, m), 7.72 (1H, d), 7.90 (1H, d), 8.06 (1H, d), 8.18 (1H, d).

EXAMPLE 393 (acid)

¹H NMR (CD₃COCD₃) δ: 2.28 (2H, m), 2.50 (2H, m), 2.63 (2H, m), 2.75–3.00 (2H, m), 4.02 (1H, dd), 6.86 (1H, br s), 7.20–7.65 (10H, m), 7.75–8.05 (5H, m), 8.32 (1H, d).

EXAMPLE 394 (acid)

¹H NMR (CD₃COCD₃) δ: 1.41 (9H, s), 2.25 (2H, m), 2.48 (2H, m), 2.60 (2H, m), 2.68–2.93 (2H, m), 4.02 (1H, m), 6.93 (1H, br s), 7.20–7.30 (4H, m), 7.48–7.70 (5H, m), 7.76–8.05 (5H, m), 8.33 (1H, d).

EXAMPLE 399 (acid)

¹H NMR (CD₃COCD₃) δ: 2.22 (2H, t), 2.45–2.5 (1H, m), 2.5 (1H, d), 2.55–2.62 (1H, m), 2.6 (1H, d), 2.9–3.0 (1H, m), 3.0–3.1 (1H, m), 4.0–4.1 (1H, m), 7.38 (2H, t), 7.45–7.6 (4H, m), 7.62 (1H, d), 7.75 (1H, s), 7.8–8.0 (4H, m), 8.05 (1H, s), 8.35 (1H, d).

EXAMPLE 401 (acid)

¹H NMR (CD₃COCD₃) δ: 1.42 (9H, s), 2.25 (2H, m), 2.50 (2H, m), 2.60 (2H, m), 2.79 (2H, m), 4.02 (1H, t), 7.12 (1H, s, NH), 7.28 (3H, m), 7.41–7.55 (4H, m), 7.65 (1H, m), 7.79–8.03 (5H, m), 8.35 (1H, d).

EXAMPLE 411 (acid)

¹H NMR (CD₃COCD₃) δ: 1.05–1.10 (3H, 2d, mixture of diasteromers), 2.07–3.00 (7H, m), 3.96 (1H, 2t), 5.43 (2H, s), 6.96 (2H, m), 7.15–7.30 (2H, m), 7.45 (2H, m), 7.60 (2H, m), 7.75 (1H, d), 7.90 (1H, d), 8.00 (2H, m), 8.40 (1H, d).

EXAMPLE 412 (diacid)

¹H NMR (CD₃COCD₃) δ: 2.25 (2H, m), 2.72 (2H, m), 2.95 (1H, m), 3.02 (1H, m), 3.34–3.37 (3H, 2s, mixture of diastereoisomers), 3.88 (1H, m), 4.17 (1H, m), 7.05–7.70 (9H, m), 7.70–8.05 (5H, m), 8.35 (1H, d).

TABLE 7

The following compounds (formula I'') are within the scope of the invention:

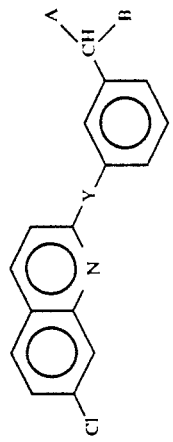

| Ex | Y | A | B |
|---|---|---|---|
| 97 | —CH=CH— | —S(CH$_2$)$_2$CO$_2$H | —(CH$_2$)$_2$(1,2-Phe)CON(CH$_3$)$_2$ |
| 98 | —CH$_2$—CH$_2$— | —S(CH$_2$)$_2$CO$_2$H | —(CH$_2$)$_2$(1,2-Phe)CON(CH$_3$)$_2$ |
| 99 | —CH=CH— | —S(CH$_2$)$_2$CO$_2$H | —(CH$_2$)$_2$(1,2-Phe)CONHCH$_3$ |
| 100 | —CH$_2$O— | —SCH$_2$C(CH$_3$)$_2$COOH | —(CH$_2$)$_2$(1,2-Phe)CON(CH$_3$)$_2$ |
| 101 | —CH$_2$—CH$_2$— | —SCH$_2$CH(CH$_3$)COOH | —(CH$_2$)$_2$(1,2-Phe)CON(CH$_2$CH$_3$)$_2$ |
| 102 | —CH$_2$O— | —S(CH$_2$)$_2$CO$_2$H | —(CH$_2$)$_2$(1,2-Phe)CON(CH$_3$)$_2$ |
| 103 | —CH$_2$—CH$_2$— | —SCH$_2$C(CH$_3$)$_2$COOH | —(CH$_2$)$_2$(1,2-Phe)CONHCH$_2$CH(CH$_3$)$_2$ |
| 104 | —CH$_2$O— | —S(CH$_2$)$_2$CO$_2$H | —(CH$_2$)$_2$(1,2-Phe)CON(CH$_3$)$_2$ |
| 105 | —CH$_2$O— | —SCH$_2$C(CH$_2$CH$_3$)$_2$COOH | —(CH$_2$)$_2$(1,2-Phe)CON(CH$_3$)$_2$ |
| 106 | —CH$_2$O— | —SCH$_2$C(CH$_2$CH$_3$)$_2$COOH | —(CH$_2$)$_2$(1,2-Phe)CON(CH$_3$)$_2$ |
| 107 | —CH$_2$O— | —S(CH$_2$)$_2$CO$_2$H | —(CH$_2$)$_2$(1,2-Phe)CON(CH$_2$)$_4$ |
| 108 | —CH$_2$—CH$_2$— | —SCH$_2$C(CH$_2$CH$_3$)$_2$COOH | —(CH$_2$)$_2$(1,2-Phe)CON(CH$_3$)$_2$ |
| 109 | —CH$_2$O— | —S(CH$_2$)$_2$CO$_2$H | —(CH$_2$)$_2$(4-Cl—Phe)CON(CH$_3$)$_2$ |
| 110 | —CH$_2$O— | —S(CH$_2$)$_2$CN$_4$H | —(CH$_2$)$_2$(1,2-Phe)CON(CH$_3$)$_2$ |
| 111 | —CH$_2$O— | —SCH$_2$CH(CH$_3$)CN$_4$H | —(CH$_2$)$_2$(1,2-Phe)CON(CH$_3$)$_2$ |
| 112 | —CH(CH$_2$)CH— | —SCH$_2$CH(CH$_3$)COOH | —(CH$_2$)$_2$(1,2-Phe)CONH$_2$ |
| 113 | —CH$_2$O— | —SCH$_2$CH(CH$_2$CH$_3$)COOH | —(CH$_2$)$_2$(1,2-Phe)CONHCH$_3$ |
| 114 | —CH$_2$—CH$_2$— | —SCH$_2$CH(CH$_3$)COOH | —(CH$_2$)$_2$(1,2-Phe)CON(CH$_3$)$_2$ |
| 115 | —CH$_2$—CH$_2$— | —SCH$_2$CH(CH$_3$)COOH | —(CH$_2$)$_2$(1,2-Phe)CONHCH$_3$ |
| 116 | —CH$_2$—CH$_2$— | —SCH$_2$CH$_2$CH$_3$COOH | —(CH$_2$)$_2$(1,2-Phe)CONH$_2$ |
| 117 | —CH$_2$—CH$_2$— | —SCH$_2$CH$_2$CH$_3$COOH | —(CH$_2$)$_2$(1,2-Phe)COOH |
| 118 | —CH$_2$O— | —S(CH$_2$)$_2$COOH | —(CH$_2$)$_2$(1,2-Phe)CON(CH$_3$)$_2$ |
| 119 | —CH$_2$O— | —SCH$_2$CH(CH$_2$CH$_3$)COOH | —(CH$_2$)$_2$(1,2-Phe)CONHCH$_2$CH$_3$ |
| 120 | —CH$_2$O— | —SCH$_2$CH(CH$_3$)CH$_2$COOH | —(CH$_2$)$_2$(1,2-Phe)CONH$_2$ |
| 121 | —CH$_2$O— | —SCH$_2$CH((CH$_2$)$_2$CH$_3$)COOH | —(CH$_2$)$_2$(1,2-Phe)CONHCH$_2$CH$_3$ |
| 122 | —CH$_2$O— | —SCH$_2$CH(CH$_2$CH$_3$)COOH | —(CH$_2$)$_2$(1,2-Phe)CONH$_2$ |
| 123 | —CH$_2$O— | —SCH$_2$CH(CH$_2$CH$_3$)COOH | —(CH$_2$)$_2$(4-Cl—Phe)CONH$_2$ |
| 124 | —CH$_2$O— | —S(CH$_2$)$_2$CO$_2$H | —(CH$_2$)$_2$(4-Cl—Phe)CONH$_2$ |
| 125 | —CH$_2$—CH$_2$— | —SCH$_2$C(CH$_3$)$_2$COOH | —(CH$_2$)$_2$(4-Cl—Phe)CONH$_2$ |
| 126 | —CH$_2$O— | —SCH$_2$CH(CH$_2$CH$_3$)COOH | —(CH$_2$)$_2$(1,2-Phe)CONH$_2$ |
| 127 | —CH$_2$O— | —SCH$_2$CH(CH$_2$CH$_3$)COOH | —(CH$_2$)$_2$(1,3-Phe)CN$_4$H |
| 128 | —CH$_2$O— | —SCH$_2$CH(CH$_2$CH$_3$)COOH | —(CH$_2$)$_2$(1,3-Phe)SO$_2$N(CH$_3$)$_2$ |
| 129 | —CH$_2$O— | —SCH$_2$CH(CH$_2$CH$_3$)COOH | —(CH$_2$)$_2$(1,3-Phe)CON(CH$_3$)$_2$ |
| 130 | —CH$_2$O— | —SCH$_2$CH(CH$_2$CH$_3$)COOH | —(CH$_2$)$_2$(1,3-Phe)NHCO$_2$CH$_2$CH$_3$ |
| 131 | —CH$_2$O— | —SCH$_2$CH(CH$_2$CH$_3$)COOH | —(CH$_2$)$_2$(1,3-Phe)N(CH$_3$)CO$_2$CH$_3$ |
| 132 | —CH$_2$O— | —SCH$_2$CH(CH$_2$CH$_3$)COOH | —(CH$_2$)$_2$(1,3-Phe)NHCO$_2$(4-Cl—Ph) |
| 133 | —CH$_2$O— | —SCH$_2$CH(CH$_2$CH$_3$)COOH | —(CH$_2$)$_2$(1,3-Phe)CN |
| 134 | —CH$_2$O— | —SCH$_2$CH(CH$_2$CH$_3$)COOH | —(CH$_2$)$_2$(1,3-Phe)COCF$_3$ |
| 135 | —CH$_2$O— | —SCH$_2$CH(CH$_2$CH$_3$)COOH | —(CH$_2$)$_2$(1,3-Phe)COPh |
| 136 | —CH$_2$O— | —SCH$_2$CH(CH$_2$CH$_3$)COOH | —(CH$_2$)$_2$(1,3-Phe)SO$_2$Ph |
| 137 | —CH$_2$O— | —SCH$_2$CH(CH$_2$CH$_3$)COOH | —(CH$_2$)$_2$(1,3-Phe)SO$_2$CF$_3$ |

TABLE 7-continued

The following compounds (formula I'') are within the scope of the invention:

| Ex | Y | A | B |
|---|---|---|---|
| 138 | —CH₂O— | SCH₂CH(CH₂CH₃)COOH | —(CH₂)₂(1,3-Phe)NHCOC(CH₃)₃ |
| 139 | —CH₂—CH₂— | SCH₂CH(CH₂CH₃)COOH | —(CH₂)₂(1,3-Phe)COOH |
| 140 | —CH₂—CH₂— | SCH₂CH(CH₂CH₃)COOH | —(CH₂)₂(1,3-Phe)CN₄H |
| 141 | —CH₂—CH₂— | SCH₂CH(CH₂CH₃)COOH | —(CH₂)₂(1,3-Phe)SO₂N(CH₃)₂ |
| 142 | —CH₂—CH₂— | SCH₂CH(CH₂CH₃)COOH | —(CH₂)₂(1,3-Phe)CON(CH₃)₂ |
| 143 | —CH₂—CH₂— | SCH₂CH(CH₂CH₃)COOH | —(CH₂)₂(1,3-Phe)NHCO₂CH₂CH₃ |
| 144 | —CH₂—CH₂— | SCH₂CH(CH₂CH₃)COOH | —(CH₂)₂(1,3-Phe)N(CH₃)CO₂CH₃ |
| 145 | —CH₂—CH₂— | SCH₂CH(CH₂CH₃)COOH | —(CH₂)₂(1,3-Phe)NHCO₂(4-Cl—Ph) |
| 146 | —CH₂—CH₂— | SCH₂CH(CH₂CH₃)COOH | —(CH₂)₂(1,3-Phe)CN |
| 147 | —CH₂—CH₂— | SCH₂CH(CH₂CH₃)COOH | —(CH₂)₂(1,3-Phe)COCF₃ |
| 148 | —CH₂—CH₂— | SCH₂CH(CH₂CH₃)COOH | —(CH₂)₂(1,3-Phe)COPh |
| 149 | —CH₂—CH₂— | SCH₂CH(CH₂CH₃)COOH | —(CH₂)₂(1,3-Phe)SO₂Ph |
| 150 | —CH₂—CH₂— | SCH₂CH(CH₂CH₃)COOH | —(CH₂)₂(1,3-Phe)SO₂CF₃ |
| 151 | —CH₂—CH₂— | SCH₂CH(CH₂CH₃)COOH | —(CH₂)₂(1,2-Phe)CN₄H |
| 152 | —CH₂—CH₂— | SCH₂CH(CH₂CH₃)COOH | —(CH₂)₂(1,2-Phe)CONHSO₂(4-CH₃,—Ph) |
| 153 | —CH₂O— | SCH₂C(CH₃)₂COOH | —(CH₂)₂(1,2-Phe)CONH₂ |
| 154 | —CH₂O— | S(CH₂)₂CH(CH₃)COOH | —(CH₂)₂(1,2-Phe)CONH₂ |
| 155 | —CH₂O— | SCH₂CH(CH₂CH₃)COOH | —(CH₂)₂(1,2-Phe)CN₄CH₃ |
| 156 | —CH₂O— | SCH₂C(CH₃)₂COOH | —(CH₂)₂(1,2-Phe)CN₄H |
| 157 | —CH₂O— | SCH₂CH(CH₂CH₃)COOH | —(CH₂)₂(1,2-Phe)CONHCH₃ |
| 158 | —CH₂O— | SCH₂C(CH₃)₂COOH | —(CH₂)₂(1,2-Phe)CN₄H |
| 159 | —CH₂O— | SCH₂CH((CH₂)₂CH₃)COOH | —(CH₂)₂(1,2-Phe)CON(CH₃)₂ |
| 160 | —CH₂O— | SCH₂CH(CH₂CH₃)COOH | —(CH₂)₂—(1,2-Phe)COOH |
| 162 | —CH₂O— | SCH₂CH(CH₂CH₃)CON(CH₃)₂ | —(CH₂)₂—(1,2-Phe)CN₄H |
| 163 | —CH₂O— | SCH₂CH(CH₂CH₃)CON(CH₃)₂ | —(CH₂)₂—(1,2-Phe)CONH(SO₂Ph) |
| 164 | —CH₂—CH₂— | SCH₂CH(CH₂CH₃)CON(CH₃)₂ | —(CH₂)₂—(1,2-Phe)COOH |
| 165 | —CH₂—CH₂— | SCH₂CH(CH₂CH₃)CON(CH₃)₂ | —(CH₂)₂—(1,2-Phe)CN₄H |
| 166 | —CH₂—CH₂— | SCH₂CH(CH₂CH₃)CON(CH₃)₂ | —(CH₂)₂—(1,2-Phe)CONH(SO₂Ph) |
| 167 | —CH₂—CH₂— | SCH₂CH(CH₂CH₃)CON(CH₃)₂ | —(CH₂)₂—(1,2-(4-Cl—Phe))COOH |
| 168 | —CH₂—CH₂ | S(CH₂)₂CO₂H | —(CH₂)₂(1,2-(4-Cl—Phe))COOH |
| 169 | —CH₂O— | S(CH₂)₂CO₂H | —(CH₂)₂(1,2-Phe)NHCO₂CH₃ |
| 170 | —CH₂O— | S(CH₂)₂CO₂H | —(CH₂)₂(1,2-Phe)NHCO₂CH₃ |
| 171 | —CH₂—CH₂— | S(CH₂)₂CO₂H | —(CH₂)₂(1,2-Phe)NHCO₂CH₃ |
| 172 | —CH₂—CH₂— | S(CH₂)₂CO₂H | —(CH₂)₂(1,2-Phe)NHCO₂CH₃ |
| 173 | —CH₂O— | SCH₂CH(CH₃)COOH | —(CH₂)₂(1,2-Phe)NHCO₂CH₂CH₃ |
| 174 | —CH₂—CH₂— | SCH₂CH(CH₃)COOH | —(CH₂)₂(1,2-Phe)NHCO₂CH₃ |
| 175 | —CH₂—CH₂— | SCH₂CH(CH₃)COOH | —(CH₂)₂(1,2-Phe)NHCO₂CH₃ |
| 176 | —CH₂—CH₂— | SCH₂CH(CH₂CH₃)COOH | —(CH₂)₂(1,2-Phe)NHCO₂CH₂CH₃ |
| 177 | —CH₂—CH₂— | SCH₂CH(CH₂CH₃)COOH | —(CH₂)₂(1,2-Phe)NHCO₂CH₃ |
| 178 | —CH₂—CH₂— | SCH₂CH(CH₂CH₃)COOH | —(CH₂)₂(1,2-Phe)NHCO₂CH₃ |
| 179 | —CH₂O— | SCH₂CH(CH₂CH₃)COOH | —(CH₂)₂(1,2-Phe)NHCO₂CH₂CH₃ |

TABLE 7-continued

The following compounds (formula I") are within the scope of the invention:

| Ex | Y | A | B |
|---|---|---|---|
| 180 | —CH₂O— | SCH₂CH(CH₂CH₃)COOH | —(CH₂)₂(1,2-Phe)NHCO₂CH₂CH₃ |
| 181 | —CH₂O— | S(CH₂)₂CO₂H | —(CH₂)₂(1,2-Phe)NHCO₂CH((CH₂)₄ |
| 182 | —CH₂O— | S(CH₂)₂CO₂H | —(CH₂)₂(1,2-Phe)NHCO₂Ph |
| 183 | —CH₂—CH₂ | S(CH₂)₂CO₂H | —(CH₂)₂(1,2-Phe)NHCO₂CH((CH₂)₄ |
| 184 | —CH₂—CH₂ | S(CH₂)₂CO₂H | —(CH₂)₂(1,2-Phe)NHCO₂Ph |
| 185 | —CH₂O— | SCH₂CH(CH₃)COOH | —(CH₂)₂(1,2-Phe)NHCO₂CH((CH₂)₄ |
| 186 | —CH₂O— | SCH₂CH(CH₃)COOH | —(CH₂)₂(1,2-Phe)NHCO₂CH((CH₂)₄ |
| 187 | —CH₂—CH₂ | SCH₂CH(CH₃)COOH | —(CH₂)₂(1,2-Phe)NHCO₂CH((CH₂)₄ |
| 188 | —CH₂—CH₂ | SCH₂CH(CH₃)COOH | —(CH₂)₂(1,2-Phe)NHCO₂Ph |
| 189 | —CH₂O— | SCH₂CH(CH₂CH₃)COOH | —(CH₂)₂(1,2-Phe)NHCO₂CH((CH₂)₄ |
| 190 | —CH₂O— | SCH₂CH(CH₂CH₃)COOH | —(CH₂)₂(1,2-Phe)NHCO₂Ph |
| 191 | —CH₂—CH₂ | SCH₂CH(CH₂CH₃)COOH | —(CH₂)₂(1,2-Phe)NHCO₂CH((CH₂)₄ |
| 192 | —CH₂—CH₂ | SCH₂CH(CH₂CH₃)COOH | —(CH₂)₂(1,2-Phe)NHCO₂C(CH₃)₃ |
| 193 | —CH₂O— | SCH₂CH(CH₃)COOH | —(CH₂)₂(1,2-Phe)COOH |
| 194 | —CH₂O— | SCH₂CH(CH₃)COOH | —(CH₂)₂(1,2-Phe)COOH |
| 195 | —CH₂—CH₂ | SCH₂CH(CH₂CH₃)COOH | —(CH₂)₂(1,2-Phe)COOH |
| 196 | —CH₂—CH₂ | SCH₂CH(CH₂CH₃)COOH | —(CH₂)₂(1,2-Phe)CN₄H |
| 197 | —CH₂O— | SCH₂CH(CH₃)COOH | —(CH₂)₂(1,2-Phe)CN₄H |
| 198 | —CH₂O— | SCH₂CH(CH₂CH₃)COOH | —(CH₂)₂(1,2-Phe)CONHSO₂Ph |
| 199 | —CH₂O— | SCH₂CH(CH₂CH₃)COOH | —(CH₂)₂(1,2-Phe)CONHSO₂CF₃ |
| 200 | —CH₂O— | SCH₂CH(CH₂CH₃)COOH | —(CH₂)₂(1,2-Phe)CONHSO₂CH₃ |
| 201 | —CH₂O— | SCH₂CH(CH₃)COOH | —(CH₂)₂(1,2-Phe)CONHSO₂Ph |
| 202 | —CH₂O— | SCH₂CH(CH₃)COOH | —(CH₂)₂(1,2-Phe)CONHSO₂CF₃ |
| 203 | —CH₂O— | SCH₂CH(CH₃)COOH | —(CH₂)₂(1,2-Phe)CONHSO₂CH₃ |
| 204 | —CH₂—CH₂ | SCH₂CH(CH₃)COOH | —(CH₂)₂(1,2-Phe)CONHSO₂Ph |
| 205 | —CH₂—CH₂ | SCH₂CH(CH₃)COOH | —(CH₂)₂(1,2-Phe)CONHSO₂CF₃ |
| 206 | —CH₂—CH₂ | SCH₂CH(CH₃)COOH | —(CH₂)₂(1,2-Phe)CONHSO₂CH₃ |
| 207 | —CH₂—CH₂ | SCH₂CH(CH₂CH₃)COOH | —(CH₂)₂(1,2-Phe)CONHSO₂Ph |
| 208 | —CH₂—CH₂ | SCH₂CH(CH₂CH₃)COOH | —(CH₂)₂(1,2-Phe)CONHSO₂CF₃ |
| 209 | —CH₂—CH₂ | SCH₂CH(CH₂CH₃)COOH | —(CH₂)₂(1,2-Phe)CONHSO₂CH₃ |
| 210 | —CH₂O— | SCH₂CH(CH₂CH₃)COOH | —(CH₂)₂(1,2-(3-Cl—Ph))COOH |
| 211 | —CH₂O— | S(CH₂)₂CO₂H | —(CH₂)₂(1,2-(3-Cl—Ph))COOH |
| 212 | —CH₂—CH₂ | SCH₂CH(CH₂CH₃)COOH | —(CH₂)₂(1,2-(3-Cl—Ph))COOH |
| 213 | —CH₂—CH₂ | SCH₂CH(CH₃)COOH | —(CH₂)₂(1,2-(3-Cl—Ph))COOH |
| 214 | —CH₂—CH₂ | SCH₂CH(OCH₃)COOH | —(CH₂)₂(1,2-Phe)COOH |
| 215 | —CH₂—CH₂ | S(CH₂)₂CO₂H | —(CH₂)₂(1,2-Phe)CON(CH₃)₂ |
| 216 | —CH₂O— | SCH₂CH(OCH₃)COOH | —(CH₂)₂(1,2-Phe)CON(CH₃)₂ |
| 217 | —CH₂O— | SCH₂CH(OCH₃)COOH | —(CH₂)₂(1,2-Phe)CON(CH₃)₂ |
| 218 | —CH₂—CH₂— | SCH₂C(CH₃)(OCH₃)COOH | —(CH₂)₂(1,2-Phe)CON(CH₃)₂ |
| 219 | —CH₂O— | SCH₂C(CH₃)(OCH₃)COOH | —(CH₂)₂(1,2-Phe)CON(CH₃)₂ |
| 220 | —CH₂—CH₂— | SCH₂CH(OCH₃)COOH | —(CH₂)₂(1,2-Phe)COOH |

TABLE 7-continued

The following compounds (formula I") are within the scope of the invention:

| Ex | Y | A | B |
|---|---|---|---|
| 221 | —CH₂—CH₂— | —SCH₂C(CH₃)(OCH₃)COOH | —(CH₂)₂(1,2-Phe)COOH |
| 222 | —CH₂—CH₂— | —SCH₂CH(OCH₃)COOH | —(CH₂)₂(1,2-Phe)CN₄H |
| 223 | —CH₂—CH₂— | —SCH₂CH(OCH₃)COOH | —(CH₂)₂(1,2-Phe)CN₄H |
| 224 | —CH₂—CH₂— | —SCH₂C(CH₃)(OCH₃)COOH | —(CH₂)₂(1,2-Phe)CN₄H |
| 225 | —CH₂O— | —SCH₂CH(OCH₃)COOH | —(CH₂)₂(1,2-Phe)CN₄H |
| 226 | —CH₂—CH₂— | —SCH₂C(CH₃)(OCH₃)COOH | —(CH₂)₂(1,2-Phe)CN₄H |
| 227 | —CH₂—CH₂— | —SCH₂C(CH₃)(OCH₃)COOH | —(CH₂)₂(1,2-Phe)NHCO₂CH₂CH₃ |
| 228 | —CH₂O— | —S(CH₂)₂CO₂H | —(CH₂)₂(1,2-Phe)NHCO₂CH₂CH₃ |
| 229 | —CH₂O— | —SCH₂CH(OCH₃)COOH | —(CH₂)₂(1,2-Phe)CON(CH₃)₂ |
| 230 | —CH₂—CH₂— | —SCH₂C(CH₃)(OH)COOH | —(CH₂)₂(1,2-Phe)CONH₂ |
| 231 | —CH₂—CH₂— | —SCH₂CH(CH₃)COOH | —(CH₂)₂(1,2-Phe)NHSO₂CF₃ |
| 232 | —CH₂O— | —SCH₂CH(CH₂CH₃)COOH | —(CH₂)₂(1,2-Phe)COCF₃ |
| 233 | —CH₂O— | —SCH₂CH(CH₂CH₃)COOH | —(CH₂)₂(1,2-Phe)COPh |
| 234 | —CH₂O— | —SCH₂CH(CH₂CH₃)COOH | —(CH₂)₂(1,2-Phe)CO(2-Me—Ph) |
| 235 | —CH₂O— | —SCH₂CH(CH₂CH₃)COOH | —(CH₂)₂(1,2-Phe)CHO |
| 236 | —CH₂O— | —SCH₂CH(CH₂CH₃)COOH | —(CH₂)₂(1,2-Phe)CH₂OH |
| 237 | —CH₂O— | —SCH₂CH(CH₃)COOH | —(CH₂)₂(1,2-Phe)COCF₃ |
| 238 | —CH₂O— | —SCH₂CH(CH₃)COOH | —(CH₂)₂(1,2-Phe)COPh |
| 239 | —CH₂O— | —SCH₂CH(CH₃)COOH | —(CH₂)₂(1,2-Phe)CO(2-Me—Ph) |
| 240 | —CH₂O— | —SCH₂CH(CH₃)COOH | —(CH₂)₂(1,2-Phe)CHO |
| 241 | —CH₂O— | —SCH₂CH(CH₃)COOH | —(CH₂)₂(1,2-Phe)CH₂OH |
| 242 | —CH₂—CH₂— | —SCH₂CH(CH₂CH₃)COOH | —(CH₂)₂(1,2-Phe)COCF₃ |
| 243 | —CH₂—CH₂— | —SCH₂CH(CH₂CH₃)COOH | —(CH₂)₂(1,2-Phe)COPh |
| 244 | —CH₂—CH₂— | —SCH₂CH(CH₂CH₃)COOH | —(CH₂)₂(1,2-Phe)CO(2-Me—Ph) |
| 245 | —CH₂—CH₂— | —SCH₂CH(CH₂CH₃)COOH | —(CH₂)₂(1,2-Phe)CHO |
| 246 | —CH₂—CH₂— | —SCH₂CH(CH₂CH₃)COOH | —(CH₂)₂(1,2-Phe)CH₂OH |
| 247 | —CH₂—CH₂— | —SCH₂CH(CH₃)COOH | —(CH₂)₂(1,2-Phe)COCF₃ |
| 248 | —CH₂—CH₂— | —SCH₂CH(CH₃)COOH | —(CH₂)₂(1,2-Phe)COPh |
| 249 | —CH₂—CH₂— | —SCH₂CH(CH₃)COOH | —(CH₂)₂(1,2-Phe)CO(2-Me—Ph) |
| 250 | —CH₂—CH₂— | —SCH₂CH(CH₃)COOH | —(CH₂)₂(1,2-Phe)CHO |
| 251 | —CH₂—CH₂— | —SCH₂CH(CH₃)COOH | —(CH₂)₂(1,2-Phe)CH₂OH |
| 252 | —CH₂O— | —SCH₂CH(CH₃)COOH | —(CH₂)₂(1,2-Phe)SO₂Ph |
| 253 | —CH₂O— | —SCH₂CH(CH₃)COOH | —(CH₂)₂(1,2-Phe)SOPh |
| 254 | —CH₂O— | —SCH₂CH(CH₃)COOH | —(CH₂)₂(1,2-Phe)SO₂CF₃ |
| 255 | —CH₂O— | —SCH₂CH(CH₃)COOH | —(CH₂)₂(1,2-Phe)SO₂CH₃ |
| 256 | —CH₂O— | —SCH₂CH(CH₃)COOH | —(CH₂)₂(1,2-Phe)SOCH₃ |
| 257 | —CH₂O— | —SCH₂CH(CH₃)COOH | —(CH₂)₂(1,2-Phe)CHO |
| 258 | —CH₂O— | —SCH₂CH(CH₃)COOH | —(CH₂)₂(1,2-Phe)NO₂ |
| 259 | —CH₂O— | —SCH₂CH(CH₃)COOH | —(CH₂)₂(1,2-Phe)SO₂Ph |
| 260 | —CH₂O— | —SCH₂CH(CH₃)COOH | —(CH₂)₂(1,2-Phe)SO₂CF₃ |
| 261 | —CH₂O— | —SCH₂CH(CH₃)COOH | —(CH₂)₂(1,2-Phe)SO₂CH₃ |

TABLE 7-continued

The following compounds (formula I") are within the scope of the invention:

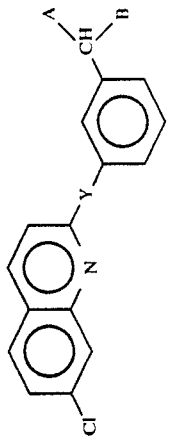

| Ex | Y | A | B |
|---|---|---|---|
| 262 | —CH₂O— | —SCH₂CH(CH₃)COOH | —(CH₂)₂(1,2-Phe)SOCH₃ |
| 263 | —CH₂O— | —SCH₂CH(CH₃)COOH | —(CH₂)₂(1,2-Phe)S(4-Cl—Ph) |
| 264 | —CH₂—CH₂— | —SCH₂CH(CH₂CH₃)COOH | —(CH₂)₂(1,2-Phe)SO₂Ph |
| 265 | —CH₂—CH₂— | —SCH₂CH(CH₂CH₃)COOH | —(CH₂)₂(1,2-Phe)SOPh |
| 266 | —CH₂—CH₂— | —SCH₂CH(CH₂CH₃)COOH | —(CH₂)₂(1,2-Phe)SO₂CF₃ |
| 267 | —CH₂—CH₂— | —SCH₂CH(CH₂CH₃)COOH | —(CH₂)₂(1,2-Phe)SO₂CH₃ |
| 268 | —CH₂—CH₂— | —SCH₂CH(CH₂CH₃)COOH | —(CH₂)₂(1,2-Phe)SOCH₃ |
| 269 | —CH₂—CH₂— | —SCH₂CH(CH₂CH₃)COOH | —(CH₂)₂(1,2-Phe)S(4-Cl—Ph) |
| 270 | —CH₂—CH₂— | —SCH₂CH(CH₃)COOH | —(CH₂)₂(1,2-Phe)SO₂Ph |
| 271 | —CH₂—CH₂— | —SCH₂CH(CH₃)COOH | —(CH₂)₂(1,2-Phe)SOPh |
| 272 | —CH₂—CH₂— | —SCH₂CH(CH₃)COOH | —(CH₂)₂(1,2-Phe)SO₂CF₃ |
| 273 | —CH₂—CH₂— | —SCH₂CH(CH₃)COOH | —(CH₂)₂(1,2-Phe)SO₂CH₃ |
| 274 | —CH₂—CH₂— | —SCH₂CH(CH₃)COOH | —(CH₂)₂(1,2-Phe)SOCH₃ |
| 275 | —CH₂—CH₂— | —SCH₂CH(CH₃)COOH | —(CH₂)₂(1,2-Phe)S(4-Cl—Ph) |
| 276 | —CH₂O— | —SCH₂CH(CH₂CH₃)COOH | —(CH₂)₂(1,2-Phe)SO₂NH₂ |
| 277 | —CH₂O— | —SCH₂CH(CH(CH₂)₂CH₃)COOH | —(CH₂)₂(1,2-Phe)SO₂NH₂ |
| 278 | —CH₂O— | —SCH₂CH(CH(CH₂)₂CH₃)COOH | —(CH₂)₂(1,2-Phe)SO₂NH₂ |
| 279 | —CH₂O— | —SCH₂CH(CH(CH₂)₂CH₃)COOH | —(CH₂)₂(1,2-Phe)SO₂NH₂ |
| 280 | —CH₂O— | —SCH₂CH(CH(CH₂)₂CH₃)COOH | —(CH₂)₂(1,2-Phe)SO₂NH₂ |
| 281 | —CH₂—CH₂— | —SCH₂CH(CH₂CH₃)COOH | —(CH₂)₂(1,2-Phe)SO₂NH₂ |
| 282 | —CH₂—CH₂— | —SCH₂CH₂CH₃)COOH | —(CH₂)₂(1,2-Phe)SO₂NH₂ |
| 283 | —CH₂O— | —SCH₂CH₂CH₃)COOH | —(CH₂)₂(1,2-Phe)SO₂N(CH₃)₂ |
| 284 | —CH₂O— | —SCH₂CH₂CH₃)COOH | —(CH₂)₂(1,2-Phe)SO₂N(CH₂CF₃)₂ |
| 285 | —CH₂O— | —SCH₂CH₂CH₃)COOH | —(CH₂)₂(1,2-Phe)SO₂NHCH₂(4-Cl—Ph) |
| 286 | —CH₂O— | —SCH₂CH₂CH₃)COOH | —(CH₂)₂(1,2-Phe)SO₂NH(4-Cl—Ph) |
| 287 | —CH₂O— | —SCH₂CH₂CH₃)COOH | —(CH₂)₂(1,2-Phe)SO₂N(CH₃)₂ |
| 288 | —CH₂—CH₂— | —SCH₂CH₂CH₃)COOH | —(CH₂)₂(1,2-Phe)SO₂N(CH₂CF₃)₂ |
| 289 | —CH₂—CH₂— | —SCH₂CH₂CH₃)COOH | —(CH₂)₂(1,2-Phe)SO₂NHCH₂(4-Cl—Ph) |
| 290 | —CH₂—CH₂— | —SCH₂CH(CH₃)COOH | —(CH₂)₂(1,2-Phe)SO₂NH(4-Cl—Ph) |
| 291 | —CH₂O— | —SCH₂CH(CH₃)COOH | —(CH₂)₂(1,2-Phe)SO₂N(CH₃)₂ |
| 292 | —CH₂O— | —SCH₂CH(CH₃)COOH | —(CH₂)₂(1,2-Phe)SO₂N(CH₂CF₃)₂ |
| 293 | —CH₂O— | —SCH₂CH(CH₃)COOH | —(CH₂)₂(1,2-Phe)SO₂NHCH₂(4-Cl—Ph) |
| 294 | —CH₂O— | —SCH₂CH(CH₃)COOH | —(CH₂)₂(1,2-Phe)SO₂NH(4-Cl—Ph) |
| 295 | —CH₂—CH₂— | —SCH₂CH(CH₃)COOH | —(CH₂)₂(1,2-Phe)SO₂N(CH₃)₂ |
| 296 | —CH₂—CH₂— | —SCH₂CH(CH₃)COOH | —(CH₂)₂(1,2-Phe)SO₂N(CH₂CF₃)₂ |
| 297 | —CH₂—CH₂— | —SCH₂CH(CH₃)COOH | —(CH₂)₂(1,2-Phe)SO₂NHCH₂(4-Cl—Ph) |
| 298 | —CH₂—CH₂— | —SCH₂CH(CH₃)COOH | —(CH₂)₂(1,2-Phe)SO₂NHCH₂(4-Cl—Ph) |
| 299 | —CH₂O— | —SCH₂CH(CH₃)COOH | —(CH₂)₂(1,2-Phe)NH(COPh) |
| 300 | —CH₂O— | —SCH₂CH(CH₃)COOH | —(CH₂)₂(1,2-Phe)N(CH₃)COPh |
| 301 | —CH₂O— | —SCH₂CH(CH₃)COOH | —(CH₂)₂(1,2-Phe)NH(COC(CH₃)₃) |
| 302 | —CH₂O— | —SCH₂CH(CH₃)COOH | —(CH₂)₂(1,2-Phe)N(CH₃)COC(CH₃)₃) |
| | | | —(CH₂)₂(1,2-Phe)NH(COCH₂Ph) |

TABLE 7-continued

The following compounds (formula I'') are within the scope of the invention:

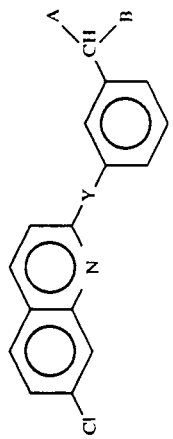

| Ex | Y | A | B |
|---|---|---|---|
| 303 | —CH₂O— | —SCH₂CH(CH₃)COOH | —(CH₂)₂(1,2-Phe)NH(SO₂Ph) |
| 304 | —CH₂O— | —SCH₂CH(CH₃)COOH | —(CH₂)₂(1,2-Phe)N(CH₃)SO₂Ph |
| 305 | —CH₂O— | —SCH₂CH(CH₃)COOH | —(CH₂)₂(1,2-Phe)NH(SO₂CF₃) |
| 306 | —CH₂O— | —SCH₂CH(CH₃)COOH | —(CH₂)₂(1,2-Phe)N(CH₃)SO₂CF₃ |
| 307 | —CH₂—CH₂— | —SCH₂CH(CH₂CH₃)COOH | —(CH₂)₂(1,2-Phe)NH(COPh) |
| 308 | —CH₂—CH₂— | —SCH₂CH(CH₂CH₃)COOH | —(CH₂)₂(1,2-Phe)N(CH₃)COPh |
| 309 | —CH₂—CH₂— | —SCH₂CH(CH₂CH₃)COOH | —(CH₂)₂(1,2-Phe)NH(COC(CH₃)₃) |
| 310 | —CH₂—CH₂— | —SCH₂CH(CH₃)COOH | —(CH₂)₂(1,2-Phe)N(CH₃)COC(CH₃)₃) |
| 311 | —CH₂—CH₂— | —SCH₂CH(CH₃)COOH | —(CH₂)₂(1,2-Phe)NH(COCH₂Ph) |
| 312 | —CH₂—CH₂— | —SCH₂CH(CH₃)COOH | —(CH₂)₂(1,2-Phe)N(CH₃)COCH₂Ph |
| 313 | —CH₂—CH₂— | —SCH₂CH(CH₃)COOH | —(CH₂)₂(1,2-Phe)NH(SO₂Ph) |
| 314 | —CH₂—CH₂— | —SCH₂CH(CH₃)COOH | —(CH₂)₂(1,2-Phe)N(CH₃)SO₂Ph |
| 315 | —CH₂—CH₂— | —SCH₂CH(CH₃)COOH | —(CH₂)₂(1,2-Phe)NH(SO₂CF₃) |
| 316 | —CH₂—CH₂— | —SCH₂CH(CH₃)COOH | —(CH₂)₂(1,2-Phe)N(CH₃)SO₂CF₃ |
| 317 | —CH₂—CH₂— | —SCH₂CH(CH₃)COOH | —(CH₂)₂(1,2-Phe)NH(COPh) |
| 318 | —CH₂—CH₂— | —SCH₂CH(CH₃)COOH | —(CH₂)₂(1,2-Phe)N(CH₃)COPh |
| 319 | —CH₂—CH₂— | —SCH₂CH(CH₃)COOH | —(CH₂)₂(1,2-Phe)NH(COC(CH₃)₃) |
| 320 | —CH₂—CH₂— | —SCH₂CH(CH₃)COOH | —(CH₂)₂(1,2-Phe)N(CH₃)COC(CH₃)₃ |
| 321 | —CH₂—CH₂— | —SCH₂CH(CH₃)COOH | —(CH₂)₂(1,2-Phe)NH(COCH₂Ph) |
| 322 | —CH₂—CH₂— | —SCH₂CH(CH₃)COOH | —(CH₂)₂(1,2-Phe)N(CH₃)COCH₂Ph |
| 323 | —CH₂—CH₂— | —SCH₂CH(CH₃)COOH | —(CH₂)₂(1,2-Phe)NH(SO₂Ph) |
| 324 | —CH₂—CH₂— | —SCH₂CH(CH₃)COOH | —(CH₂)₂(1,2-Phe)N(CH₃)SO₂Ph |
| 325 | —CH₂O— | —SCH₂CH(CH₂CH₃)COOH | —(CH₂)₂(1,2-Phe)NH(SO₂CF₃) |
| 326 | —CH₂O— | —SCH₂CH(CH₂CH₃)COOH | —(CH₂)₂(1,2-Phe)N(CH₃)SO₂CF₃ |
| 327 | —CH₂O— | —SCH₂CH(CH₂CH₃)COOH | —(CH₂)₂(1,2-Phe)N(CH₃)CO₂CH₂CH₃ |
| 328 | —CH₂O— | —SCH₂CH(CH₃)COOH | —(CH₂)₂(1,2-Phe)N(CH₃)CO₂(4-Cl—Ph) |
| 329 | —CH₂O— | —SCH₂CH(CH₃)COOH | —(CH₂)₂(1,2-Phe)OC(O)N(CH₃)₂ |
| 330 | —CH₂—CH₂— | —SCH₂CH(CH₃)COOH | —(CH₂)₂(1,2-Phe)OC(O)N(CH(CH₃)CF₃)₂ |
| 331 | —CH₂—CH₂— | —SCH₂CH(CH₃)COOH | —(CH₂)₂(1,2-Phe)OC(O)NH(CH₂(4-Cl—Ph) |
| 332 | —CH₂—CH₂— | —SCH₂CH(CH₃)COOH | —(CH₂)₂(1,2-Phe)N(CH₃)CO₂CH₂CH₃ |
| 333 | —CH₂—CH₂— | —SCH₂CH(CH₃)COOH | —(CH₂)₂(1,2-Phe)N(CH₃)CO₂(4-Cl—Ph) |
| 334 | —CH₂—CH₂— | —SCH₂CH(CH₃)COOH | —(CH₂)₂(1,2-Phe)OC(O)N(CH₃)₂ |
| 335 | —CH₂O— | —SCH₂CH(CH₂(4-Cl—Ph))COOH | —(CH₂)₂(1,2-Phe)OC(O)N(CH(CH₃)CF₃)₂ |
| 336 | —CH₂O— | —SCH₂CH(CH₂(4-Cl—Ph))COOH | —(CH₂)₂(1,2-Phe)OC(O)NH(CH₂(4-Cl—Ph) |
| 337 | —CH₂O— | —SCH₂CH(CH₂(4-Cl—Ph))COOH | —(CH₂)₂(1,2-Phe)—COOH |
| 338 | —CH₂O— | —SCH₂CH(CH₂(4-Cl—Ph))COOH | —(CH₂)₂(1,2-Phe)CON(CH₃)₂ |
| 339 | —CH₂O— | —SCH₂CH(CH₂(4-Cl—Ph))COOH | —(CH₂)₂(1,2-Phe)NHCO₂CH₂CH₃ |
| 340 | —CH₂—CH₂— | —SCH₂CH(CH₂(4-Cl—Ph))COOH | —(CH₂)₂(1,2-Phe)CON(CH₃)₂ |
| 341 | —CH₂—CH₂— | —SCH₂CH(CH₂(4-Cl—Ph))COOH | —(CH₂)₂(1,2-Phe)—COOH |
| 342 | —CH₂—CH₂— | —SCH₂CH(CH₂(4-Cl—Ph))COOH | —(CH₂)₂(1,2-Phe)CN₄H |
| 343 | —CH₂—CH₂— | —SCH₂CH(CH₂CH₃)COOH | —(CH₂)₂(1,2-Phe)NHCO₂CH₂CH₃ |

TABLE 7-continued

The following compounds (formula I'') are within the scope of the invention:

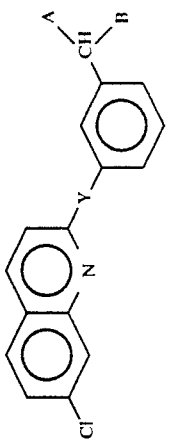

| Ex | Y | A | B |
|---|---|---|---|
| 344 | —CH₂O— | —SCH₂CH(CH₂CH₂CH₃)COOH | —(CH₂)₂(1,2-Phe)COOH |
| 345 | —CH₂O— | —SCH₂CH(CH₂CH(CH₂)₂)COOH | —(CH₂)₂(1,2-Phe)CONHCH₃ |
| 346 | —CH₂—CH₂— | —SCH₂CH(CH₂CH(CH₂)₂)COOH | —(CH₂)₂(1,2-Phe)CONHCH₃ |
| 347 | —CH₂O— | —SCH₂CH(CH₂CH(CH₂)₂)COOH | —(CH₂)₂(1,2-Phe)COOH |
| 348 | —CH₂—CH₂— | —SCH₂CH(CH₂CH(CH₂)₂)COOH | —(CH₂)₂(1,2-Phe)COOH |
| 349 | —CH₂—CH₂— | —SCH₂CH(CH₂CH(CH₂)₂)COOH | —(CH₂)₂(1,2-Phe)CN₄H |
| 350 | —CH₂O— | —SCH₂CH(CH₂CH(CH₂)₂)COOH | —(CH₂)₂(1,2-Phe)CN₄H |
| 351 | —CH₂—CH₂— | —SCH₂CH(CH₂CH(CH₂)₂)COOH | (CH₂)₂(1,2-Phe)NHCO₂CH₂CH₃ |
| 352 | —CH₂—CH₂— | —SCH₂CH(CH₂CH(CH₂)₂)COOH | (CH₂)₂(1,2-Phe)NHCO₂CH₂CH₃ |
| 353 | —CH₂O— | —SCH₂CH(CH₂CH₃)COOH | (CH₂)₂(1,3-Phe)COOH |
| 354 | —CH₂O— | —SCH₂CH(CH₂CH₃)CONH₂ | —(CH₂)₂(1,2-Phe)CO₂H |
| 355 | —CH(CH₂)CH— | —S(CH₂)₂CO₂H | —(CH₂)₂(1,2-Phe)CONH₂ |
| 356 | —CH₂O— | —S(CH₂)₂CO₂H | —(CH₂)₂(4-Cl—Phe)CONHCH₃ |
| 357 | —CH₂O— | —SCH₂CH(CH₂)CO₂H | —(CH₂)₂(4-Cl—Phe)CON(CH₃)CH₂OH |
| 358 | —CH₂O— | —SCH₂CH(CH₂)CO₂H | —(CH₂)₂(4-Cl—Phe)CON(CH₃)₂ |
| 359 | —CH₂O— | —SCH₂CH(CHCH₂CH₂)CO₂H | —(CH₂)₂(4-Cl—Phe)CON(CH₃)₂ |
| 360 | —CH₂O— | —SCH₂CH(CH₂)CO₂H | —(CH₂)₂(4-Cl—Phe)CON(CH₃)₂ |
| 361 | —CH₂O— | —S(CH₂)₂CO₂H | —(CH₂)₂(1,2-Phe)S(O)₂CH₃ |
| 362 | —CH₂O— | —S(CH₂)₂CO₂H | —(CH₂)₂(4-Cl—Phe)CO₂H |
| 363 | —CH₂—CH₂— | —S(CH₂)₂CO₂H | —(CH₂)₂(4-Cl—Phe)CON(CH₃)₂ |
| 364 | —CH₂O— | —SCH₂CH(CH₃)CO₂H | —(CH₂)₂(1,2-Phe)C(NOH)CH₃ |
| 365 | —CH₂O— | —S(CH₂)₂CO₂H | —(CH₂)₂(4-Cl—Phe)CON(CH₃)₂(+) |
| 366 | —CH₂O— | —S(CH₂)₂CO₂H | —(CH₂)₂(4-Cl—Phe)CON(CH₃)₂(−) |
| 367 | —CH₂O— | —S(CH₂)₂CO₂H | —(CH₂)₂(4-Cl—Phe)NHCO₂CH₂CH₃ |
| 368 | —CH₂O— | —S(CH₂)₂COOH | —(CH₂)₂(4-Cl—Phe)CON(CH₃)₂ |
| 369 | —CH₂O— | —S(O)(CH₂)₂CO₂H | —(CH₂)₂(6-Cl—Phe)CON(CH₃)₂ |
| 370 | —CH₂O— | —S(CH₂)₂CO₂H | —(CH₂)₂(4-Cl—Phe)CON(CH₃)₂ |
| 371 | —CH₂O— | —S(CH₂)₂CO₂H | —(CH₂)₂(3-Cl—Phe)CON(CH₃)₂ |
| 372 | —CH₂O— | —SCH₂CH(CH₃)CO₂H | —(CH₂)₂(4-Cl—Phe)CONH(CH₂)₂OH |
| 373 | —CH₂O— | —S(CH₂)₂CO₂H | —(CH₂)₂(1,2-Phe)CONH₂ |
| 374 | —CH₂O— | —S(CH₂)₂CO₂H | —(CH₂)₂(4-Cl—Phe)CON(CH₃)₂(+) |
| 375 | —CH₂O— | —S(CH₂)₂CO₂H | —(CH₂)₂(4-Cl—Phe)CON(CH₃)₂(−) |
| 376 | —CH₂O— | —S(CH₂)₂COOH | —(CH₂)₂(4-Br—Phe)CO₂H |
| 377 | —CH₂O— | —SCH(CH₃)CH₂CO₂H | —(CH₂)₂(4-Cl—Phe)CON(CH₃)₂ |
| 378 | —CH₂—CH₂— | —SCH₂CH(CH₂CH₃)CO₂H | —(CH₂)₂(1,2-Phe)CON(CH₃)₂ |
| 379 | —CH₂O— | —S(CH₂)₂CO₂H | —(CH₂)₂(2,5-Fur)CON(CH₃)₂* |
| 380 | —CH₂O— | —SCH₂CH(CH₃)CO₂H | —(CH₂)₂(4-Cl—Phe)CONH₂ |
| 381 | —CH₂O— | —S(CH₂)₂CO₂H | —(CH₂)₂(4-Cl—Phe)NHCOCH₃ |
| 382 | —CH₂O— | —S(CH₂)₂CO₂H | —(CH₂)₂(1,2-Phe)CONHS(O)₂CH₃ |
| 383 | —CH₂O— | —SCH₂CH(CH₂CH₃)CO₂H | —(CH₂)₂(4-Cl—Phe)CO₂H |
| 384 | —CH₂O— | —SCH₂CH(CH₃)CO₂H | —(CH₂)₂(4-Cl—Phe)CO₂H |

TABLE 7-continued

The following compounds (formula I'') are within the scope of the invention:

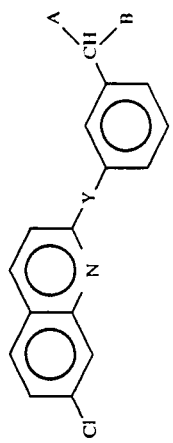

| Ex | Y | A | B |
|---|---|---|---|
| 385 | —CH₂O— | —S(CH₂)₂CO₂H | —(CH₂)₂(1,2-(4,5-diCl—Phe)CO₂H |
| 386 | —CH=CH— | —S(CH₂)₂CO₂H | —SCH₂(1,2-Phe)CO₂H |
| 387 | —CH=CH— | —S(CH₂)₂CO₂H | —SCH₂(1,2-(4-Cl—Phe)CO₂H |
| 388 | —CH₂O— | —SCH₂CH(OCH₃)CO₂H | —(CH₂)₂(1,2-(4-Cl—Phe)CO₂H |
| 389 | —CH₂—CH₂— | —S(CH₂)₂CO₂H | —(CH₂)₂(1,2-(4-Cl—Phe)CO₂H |
| 390 | —CH=CH— | —S(CH₂)₂CON(CH₃)₂ | —SCH₂(1,2-Phe)CO₂H |
| 391 | —CH=CH— | —S(CH₂)₂CON(CH₃)₂ | —SCH₂(1,2-(4-Cl—Phe)CO₂H |
| 392 | —CH₂O— | —S(CH₂)₂CO₂H | —(CH₂)₂(3,2-Pye)CO₂H |
| 393 | —CH₂O— | —S(CH₂)₂CO₂H | —(CH₂)₂(1,2-Phe)CONH₂ |
| 394 | —CH=CH— | —S(CH₂)₂CO₂H | —(CH₂)₂(1,2-Phe)CONHC(CH₃)₃ |
| 395 | —CH₂O— | —S(CH₂)₂CO₂H | —(CH₂)₂(1,2-(4-Ph—Phe)CO₂H |
| 396 | —CH=CH— | —S(CH₂)₂CO₂H | —(CH₂)₂(1,2-(4-Cl—Phe)CO₂H |
| 397 | —CH=CH— | —S(CH₂)₂CON(CH₃)₂ | —(CH₂)₂(1,2-(4-Cl—Phe)CO₂H |
| 398 | —CH=CH— | —S(CH₂)₂CO₂H | —(CH₂)₂(1,2-(4-Cl—Phe)CONH₂ |
| 399 | —CH=CH— | —S(CH₂)₂CO₂H | —(CH₂)₂(1,2-(4-Cl—Phe)CN₄H |
| 400 | —CH=CH— | —S(CH₂)₂CO₂H | —(CH₂)₂(3,2-Pye)CON(CH₃)₂ |
| 401 | —CH=CH— | —S(CH₂)₂CO₂H | —(CH₂)₂(1,2-(4-Cl—Phe)CONHC(CH₃)₃ |
| 402 | —CH=CH— | —S(CH₂)₂CO₂H | —(CH₂)₂(1,2-(4-Cl—Phe)CON(CH₃)₂ |
| 403 | —CH₂O— | —S(CH₂)₂CO₂H | —(CH₂)₂(1,2-(4-Cl—Phe)CN₄H |
| 404 | —CH=CH— | —SCH₂CH(CH₃)CO₂H | —(CH₂)₂(1,2-Phe)CN |
| 405 | —CH=CH— | —S(CH₂)₂CO₂H | —SCH₂(1,2-Phe)CN₄H |
| 406 | —CH=CH— | —S(CH₂)₂CON(CH₃)₂ | —SCH₂(1,2-Phe)CN₄H |
| 407 | —CH=CH— | —SCH₂(1,2-Phe)CO₂H | —SCH₂(1,2-Phe)CO₂H |
| 408 | —CH=CH— | —SCH₂(1,2-(4-Cl—Phe)CO₂H | —SCH₂(1,2-(4-Cl—Phe)CO₂H |
| 409 | —CH=CH— | —S(CH₂)₂CO₂H | —SCH₂(1,2-Phe)CON(CH₃)₂ |
| 410 | —CH=CH— | —S(CH₂)₂CO₂H | —SCH₂(1,2-(4-Cl—Phe)CON(CH₃)₂ |
| 411 | —CH₂O— | —SCH₂CH(CH₃)CO₂H | —(CH₂)₂(1,2-Phe)NO₂ |
| 412 | —CH=CH— | —SCH₂CH(OCH₃)CO₂H | —(CH₂)₂(1,2-Phe)CO₂H |
| 413 | —CH₂O— | —SCH₂CH(CH₃)CO₂H | —(CH₂)₂(1,4-(2-(CH₃O)—Phe)CO₂H |
| 414 | —CH=CH— | —SCH₂CH(CH₃)CO₂H | —(CH₂)₂(1,4-(2-(CH₃O)—Phe)CO₂H |
| 415 | —CH=CH— | —S(CH₂)₂CO₂H | —(CH₂)₂(1,2-Phe)CH(CH₃)CO₂H |
| 416 | —CH₂O— | —SCH₂CH(CH₃)CO₂H | —(CH₂)₂(1,2-Phe)CH(CH₃)NHCO₂CH₂CH₃ |
| 417 | —CH=CH— | —S(CH₂)₂CO₂H | —(CH₂)₂(1,3-Phe)C((CH₃)₂CO₂H |
| 418 | —CH₂O— | —SCH₂CH(CH₂CH₃)CO₂H | —(CH₂)₂(1,2-Phe)C(CH₃)₂CONHS(O)₂CH₃ |
| 419 | —CH=CH— | —S(CH₂)₂CO₂H | —(CH₂)₂(1,3-Phe)CH(CH₃)CON(CH₃)₂ |
| 420 | —CH=CH— | —S(CH₂)₂CO₂H | —(CH₂)₂(1,3-Phe)CH(CH₃)CN₄H |
| 421 | —CH₂O— | —S(CH₂)₂CO₂H | —(CH₂)₂(1,2-Phe)CH₂S(O)₂CF₃ |
| 422 | —CH₂O— | —S(CH₂)₂CO₂H | —(CH₂)₂(1,2-Phe)C(CH₃)₂NHCOC(CH₃)₃ |
| 423 | —CH=CH— | —S(CH₂)₂CO₂H | —(CH₂)₂(1,2-Phe)CH₂S(O)CH₂CH₃ |

*Fur = furanediyl

What is claimed is:
1. A compound of the formula:

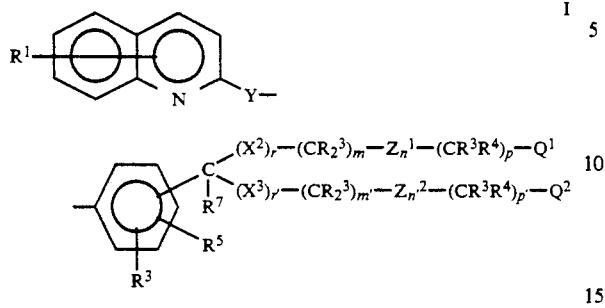

wherein:

$R^1$ is H, halogen, $C_1-C_8$ alkyl, $C_2-C_8$ alkenyl, $C_2-C_8$ alkynyl, $-CF_3$, $-SR^2$, $-S(O)R^2$, $-S(O)_2R^2$, $-OR^3$, $-COOR^3$, $-(C=O)R^3$, $-C(OH)R^3R^3$, $-CN$, $-N_3$, substituted or unsubstituted phenyl, substituted or unsubstituted benzyl, substituted or unsubstituted 2-phenethyl, or substituted or unsubstituted pyridyl;

$R^2$ is $C_1-C_8$ alkyl, $C_2-C_8$ alkenyl, $C_2-C_8$ alkynyl, $-CF_3$, substituted or unsubstituted phenyl, substituted or unsubstituted benzyl, or substituted or unsubstituted 2-phenethyl;

$R^3$ is H or $R^2$;

$R^4$ is H, halogen, $-NO_2$, $-CN$, $-OR^3$, $-SR^3$, $NR^3R^3$, or $C_1-C_8$ alkyl;

$R^5$ is H, halogen, $-N_3$, $-CN$, $-SR^2$, $-NR^3R^3$, $-OR^3$, $C_1-C_8$ alkyl, $-(C=O)R^3$;

$R^6$ is $-CH_2CONR^{12}R^{12}$;

$R^7$ is H or $C_1-C_4$ alkyl;

$R^{10}$ is $-SR^{11}$, $-OR^{12}$, or $-NR^{12}R^{12}$;

$R^{11}$ is $C_1-C_6$ alkyl, $-(C=O)R^{14}$, unsubstituted phenyl, or unsubstituted benzyl;

$R^{12}$ is H or $R^{11}$;

$R^{13}$ is $C_1-C_8$ alkyl, $C_2-C_8$ alkenyl, $C_2-C_8$ alkynyl, $-CF_3$, or unsubstituted phenyl, benzyl, or 2-phenethyl;

$R^{14}$ is H or $R^{13}$;

$R^{15}$ is $R^3$ or halogen;

$R^{16}$ is H, $C_1-C_4$ alkyl, or OH;

$R^{17}$ is $C_1-C_8$ alkyl, $C_2-C_8$ alkenyl, $C_2-C_8$ alkynyl, or substituted or unsubstituted phenyl, benzyl, or 2-phenethyl;

$R^{18}$ is $C_1-C_8$ alkyl, $C_2-C_8$ alkenyl, $C_2-C_8$ alkynyl, $-CF_3$, or substituted or unsubstituted phenyl, benzyl, or 2-phenethyl;

$R^{19}$ is $C_4-C_8$ alkyl, $C_2-C_8$ alkenyl, $C_2-C_8$ alkynyl, $-CF_3$, or unsubstituted phenyl, benzyl, or 2-phenethyl;

m and m' are independently 0-8;
n and n' are independently 0 or 1 but not both 0;
p and p' are independently 0-8;
m+n+p is 1-10 when $X^2$ is O, S, S(O), or $S(O)_2$;
m+n+p is 0-10 when $X^2$ is $CR^3R^{16}$;
m'+n'+p' is 1-10 when $X^3$ is O, S, S(O), or $S(O)_2$;
m'+n'+p' is 0-10 when $X^3$ is $CR^3R^{16}$;
r is 0 or 1 when $Z^1$ is HET ($-R^3$, $-R^5$);
r is 1 when $Z^1$ is $-CONR^3$;
r' is 0 or 1 when $Z^2$ is HET($-R^3$, $-R^5$);
r' is 1 when $Z^2$ is $CONR^3$;
$Q^1$ and $Q^2$ are independently $-COOR^3$, tetrazole, $-COOR^6$, $-CONHS(O)_2R^{13}$, $-CN$, $-CONR^{12}R^{12}$, $-CHO$, $-CH_2OH$, $-COCH_2OH$, $-NHS(O)_2R^{13}$, $-C(O)R^{19}$, $-NR^{17}C(O)OR^{17}$, $-NR^{12}C(O)NR^{12}R^{12}$, $-NHC(O)R^{18}$, $-OC(O)NHR^{12}$, $-S(O)_2R^{18}$, $-S(O)R^{18}$, $-S(O)_2NR^{12}R^{12}$, $-NO_2$,

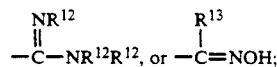

$X^1$ is O, S, $-S(O)-$, $-S(O)_2-$, $-NR^3$, or $-CR^3R^3-$;
$X^2$ and $X^3$ are independently O, S, S(O), $S(O)_2$, or $CR^3R^{16}$;
Y is $-CR^3=CR^3-$, $-C\equiv C-$, $-CR^3R^3-X^1-$, $-X^1-CR^3R^3-$, $-CR^3R^3-X^1-CR^3R^3$,

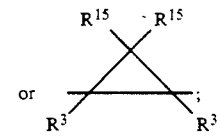

$Z^1$ and $Z^2$ are independently $-CONR^3-$or $-HET(-R^3, -R^5)-$, provided that at least one of them is $-HET(-R^3, -R^5)-$;
HET is

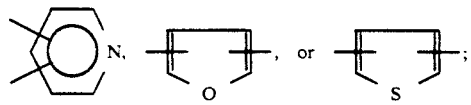

substituted phenyl, benzyl, or 2-phenethyl mean 1 or 2 substituents on the aromatic ring selected from $C_1-C_6$ alkyl, $R^{10}$, $NO_2$, $SCF_3$, halogen, $-COR^7$, $-COR^{10}$, CN, and $CF_3$;

and the pharmaceutically acceptable salts thereof.

2. A compound of claim 1 wherein the substituents are as follows:

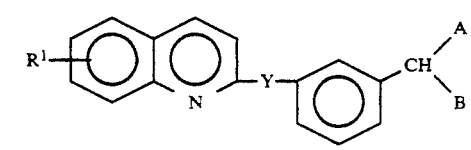

| $R^1$ | Y | A | B |
|---|---|---|---|
| 7-Cl | $-CH=CH-$ | $-S(CH_2)_2C(O)N(CH_3)_2$ | -(2,5-Thio)$CO_2H$ |
| 7-Cl | $-CH_2O-$ | $-S(CH_2)_2C(O)N(CH_3)_2$ | -(3,5-Pye)$CO_2H$ |

-continued

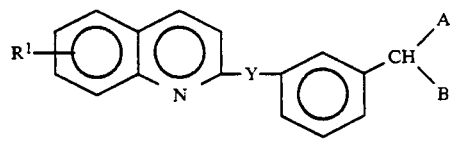

| R¹ | Y | A | B |
|---|---|---|---|
| 7-Cl | —CH=CH— | —S(CH₂)₂C(O)N(CH₃)₂ | -(3,5-Pye)CO₂H | wherein pye = ⟨pyridinyl⟩ and thio = ⟨thienyl⟩

3. A compound of claim 1 which is:
5-((3-(2-(7-chloroquinolin-2-yl)ethenyl)phenyl)(2-(dimethylcarbamoyl)ethylthio)methyl)thiophene-2-carboxylic acid;
5-((3-((7-chloro-2-quinolinyl)methoxy)phenyl)((3-dimethylamino-3-oxopropyl)thio)methyl)-3-pyridinecarboxylic acid, sodium salt; or
3-(1-(3-(2-(7-chloro-2-quinolinyl)ethenyl)phenyl)-1-((2-carboxy-4-pyridinyl)thio)methyl)benzoic acid.

4. A compound of claim 1 wherein:
$R^1$ is H, halogen, $C_1$-$C_8$ alkyl, —CF₃, —SR², —S(O)R², —S(O)₂R², —OR³, or —CN;
$R^2$ is $C_1$-$C_8$ alkyl or —CF₃;
$R^4$ is H, —OR³, —SR³, NR³R³, or $C_1$-$C_8$ alkyl;
$R^5$ is H, halogen, —CN, —SR², —OR³, $C_1$-$C_8$ alkyl, or —(C=O)R³;
$R^{13}$ is $C_1$-$C_8$ alkyl, —CF₃, or unsubstituted phenyl, benzyl, or 2-phenethyl;
m and m' are independently 0-4;
p and p' are independently 0-4;
m+n+p is 1-10 when X² is O or S;
m'+n'+p' is 1-10 when X³ is O or S;
Q¹ and Q² are independently —COOR³, tetrazole, —COOR⁶, —CONHS(O)₂R¹³, —CONR¹²R¹², or —NHS(O)₂R¹³;
X¹ is O, S, —NR³, or —CR³R³—;
X² and X³ are independently O, S, or CR³R¹⁶;
Y is —CR³=CR³—, —C=C—, —CR³R³—X¹—, or —X¹—CR³R³—;
and the pharmaceutically acceptable salts thereof.

5. A compound of claim 1 wherein:
$R^1$ is H, halogen, $C_1$-$C_8$ alkyl, —CF₃, —SR², —S(O)R², —S(O)₂R², —OR³, or —CN;
$R^2$ is $C_1$-$C_8$ alkyl or —CF₃;
$R^4$ is H, —OR³, —SR³, NR³R³, or $C_1$-$C_8$ alkyl;
$R^5$ is H, halogen, —CN, —SR², —OR³, $C_1$-$C_8$ alkyl, or —(C=O)R³;
$R^{13}$ is $C_1$-$C_8$ alkyl, —CF₃, or unsubstituted phenyl, benzyl, or 2-phenethyl;
m and m' are independently 0-4;
p and p' are independently 0-4;
m+n+p is 1-10 when X² is O or S;
m'+n'+p' is 1-10 when X³ is O or S;
Q¹ and Q² are independently —COOR³, tetrazole, or —CONR¹²R¹²;
X¹ is O, S, —NR³, or —CR³R³—;
X² and X³ are independently O, S, or CR³R¹⁶;
Y is —CH=CH—;
Z¹ and Z² are HET(—R³, —R⁵);
and the pharmaceutically acceptable salts thereof.

6. A pharmaceutical composition for preventing the action of leukotrienes in a mammal comprising a therapeutically effective amount of a compound of claim 1 and a pharmaceutically acceptable carrier.

7. A method of preventing the action of leukotrienes in a mammal which comprises administering to said mammal an effective amount of a compound of claim 1.

8. The method of claim 7 wherein the mammal is man.

* * * * *